(12) United States Patent
Kim et al.

(10) Patent No.: US 11,919,911 B2
(45) Date of Patent: Mar. 5, 2024

(54) METHYL (R)-2-(FLUOROMETHYL)-5-OXO-4-PHENYL-4,5,6,7-TETRAHYDRO-1H-CYCLOPENTA[B]PYRIDINE-3-CARBOXYLATE AND METHYL (R)-2-(FLUOROMETHYL)-5-OXO-4-PHENYL-1,4,5,7-TETRAHYDROFURO[3,4-B]PYRIDINE-3-CARBOXYLATE AS CAV1.2 ACTIVATORS

(71) Applicant: Novartis AG, Basel (CH)

(72) Inventors: Sung David C. Kim, Westwood, MA (US); Zaixing Li, Shanghai (CN); Chui Lu, Shanghai (CN); Danuta Lubicka, Peabody, MA (US); James Neef, Stow, MA (US); Hye-Yeon Park, Arlington, MA (US); Tejaskumar Pankajbhai Pathak, Boston, MA (US); Amir Masoud Sadaghiani, Dover, MA (US); Xilin Zhou, Arlington, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 17/346,006

(22) Filed: Jun. 11, 2021

(65) Prior Publication Data
US 2021/0395261 A1 Dec. 23, 2021

(30) Foreign Application Priority Data

Jun. 15, 2020 (WO) ............... PCT/CN2020/096177

(51) Int. Cl.
*C07D 491/048* (2006.01)
*C07D 221/04* (2006.01)

(52) U.S. Cl.
CPC ....... *C07D 491/048* (2013.01); *C07D 221/04* (2013.01); *C07B 2200/13* (2013.01)

(58) Field of Classification Search
CPC ................................. C07D 491/048
USPC ...................................... 514/302
See application file for complete search history.

(56) References Cited

U.S. PATENT DOCUMENTS

| | | | |
|---|---|---|---|
| 4,532,248 A | 7/1985 | Franckowiak et al. | |
| 4,567,268 A | 1/1986 | Young | |
| 5,026,714 A | 6/1991 | Goldmann et al. | |

FOREIGN PATENT DOCUMENTS

| | | |
|---|---|---|
| EP | 0111455 A2 | 6/1984 |
| EP | 0158138 A1 | 10/1985 |
| WO | 2010/015037 A1 | 2/2010 |

OTHER PUBLICATIONS

Skrastins et al., Khimya Geterotsiklcheskikh Soedinenii (1992), vol. 4, pp. 570-571.*

Andrade, A., et al., "Genetic Associations between Voltage-Gated Calcium Channels and Psychiatric Disorders," Int. J. Mol. Sci., 2019, 20, 3537.
Berridge, M., "Calcium signalling and psychiatric disease: bipolar disorder and schizophrenia," Cell Tissue Res, 2014, 357:477-492.
Ferreira et al, "Collaborative genome-wide association analysis supports a role for ANK3 and CACNA1C in bipolar disorder," Nat Genet 40:1056-1058, 2008.
Goerlitzer, K., et al., ;"Anellated lactones form Bay-K-8644 and dihydropyridine byproducts in the Hantzsch synthesis"; Inst. Pharm. Chem., Tech. Univ. Braunschweig, Braunschweig, 3300, Germany (English abstract attached) Archiv der Pharmazie (Weinheim, Germany) (1991), 324(11), 879-86.
Gunduz, M., et al., "Synthesis of cyclopentapyridine and thienopyridine derivatives as potential calcium channel modulators," Arzneimittelforschung. Apr. 2012;62(4):167-75.
Hopp, S., "Targeting microglia L-type voltage-dependent calcium channels for the treatment of central nervous system disorders," J Neurosci Res., Jan. 2021;99(1):141-162.
Ishikawa, et al., "Survival of rat motoneurons in culture by L-type calcium channel agonists, FPL64176 and (S)-Bay K8644," Journal of neurochemistry , 2012, vol. 123, p. 82-83.
Kabir, Z., et al., "From Gene to Behavior: L-Type Calcium Channel Mechanisms Underlying Neuropsychiatric Symptoms," Neurotherapeutics. Jul. 2017; 14(3): 588-613.
McInally, T., et al. "A novel, base-induced fragmentation of Hantzsch-type 4-aryl-1,4-dihydropyridines"; Journal of the Chemical Society, Perkin Transactions 1: Organic and Bio-Organic Chemistry (1972-1999) (1988), (7), 1837-44.

(Continued)

*Primary Examiner* — Taofiq A Solola
(74) *Attorney, Agent, or Firm* — McCarter & English, LLP

(57) ABSTRACT

The present disclosure provides for a compound according to formula (I)

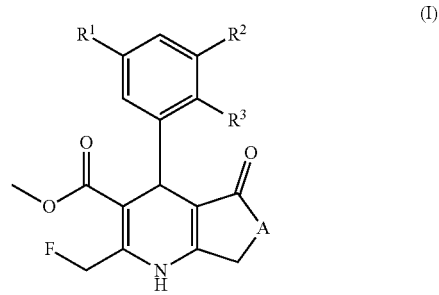

Figure 1:
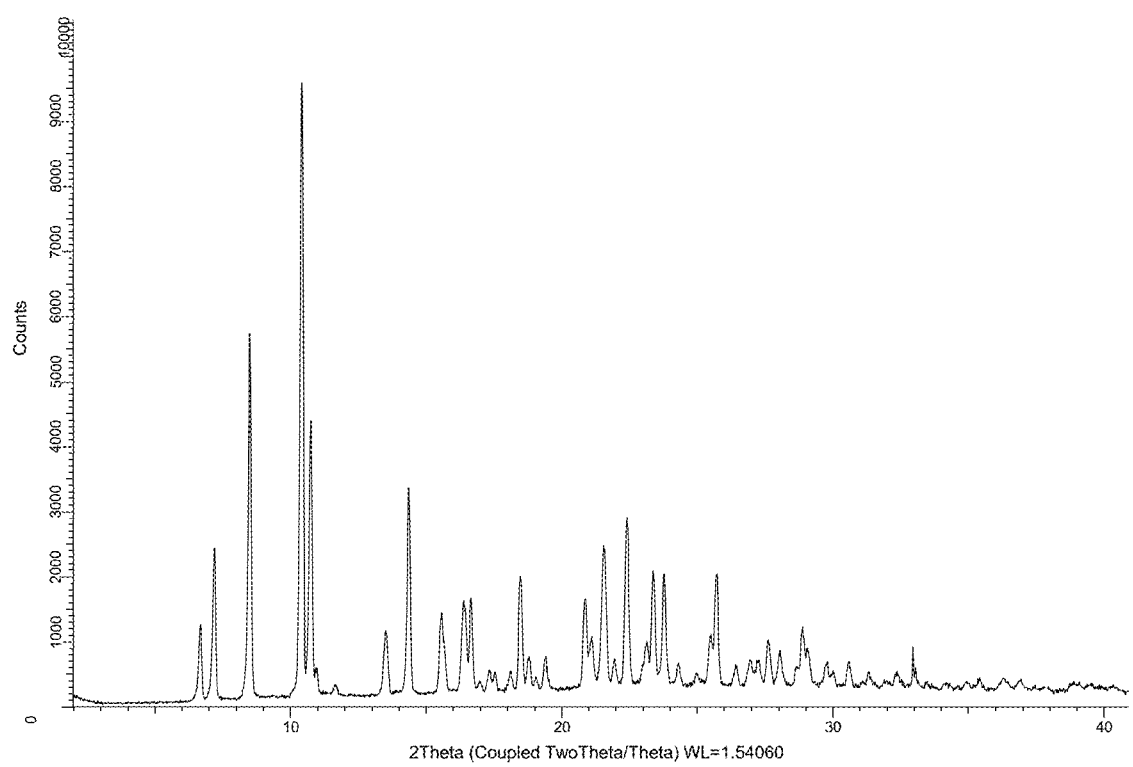

or a pharmaceutically acceptable salt thereof as Ca$_V$1.22 activators for the treatment of schizophrenia, bipolar disorder, major depressive disorder, substance use disorder, ADHD, Phelan-McDermid Syndrome, autism spectrum disorder, multiple sclerosis, frontotemporal dementia, Alzheimer's disease, Brugada Syndrome, Short QT syndrome, or early repolarization syndrome.

22 Claims, 9 Drawing Sheets

(56) References Cited

OTHER PUBLICATIONS

Patmore, L., et al., "RS 30026: a potent and effective calcium channel agonist"; British Journal of Pharmacology (1990), 99(4), 687-94.

Sausin'sh, A., et al. "Methods of synthesis of 4-(pyrazolyl)—and 4-(pyridyl)-5-oxo-1,4,5,7-tetrahydrofuro[3,4-b] byridines"; Chemistry of Heterocyclic Compounds, (1995), (7), pp. 966-972.

Skrastin'sh, I.P., et al. "Bromination of 4-aryl-3,5-bis(alkoxycarbonyl)-2,6-dimethyl-1,4-dihydropyridines"; Chemistry of Heterocyclic Compounds, (1991), (9), 1230-5.

Skrastin'sh, I.P., et al., "Bromination of 2,6-dimethyl-3,5-bis(methoxycarbonyl)-4-[2- (difluoromethoxy)phenyl]-1,4-dihydropyridine (foridone)"; Chemistry of Heterocyclic Compounds, 1989 (7), 948-52.

Skrastin'sh, I.P, et al., "Synthesis and pharmacological activity of furo-1,4-dihydropyridines"; Pharmaceutical Chemistry Journal, (1989), 23(11), 1323-6.

Young, S. D., "Facile conversion of Hantzsch type 4-aryl-2,6-dimethyl-1,4-dihydropyridine-3,5- carboxylates into 4-aryl-2-methyl-5-oxo-1,4,5,7-tetrahydrofuro[3,4- b]pyridine-3-carboxylates"; Merck Sharp and Dohme Res. Lab., West Point, PA; Synthesis (1984), (7), 617-18.

International Search Report and Written Opinion for International Application No. PCT/IB2021/055184, dated Sep. 2, 2021, 13 pages.

International Search Report and Written Opinion for International Application No. PCT/IB2021/055183, dated Aug. 26, 2021, 14 pages.

Patani et al, Bioisosterism: a Rational Approach in Drug Design, Chemical reviews, 1996, 3147-3176, 96.8.

* cited by examiner

METHYL (R)-2-(FLUOROMETHYL)-5-OXO-4-PHENYL-4,5,6,7-TETRAHYDRO-1H-CYCLOPENTA[B]PYRIDINE-3-CARBOXYLATE AND METHYL (R)-2-(FLUOROMETHYL)-5-OXO-4-PHENYL-1,4,5,7-TETRAHYDROFURO[3,4-B]PYRIDINE-3-CARBOXYLATE AS CAV1.2 ACTIVATORS

This application claims the benefit of priority to International Application No.: PCT/CN2020/096177, filed Jun. 15, 2020, the disclosure of which is incorporated herein by reference in its entirety.

1. FIELD OF THE INVENTION

The present invention relates to methyl 2-(fluoromethyl)-5-oxo-4-phenyl-4,5,6,7-tetrahydro-1H-cyclopenta[b]pyridine-3-carboxylate and methyl 2-(fluoromethyl)-5-oxo-4-phenyl-1,4,5,7-tetrahydrofuro[3,4-b]pyridine-3-carboxylate compounds, pharmaceutical compositions containing them, and the use of such compounds as $Ca_V1.2$ activators for the treatment of calcium signaling deficit and/or synaptic dysfunction in psychiatric disorders including schizophrenia, bipolar disorder, major depressive disorder, and substance use disorders; neurodevelopmental disorders, such as attention deficit hyperactivity disorder, Phelan-McDermid Syndrome, and autism spectrum disorders; neurodegenerative disorders, such as multiple sclerosis, frontotemporal dementia, and Alzheimer's disease; and cardiac conditions such as Brugada Syndrome, Short QT syndrome, and early repolarization syndrome.

2. BACKGROUND OF THE INVENTION

Advancements in human genomics have shed light on the genetic basis of psychiatric disorders. Genome wide association studies (GWAS) in schizophrenia have identified over one hundred disease-associated loci, including $Ca_V1.2$ and other genes involved in neuronal calcium signaling. A cross-disorder GWAS analysis has identified $Ca_V1.2$ and its channel-forming beta subunit (CACNB2) as strongly associated with schizophrenia, bipolar disorder, major depressive disorder, ADHD, and autism spectrum disorders. In addition to evidence from GWAS, exome sequencing in patients with schizophrenia showed enrichment of disruptive mutations in $Ca_V1.2$ and other gene members of the neuronal calcium-signaling pathway including the CACNA2D, CACNB, CAMK2 genes. $Ca_V1.2$ has been shown to be important for neuronal differentiation and migration, neurite outgrowth, synaptic signaling, gene expression and brain plasticity. It has been shown to play a role in emotion, learning and memory, executive function, and reward responses of the brain.

$Ca_V1.2$ is broadly expressed throughout the body and plays a major role in multiple organ systems including the cardiovascular system; however, the physiological function of $Ca_V1.2$ in the cardiovascular system is distinct from its function in the brain. Studies have shown that $Ca_V1.2$ is a key contributor to action potential generation in the heart while it is a key driver of intracellular signaling and gene expression in neurons with minimal role in action potential generation. In Timothy Syndrome, $Ca_V1.2$ mutation p.G406R leads to distinct cellular phenotypes between cardiomyocytes and neurons. $Ca_V1.2$ mutations that cause cardiovascular specific disorders (Brugada Syndrome and Long QT syndrome type 8) are further evidence for the divergent functions of $Ca_V1.2$ in heart and brain.

Calcium channel activators have been previously reported, but further investigation into their use for neuropsychiatric disorders has been limited due to their effects on the cardiovascular system. In fact, many of these molecules were initially investigated and developed for their potential therapeutic use in heart failure. Most of the $Ca_V1.2$ SNPs associated from psychiatric GWAS studies reside in introns of the gene, and these risk SNPs have been shown to be associated with reduction of mRNA expression that in many cases results in overall reduction of calcium current amplitude. Therefore, small molecules that can increase the overall current amplitude could be the most beneficial to patients.

3. SUMMARY OF THE INVENTION

The present disclosure provides a compound according to formula (I) or a pharmaceutically acceptable salt thereof

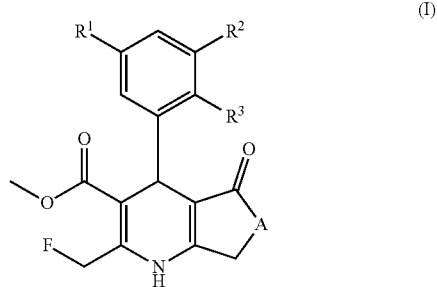

(I)

wherein:
   A is O or $CH_2$;
   $R^1$ is H or F;
   $R^2$ is H or F; and
   $R^3$ is $OCHF_2$, methyl, ethyl, or cyclopropyl each of which is optionally substituted with 1 to 3 F.

In a second aspect, the disclosure provides a compound according to formula (III) or a pharmaceutically acceptable salt or solvate thereof,

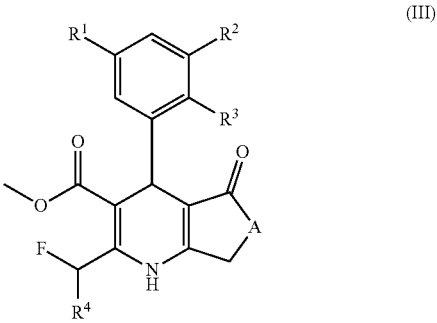

(III)

wherein:
   A is O or $CH_2$;
   $R^1$ is H or F;
   $R^2$ is H or F;
   $R^3$ is $OCHF_2$, methyl, ethyl, or cyclopropyl each of which is optionally substituted with 1 to 3 F; and
   $R^4$ is H or F.

In a third aspect, the disclosure provides a pharmaceutical composition comprising a compound of formula (I) or a pharmaceutically acceptable salt thereof.

In a fourth aspect, the disclosure provides for a compound of formula (I), or a pharmaceutically acceptable salt thereof for use in therapy, in particular in the treatment of psychiatric disorders including schizophrenia, bipolar disorder, major depressive disorder, and substance use disorders; neurodevelopmental disorders, such as attention deficit hyperactivity disorder, Phelan-McDermid Syndrome, and autism spectrum disorders; neurodegenerative disorders, such as multiple sclerosis, frontotemporal dementia and Alzheimer's disease; and cardiac conditions such as Brugada Syndrome, Short QT syndrome, and early repolarization syndrome.

In a fifth aspect, the disclosure provides a method for the treatment of psychiatric disorders including schizophrenia, bipolar disorder, major depressive disorder, and substance use disorders; neurodevelopmental disorders, such as attention deficit hyperactivity disorder, Phelan-McDermid Syndrome, and autism spectrum disorders; neurodegenerative disorders, such as multiple sclerosis, frontotemporal dementia and Alzheimer's disease; and cardiac conditions such as Brugada Syndrome, Short QT syndrome, and early repolarization syndrome. comprising administration of an effective amount of a compound according to formula (I), or a pharmaceutically acceptable salt thereof, to a patient in need of treatment thereof.

In a sixth aspect, the disclosures provides for the use of a compound of formula (I) or a pharmaceutically acceptable salt thereof in the manufacture of a medicament for the treatment of psychiatric disorders including schizophrenia, bipolar disorder, major depressive disorder, and substance use disorders; neurodevelopmental disorders, such as attention deficit hyperactivity disorder, Phelan-McDermid Syndrome, and autism spectrum disorders; neurodegenerative disorders, such as multiple sclerosis, frontotemporal dementia and Alzheimer's disease; and cardiac conditions such as Brugada Syndrome, Short QT syndrome, and early repolarization syndrome.

In a seventh aspect, the disclosure provides a method for the treatment of psychiatric disorders including schizophrenia, bipolar disorder, major depressive disorder, and substance use disorders; neurodevelopmental disorders, such as attention deficit hyperactivity disorder, Phelan-McDermid Syndrome, and autism spectrum disorders; neurodegenerative disorders, such as multiple sclerosis, frontotemporal dementia and Alzheimer's disease; and cardiac conditions such as Brugada Syndrome, Short QT syndrome, and early repolarization syndrome. comprising administration of a compound according to formula (I), or a pharmaceutically acceptable salt thereof, to a patient in need of treatment thereof.

In an eighth aspect, the disclosure provides a pharmaceutical composition comprising a compound of formula (III) or a pharmaceutically acceptable salt thereof.

In a ninth aspect, the disclosure provides for a compound of formula (III), or a pharmaceutically acceptable salt thereof for use in therapy, in particular in the treatment of psychiatric disorders including schizophrenia, bipolar disorder, major depressive disorder, and substance use disorders; neurodevelopmental disorders, such as attention deficit hyperactivity disorder, Phelan-McDermid Syndrome, and autism spectrum disorders; neurodegenerative disorders, such as multiple sclerosis, frontotemporal dementia and Alzheimer's disease; and cardiac conditions such as Brugada Syndrome, Short QT syndrome, and early repolarization syndrome.

In a tenth aspect, the disclosure provides a method for the treatment of psychiatric disorders including schizophrenia, bipolar disorder, major depressive disorder, and substance use disorders; neurodevelopmental disorders, such as attention deficit hyperactivity disorder, Phelan-McDermid Syndrome, and autism spectrum disorders; neurodegenerative disorders, such as multiple sclerosis, frontotemporal dementia and Alzheimer's disease; and cardiac conditions such as Brugada Syndrome, Short QT syndrome, and early repolarization syndrome. comprising administration of an effective amount of a compound according to formula (III), or a pharmaceutically acceptable salt thereof, to a patient in need of treatment thereof.

In a eleventh aspect, the disclosures provides for the use of a compound of formula (III) or a pharmaceutically acceptable salt thereof in the manufacture of a medicament for the treatment of psychiatric disorders including schizophrenia, bipolar disorder, major depressive disorder, and substance use disorders; neurodevelopmental disorders, such as attention deficit hyperactivity disorder, Phelan-McDermid Syndrome, and autism spectrum disorders; neurodegenerative disorders, such as multiple sclerosis, frontotemporal dementia and Alzheimer's disease; and cardiac conditions such as Brugada Syndrome, Short QT syndrome, and early repolarization syndrome.

In a twelfth aspect, the disclosure provides a method for the treatment of psychiatric disorders including schizophrenia, bipolar disorder, major depressive disorder, and substance use disorders; neurodevelopmental disorders, such as attention deficit hyperactivity disorder, Phelan-McDermid Syndrome, and autism spectrum disorders; neurodegenerative disorders, such as multiple sclerosis, frontotemporal dementia and Alzheimer's disease; and cardiac conditions such as Brugada Syndrome, Short QT syndrome, and early repolarization syndrome. comprising administration of a compound according to formula (III), or a pharmaceutically acceptable salt thereof, to a patient in need of treatment thereof.

4. BRIEF DESCRIPTION OF THE DRAWINGS

FIG. 1: illustrates a representative XRPD of Form A of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate of the present disclosure. The x-axis shows the scattering angle in ° 2-Theta, the y-axis shows the intensity of the scattered X-ray beam in counts of detected photons.

Figure 2:
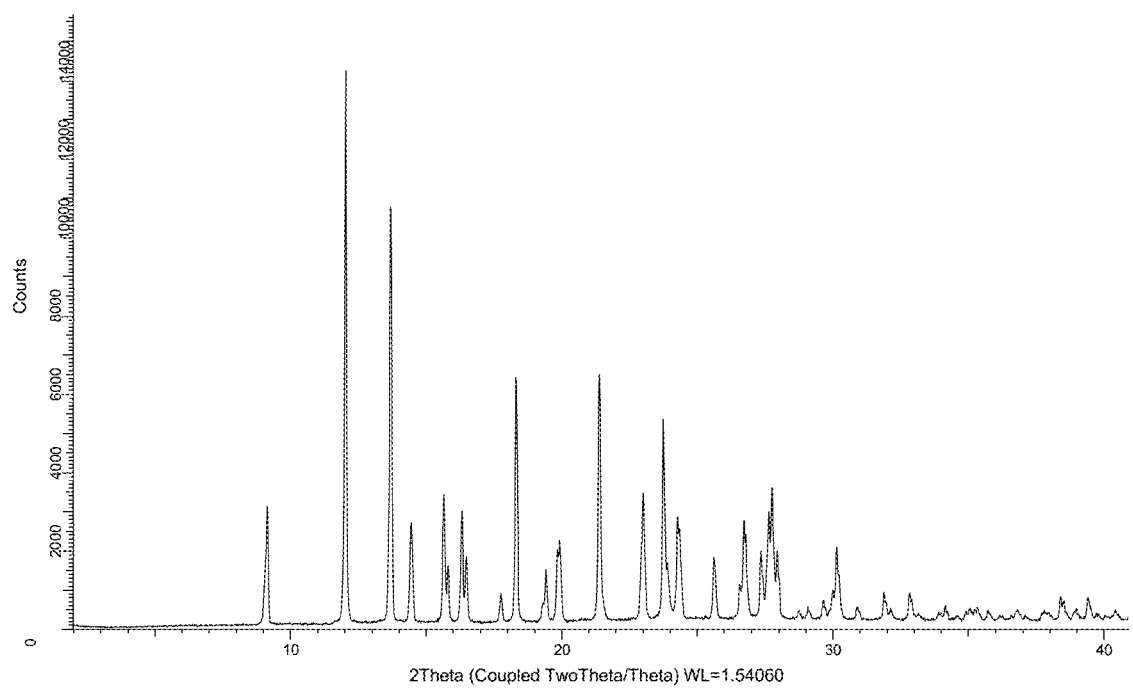

FIG. 2: illustrates a representative XRPD of Form B of [methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate of the present disclosure. The x-axis shows the scattering angle in ° 2-Theta, the y-axis shows the intensity of the scattered X-ray beam in counts of detected photons.

Figure 3:
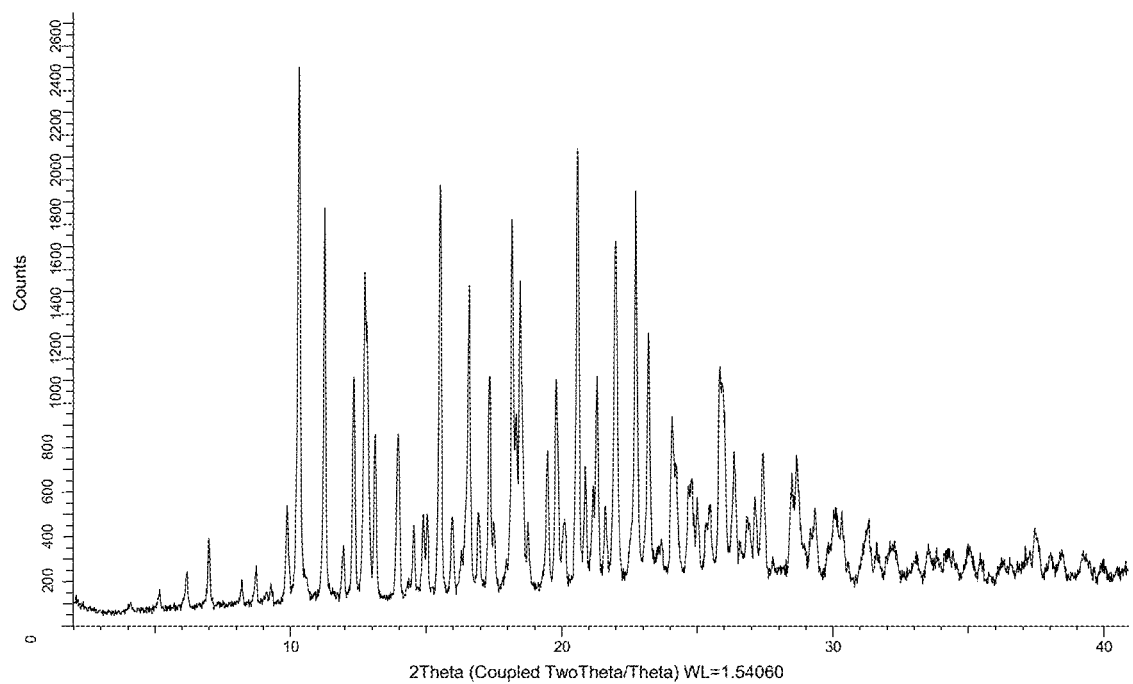

FIG. 3: illustrates a representative XRPD of Form C of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate of the present disclosure of the present invention. The x-axis shows the scattering angle in ° 2-Theta, the y-axis shows the intensity of the scattered X-ray beam in counts of detected photons.

Figure 4:
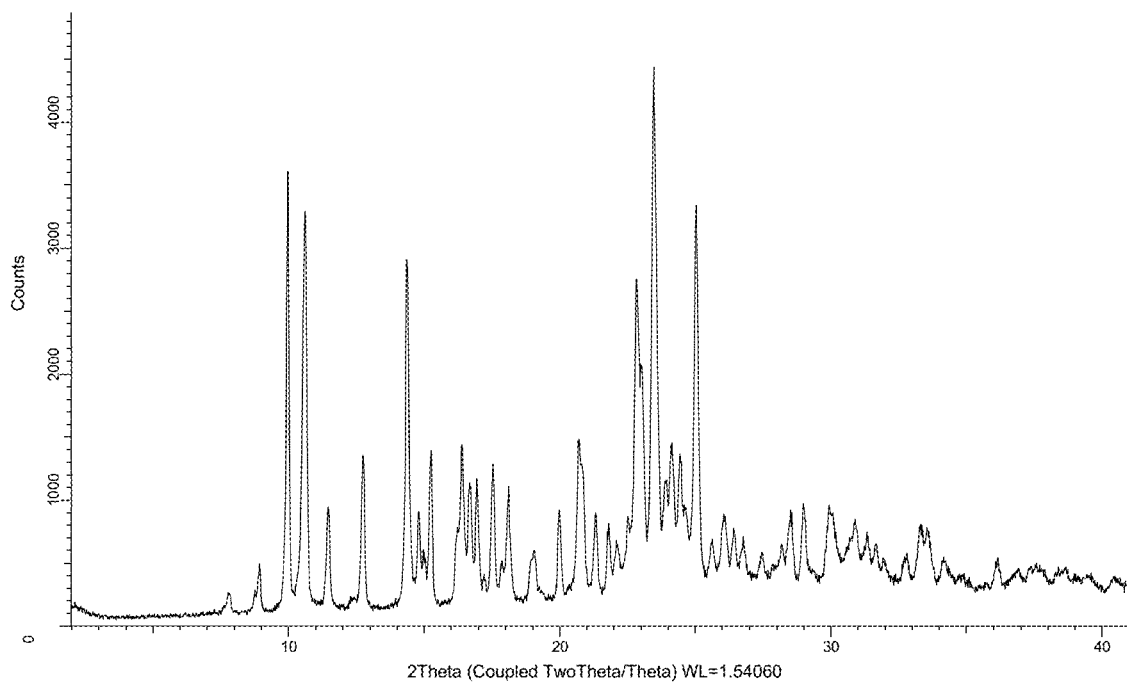

FIG. 4: illustrates a representative XRPD of Hydrate A of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate of the present disclosure. The x-axis shows the scattering angle in ° 2-Theta, the y-axis shows the intensity of the scattered X-ray beam in counts of detected photons.

Figure 5:
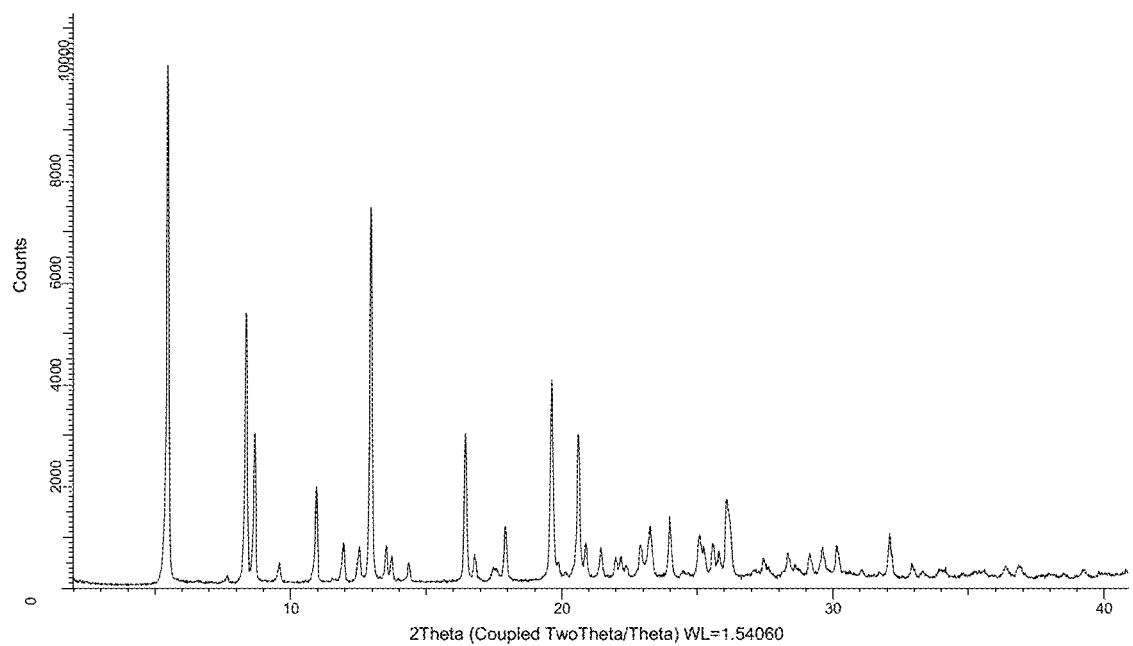

FIG. 5: illustrates a representative XRPD of Hydrate B of methyl (R)-4-(3-fluoro-2-((R)-1-fluoroethyl)phenyl)-2-

(fluoromethyl)-5-oxo-1,4,5,7-tetrahydrofuro[3,4-b]pyridine-3-carboxylate of the present disclosure. The x-axis shows the scattering angle in ° 2-Theta, the y-axis shows the intensity of the scattered X-ray beam in counts of detected photons.

Figure 6:
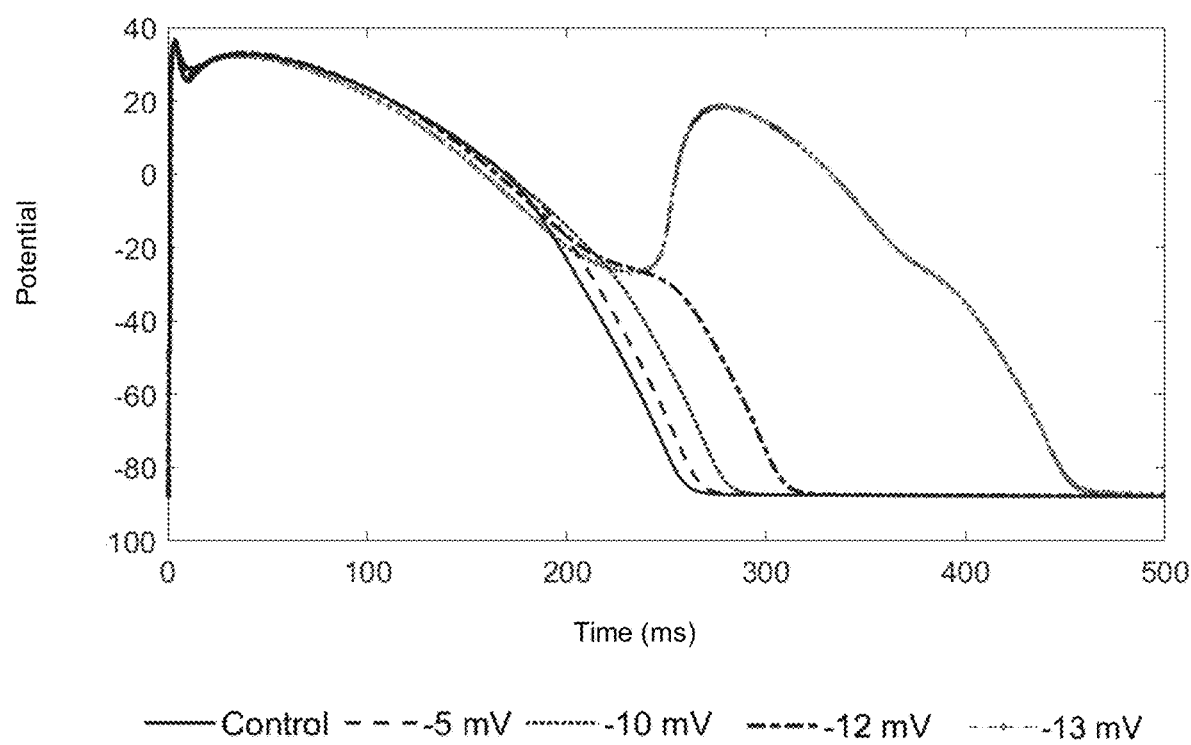

FIG. 6: illustrates simulated cardiac action potentials from an epicardial environment showing the impact of shifting the voltage of $Ca_V1.2$ activation to more negative membrane potentials. The x-axis is time (ms) and the y-axis is potential.

Figure 7:
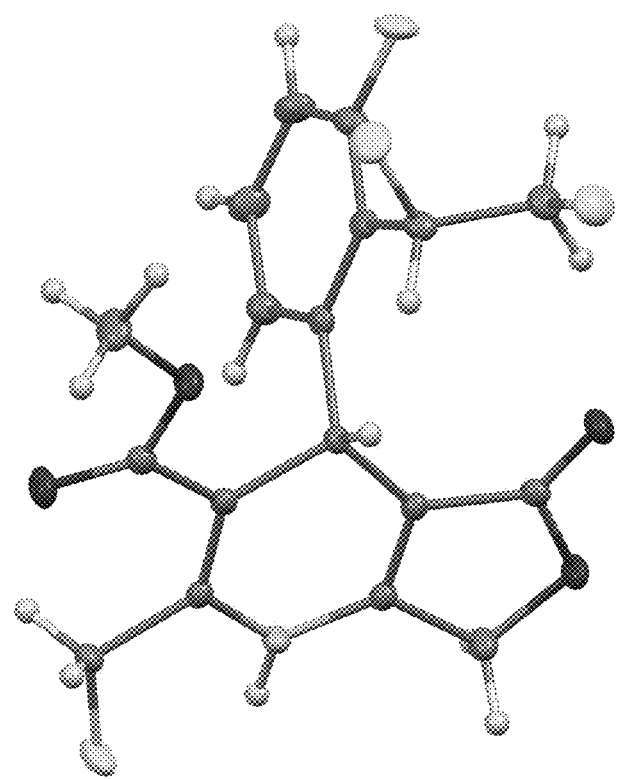

FIG. 7: illustrates the single X-ray crystal of Example 6, methyl (R)-4-(2-((S)-1,2-difluoroethyl)-3-fluorophenyl)-2-(fluoromethyl)-5-oxo-1,4,5,7-tetrahydrofuro[3,4-b]pyridine-3-carboxylate, confirming that active enantiomer is the R-enantiomer.

Figure 8:
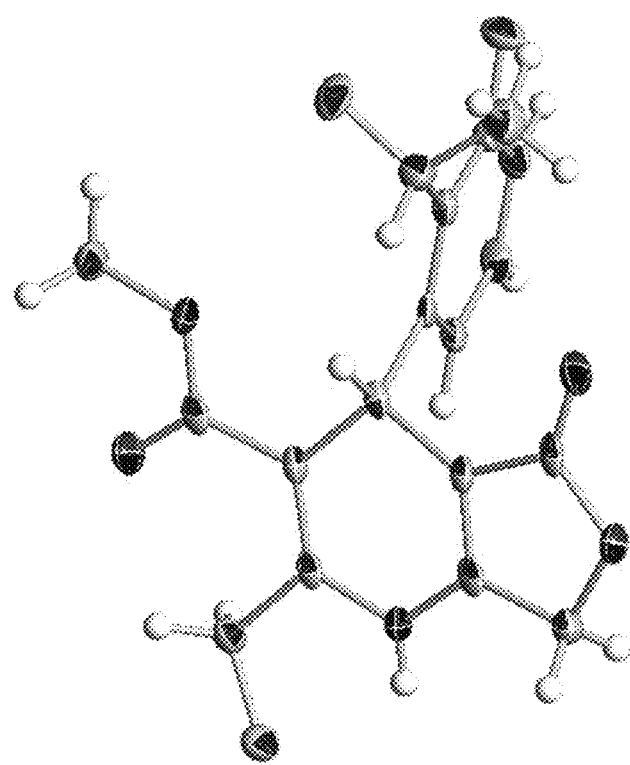

FIG. 8: illustrates the single X-ray crystal of Example 8, methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate, confirming that active enantiomer is the R-enantiomer.

Figure 9:
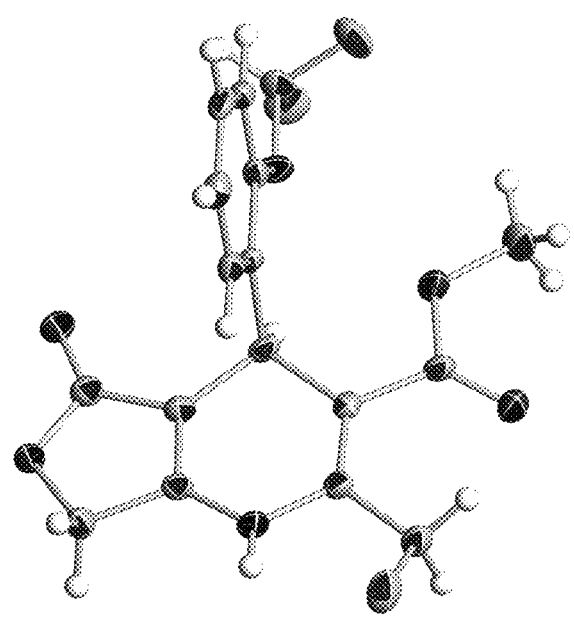

FIG. 9: illustrates the single X-ray crystal of Example 9, methyl (R)-4-(2-(difluoromethoxy)phenyl)-2-(fluoromethyl)-5-oxo-1,4,5,7-tetrahydrofuro[3,4-b]pyridine-3-carboxylate, confirming that active enantiomer is the R-enantiomer.

5. DETAILED DESCRIPTION OF THE INVENTION

5.1. Definitions

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

As used herein, "administration" and "administering" and "administer" refer to the manner in which a compound described herein is presented to a subject.

As used herein, "optionally substituted" means the group referred to can be substituted at one or more positions by any one or any combination of the radicals listed thereafter.

As used herein, "halo" or "halogen", as used herein, may be fluorine, chlorine, bromine or iodine.

As used herein, "subject" refers to a living organism suffering from one or more of the diseases or disorders described here (e.g., psychiatric disorders including schizophrenia, bipolar disorder, major depressive disorder, and substance use disorders; neurodevelopmental disorders, such as attention deficit hyperactivity disorder, Phelan-McDermid Syndrome, and other autism spectrum disorders; neurodegenerative disorders, such as multiple sclerosis, frontotemporal dementia, and Alzheimer's disease; and cardiac conditions such as Brugada Syndrome, Short QT syndrome, and early repolarization syndrome) that can be treated by administration of a pharmaceutical composition described herein. Examples of subjects include mammals (e.g., humans and animals such as dogs, cows, horses, monkeys, pigs, sheep, goats, cats, mice, rabbits, rats, and transgenic non-human animals). In certain embodiments, the subject is a human, e.g., a human suffering from, at risk of suffering from, or potentially capable of suffering from a disease described herein (e.g., psychiatric disorders including schizophrenia, bipolar disorder, major depressive disorder, and substance use disorders; neurodevelopmental disorders, such as attention deficit hyperactivity disorder, Phelan-McDermid Syndrome, and other autism spectrum disorders; neurodegenerative disorders, such as multiple sclerosis, frontotemporal dementia, and Alzheimer's disease; and cardiac conditions such as Brugada Syndrome, Short QT syndrome, and early repolarization syndrome).

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

If there is a discrepancy between a depicted structure and a chemical name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure of portion of the structure.

5.2. Compounds

A compound according to formula (I) or a pharmaceutically acceptable salt or solvate thereof

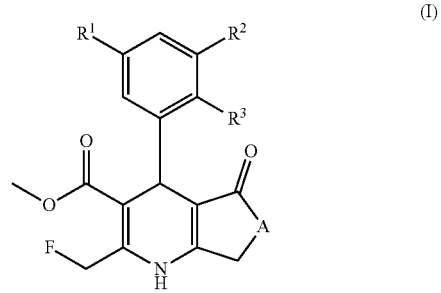

(I)

wherein:

A is O or $CH_2$;

$R^1$ is H or F;

$R^2$ is H or F; and $R^3$ is $OCHF_2$, methyl, ethyl, or cyclopropyl each of which is optionally substituted with 1 to 3 F.

One embodiment is a compound of formula (Ia) or a pharmaceutically acceptable salt or solvate thereof,

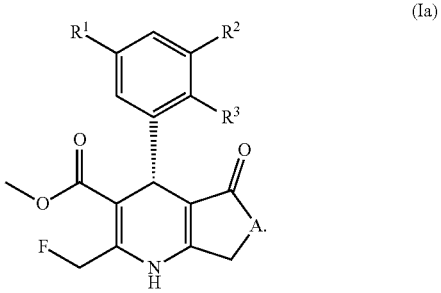

(Ia)

Another embodiment is a compound of formula (Ib) or a pharmaceutically acceptable salt or solvate thereof,

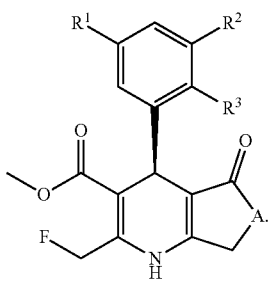

(Ib)

In another embodiment, A is O.
In another embodiment, A is $CH_2$.
In another embodiment, $R^1$ is H.
In another embodiment, $R^1$ is F.
In another embodiment, $R^2$ is H.
In another embodiment, $R^2$ is F.
In another embodiment, $R^3$ is $OCHF_2$.
In another embodiment, $R^3$ is methyl, ethyl, or cyclopropyl each of which is optionally substituted with 1 to 3 F.
In another embodiment, $R^3$ is methyl, ethyl, or cyclopropyl each of which is substituted with 1 to 3 F.
In another embodiment, $R^3$ is $CHF_2$ or $CF_3$.
In another embodiment, $R^3$ is ethyl substituted with 1 or 2 F.
In another embodiment, $R^3$ is ethyl unsubstituted.
In another embodiment, $R^3$ is cyclopropyl unsubstituted or substituted with 2 F.

A compound according to formula (III) or a pharmaceutically acceptable salt or solvate thereof,

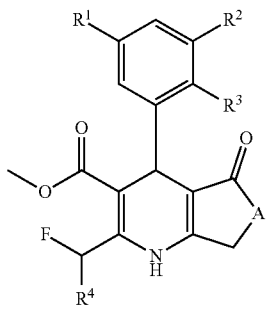

(III)

wherein:
A is O or $CH_2$;
$R^1$ is H or F;
$R^2$ is H or F;
$R^3$ is $OCHF_2$, methyl, ethyl, or cyclopropyl each of which is optionally substituted with 1 to 3 F; and
$R^4$ is H or F.

In another embodiment, A is O.
In another embodiment, A is $CH_2$.
In another embodiment, $R^1$ is H.
In another embodiment, $R^1$ is F.
In another embodiment, $R^2$ is H.
In another embodiment, $R^2$ is F.
In another embodiment, $R^3$ is $OCHF_2$.
In another embodiment, $R^3$ is methyl, ethyl, or cyclopropyl each of which is optionally substituted with 1 to 3 F.
In another embodiment, $R^3$ is methyl, ethyl, or cyclopropyl each of which is substituted with 1 to 3 F.

In another embodiment, $R^3$ is $CHF_2$ or $CF_3$.
In another embodiment, $R^3$ is ethyl substituted with 1 or 2 F.
In another embodiment, $R^3$ is ethyl unsubstituted.
In another embodiment, $R^3$ is cyclopropyl unsubstituted or substituted with 2 F.
In another embodiment, $R^4$ is F.
In another embodiment, $R^4$ is H.

Specific compounds include:
methyl (R)-4-(2-((R)-2,2-difluorocyclopropyl)-3-fluorophenyl)-2-(fluoromethyl)-5-oxo-1,4,5,7-tetrahydrofuro[3,4-b]pyridine-3-carboxylate;
methyl (R)-4-(2-((S)-2,2-difluorocyclopropyl)-3-fluorophenyl)-2-(fluoromethyl)-5-oxo-1,4,5,7-tetrahydrofuro[3,4-b]pyridine-3-carboxylate;
(R)-4-(2-cyclopropyl-3-fluorophenyl)-2-(fluoromethyl)-5-oxo-1,4,5,7-tetrahydrofuro[3,4-b]pyridine-3-carboxylate;
methyl (R)-4-(2-((R)-2,2-difluorocyclopropyl)-3,5-difluorophenyl)-2-(fluoromethyl)-5-oxo-1,4,5,7-tetrahydrofuro[3,4-b]pyridine-3-carboxylate;
methyl (R)-4-(2-((S)-2,2-difluorocyclopropyl)-3,5-difluorophenyl)-2-(fluoromethyl)-5-oxo-1,4,5,7-tetrahydrofuro[3,4-b]pyridine-3-carboxylate;
methyl (R)-4-(3,5-difluoro-2-((R)-1-fluoroethyl)phenyl)-2-(fluoromethyl)-5-oxo-1,4,5,7-tetrahydrofuro[3,4-b]pyridine-3-carboxylate;
methyl (R)-4-(3,5-difluoro-2-((S)-1-fluoroethyl)phenyl)-2-(fluoromethyl)-5-oxo-1,4,5,7-tetrahydrofuro[3,4-b]pyridine-3-carboxylate;
methyl (R)-4-(2-((S)-1,2-difluoroethyl)-3-fluorophenyl)-2-(fluoromethyl)-5-oxo-1,4,5,7-tetrahydrofuro[3,4-b]pyridine-3-carboxylate;
methyl (R)-4-(2-((R)-1,2-difluoroethyl)-3-fluorophenyl)-2-(fluoromethyl)-5-oxo-4,5,6,7-tetrahydro-1H-cyclopenta[b]pyridine-3-carboxylate;
methyl (R)-4-(2-((S)-1,2-difluoroethyl)-3-fluorophenyl)-2-(fluoromethyl)-5-oxo-4,5,6,7-tetrahydro-1H-cyclopenta[b]pyridine-3-carboxylate;
methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate;
methyl (R)-4-(3-fluoro-2-((S)-1-fluoroethyl)phenyl)-2-(fluoromethyl)-5-oxo-1,4,5,7-tetrahydrofuro[3,4-b]pyridine-3-carboxylate;
methyl (R)-4-(2-(difluoromethoxy)phenyl)-2-(fluoromethyl)-5-oxo-1,4,5,7-tetrahydrofuro[3,4-b]pyridine-3-carboxylate;
methyl (R)-4-(3,5-difluoro-2-(trifluoromethyl)phenyl)-2-(fluoromethyl)-5-oxo-1,4,5,7-tetrahydrofuro[3,4-b]pyridine-3-carboxylate;
methyl (R)-4-(2-(2,2-difluoroethyl)-3-fluorophenyl)-2-(fluoromethyl)-5-oxo-1,4,5,7-tetrahydrofuro[3,4-b]pyridine-3-carboxylate;
methyl (R)-4-(2-(2,2-difluoroethyl)-3,5-difluorophenyl)-2-(fluoromethyl)-5-oxo-1,4,5,7-tetrahydrofuro[3,4-b]pyridine-3-carboxylate;
methyl (R)-4-(2-cyclopropyl-3,5-difluorophenyl)-2-(fluoromethyl)-5-oxo-1,4,5,7-tetrahydrofuro[3,4-b]pyridine-3-carboxylate;
methyl (R)-4-(2-cyclopropyl-3,5-difluorophenyl)-2-(fluoromethyl)-5-oxo-4,5,6,7-tetrahydro-1H-cyclopenta[b]pyridine-3-carboxylate;
methyl (R)-4-(2-(difluoromethyl)-3-fluorophenyl)-2-(fluoromethyl)-5-oxo-1,4,5,7-tetrahydrofuro[3,4-b]pyridine-3-carboxylate;

methyl (R)-4-(2-((R)-1,2-difluoroethyl)-3,5-difluorophenyl)-2-(fluoromethyl)-5-oxo-1,4,5,7-tetrahydrofuro[3,4-b]pyridine-3-carboxylate;
methyl (R)-4-(2-((S)-1,2-difluoroethyl)-3,5-difluorophenyl)-2-(fluoromethyl)-5-oxo-1,4,5,7-tetrahydrofuro[3,4-b]pyridine-3-carboxylate;
methyl (R)-4-(3-fluoro-2-(trifluoromethyl)phenyl)-2-(fluoromethyl)-5-oxo-1,4,5,7-tetrahydrofuro[3,4-b]pyridine-3-carboxylate;
methyl (R)-4-(2-(difluoromethyl)-3,5-difluorophenyl)-2-(fluoromethyl)-5-oxo-1,4,5,7-tetrahydrofuro[3,4-b]pyridine-3-carboxylate;
methyl (R)-4-(2-(difluoromethoxy)-3-fluorophenyl)-2-(fluoromethyl)-5-oxo-1,4,5,7-tetrahydrofuro[3,4-b]pyridine-3-carboxylate;
methyl 4-(2-(difluoromethoxy)-5-fluorophenyl)-2-(fluoromethyl)-5-oxo-1,4,5,7-tetrahydrofuro[3,4-b]pyridine-3-carboxylate;
methyl (R)-4-(2-cyclopropyl-5-fluorophenyl)-2-(fluoromethyl)-5-oxo-1,4,5,7-tetrahydrofuro[3,4-b]pyridine-3-carboxylate;
methyl (R)-4-(2-cyclopropylphenyl)-2-(fluoromethyl)-5-oxo-1,4,5,7-tetrahydrofuro[3,4-b]pyridine-3-carboxylate;
methyl (R)-4-(5-fluoro-2-(trifluoromethyl)phenyl)-2-(fluoromethyl)-5-oxo-1,4,5,7-tetrahydrofuro[3,4-b]pyridine-3-carboxylate;
methyl (R)-2-(fluoromethyl)-5-oxo-4-(2-(trifluoromethyl)phenyl)-1,4,5,7-tetrahydrofuro[3,4-b]pyridine-3-carboxylate;
(R)-4-(3-fluoro-2-(2,2,2-trifluoroethyl)phenyl)-2-(fluoromethyl)-5-oxo-4,5,6,7-tetrahydro-1H-cyclopenta[b]pyridine-3-carboxylate;
methyl (R)-4-(2-(2,2-difluoroethyl)-3-fluorophenyl)-2-(fluoromethyl)-5-oxo-4,5,6,7-tetrahydro-1Hcyclopenta[b]pyridine-3-carboxylate;
methyl (R)-4-(3-fluoro-2-((R)-1-fluoroethyl)phenyl)-2-(fluoromethyl)-5-oxo-4,5,6,7-tetrahydro-1H-cyclopenta[b]pyridine-3-carboxylate;
methyl (R)-4-(3-fluoro-2-((S)-1-fluoroethyl)phenyl)-2-(fluoromethyl)-5-oxo-4,5,6,7-tetrahydro-1H-cyclopenta[b]pyridine-3-carboxylate;
methyl (R)-4-(2-cyclopropyl-3-fluorophenyl)-2-(fluoromethyl)-5-oxo-4,5,6,7-tetrahydro-1H-cyclopenta[b]pyridine-3-carboxylate;
methyl (S)-4-(3,5-difluoro-2-((S)-1-fluoroethyl)phenyl)-2-(fluoromethyl)-5-oxo-4,5,6,7-tetrahydro-1H-cyclopenta[b]pyridine-3-carboxylate; and
methyl (S)-4-(3,5-difluoro-2-((R)-1-fluoroethyl)phenyl)-2-(fluoromethyl)-5-oxo-4,5,6,7-tetrahydro-1H-cyclopenta[b]pyridine-3-carboxylate.

Specific compounds further include:
methyl (R)-4-(2-ethylphenyl)-2-(fluoromethyl)-5-oxo-1,4,5,7-tetrahydrofuro[3,4-b]pyridine-3-carboxylate; and
methyl (R)-2-(difluoromethyl)-4-(3-fluoro-2-(1-fluoroethyl)phenyl)-5-oxo-1,4,5,7-tetrahydrofuro[3,4-b]pyridine-3-carboxylate.

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present disclosure is meant to include all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the present disclosure. "Salts" include in particular "pharmaceutically acceptable salts". The term "pharmaceutically acceptable salts" refers to salts that retain the biological effectiveness and properties of the compounds of this disclosure and, which typically are not biologically or otherwise undesirable. In many cases, the compounds of the present disclosure are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present disclosure provides compounds of the present disclosure in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Compounds of the disclosure, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the disclosure further provides co-crystals comprising a compound of formula (I).

Furthermore, the compounds of the present disclosure, including their salts, can also be obtained in the form of their hydrates, or include other solvents used for their crystallization. The compounds of the present disclosure may inherently or by design form solvates with pharmaceutically acceptable solvents (including water); therefore, it is intended that the disclosure embrace both solvated and unsolvated forms. The term "solvate" refers to a molecular complex of a compound of the present disclosure (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The disclosure includes unlabeled forms as well as isotopically labeled forms of compounds of formula (I). Isotopically labeled compounds have structures depicted by the formulae given herein except that one or more atoms are replaced by an atom having a selected atomic mass or mass number. Isotopes that can be incorporated into compounds of the disclosure include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present disclosure. The concentration of deuterium, may be defined by the isotopic enrichment factor. The term "isotopic enrichment factor" as used herein means the ratio between the isotopic abundance and the natural abundance of a specified isotope. If a substituent in a compound of this disclosure is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

For example, formula (I) is deuterated as shown in formula (II):

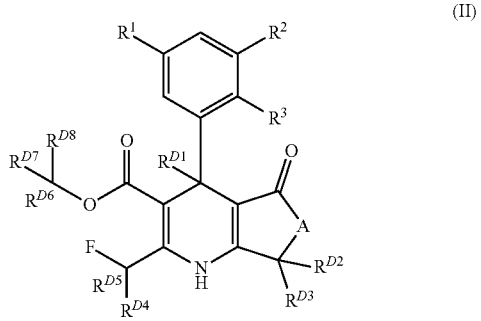

or a pharmaceutically acceptable salt thereof, wherein $R^1$, $R^2$ $R^3$, and A are as defined in formula (I); $R^{D1}$ through $R^{D8}$ are each independently H or D.

Other examples of isotopes that can be incorporated into compounds of the disclosure include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F, $^{31}$P, $^{32}$P, $^{35}$S, $^{36}$Cl, $^{123}$I, $^{124}$I, $^{125}$I respectively. Accordingly, it should be understood that the disclosure includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of the present disclosure can generally be prepared by conventional techniques known to those skilled in the art or by processes analogous to those described in the accompanying Examples and Preparations using an appropriate isotopically-labeled reagents in place of the non-labeled reagent previously employed.

Any asymmetric atom (e.g., carbon or the like) of the compound(s) of the present disclosure can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans- (E)-form.

Accordingly, as used herein a compound of the present disclosure can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present disclosure or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present disclosure into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the present disclosure or racemic intermediates can also be resolved by chiral chromatography, e.g., high pressure liquid chromatography (HPLC) using a chiral adsorbent.

Methods of Use

The compounds of the present disclosure in free form or in pharmaceutically acceptable salt form, exhibit valuable pharmacological properties, e.g. $Ca_V1.2$ activation properties, e.g. as indicated in vitro and in vivo tests as provided in the next sections, and are therefore indicated for therapy or for use as research chemicals, e.g. as tool compounds.

Compounds of the present disclosure may be useful in the treatment of an indication selected from the following list: psychiatric disorders including schizophrenia, bipolar disorder, major depressive disorder, and substance use disorders;
neurodevelopmental disorders, such as attention deficit hyperactivity disorder, Phelan-McDermid Syndrome, and autism spectrum disorders; and
neurodegeneration disorders, such as multiple sclerosis, frontotemporal dementia and Alzheimer's disease and
cardiac conditions, such as Brugada Syndrome, Short QT syndrome, and early repolarization syndrome. In one embodiment, the indication is a psychiatric disorder such as schizophrenia, bipolar disorder, major depressive disorder, and substance use disorders. In another embodiment, the indication is schizophrenia or bipolar disorder.

Thus, as a further aspect, the present disclosure provides the use of a compound of the present disclosure or a pharmaceutically acceptable salt thereof in therapy. In a further embodiment, the therapy is selected from a disease which may be treated by activation of $Ca_V1.2$. In another embodiment, the disease is selected from the afore-mentioned list of indications.

Thus, as a further aspect, the present disclosure provides a compound of the present disclosure or a pharmaceutically acceptable salt thereof for use in therapy. In a further embodiment, the therapy is selected from a disease which may be treated by activation of $Ca_V1.2$. In another embodiment, the disease is selected from the afore-mentioned list of indications.

In another aspect, the disclosure provides a method of treating a disease which is treated by activation of $Ca_V1.2$ comprising administration of a therapeutically effective amount of a compound of the present disclosure or a pharmaceutically acceptable salt thereof. In a further embodiment, the disease is selected from the afore-mentioned list of indications.

In another aspect, the disclosure provides a method of treating a disease which is treated by activation of $Ca_V1.2$ comprising administration of a compound of the present disclosure or a pharmaceutically acceptable salt thereof. In a further embodiment, the disease is selected from the afore-mentioned list of indications.

Thus, as a further aspect, the present disclosure provides the use of a compound of the present disclosure or a pharmaceutically acceptable salt thereof for the manufacture of a medicament. In a further embodiment, the medicament is for treatment of a disease which may be treated by activation of $Ca_V1.2$. In another embodiment, the disease is selected from the afore-mentioned list of indications.

In another aspect, the present disclosure provides a method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome which is treated by activation of $Ca_V1.2$ comprising administration of a therapeutically effective amount of a compound of the present disclosure or a pharmaceutically acceptable salt thereof.

In another aspect, the present disclosure provides a method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome which is treated by activation of $Ca_V1.2$ comprising administration of a compound of the present disclosure or a pharmaceutically acceptable salt thereof.

Thus, as a further aspect, the present disclosure provides the use of a compound of the present disclosure or a pharmaceutically acceptable salt thereof for treating a disease selected from schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome.

Thus, as a further aspect, the present disclosure provides a compound of the present disclosure or a pharmaceutically acceptable salt thereof for use in treating a disease selected from schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome.

In another aspect, the present disclosure provides a method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome comprising administration of a therapeutically effective amount of a compound of the present disclosure or a pharmaceutically acceptable salt thereof.

In another aspect, the present disclosure provides a method for the treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome comprising administration of a compound of the present disclosure or a pharmaceutically acceptable salt thereof.

Thus, as a further aspect, the present disclosure provides the use of a compound of the present disclosure or a pharmaceutically acceptable salt thereof for the manufacture of a medicament. for treatment of schizophrenia, bipolar disorder, major depressive disorder, substance use disorder, ADHD, Phelan McDermid Syndrome, autism spectrum disorder, multiple sclerosis, frontotemporal dementia, Alzheimer's disease, Brugada Syndrome, Short QT syndrome, or early repolarization syndrome.

Pharmaceutical Compositions

In another aspect, the present disclosure provides a pharmaceutical composition comprising a compound of the present disclosure, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present disclosure can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

The pharmaceutical composition or combination of the present disclosure can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present disclosure can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

Crystalline Forms

The present disclosure relates to crystalline forms of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate and to a process for its preparation. Furthermore, the disclosure relates to a pharmaceutical composition comprising said crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate, preferably in a predetermined and/or effective amount, and at least one pharmaceutically acceptable excipient. The pharmaceutical composition of the present disclosure can be used as a medicament, in particular for the treatment and/or prophylaxis of schizophrenia, bipolar disorder, major depressive disorder, substance use disorder, ADHD, Phelan-McDermid Syndrome, autism spectrum disorder, multiple sclerosis, frontotemporal dementia, Alzheimer's disease, Brugada Syndrome, Short QT syndrome, or early repolarization syndrome.

Different solid state forms of an active pharmaceutical ingredient often possess different properties. Differences in physicochemical properties of solid forms can play a crucial role for the improvement of pharmaceutical compositions, for example, pharmaceutical formulations with improved dissolution profile or with improved stability or shelf-life can become accessible due to an improved solid state form of an active pharmaceutical ingredient. Also processing or handling of the active pharmaceutical ingredient during the formulation process may be improved. New solid state forms of an active pharmaceutical ingredient can thus have desirable processing properties. They can be easier to handle, better suited for storage, and/or allow for better purification, compared to previously known solid forms.

Crystalline forms of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate may be characterized by analytical methods well known in the field of the pharmaceutical industry for characterizing solids. Such methods comprise, but are not limited to, XRPD, SXRD, FTIR, Raman, DSC, TGA, and GMS (gravimetric measurement system). The forms may be characterized by one of the aforementioned analytical methods or by combining two or more of them.

Crystalline forms of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate may be referred to herein as being characterized by graphical data "as shown in" a figure. Such data include, for example, powder X-ray diffraction, FTIR and Raman spectroscopy. The person skilled in the art understands that factors such as variations in instrument type, response and variations in sample directionality, sample concentration and sample purity may lead to small variations for such data when presented in graphical form, for example variations relating to the exact peak positions and intensities. However, a comparison of the graphical data in the figures herein with the graphical data generated for another or an unknown solid form and the confirmation that two sets of graphical data relate to the same crystal form is well within the knowledge of a person skilled in the art.

The term "reflection" with regard to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately 100 to 1000 atoms, whereas short-range order is over a few atoms only (see *Fundamentals of Powder Diffraction and Structural Characterization of Materials*" by Vitalij K. Pecharsky and Peter Y. Zavalij, Kluwer Academic Publishers, 2003, page 3).

The term "essentially the same" with reference to powder X-ray diffraction means that variabilities in reflection positions and relative intensities of the reflections are to be taken into account. For example, a typical precision of the 2-Theta values is in the range of ±0.2° 2-Theta, preferably in the range of ±0.1° 2-Theta.

Furthermore, one skilled in the art will appreciate that relative reflection intensities will show inter-apparatus variability as well as variability due to degree of crystallinity, preferred orientation, particle size, sample preparation and other factors known to those skilled in the art and should be taken as qualitative measure only.

The terms "solid form" or "solid state form" as used herein interchangeably refer to any crystalline and/or amorphous phase of a compound.

As used herein, the term "amorphous" refers to a solid form of a compound that is not crystalline. An amorphous compound possesses no long-range order and does not display a definitive X-ray diffraction pattern with reflections.

As used herein the term "polymorph" refers to crystalline forms having the same chemical composition but different spatial arrangements of the molecules, atoms, and/or ions forming the crystal.

The term "co-crystal" as used herein refers to a crystalline material comprising two or more different molecular and/or ionic compounds in the same crystal lattice that are associated by nonionic and noncovalent bonds, wherein at least two of the individual molecular and/or ionic compounds are solids at room temperature.

The term "hydrate" as used herein, refers to a crystalline solid where either water is cooperated in or accommodated by the crystal structure e.g. is part of the crystal structure or entrapped into the crystal (water inclusions). Thereby, water can be present in a stoichiometric or non-stoichiometric amount. When water is present in stoichiometric amount, the hydrate may be referred to by adding greek numeral prefixes. For example, a hydrate may be referred to as a hemihydrate or as a monohydrate depending on the water/compound stoichiometry. The water content can be measured, for example, by Karl-Fischer-Coulometry.

The terms "dehydrating" or "dehydration" as used herein, describe the at least partial removal of water from the crystal structure of the host molecule.

The term "solvate" as used herein, refers to a crystalline solid were either one or more organic solvent(s) is/are cooperated in or accommodated by the crystal structure e.g. is/are part of the crystal structure or entrapped into the crystal (water inclusions). Thereby, the one or more organic solvent(s) can be present in a stoichiometric or non-stoichiometric amount. When the one or more organic solvent(s) is/are present in stoichiometric amount(s), the solvate may be referred to by adding greek numeral prefixes. For example, a solvate may be referred to as a hemisolvate or as a monosolvate depending on the solvent(s)/compound stoichiometry. The solvent content can be measured, for example, by GC, NMR, SXRD and/or TGA/MS.

The term "non-hygroscopic" as used herein refers to a compound showing a water uptake of at most 2 w-% in the sorption cycle when measured with GMS at a relative humidity in the range of from 0 to 95% RH and a temperature of (25.0±0.1°) C., based on the weight of the compound.

As used herein, the term "about" means within a statistically meaningful range of a value. Such a range can be within an order of magnitude, typically within 10%, more typically within 5%, even more typically within 1% and most typically within 0.1% of the indicated value or range. Sometimes, such a range can lie within the experimental error, typical of standard methods used for the measurement and/or determination of a given value or range.

As used herein, the term "substantially free of any other solid form" with reference to a composition comprising a particular solid form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate means that the composition includes at most 20 w-%, preferably at most 10 w-%, more preferably at most 5 w-%, even more preferably at most 2 w-% and most preferably at most 1 w-% of any other solid form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate, based on the weight of the composition.

As used herein, "substantially pure," when used in reference to a form, means a compound having a purity greater than 90 w-%, including greater than 90, 91, 92, 93, 94, 95, 96, 97, 98, and 99 w-%, and also including equal to about 100 w-% of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate, based on the weight of the compound. The remaining material comprises other form(s) of the compound, and/or reaction impurities and/or processing impurities arising from its preparation. For example, a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate may be deemed substantially pure in that it has a purity greater than 90 w-%, as measured by means that are at this time known and generally accepted in the art, where the remaining less than 10 w-% of material comprises other form(s) of [Compound ABC] and/or reaction impurities and/or processing impurities.

Crystalline Form A

In a further aspect, the disclosure provides crystalline Form A of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate. The most prominent X-ray powder diffraction peaks for Form A of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate are shown in Table 1.

TABLE 1

The most prominent X-ray powder diffraction peaks for Form A

| Peak | Angle [° 2theta] | d Value [Å] |
|---|---|---|
| 1 | 6.7 | 13.218 |
| 2 | 7.2 | 12.255 |
| 3 | 8.5 | 10.387 |
| 4 | 10.4 | 8.481 |
| 5 | 10.8 | 8.220 |
| 6 | 13.5 | 6.543 |
| 7 | 14.4 | 6.160 |
| 8 | 15.6 | 5.685 |
| 9 | 18.5 | 4.795 |
| 10 | 21.6 | 4.116 |
| 11 | 22.4 | 3.963 |

One embodiment of the disclosure provides Form A of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate characterized by having a XRPD pattern comprising reflections at 2-Theta angles of:

(8.5±0.2°), (10.4±0.2°) and (10.8±0.2°); or
(8.5±0.2°), (10.4±0.2°), (10.8±0.2°) and (22.4±0.2°); or
(8.5±0.2°), (10.4±0.2°), (10.8±0.2°), (14.4±0.2°) and (22.4±0.2°); or
(8.5±0.2°), (10.4±0.2°), (10.8±0.2°), (14.4±0.2°), (21.6±0.2°) and (22.4±0.2°); or
(7.2±0.2°), (8.5±0.2°), (10.4±0.2°), (10.8±0.2°), (14.4±0.2°), (21.6±0.2°) and (22.4±0.2°); or
(7.2±0.2°), (8.5±0.2°), (10.4±0.2°), (10.8±0.2°), (14.4±0.2°), (18.5±0.2°), (21.6±0.2°) and (22.4±0.2°); or
(7.2±0.2°), (8.5±0.2°), (10.4±0.2°), (10.8±0.2°), (14.4±0.2°), (15.6±0.2°), (18.5±0.2°), (21.6±0.2°) and (22.4±0.2°); or (6.7±0.2°), (7.2±0.2°), (8.5±0.2°), (10.4±0.2°), (10.8±0.2°), (14.4±0.2°), (15.6±0.2°), (18.5±0.2°), (21.6±0.2°) and (22.4±0.2°); or (6.7±0.2°), (7.2±0.2°), (8.5±0.2°), (10.4±0.2°), (10.8±0.2°), (13.5±0.2°), (14.4±0.2°), (15.6±0.2°), (18.5±0.2°), (21.6±0.2°) and (22.4±0.2°) when measured at a temperature in the range of from 20 to 30° C. with Cu-Kalpha$_{1,2}$ radiation having a wavelength of 0.15419 nm.

In yet another embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate, Form A characterized by having a XRPD pattern essentially the same as that shown in FIG. 1 of the present disclosure, when measured at a temperature in the range of from 20 to 30° C. with Cu-Kalpha$_{1,2}$ radiation having a wavelength of 0.15418 nm.

In another embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate, Form A characterized by having a melting point onset temperature of 98±5° C., when measured with DSC at a heating rate of 10 K/min.

In another embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Form A characterized by having a melting point peak maximum temperature of 104±5° C., when measured with DSC at a heating rate of 10 K/min.

Crystalline Form B

In a further aspect, the disclosure provides Form B of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate. The most prominent X-ray powder diffraction peaks for Form B of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate are shown in Table 2.

TABLE 2

The most prominent X-ray powder diffraction peaks for Form B

| Peak | Angle [° 2theta] | d Value [Å] |
| --- | --- | --- |
| 1 | 9.1 | 9.658 |
| 2 | 12.0 | 7.344 |
| 3 | 13.7 | 6.458 |
| 4 | 14.5 | 6.122 |
| 5 | 15.7 | 5.637 |
| 6 | 18.3 | 4.838 |
| 7 | 21.4 | 4.151 |
| 8 | 23.0 | 3.861 |
| 9 | 23.8 | 3.736 |

In one embodiment, the disclosure provides Form B of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate characterized by having a XRPD pattern comprising reflections at 2-Theta angles of:

(12.0±0.2°), (13.7±0.2°) and (21.4±0.2°); or
(12.0±0.2°), (13.7±0.2°), (18.3±0.2°) and (21.4±0.2°); or
(12.0±0.2°), (13.7±0.2°), (18.3±0.2°), (21.4±0.2°) and (23.8±0.2°); or
(12.0±0.2°), (13.7±0.2°), (18.3±0.2°), (21.4±0.2°), (23.0±0.2°) and (23.8±0.2°); or
(9.1±0.2°), (12.0±0.2°), (13.7±0.2°), (18.3±0.2°), (21.4±0.2°), (23.0±0.2°) and (23.8±0.2°); or (9.1±0.2°), (12.0±0.2°), (13.7±0.2°), (14.5±0.2°), (18.3±0.2°), (21.4±0.2°), (23.0±0.2°) and (23.8±0.2°); or (9.1±0.2°), (12.0±0.2)°, (13.7±0.2°), (14.5±0.2°), (15.7±0.2°), (18.3±0.2°), (21.4±0.2°), (23.0±0.2°) and (23.8±0.2°) when measured at a temperature in the range of from 20 to 30° C. with Cu-Kalpha$_{1,2}$ radiation having a wavelength of 0.15419 nm.

In yet another embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Form B characterized by having a XRPD pattern essentially the same as that shown in FIG. 2 of the present invention, when measured at a temperature in the range of from 20 to 30° C. with Cu-Kalpha$_{1,2}$ radiation having a wavelength of 0.15418 nm.

In another embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Form B characterized by having a melting point onset temperature of 184±5° C., when measured with DSC at a heating rate of 10 K/min.

In another embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Form B characterized by having a melting point peak maximum temperature of 185±5° C., when measured with DSC at a heating rate of 10 K/min.

Crystalline Form C

In a further embodiment, the disclosure provides Form C of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate. The most prominent X-ray powder diffraction peaks for Form C of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate are shown in Table 3.

TABLE 3

The most prominent X-ray powder diffraction peaks for Form C

| Peak | Angle [° 2theta] | d Value [Å] |
| --- | --- | --- |
| 1 | 7.0 | 12.613 |
| 2 | 10.3 | 8.554 |
| 3 | 11.3 | 7.844 |
| 4 | 12.3 | 7.162 |
| 5 | 12.8 | 6.914 |
| 6 | 14.0 | 6.331 |
| 7 | 15.5 | 5.701 |
| 8 | 16.6 | 5.338 |
| 9 | 17.3 | 5.109 |
| 10 | 18.2 | 4.874 |
| 11 | 20.6 | 4.310 |
| 12 | 22.0 | 4.036 |
| 13 | 22.7 | 3.908 |
| 14 | 23.2 | 3.831 |

In one embodiment, the disclosure provides Form C of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate characterized by having a XRPD pattern comprising reflections at 2-Theta angles of:

(10.3±0.2°), (15.5±0.2°) and (20.6±0.2°); or
(10.3±0.2°), (11.3±0.2°), (15.5±0.2°) and (20.6±0.2°); or
(10.3±0.2°), (11.3±0.2°), (15.5±0.2°), (20.6±0.2°) and (22.7±0.2°); or (10.3±0.2°), (11.3±0.2°), (15.5±0.2°), (18.2±0.2°), (20.6±0.2°) and (22.7±0.2°); or (10.3±0.2°), (11.3±0.2°), (15.5±0.2°), (18.2±0.2°), (20.6±0.2°), (22.7±0.2°) and (22.0±0.2°); or (10.3±0.2°), (11.3±0.2°), (15.5±0.2°), (16.6±0.2°), (18.2±0.2°), (20.6±0.2°), (22.7±0.2°) and (22.0±0.2°); or (10.3±0.2°), (11.3±0.2°), (12.8±0.2°), (15.5±0.2°), (16.6±0.2°), (18.2±0.2°), (20.6±0.2°), (22.7±0.2°) and (22.0±0.2°); or (10.3±0.2°), (11.3±0.2°), (12.8±0.2°), (15.5±0.2°), (16.6±0.2°), (18.2±0.2°), (20.6±0.2°), (22.7±0.2°), (22.0±0.2°) and (23.2±0.2°); or (10.3±0.2°), (11.3±0.2°), (12.3±0.2°), (12.8±0.2°), (15.5±0.2°), (16.6±0.2°), (18.2±0.2°), (20.6±0.2°), (22.7±0.2°), (22.0±0.2°) and (23.2±0.2°); or (10.3±0.2°), (11.3±0.2°), (12.3±0.2°), (12.8±0.2°), (15.5±0.2°), (16.6±0.2°), (17.3±0.2°), (18.2±0.2°), (20.6±0.2°), (22.7±0.2°), (22.0±0.2°) and (23.2±0.2°); or (10.3±0.2°), (11.3±0.2°), (12.3±0.2°), (12.8±0.2°), (14.0±0.2°), (15.5±0.2°), (16.6±0.2°), (17.3±0.2°), (18.2±0.2°), (20.6±0.2°), (22.7±0.2°), (22.0±0.2°) and (23.2±0.2°); or (7.0±0.2°), (10.3±0.2°), (11.3±0.2°), (12.3±0.2°), (12.8±0.2°), (14.0±0.2°), (15.5±0.2°), (16.6±0.2°), (17.3±0.2°), (18.2±0.2°), (20.6±0.2°), (22.7±0.2°), (22.0±0.2°) and (23.2±0.2°) when measured at a temperature in the range of from 20 to 30° C. with Cu-Kalpha$_{1,2}$ radiation having a wavelength of 0.15419 nm.

In yet another embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Form C characterized by having a XRPD pattern essentially the same as that shown in FIG. 3 of the present invention, when measured at a temperature in the range of from 20 to 30° C. with Cu-Kalpha$_{1,2}$ radiation having a wavelength of 0.15418 nm.

In another embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Form C characterized by having a melting point onset temperature of 178±5° C., when measured with DSC at a heating rate of 10 K/min.

In one embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Form C characterized by having a melting point peak maximum temperature of 178±5° C., when measured with DSC at a heating rate of 10 K/min.

Hydrate A

In a further aspect, the disclosure provides Hydrate A of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate. The most prominent X-ray powder diffraction peaks for crystalline form Hydrate A of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate are shown in Table 4.

TABLE 4

The most prominent X-ray powder diffraction peaks for Hydrate A

| Peak | Angle [° 2theta] | d Value [Å] |
| --- | --- | --- |
| 1 | 10.0 | 8.857 |
| 2 | 10.6 | 8.323 |
| 3 | 11.5 | 7.709 |
| 4 | 12.8 | 6.937 |
| 5 | 14.4 | 6.154 |
| 6 | 17.5 | 5.051 |
| 7 | 18.1 | 4.893 |
| 8 | 20.0 | 4.436 |
| 9 | 20.8 | 4.273 |
| 10 | 22.9 | 3.878 |
| 11 | 23.5 | 3.787 |
| 12 | 25.0 | 3.553 |

In one embodiment, the disclosure provides Hydrate A methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate characterized by having a XPRD pattern comprising reflections at 2-Theta angles of:

(10.0±0.2°), (10.6±0.2°) and (23.5±0.2°); or (10.0±0.2°), (10.6±0.2°), (23.5±0.2°) and (25.0±0.2°); or (10.0±0.2°), (10.6±0.2°), (14.4±0.2°), (23.5±0.2°) and (25.0±0.2°); or (10.0±0.2°), (10.6±0.2°), (14.4±0.2°), (22.9±0.2°), (23.5±0.2°) and (25.0±0.2°); or (10.0±0.2°), (10.6±0.2°), (12.8±0.2°), (14.4±0.2°), (22.9±0.2°), (23.5±0.2°) and (25.0±0.2°); or (10.0±0.2°), (10.6±0.2°), (12.8±0.2°), (14.4±0.2°), (17.5±0.2°), (22.9±0.2°), (23.5±0.2°) and (25.0±0.2°); or (10.0±0.2°), (10.6±0.2°), (12.8±0.2°), (14.4±0.2°), (17.5±0.2°), (18.1±0.2°), (22.9±0.2°), (23.5±0.2°) and (25.0±0.2°); or (10.0±0.2°), (10.6±0.2°), (11.1±0.2°), (12.8±0.2°), (14.4±0.2°), (17.5±0.2°), (18.1±0.2°), (22.9±0.2°), (23.5±0.2°) and (25.0±0.2°); or (10.0±0.2°), (10.6±0.2°), (11.1±0.2°), (12.8±0.2°), (14.4±0.2°), (17.5±0.2°), (18.1±0.2°), (20.0±0.2°), (22.9±0.2°), (23.5±0.2°) and (25.0±0.2°); when measured at a temperature in the range of from 20 to 30° C. with Cu-Kalpha$_{1,2}$ radiation having a wavelength of 0.15419 nm.

In yet another embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Hydrate A characterized by having a XRPD pattern essentially the same as that shown in FIG. 4 of the present invention, when measured at a temperature in the range of from 20 to 30° C. with Cu-Kalpha$_{1,2}$ radiation having a wavelength of 0.15418 nm.

In another embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Hydrate A characterized by having a broad endothermic event with a peak maximum at temperature of 109±10° C., when measured with DSC at a heating rate of 10 K/min.

Hydrate B

In a further aspect, the disclosure provides Hydrate B of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate. The most prominent X-ray powder diffraction peaks for crystalline Hydrate B of methyl (R)-4-(3- fluoro-2-((R)-1-fluoroethyl)phenyl)-2-(fluoromethyl)-5-oxo-1,4,5,7-tetrahydrofuro[3,4-b]pyridine-3-carboxylate are shown in Table 5.

TABLE 5

The most prominent X-ray powder diffraction peaks for Hydrate B

| Peak | Angle [° 2theta] | d Value [Å] |
|---|---|---|
| 1 | 5.5 | 16.076 |
| 2 | 8.4 | 10.545 |
| 3 | 8.7 | 10.168 |
| 4 | 11.0 | 8.066 |
| 5 | 13.0 | 6.817 |
| 6 | 16.5 | 5.380 |
| 7 | 17.9 | 4.941 |
| 8 | 19.6 | 4.517 |
| 9 | 20.6 | 4.305 |
| 10 | 24.0 | 3.706 |

In one embodiment, the disclosure provides Hydrate B of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate characterized by having a XRPD pattern comprising reflections at 2-Theta angles of:
(5.5±0.2°), (8.4±0.2°) and (13.0±0.2°); or
(5.5±0.2°), (8.4±0.2°), (13.0±0.2°) and (19.6±0.2°); or
(5.5±0.2°), (8.4±0.2°), (8.7±0.2°), (13.0±0.2°) and (19.6±0.2°); or
(5.5±0.2°), (8.4±0.2°), (8.7±0.2°), (13.0±0.2°), (16.5±0.2°) and (19.6±0.2°); or
(5.5±0.2°), (8.4±0.2°), (8.7±0.2°), (13.0±0.2°), (16.5±0.2°), (19.6±0.2°) and (20.6±0.2°); or
(5.5±0.2°), (8.4±0.2°), (8.7±0.2°), (11.0±0.2°), (13.0±0.2°), (16.5±0.2°), (19.6±0.2°) and (20.6±0.2°); or
(5.5±0.2°), (8.4±0.2°), (8.7±0.2°), (11.0±0.2°), (13.0±0.2°), (16.5±0.2°), (17.9±0.2°), (19.6±0.2°) and (20.6±0.2°); or
(5.5±0.2°), (8.4±0.2°), (8.7±0.2°), (11.0±0.2°), (13.0±0.2°), (16.5±0.2°), (17.9±0.2°), (19.6±0.2°) (20.6±0.2°) and (24.0±0.2°); when measured at a temperature in the range of from 20 to 30° C. with Cu-Kalpha$_{1,2}$ radiation having a wavelength of 0.15419 nm.

In yet another embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Hydrate B characterized by having a XRPD pattern essentially the same as that shown in FIG. 5 of the present invention, when measured at a temperature in the range of from 20 to 30° C. with Cu-Kalpha$_{1,2}$ radiation having a wavelength of 0.15418 nm.

In another embodiment, the present disclosure relates to a crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Hydrate B characterized by having a broad endothermic event with a peak maximum at temperature of 93±10° C., when measured with DSC at a heating rate of 10 K/min.

In another aspect, the present invention relates to a composition comprising crystalline forms of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate as defined in any one of the embodiments described above, said composition being essentially free of any other solid form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate. For example, a composition comprising the crystalline Hydrate A of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate of the present disclosure comprises at most 20 w-%, preferably at most 10 w-%, more preferably at most 5, 4, 3, 2 or 1 w-% of any other solid form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate], based on the weight of the composition.

Ca$_v$1.2-HEK293(AUX) Cell Line

In one aspect, the present disclosure relates to a cell comprising a human CaV1.2 alpha1C (α1C) subunit (encoded by human CACNA1C transcript variant 14; GenBank ID: NM_001129840), an alpha2delta (α2Δ2) auxiliary subunit (encoded by human CACNA2D2 transcript variant 3; GenBank ID: NM_001174051), and a beta2 (β2) auxiliary subunit (encoded by human CACNB2 transcript variant 2; GenBank ID: NM_201596), wherein the α1C subunit is constitutively expressed, and the α2Δ2 subunit and β2 subunit are doxycycline-inducibly expressed. In another aspect, the present disclosure relates to the cell for use in a method for screening compounds for biological activity. In one aspect, the cell is comprised in a stable cell line, e.g., HEK293, constitutively expressing the α1C subunit and doxycycline-inducibly expressing the α2Δ2 subunit and the β2 subunit. In another aspect, the stable cell line is generated by DNA transfection or viral transduction, e.g., via lentivirus or baculovirus. In one aspect, the cell is comprised in a cell line, e.g., HEK293, from transient DNA transfection constitutively expressing the α1C subunit and doxycycline-inducibly expressing the α2Δ2 subunit and the β2 subunit. In another aspect of the present disclosure, the compounds are Ca$_v$1.2 activators. In another aspect, the present disclosure relates to the cell for use in a method to identify an agent for treating, preventing, and/or diagnosing a disease or disorder, e.g., schizophrenia, bipolar disorder, major depressive disorder, substance use disorder, ADHD, Phelan-McDermid Syndrome, autism spectrum disorder, multiple sclerosis, frontotemporal dementia, Alzheimer's disease, Brugada Syndrome, Short QT syndrome, or early repolarization syndrome. In some aspects, the agent is a Ca$_v$1.2 activator.

INTERMEDIATES AND EXAMPLES

The following examples are intended to illustrate the disclosure and are not to be construed as being limitations thereon.

The examples were all separated into their single enantiomers and were tested in the Sophion Qpatch assay described in the Biological Data section below. However, the stereochemistry of each enantiomer was not determined. The stereochemistry of the active enantiomer for Example 6, methyl (R)-4-(2-((S)-1,2-difluoroethyl)-3-fluorophenyl)-2-(fluoromethyl)-5-oxo-1,4,5,7-tetrahydrofuro[3,4-b]pyridine-3-carboxylate, and Example 9, methyl (R)-4-(2-(difluoromethoxy)phenyl)-2-(fluoromethyl)-5-oxo-1,4,5,7-tetrahydrofuro[3,4-b]pyridine-3-carboxylate, were analyzed using single crystal x-ray crystallography and it was determined that the active enantiomer was the R-enantiomer. Therefore, it is assumed that the R-enantiomer of methyl 2-(fluoromethyl)-5-oxo-4-phenyl-4,5,6,7-tetrahydro-1H-cyclopenta[b]pyridine-3-carboxylate and methyl 2-(fluoromethyl)-5-oxo-4-phenyl-1,4,5,7-tetrahydrofuro[3,4-b]pyridine-3-carboxylate compounds, depicted below, are the active enantiomers.

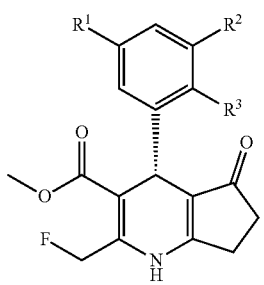

methyl (R)-2-(fluoromethyl)-5-oxo-4-phenyl-4,5,6,7-tetrahydro-1H-cyclopenta[b]pyridine-3-carboxylate

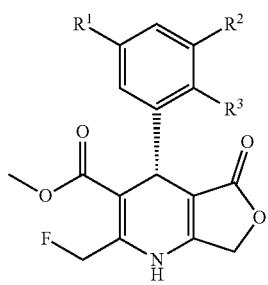

methyl (R)-2-(fluoromethyl)-5-oxo-4-phenyl-1,4,5,7-tetrahydrofuro[3,4-b]pyridine-3-carboxylate Example numbers (Example 1, 2, 3, etc.) are given for the active enantiomers which are all assumed to have the R-configuration. All other isomers isolated from the synthesis were given example numbers with letters (Example 1 b, 2b, 3b etc.). Although there is strong evidence to suggest that the R-configuration is the desired stereochemistry, there is still the possibility that the S-enantiomer could be the active enantiomer.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR.

All starting materials, building blocks, reagents, acids, bases, dehydrating agents, solvents, and catalysts utilized to synthesis the compounds of the present disclosure are either commercially available or can be produced by organic synthesis methods known to one of ordinary skill in the art.

Further, the compounds of the present disclosure can be produced by organic synthesis methods known to one of ordinary skill in the art as shown in the following examples. Abbreviations used are those conventional in the art or the following:

$^1$H NMR proton nuclear magnetic resonance
AUX auxiliary subunit of Ca$_V$1.2 channel
C Celsius
CD3OD methanol-d4
CDCl3 chloroform-d
CHO Chinese Hamster Ovary cells
Ct threshold cycle in a quantitative polymerase chain reaction assay
d doublet
DAST diethylaminosulfur trifluoride
DCM dichloromethane
dd doublet of doublets
DME 1,4-dimethoxyethane
DMEM Dulbecco's Modified Eagle Medium
DMF N,N-dimethylformamide
DMSO dimethylsulfoxide
DMSO-d6 dimethylsulfoxide-d6
D-PBS Dulbecco's Phosphate Buffered Saline
EC50 Half maximal effective concentration
EDTA Ethylenediaminetetraacetic acid
EGTA Ethylene glycol-bis(β-aminoethyl ether)-N,N,N',N'-tetraacetic acid
Eq equivalents
EtOAc ethyl acetate
FAM 6-carboxyfluorescein
FCS Furin Cleavage Site
FRT Flippase recognition target site
g gram
h hour(s)
H$_2$O water
HEPES 4-(2-hydroxyethyl)-1-piperazineethanesulfonic acid
HOBt 1-hydroxy-7-azabenzotriazole
HPLC high pressure liquid chromatography
HRMS high resolution mass spectrometry
Hrs hours
Hz hertz
IACUC Institutional Animal Care and Use Committee
IPA isopropyl alcohol
kg kilogram
L liter
LCMS liquid chromatography mass spectrometry
M molar
m multiplet
m/z mass to charge ratio
mg milligram
MHz mega hertz
min minutes
mL milliliter
ml milliliter
mL/min milliliters per minute
mm millimeter
mM millimolar
mmol millimoles
mRNA messenger ribonucleic acid
MS mass spectrometry
mV millivoltμl
N normal
n-BuLi n-butyllithium
NMR nuclear magnetic resonance
NOESY nuclear Overhauser effect spectroscopy
pCMV the cytomegalovirus promoter
P2A a peptide self-cleavage sequence derived from porcine teschovirus-1
PdCl2(dppf) Dichloro[1,1'-bis(diphenylphosphino)ferrocene]palladium(II)
PD Pharmacodynamics
PK Pharmacokinetics
ppm parts per million
PyBOP benzotriazol-1-yloxytripyrrolidinophosphonium hexafluorophosphate
QT the time interval between the Q wave and T wave of an electrocardiograph rac racemic
rpm round per minute
RNA ribonucleic acid
RT room temperature
Rt retention time
RT-PCR Reverse Transcription-Polymerase Chain Reaction
s singlet
SFC supercritical fluid chromatography
SFM Serum Free Medium
SNP Single Nucleotide Polymorphism
t triplet
TFA trifluoroacetic acid
THF tetrahydrofuran
uL microliter
Um micrometer
UPLC ultra performance liquid chromatography
UV ultraviolet
VIC 2'-chloro-7'phenyl-1,4-dichloro-6-carboxy-fluorescein
v/v volume/volume percent
Small Molecule X-Ray Crystallography
Data Collection Intensity data were collected at 100 K on a Bruker AXS three-circle diffractometer with monochromated Cu(Kα)-radiation, microfocus rotating anode generator, and a Smart 6000 CCD detector using the SMART software (Bruker AXS (2003)). 16 ω-scans at different ϕ-Positions were performed to ensure appropriate data redundancy. Data processing and global cell refinement were performed with Saint (Bruker AXS (2012)). A semi-empirical absorption correction was applied, based on the intensities of symmetry-related reflections measured at different angular settings, using SADABS version 2016/2 (Krause L (2015)). The extinction coefficient refined to 0.00048(11). Crystal data, data collection parameters, and convergence results are listed.

Structure Solution and Refinement

The structure was solved by dual space-recycling methods and subsequent DF syntheses and refined based on full-matrix least-squares on F2 using the SHELXTL program suite (Sheldrick G M (2001)) with SHELXL-2013/4.

REFERENCES

Allen F H, Kennard O, Watson D et al (1987) Tables of Bond Lengths determined by X-Ray and Neutron Diffraction. Part 1, Bond Lengths in Organic Compounds. J. Chem. Soc. Perkin Trans II; S1-S19.
Bruker AXS (2005) SMART V5.632. Bruker AXS Inc., Madison, WI, USA.
Bruker AXS (2012) SAINT V7.36A. Bruker AXS Inc., Madison, WI, USA.
Krause L, Herbst-Irmer R, Sheldrick G M et al (2015) Comparison of silver and molybdenum microfocus X-ray sources for single-crystal structure determination. J. Appl. Cryst.; 48: 3-10.
Spek A L (2003) Single-crystal structure validation with the program PLATON. J. Appl. Cryst.; 36: 7-13.
Sheldrick G M (2001) SHELXTL V6.12. Bruker AXS Inc. Madison, WI, USA.

LCMS Method 1:
Instrument: Waters Acquity UPLC, photodiode array detector; Column: Acquity UPLC BEH $C_{18}$ 1.7 μm, 21×30 mm; 2 min run time, 2% solvent B from 0 to 0.1 min, 2→98% solvent B:solvent A from 0.1 to 1.8 min, 98% solvent B for 0.2 min. Solvents: Solvent A=0.1% formic acid in water (v/v), Solvent B=0.1% formic acid in acetonitrile (v/v). Injection volume 2-5 μL; UV detection array 210-400, Mass detection 120-1250 (electrospray ionization); column at 50° C.; flow rate 1.0 mL/min.

LCMS Method 2:
Instrument: Waters Acquity UPLC, photodiode array detector; Column: Acquity UPLC BEH $C_{18}$ 1.7 μm 21×50 mm; 2 min run time, 2% solvent B from 0 to 0.1 min, 2→98% solvent B:solvent A from 0.1 to 1.8 min, 98% solvent B for 0.2 min. Solvents: Solvent A=5 mM ammonium hydroxide in water, solvent B=5 mM ammonium hydroxide in acetonitrile. Injection volume 2-5 μL; UV detection array 210-400, Mass detection 120-1250 (electrospray ionization); column at 50° C.; flow rate 1.0 mL/min.

LCMS Method 3:
Instrument: Waters Acquity UPLC, photodiode array detector; Column Acquity UPLC BEH $C_{18}$ 1.7 μm 21×30 mm; 5.2 min run time, 2→98% solvent B:solvent A from 0 to 5.15 min, 98% solvent B from 5.15 to 5.20 min. Solvents: Solvent A=0.1% formic acid in water (v/v), solvent B=0.1% formic acid in acetonitrile (v/v). Injection volume 2-5 μL; UV detection array 210-400, Mass detection 120-1600; column at 50° C., flow rate 1.0 mL/min.

LCMS Method 4:
Instrument: Waters Acquity UPLC, photodiode array detector; Column Acquity UPLC BEH $C_{18}$ 1.7 μm 21×30 mm; 5.2 min run time, 2→98% solvent B:solvent A from 0 to 5.15 min, 98% solvent B from 5.15 to 5.20 min. Solvents: Solvent A=5 mM ammonium hydroxide in water, solvent B=5 mM ammonium hydroxide in acetonitrile. Injection volume 2-5 μL; UV detection array 210-400, Mass detection 120-1600; column at 50° C., flow rate 1.0 mL/min.

LCMS Method 5:
Instrument: Agilent 1200 LC/G1956A, diode array detector; Column: Chromolith Flash $C_{18}$, 1.6 micron 2×25 mm; 1.5 minute run time, 5→95% solvent B: solvent A from 0→1.2 minutes and then 95% solvent B from 1.21→1.5 minutes. Solvents: Solvent A=0.0375% TFA in Water (v/v), Solvent B=0.01875% TFA in Acetonitrile (v/v). Injection volume 2-5 μL; UV detection 220 and 254 nM, Mass detection 100-1000 (electrospray ionization); column at 50° C.; Flow rate 1.5 mL/min.

LCMS Method 6:
Instrument: SHIMADZU LCMS-2020, photo diode array detector; Column: Kinetex EVO $C_{18}$, 5 uM, 1×30 mm; 1.55 minute run time, 5→95% solvent B:solvent A from 0→1.20 minutes and then 95% solvent B from 1.21 minutes to 1.55 minutes. Solvents: Solvent A=0.025% $NH_4OH$ in water (v/v), Solvent B=acetonitrile. Injection volume 2-5 μL; UV detection 220 and 254 nM, Mass detection 100-1000 (electrospray ionization); column at 40° C.; Flow rate 1.5 mL/min.

LCMS Method 7:
Instrument: API2000, column: Mercury MS Synergi 2 μm, 20×4.0 mm, C12; gradient: A—0.1% formic acid in water/B—acetonitrile: Time/% B: 0.0/30, 0.5/30, 1.5/95, 2.0/95, 2.5/30, 3.0/30, flow 2.0 mL/min; UV detection array 190-400, Mass detection 100-1000 (electrospray ionization); column temperature 30° C.

LCMS Method 8:
Instrument: API3000, column: Synergi 2.5 μm MAX-RP, 20×4.0 mm 100 A Mercury; gradient: 0.1% Formic acid in water B: acetonitrile: Time % B 0/10, 0.5/20, 1.5/95, 2.0/95, 2.5/10, 3/10, flow 2.0 mL/min; UV detection array 190-400 (Total Wavelength Chromatogram), Mass detection 100-1000 (electrospray ionization); column temperature 30° C.

LCMS Method 9:

Instrument: API3000, column: Synergi 2.5 μm, 50×4.6 mm, MAX-RP 100 A; gradient: 0.1% formic acid in water B: acetonitrile: Time 0.0/10, 0.2/50, 1.0/95, 1.5/100, 2.5/95, 2.9/50, 3.2/10, 4/10, flow 1.2 mL/min; UV detection array 190-400 (Total Wavelength Chromatogram), Mass detection 100-1000 (electrospray ionization); column temperature 30° C.

LCMS Method 10:

Shimadzu, column: Mercury MS Synergi 2.5 μm, 20×4.0 mm, C12; gradient: A—0.1% formic acid in water/B—acetonitrile: Time/% B: 0.1/5, 0.5/5, 1.0/95, 1.5/95, 2.0/5, 3.0/5, flow 2.0 mL/min; UV detection array 200-400, Mass detection 100-1000 (electrospray ionization); column temperature 40° C.

LCMS Method 11:

Shimadzu, column: Kinetex 5 μm EVO C18 100 A, (100×2.1 mm); gradient: A—0.1% formic acid in water/B—acetonitrile: Time/% B: 0/5, 1/30, 3/95, 4/95, 4.1/5, 6/5, flow 1.4 mL/min; UV detection array 200-400, Mass detection 100-1000 (electrospray ionization); column temperature 40° C.

LCMS Method 12:

Shimadzu, column: Synergi 2.5 μm MAX-RP 100 A, (20×4.0 mm) Mercury; gradient: A—0.1% formic acid in water/B—acetonitrile: Time/% B: 0.1/5, 0.5/5, 1.0/95, 1.5/95, 2.0/5, 3.0/5, flow 2.0 mL/min; UV detection array 200-400, Mass detection 100-1000 (electrospray ionization); column temperature 40° C.

LCMS Method 13:

Acquity, Column: UPLC BEH C18 1.7 μm 2.1×50 mm; Gradient: A—0.1% formic acid in water/B—acetonitrile: 2.2 min run time, 2→98% solvent B: solvent A from 0→1.76 minutes and then 95% solvent B from 1.76 minutes to 2.0 minutes; flow 1.0 mL/min; UV detection array 210-400 nm; Mass Range 100-2050 Da; HRMS_2 min; Column Temperature 50° C.

Preparative HPLC Methods for Purification:

Method 1: HPLC Column: XBRIDGE-C18 (19.0×150 mm, 5 micron), Mobile phase-A: 0.1% TFA in H$_2$O, B: CH$_3$CN, gradient (Time/% B): 0/20, 2/20, 8/50) Flow rate: [19 mL/min].

Method 2: HPLC Column: ZORBAX ECLIPSE XDB C18 (21.2×150 mm, 5 micron), Mobile phase-A: 0.1% TFA in H$_2$O, B: CH$_3$CN, gradient (Time/% B): 0/10, 2/20, 10/40 and Flow rate: [20 mL/min].

Method 3: HPLC [Column: XBRIDGE C18 (21.2×150 mm, 5 micron), Mobile phase-A: 10 mM NH$_4$HCO$_3$ in water, B: CH$_3$CN, gradient (Time/% B): 0/10, 2/20, 8/50 and Flow rate: [18 mL/min].

Method 4: HPLC Column: Gemini NX C18 (21.2×150.00 mm, 5 micron); Mobile Phase-(A): 0.1% TFA in water (B): Acetonitrile/Methanol; Flow: 15 mL/min; (Time/% B 0/20, 2/20, 8/20)

Method 5: HPLC Column: KINETEX EVO 5μ C18 (21.2×150 mm), Mobile Phase: WATER (A) CH$_3$CN (B), gradient (Time/% B): 0/20, 2/30, 7/70 and Flow rate: [18 mL/min].

Method 6: HPLC column: KINETEX C18, (21.2×150 mm), Mobile phases: A: WATER, B: CH$_3$CN:MeOH, gradient (Time/% B): 0/20, 2/30, 7/70, Flow rate: 18 mL/min].

Method 7: HPLC Column: KINETEX (21.2×150 mm, 5 micron), Mobile phases: A=0.05% TFA in water, B=CH$_3$CN, gradient (Time/% B): 0/20, 2/30, 10/60, Flow rate: 20 mL/min].

Chiral Preparative HPLC Methods for Separation of Isomers:

Method 1: Column: CHIRALPAK IC (10×250 mm, 5 micron), Mobile Phase: Hexane (A) IPA:MeOH, 1:1 (B); Flow rate: 8 mL/min; Isocratic: 96:04 (A:B).

Method 2: Column: REGIS WELKO (250×10 mm, 5 micron), Mobile Phase: Hexane (A): EtOH, 1:1 (B); Flow rate: 9 mL/min; Isocratic: 85:15 (A:B).

Method 3: Column: CHIRALPAC IG (250×10 mm, 5 micron), Mobile Phase: IPA (A): MeOH, 1:1 (B); Flow rate: 6 mL/min; Isocratic: 98:2 (A:B).

Method 4: Column: LUX CELLULOSE-4 (10×250 mm, 5 micron), Mobile Phase: Hexane (A) EtOH:IPA 1:1 (B); Flow rate: 8 mL/min; Isocratic: 90:10 (A:B).

Method 5: Column: LUX CELLULOSE-4 (10×250 mm, 5 micron), Mobile Phase: Hexane (A) EtOH: 1:1 (B); Flow rate: 8 mL/min; Isocratic: 90:10 (A:B).

Method 6: Column: LUX CELLULOSE-4 (10×250 mm, 5 micron), Mobile Phase: Hexane (A); EtOH:MeOH 1:1 (B); Flow rate: 18 mL/min; Isocratic: 90:10 (A:B).

Method 7: Column: LUX CELLULOSE-4 (21.2×250 mm, 5 micron), Mobile Phase: Hexane (A); EtOH:MeOH 1:1 (B); Flow rate: 19 mL/min; Isocratic: 80:20 (A:B).

Method 8: Column: REGIS (10×250 mm, 5 micron), MOBILE PHASE: CO$_2$ (A) MeOH:EtOH 1:1 (B); FLOW: 13 mL/min, Isocratic: 80:20 (A:B).

Method 9: Column: LUX CELLULOSE-4 (10×250 mm, 5 micron), Mobile Phase: Hexane (A) 0.1% DEA IN EtOH: MeOH (50:50) (B); Flow rate: 7 mL/min; Isocratic: 93:07 (A:B).

Chiral Analytical HPLC Methods for Analysis of Separated Isomers:

Method 1: Column: Lux, Cellulose-4 (250×4.6 mm, 5 micron; Mobile Phase: A=n-HEXANE, B=0.1% TFA IN ETHANOL; 1 mL/min; Isocratic: 70:30 (A:B)

Method 2: Column: LUX CELLULOSE-4 (4.6×250 mm, 5 micron; Mobile Phase: Hexane (A) EtOH: 1:1 (B); Flow rate: 1 mL/min; Isocratic: 50:50 (A:B).

Method 3: Column: REGIS, (S, S) WHELK-01 (250×4.6 mm, 5 micron; Mobile Phase: A=n-HEXANE, B=ETHANOL; Flow rate: 1 mL/min; Isocratic: 70:30 (A:B).

Intermediate A: Formation of ethyl 4-acetoxy-3-oxobutanoate

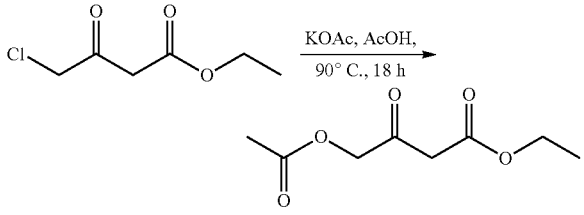

To a solution of ethyl 4-chloro-3-oxobutanoate (200 g, 1215.1 mmol) in acetic acid (1500 mL) was added potassium acetate (357 g, 3645.4 mmol). The resulting solution was stirred at 90° C. for 18 hrs. The solvent was dissolved in water (2 L) and extracted into ethyl acetate (1 L×4 times). EtOAc phases were combined and washed with saturated NaHCO$_3$ solution (2 L), brine and dried over Na$_2$SO$_4$. The solvent was removed under reduced pressure and purification of the crude product by silica flash chromatography (0→15%) ethyl acetate in petroleum ether afforded the title compound as a light brown liquid ethyl 4-acetoxy-3-oxobutanoate. (152 g).

¹H NMR (400 MHz, CDCl₃) δ 4.78 (s, 2H), 4.20 (q, J=14.1, 7.2 Hz, 2H), 3.49 (s, 2H), 2.16 (s, 3H), 1.28 (t, J=7.2 Hz, 3H).

Intermediate B: Formation of methyl (Z)-3-amino-4-fluorobut-2-enoate

Method 1:

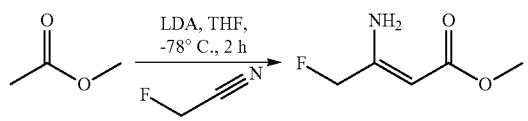

A solution of methyl acetate (36.5 g, 492.71 mmol) in tetrahydrofuran (200 mL) under nitrogen atmosphere was cooled to −78° C., lithium diisopropylamide in THF (246.44 mL, 2.0 M, 492.71 mmol) was added to reaction slowly over a period of 20 min, the resulting mixture was stirred for 1 h at −78° C. followed by addition of 2-fluoroacetonitrile (19.4 g, 328.9 mmol) in a solution of tetrahydrofuran (150 mL) dropwise. Reaction mixture and stirred at −78° C. for another 1 h before addition of saturated ammonium chloride solution (200 mL) was added and product extracted into ethyl acetate (5 L). EtOAc was washed with saturated brine solution (500 mL) and dried over Na₂SO₄. The solvent was removed under reduced pressure and purification of the crude product by silica flash chromatography (0→10%) ethyl acetate in petroleum ether afforded the title compound as a white crystalline solid methyl (Z)-3-amino-4-fluorobut-2-enoate (16 g).

Method 2:

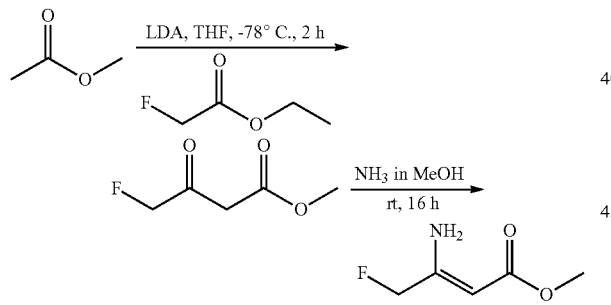

Step 1: A solution of methyl acetate (83.78 g, 1131.0 mmol) in tetrahydrofuran (800 mL) under nitrogen atmosphere was cooled to −78° C., then lithium diisopropylamide in THF (565.5 mL, 2.0 M, 1131.0 mmol) was added to reaction slowly over a period of 20 min. Resulting mixture was stirred for 1 h at −78° C. and then ethyl 2-fluoroacetate (100 g, 942.5 mmol) was added in a solution of tetrahydrofuran (200 mL) drop wise and the reaction mixture and stirred at −78° C. for another 1 h. Saturated ammonium chloride solution (200 mL) was added to reaction mixture and product extracted into ethyl acetate (5 L). EtOAc was washed with saturated brine solution (500 mL) and dried over Na₂SO₄. The solvent was removed under reduced pressure and purification of the crude product by silica flash chromatography (0→10%) ethyl acetate in petroleum ether to give yellow crystals of methyl 4-fluoro-3-oxobutanoate (60 g).

¹H NMR (400 MHz, CDCl3) δ 4.97 (s, 1H), 4.85 (s, 1H), 3.76 (d, J=2.3 Hz, 3H), 3.62 (d, J=3.7 Hz, 2H).

Step 2: To methyl 4-fluoro-3-oxobutanoate (from step 1, 60 g) in a sealed tube was added saturated ammonia solution in methanol (300 mL) at room temperature. The resulting mixture was stirred at room temperature for 16 hrs. The solvent was removed under reduced pressure afforded the title compound as a white solid methyl (Z)-3-amino-4-fluorobut-2-enoate (51 g).

¹H NMR (300 MHz, DMSO-d6) δ 4.98 (t, J=0.7, 0.7 Hz, 1H), 4.82 (t, J=0.7, 0.7 Hz, 1H), 4.53 (q, 1H), 3.53 (d, J=1.2 Hz, 3H).

General Procedure I

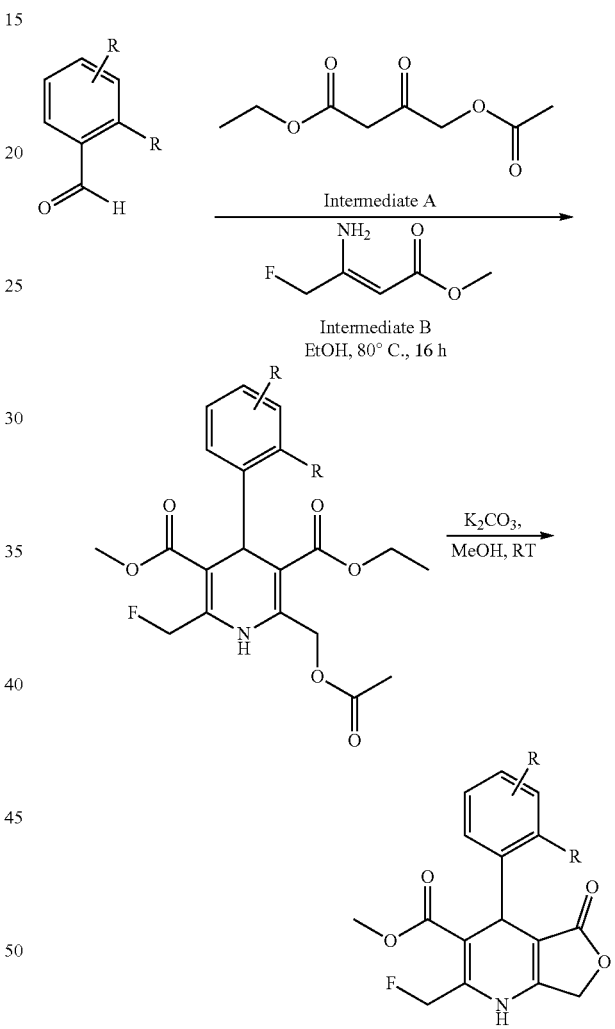

Step 1: To a solution of aldehyde (1 mmol) in EtOH (10 mL) was added methyl (Z)-3-amino-4-fluorobut-2-enoate (intermediate B, 1 mmol or 1.2 mmol) and ethyl 4-acetoxy-3-oxobutanoate (intermediate A, 1 mmol or 1.2 mmol). The resulting solution was stirred at 80° C. for 16 hrs. The solvent was removed under reduced pressure afforded the title compound (crude).

Step 2: To a crude intermediate from step 1 in methanol (10 mL) was added potassium carbonate (5 mmol). The resulting solution was stirred at room temperature for 2 hrs. The solvent was removed under reduced pressure and this added to water. Product extracted into ethyl acetate (100 mL), washed with brine and dried over Na₂SO₄. The solvent was removed under reduced pressure and purification of the crude product by silica flash chromatography.

General Procedure II

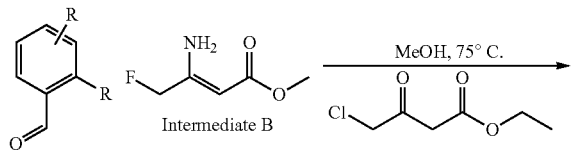

To a solution of aldehyde (1 mmol) in MeOH (10 mL) was added methyl (Z)-3-amino-4-fluorobut-2-enoate (intermediate B, 1 mmol or 1.2 mmol) and ethyl 4-acetoxy-3-oxobutanoate (intermediate A, 1 mmol or 1.2 mmol). The resulting solution was stirred at 75° C. for 16-48 hrs. The solvent was removed under reduced pressure and the product was purified using silica flash chromatography.

Example 1: methyl (R)-4-(2-((R or S)-2,2-difluorocyclopropyl)-3-fluorophenyl)-2-(fluoromethyl)-5-oxo-1,4,5,7-tetrahydrofuro[3,4-b]pyridine-3-carboxylate

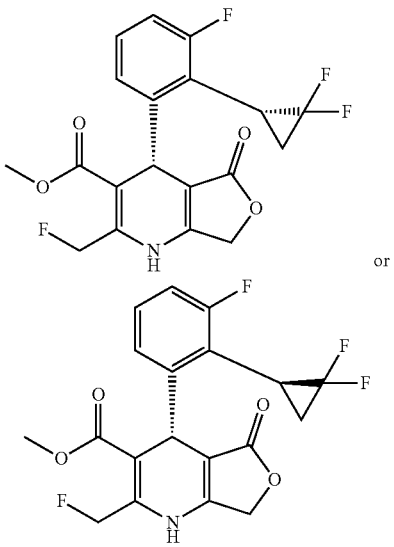

Step 1: 2-(2-bromo-3-fluorophenyl)-1,3-dioxolane

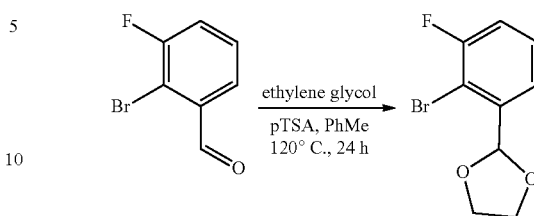

To a solution of 2-bromo-3-fluorobenzaldehyde (60 g, 295.56 mmol) and ethylene glycol (65.4 mL, 1182.2 mmol) in toluene (600 mL) was added p-toluenesulfonic acid monohydrate (28.11 g, 147.78 mmol). The resulting solution was stirred at 120° C. for 24 hrs using dean-stark apparatus. Reaction mixture was poured into water (2 L) and extracted into ethyl acetate (3 L). EtOAc was washed with saturated NaHCO$_3$ solution (1 L), brine and dried over Na$_2$SO$_4$. The solvent was removed under reduced pressure and purification of the crude product by silica flash chromatography (0→10%) ethyl acetate in petroleum ether afforded the title compound 2-(2-bromo-3-fluorophenyl)-1,3-dioxolane (60 g) as a colorless liquid.

$^1$H NMR (400 MHz, CDCl$_3$) δ 7.42-7.37 (m, 1H), 7.34-7.29 (m, 1H), 7.16-7.10 (m, 1H), 6.10 (s, 1H), 4.19-4.09 (m, 4H).

Step 2: 2-(3-fluoro-2-vinylphenyl)-1,3-dioxolane

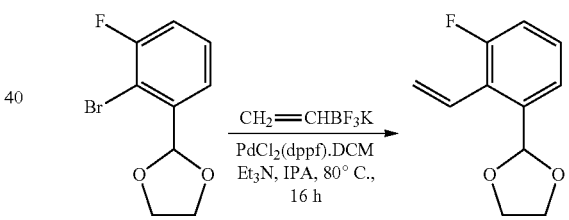

To a solution of 2-(2-bromo-3-fluorophenyl)-1,3-dioxolane (from step 1, 15 g, 60.72 mmol) and potassium vinyltrifluoroborate (16.26 g, 121.45 mmol) in isopropyl alcohol (200 mL) was added triethylamine (25.5 mL, 182.16 mmol) and [1,1'-Bis(diphenylphosphino)ferrocene] dichloropalladium(II).DCM (4.95 g, 6.07 mmol). The resulting solution was degassed with Argon gas for 10 min and stirred at 80° C. for 16 hrs. The reaction mixture was filtered and washed with ethyl acetate (100 mL). The filtrate was added to water (1 L) and product extracted into ethyl acetate (2 L). EtOAc phase was washed with brine and dried over Na$_2$SO$_4$. The solvent was removed under reduced pressure and purification of the crude product by silica flash chromatography (0→10%) ethyl acetate in petroleum ether afforded the title compound 2-(3-fluoro-2-vinylphenyl)-1,3-dioxolane (7.5 g) as a colorless liquid.

$^1$H NMR (400 MHz, CDCl$_3$) δ 7.45-7.41 (m, 1H), 7.27-7.20 (m, 1H), 7.10-7.03 (m, 1H), 6.82 (dd, J=17.7, 11.7 Hz, 1H), 5.82-5.78 (m, 1H), 5.66-5.60 (m, 1H), 5.95 (s, 1H), 4.18-4.02 (m, 4H).

Step 3: 2-(2-(2,2-difluorocyclopropyl)-3-fluorophenyl)-1,3-dioxolane

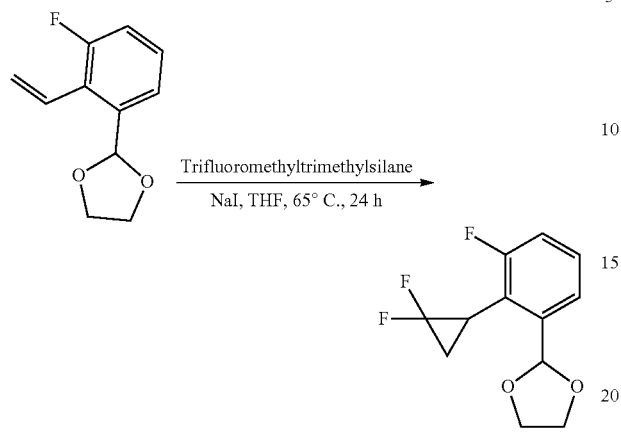

To a solution of 2-(3-fluoro-2-vinylphenyl)-1,3-dioxolane (from step 2, 6.5 g, 33.47 mmol) and trifluoromethyltrimethylsilane (50 mL, 334.7 mmol) in tetrahydrofuran (120 mL) was added sodium iodide (2.5 g, 16.73 mmol). The resulting solution was stirred at 65° C. for 24 hrs. The solvent was evaporated under reduced pressure and the residue was dissolved in dichloromethane (100 mL). This was washed with water (50 mL), brine and dried over $Na_2SO_4$. The solvent was removed under reduced pressure which afforded the title compound 2-(2-(2,2-difluorocyclopropyl)-3-fluorophenyl)-1,3-dioxolane (8 g) as a colorless liquid.

$^1$H NMR (400 MHz, $CDCl_3$) δ 7.42 (d, J=7.5 Hz, 1H), 7.34-7.28 (m, 1H), 7.16-7.03 (m, 1H), 6.06 (s, 1H), 4.20-4.01 (m, 4H), 2.77-2.66 (m, 1H), 2.02-1.72 (m, 2H).

Step 4: 2-(2,2-difluorocyclopropyl)-3-fluorobenzaldehyde

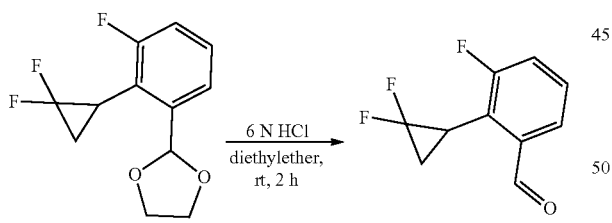

To a solution of 2-(2-(2,2-difluorocyclopropyl)-3-fluorophenyl)-1,3-dioxolane (from step 3, 8 g, 32.76 mmol) and in diethyl ether (80 mL) was added 6N HCl (10 mL). The resulting solution was stirred at room temperature for 2 hrs. This was washed with water (50 mL), saturated $NaHCO_3$ solution (100 mL), brine and dried over $Na_2SO_4$. The solvent was removed under reduced pressure and purification of the crude product by silica flash chromatography (0→5%) ethyl acetate in petroleum ether afforded the title compound 2-(2,2-difluorocyclopropyl)-3-fluorobenzaldehyde (3.8 g) as a colorless liquid.

$^1$H NMR (400 MHz, $CDCl_3$) δ 10.28 (s, 1H), 7.70 (d, J=6.9 Hz, 1H), 7.50-7.43 (m, 1H), 7.36-7.26 (m, 1H), 2.92-2.81 (m, 1H), 2.16-2.06 (m, 1H), 1.67-1.53 (m, 1H).

Step 5: 3-ethyl 5-methyl 2-(acetoxymethyl)-4-(2-(2,2-difluorocyclopropyl)-3-fluorophenyl)-6-(fluoromethyl)-1,4-dihydropyridine-3,5-dicarboxylate

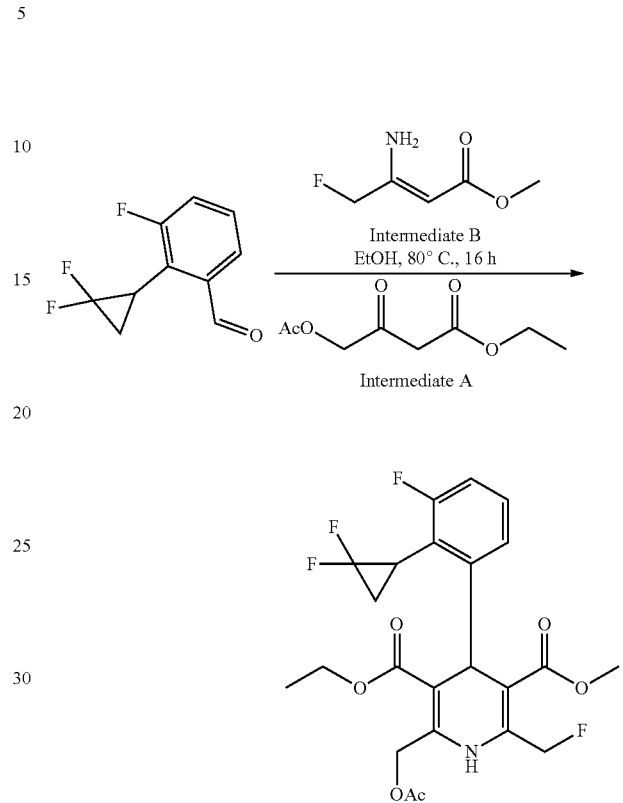

Title compound was synthesized using step 1 of general procedure I (using the aldehyde from step 4, (1.0 g, 4.996 mmol), intermediate A, (945 mg, 4.996 mmol) and intermediate B, (665 mg, 4.996 mmol) to give 3-ethyl 5-methyl 2-(acetoxymethyl)-4-(2-(2,2-difluorocyclopropyl)-3-fluorophenyl)-6-(fluoromethyl)-1,4-dihydropyridine-3,5-dicarboxylate (1.4 g, crude). The crude product was taken as such to next step without further purification and analysis.

Step 6: methyl 4-(2-(2,2-difluorocyclopropyl)-3-fluorophenyl)-2-(fluoromethyl)-5-oxo-1,4,5,7-tetrahydrofuro[3,4-b]pyridine-3-carboxylate

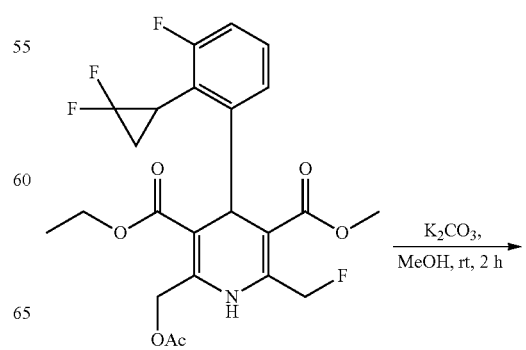

-continued

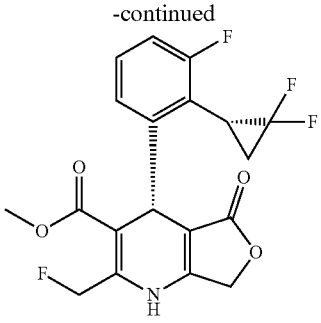

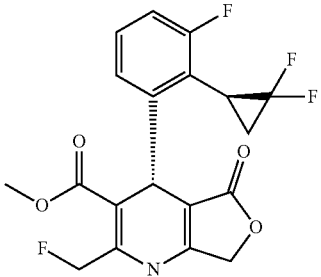

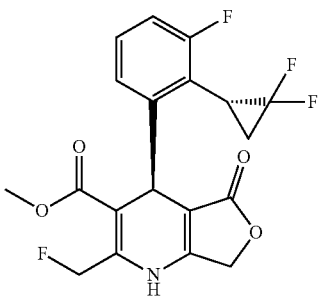

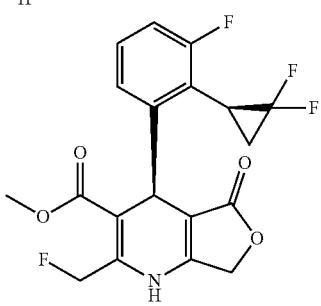

Title compound was synthesized using step 2 of general procedure I (using the intermediate from step 5, 1.4 g, 2.884 mmol). Crude product was purified by silica flash chromatography (0→50%) ethyl acetate in petroleum ether which afforded the title compound methyl 4-(2-(2,2-difluorocyclopropyl)-3-fluorophenyl)-2-(fluoromethyl)-5-oxo-1,4,5,7-tetrahydrofuro[3,4-b]pyridine-3-carboxylate (125 mg) as an off white solid. The sample was chirally separated into two products using chiral SFC: Column: Lux-cellulose-2 21×250 mm 5 um; Flow rate: 80 g per minute; Cosolvent: 20% 1:1 MeOH:IPA; Detection: 344 nm; BPR Set Point: 125 bar.

Resulting peak 1 & 2 from previous separation were separated into 4 isomers using chiral SFC:

Column: WO1 SS 21×250 mm; Flow Rate: 80 g per minute; Cosolvent: 15% IPA; Detection: 344 nm; BPR Set Point: 150 bar.

Example 1

20 mg of the title compounds as the second eluting stereoisomer as a white solid (61%)

SFC Rt=2.49; Mobile Phase: 5-55% (1:1) MeOH IPA w/10 mM NH$_4$OH in CO$_2$ 5 mL/min; Column: Lux Cellulose-2 4.6×100 mm 5 μm LCMS Rt=2.12 min; MS m/z 398.3 [M+H]+; [Method 3]

$^1$H NMR (400 MHz, DMSO-d6) δ 10.13 (d, J=3.3 Hz, 1H), 7.31 (td, J=8.0, 5.6 Hz, 1H), 7.20-6.83 (m, 2H), 5.78-5.41 (m, 2H), 5.22 (s, 1H), 5.03-4.73 (m, 2H), 3.51 (s, 3H), 2.86 (td, J=12.4, 8.5 Hz, 1H), 2.64-2.53 (m, 1H), 2.18 (dt, J=12.2, 5.5 Hz, 1H).

Example 1b 15 mg of first eluting stereoisomer as a white solid (46%)

SFC Rt=2.42; Mobile Phase: 5-55% (1:1) MeOH IPA w/10 mM NH$_4$OH in CO$_2$ 5 mL/min; Column: Lux Cellulose-2 4.6×100 mm 5 μm LCMS Rt=2.15 min; MS m/z 398.2 [M+H]+; [Method 3]

$^1$H NMR (400 MHz, DMSO-d6) δ 10.08 (d, J=3.2 Hz, 1H), 7.33 (td, J=8.1, 5.8 Hz, 1H), 7.25-6.92 (m, 2H), 5.94-5.54 (m, 2H), 5.27 (s, 1H), 4.79 (d, J=1.4 Hz, 2H), 3.44 (s, 3H), 3.15-3.04 (m, 1H), 2.35-2.19 (m, 1H), 1.88 (dtd, J=14.0, 8.2, 3.2 Hz, 1H).

Example 1c 24 mg of third eluting stereoisomer as a white solid (73%)

SFC Rt=2.73 min; Mobile Phase: 5-55% (1:1) MeOH IPA w/10 mM NH$_4$OH in CO$_2$ 5 mL/min;

Column: Lux Cellulose-2 4.6×100 mm 5 μm

LCMS Rt=2.16 mins; MS m/z 398.3 [M+H]+; [Method 3]

$^1$H NMR (400 MHz, DMSO-d6) δ 10.13 (d, J=3.3 Hz, 1H), 7.31 (td, J=8.0, 5.6 Hz, 1H), 7.18-6.87 (m, 2H), 5.61 (dd, J=47.8, 4.0 Hz, 2H), 5.22 (s, 1H), 4.98-4.78 (m, 2H), 3.51 (s, 3H), 2.86 (td, J=12.5, 8.5 Hz, 1H), 2.64-2.55 (m, 1H), 2.18 (tt, J=12.8, 6.8 Hz, 1H).

Example 1d 15 mg of fourth eluting stereoisomer as a white solid (46%)

SFC Rt=2.78 min; Mobile Phase: 5-55% (1:1) MeOH IPA w/10 mM NH$_4$OH in CO$_2$ 5 mL/min;

Column: Lux Cellulose-2 4.6×100 mm 5 μm

LCMS Rt=2.11 mins; MS m/z 398.1 [M+H]+; [Method 3]

$^1$H NMR: (400 MHz, DMSO-d6) δ 10.08 (d, J=3.3 Hz, 1H), 7.33 (td, J=8.0, 5.6 Hz, 1H), 7.14-6.94 (m, 2H), 5.72 (dd, J=47.8, 4.8 Hz, 2H), 5.27 (s, 1H), 4.79 (d, J=1.4 Hz, 2H), 3.44 (s, 3H), 3.15 (d, J=14.7 Hz, 1H), 2.33-2.20 (m, 1H), 1.99-1.79 (m, 1H).

Example 2: Methyl (R)-4-(2-cyclopropyl-3-fluorophenyl)-2-(fluoromethyl)-5-oxo-1,4,5,7-tetrahydrofuro[3,4-b]pyridine-3-carboxylate

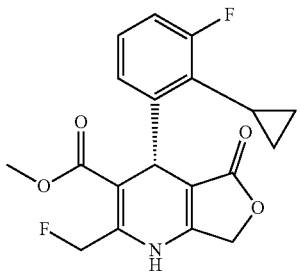 [SMILES: COC(=O)C1=C(CF)NC2=C(C(=O)OC2)[C@H]1c1cccc(F)c1C1CC1]

Step 1: 2-cyclopropyl-3-fluorobenzaldehyde

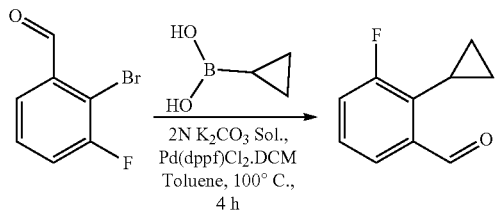

To a solution of 2-bromo-3-fluorobenzaldehyde (15 g, 73.88 mmol) and cyclopropylboronic acid (7.61 g, 88.66 mmol) in toluene (160 mL) was added 2N K₂CO₃ (25.5 mL, 182.16 mmol) and [1,1'-Bis(diphenylphosphino)ferrocene]dichloropalladium(II).DCM (6.03 g, 7.38 mmol). The resulting solution was degassed with Argon gas for 10 min and stirred at 100° C. for 4 hrs. The reaction mixture was filtered and washed with ethyl acetate (200 mL). The filtrate was added to water (500 mL) and product extracted into ethyl acetate (2 L), EtOAc phase was washed with brine and dried over Na₂SO₄. The solvent was removed under reduced pressure and purification of the crude product by silica flash chromatography (0→1%) ethyl acetate in petroleum ether afforded the title compound 2-(3-fluoro-2-vinylphenyl)-1,3-dioxolane (11.2 g) as a colorless liquid.

$^1$H NMR (300 MHz, CDCl₃) δ 10.70 (s, 1H), 7.63 (dd, J=1.2, 7.8 Hz, 1H), 7.35-7.15 (m, 2H), 2.14-2.02 (m, 1H), 1.19-1.09 (m, 2H), 0.85-0.75 (m, 2H).

Step 2: 3-ethyl 5-methyl 2-(acetoxymethyl)-4-(2-cyclopropyl-3-fluorophenyl)-6-(fluoromethyl)-1,4-dihydropyridine-3,5-dicarboxylate

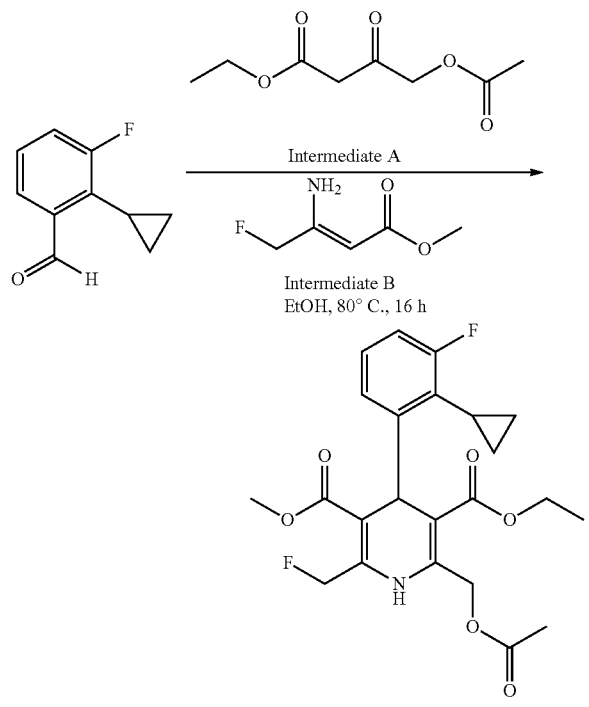

Title compound was synthesized using step 1 of general procedure I (using the aldehyde from step 1, 4.0 g, 24.36 mmol) to give 3-ethyl 5-methyl 2-(acetoxymethyl)-4-(2-cyclopropyl-3-fluorophenyl)-6-(fluoromethyl)-1,4-dihydropyridine-3,5-dicarboxylate (7.0 g, crude).

LCMS Rt=1.806 min; MS m/z 450.3 [M+H]+; [Method 7]

Step 3: methyl 4-(2-cyclopropyl-3-fluorophenyl)-2-(fluoromethyl)-5-oxo-1,4,5,7-tetrahydrofuro[3,4-b]pyridine-3-carboxylate

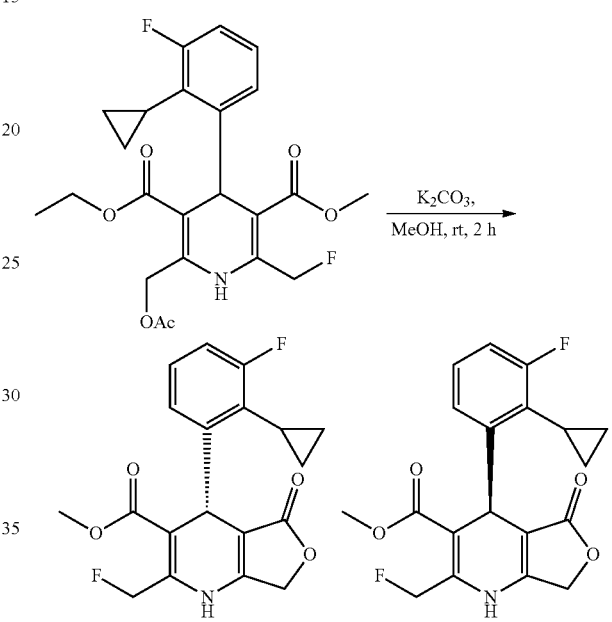

Title compound was synthesized using step 2 of general procedure I (using the intermediate from step 2, 7.0 g, 15.57 mmol). Crude product was purified by silica flash chromatography (0→50%) ethyl acetate in petroleum ether which afforded the title compound methyl 4-(2-cyclopropyl-3-fluorophenyl)-2-(fluoromethyl)-5-oxo-1,4,5,7-tetrahydrofuro[3,4-b]pyridine-3-carboxylate (1.15 g) as an off white solid.

150 mg of racemic mixture was separated into its enantiomers using chiral prep-HPLC [method 6].

Example 2

50 mg of first eluting enantiomer obtained as a white solid.

Chiral HPLC Rt=6.129 min [chiral analytical method 1]

LCMS Rt=1.538 min; MS m/z 360.0 [M−H]−; [Method 7]

$^1$H NMR (400 MHz, CDCl3) δ 7.15-7.05 (m, 1H), 6.92 (ddd, J=7.8, 1.2, 0.6 Hz, 1H), 6.82 (ddd, J=10.8, 8.2, 1.3 Hz, 1H), 5.78 (d, J=0.9 Hz, 1H), 5.71-5.59 (m, 2H), 4.80-4.69 (m, 2H), 3.55 (s, 3H), 2.19-2.15 (m, 1H), 1.34-1.20 (m, 1H), 1.06-0.96 (m, 2H), 0.82-0.71 (m, 1H). Exchangeable NH not seen in spectrum.

Example 3: Methyl (R)-4-(2-((R or S)-2,2-difluorocyclopropyl)-3,5-difluorophenyl)-2-(fluoromethyl)-5-oxo-1,4,5,7-tetrahydrofuro[3,4-b]pyridine-3-carboxylate and Example 4: Methyl (R)-4-(2-((R or S)-2,2-difluorocyclopropyl)-3,5-difluorophenyl)-2-(fluoromethyl)-5-oxo-1,4,5,7-tetrahydrofuro[3,4-b]pyridine-3-carboxylate

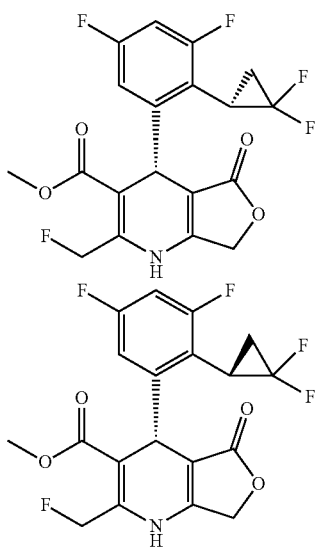

Step 1: 2-(2-bromo-3,5-difluorophenyl)-1,3-dioxolane

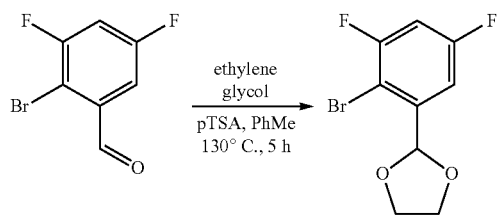 [SMILES: O=Cc1cc(F)cc(F)c1Br ; Fc1cc(F)c(Br)c(C2OCCO2)c1]

The title compound was synthesized following a procedure similar to step 1 of example 1 using 10 g of 2-bromo-3,5-difluorobenzaldehyde to obtain 11.5 g of desired product 2-(2-bromo-3,5-difluorophenyl)-1,3-dioxolane.

$^1$H NMR (300 MHz, CDCl$_3$) δ 7.20-7.15 (m, 1H), 6.49-6.87 (m, 1H), 6.08 (s, 1H), 4.17-4.04 (m, 4H).

Step 2: 2-(3,5-difluoro-2-vinylphenyl)-1,3-dioxolane

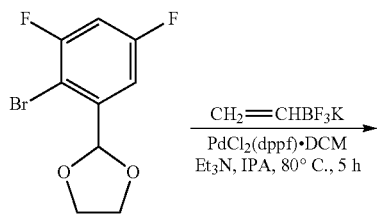

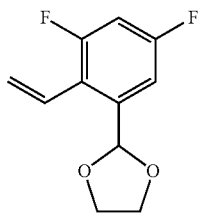

The title compound was synthesized following a procedure similar to step 2 of example 1 using 2-(2-bromo-3,5-difluorophenyl)-1,3-dioxolane producing 2-(3,5-difluoro-2-vinylphenyl)-1,3-dioxolane (3.45 g).

$^1$H NMR (300 MHz, CDCl$_3$) δ 7.20-7.16 (m, 1H), 6.94-6.83 (m, 1H), 6.82 (dd, J=17.7, 11.7 Hz, 1H), 5.60 (dd, J=1.2, 11.7 Hz, 1H), 5.66-5.60 (m, 1H), 5.95 (s, 1H), 4.18-4.02 (m, 4H).

Step 3: 2-(2-(2,2-difluorocyclopropyl)-3,5-difluorophenyl)-1,3-dioxolane

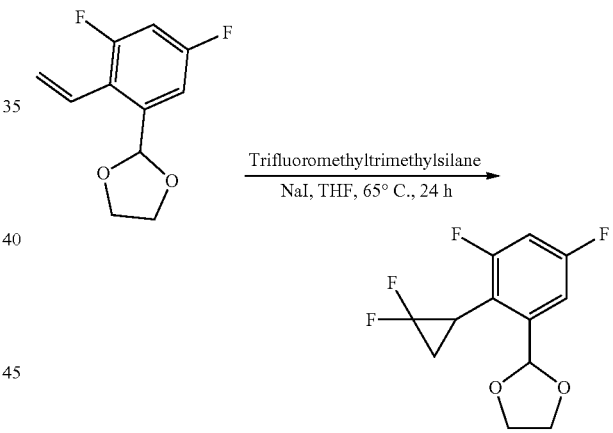

To a solution of 2-(3,5-difluoro-2-vinylphenyl)-1,3-dioxolane (from step 2, 2.4 g, 11.31 mmol) and trifluoromethyltrimethylsilane (16.1 g, 113.1 mmol) in tetrahydrofuran (15 mL) was added sodium iodide (850 mg, 5.65 mmol). The resulting solution was stirred at 65° C. for 24 hrs. The reaction mixture was cooled to room temperature and trifluoromethyltrimethylsilane (16.1 g, 113.1 mmol) and sodium iodide (850 mg, 5.65 mmol) were added, the resulting solution was stirred at 65° C. for 24 hrs. The reaction mixture was then partitioned between ethyl acetate and water, the organic phase was washed with brine, and dried over Na$_2$SO$_4$. The solvent was removed under reduced pressure which afforded the title compound 2-(2-(2,2-difluorocyclopropyl)-3,5-difluorophenyl)-1,3-dioxolane (1.5 g) as a brown liquid.

$^1$H NMR (400 MHz, CDCl$_3$) δ 7.26-7.14 (m, 1H), 6.90-6.77 (m, 1H), 6.04 (s, 1H), 4.17-4.03 (m, 4H), 2.77-2.66 (m, 1H), 1.98-1.70 (m, 2H).

Step 4: 2-(2,2-difluorocyclopropyl)-3,5-difluorobenzaldehyde

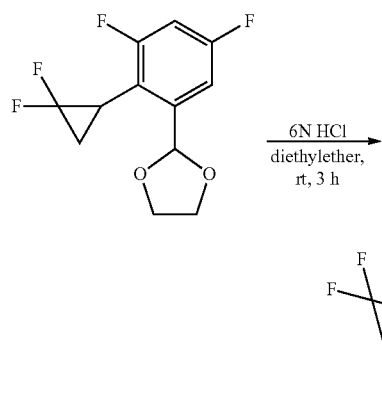

To a solution of 2-(2-(2,2-difluorocyclopropyl)-3,5-difluorophenyl)-1,3-dioxolane (from step 3, 1.5 g, 5.72 mmol) in diethyl ether (15 mL) was added 6N HCl (3 mL). The resulting solution was stirred at room temperature for 3 hrs. This was washed with water (50 mL), saturated NaHCO$_3$ solution (100 mL), and brine and dried over Na$_2$SO$_4$. The solvent was removed under reduced pressure and purification of the crude product by silica flash chromatography (0→5%) ethyl acetate in hexane afforded the title compound 2-(2,2-difluorocyclopropyl)-3,5-difluorobenzaldehyde (1.25 g) as a colorless liquid.

$^1$H NMR (300 MHz, CDCl$_3$) δ 10.22 (s, 1H), 7.50-7.39 (m, 1H), 7.20-7.05 (m, 1H), 2.80-2.60 (m, 1H), 2.18-1.89 (m, 1H), 1.65-1.53 (m, 1H).

Step 5: 3-ethyl 5-methyl 2-(acetoxymethyl)-4-(2-(2,2-difluorocyclopropyl)-3,5-difluorophenyl)-6-(fluoromethyl)-1,4-dihydropyridine-3,5-dicarboxylate

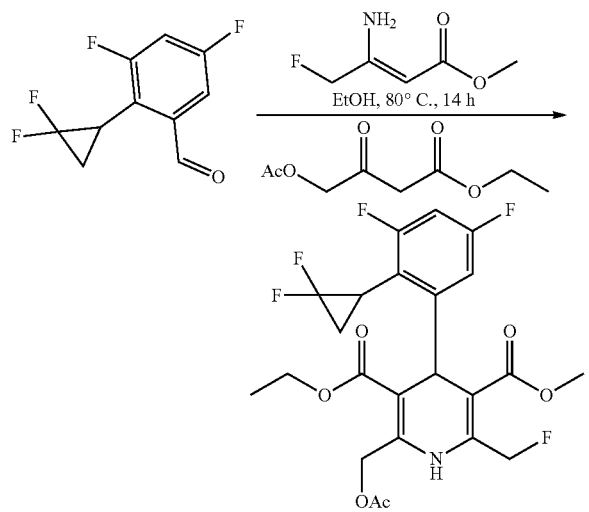

Title compound was synthesized using general step 1 of method I (using the aldehyde from step 4, (1.0 g, 4.58 mmol), Intermediate A, (862 mg, 4.58 mmol) and intermediate B, (608 mg, 4.58 mmol)) to give 3-ethyl 5-methyl 2-(acetoxymethyl)-4-(2-(2,2-difluorocyclopropyl)-3,5-difluorophenyl)-6-(fluoromethyl)-1,4-dihydropyridine-3,5-dicarboxylate (2.5 g, crude).

LCMS Rt=1.683 min; MS m/z 504 [M+H]+; [Method 7]

Step 6: methyl 4-(2-(2,2-difluorocyclopropyl)-3,5-difluorophenyl)-2-(fluoromethyl)-5-oxo-1,4,5,7-tetrahydrofuro[3,4-b]pyridine-3-carboxylate

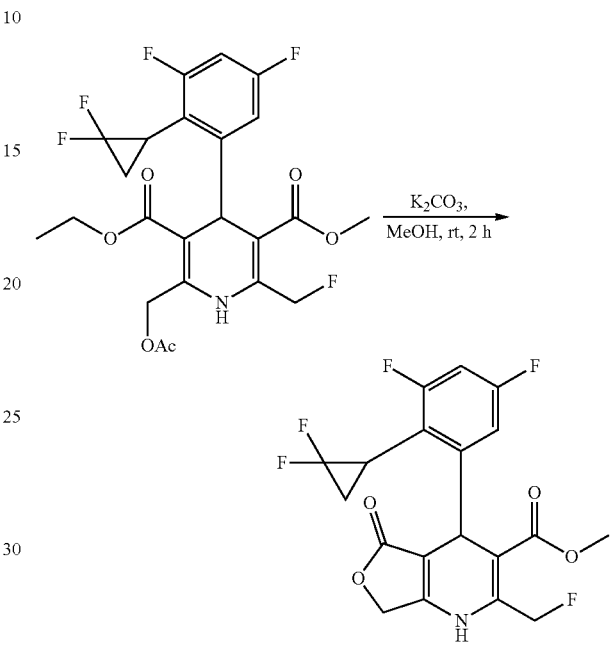

Title compound was synthesized using step 2 of general procedure I (using intermediate from step 5, 2.5 g, 4.97 mmol). Crude product was purified by silica flash chromatography (0→50%) ethyl acetate in petroleum ether which afforded the title compound methyl 4-(2-(2,2-difluorocyclopropyl)-3,5-difluorophenyl)-2-(fluoromethyl)-5-oxo-1,4,5,7-tetrahydrofuro[3,4-b]pyridine-3-carboxylate (120 mg) as an off white solid. Racemic was separated into its enantiomers by chiral SFC (Mobile Phase: 20% IPA/CO$_2$ 80 g/min; Column: Whelk-O1 SS 21×250 mm; Instrument: Thar80_SN4740).

Example 3

20.9 mg of first eluting stereoisomer as a white solid (68.8%).

SFC Rt=2.40 min ((SS) Whelk-O1 4.6×100 mm, 5 µm, 5→55% IPA in CO$_2$).

LCMS Rt=2.27 min; MS m/z 416.2 [M+H]+; [Method 4]

$^1$H NMR (400 MHz, Methanol-d4) δ 6.93-6.73 (m, 2H), 5.90-5.77 (m, 1H), 5.77-5.64 (m, 1H), 5.46 (s, 1H), 4.83 (s, 2H), 3.54 (s, 3H), 3.20-3.02 (m, 1H), 2.09 (tdd, J=11.8, 7.5, 5.9 Hz, 1H), 1.95 (ddt, J=16.5, 7.8, 3.4 Hz, 1H).

Example 4

20.6 mg of the second eluting stereoisomer as a white solid (67.8%).

SFC Rt=2.43 min ((SS) Whelk-O1 4.6×100 mm, 5 µm, 5→55% IPA in CO$_2$).

LCMS Rt=2.21 min; MS m/z 416.4 [M+H]+; [Method 4]

$^1$H NMR (400 MHz, Methanol-d4) δ 6.93-6.72 (m, 2H), 5.74 (d, J=3.6 Hz, 1H), 5.62 (d, J=4.1 Hz, 1H), 5.42 (s, 1H), 5.00-4.90 (m, 2H), 3.60 (s, 3H), 2.97-2.80 (m, 1H), 2.68-2.49 (m, 1H), 2.02 (tdd, J=11.9, 7.8, 5.9 Hz, 1H).

Remaining stereoisomers were isolated as Examples 3b and 4b

Example 3b 21.6 mg of the third eluting stereoisomer as a white solid (74.1%).

SFC Rt=2.68 min ((SS) Whelk-O1 4.6×100 mm, 5 μm, 5→55% IPA in CO$_2$).

LCMS Rt=2.22 min; MS m/z 416.6 [M+H]+; [Method 4]

$^1$H NMR (400 MHz, Methanol-d4) δ 6.78-6.63 (m, 2H), 5.76-5.64 (m, 1H), 5.64-5.52 (m, 1H), 5.33 (s, 1H), 4.70 (s, 2H), 3.41 (s, 3H), 3.07-2.91 (m, 1H), 1.96 (tdd, J=11.8, 7.6, 5.9 Hz, 1H), 1.90-1.77 (m, 1H).

Example 4b 20.6 mg of the fourth eluting stereoisomer as a white solid (70.7%).

SFC Rt=2.79 min ((SS) Whelk-O1 4.6×100 mm, 5 μm, 5→55% IPA in CO$_2$).

LCMS Rt=2.21 min; MS m/z 416.3 [M+H]+; [Method 4]

$^1$H NMR (400 MHz, Methanol-d4) δ 6.91-6.73 (m, 2H), 5.80-5.67 (m, 1H), 5.67-5.55 (m, 1H), 5.41 (d, J=1.6 Hz, 1H), 4.98-4.88 (m, 2H), 3.59 (s, 3H), 2.98-2.81 (m, 1H), 2.68-2.48 (m, 1H), 2.00 (tdd, J=11.8, 7.8, 5.9 Hz, 1H).

Example 5: methyl (R)-4-(3,5-difluoro-2-((R or S)-1-fluoroethyl)phenyl)-2-(fluoromethyl)-5-oxo-1,4,5,7-tetrahydrofuro[3,4-b]pyridine-3-carboxylate

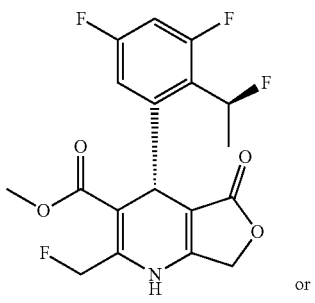

or

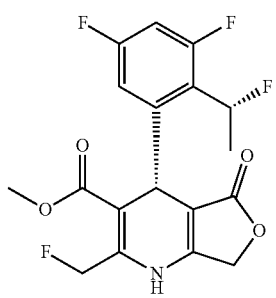

Step 1: 2-(1,3-dioxolan-2-yl)-4,6-difluorobenzaldehyde

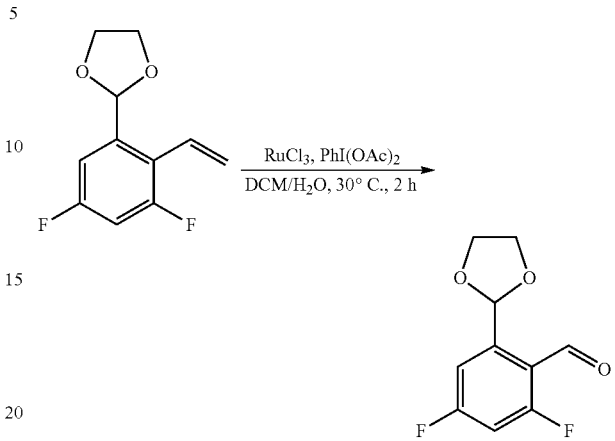

To a solution of 2-(3,5-difluoro-2-vinylphenyl)-1,3-dioxolane (prepared in example 4 from step 2, 5 g, 23.58 mmol) and ruthenium chloride·XH$_2$O (490 mg, 2.35 mmol) in dichloromethane (50 mL) and water (10 mL) was added diacetoxyiodo benzene (11.4 g, 35.37 mmol). The resulting solution was stirred at 30° C. for 2 hrs. The reaction mixture was filtered and washed with ethyl acetate (200 mL). The filtrate added to water (200 mL) and product extracted into ethyl acetate (500 mL). EtOAc phase was washed with brine and dried over Na$_2$SO$_4$. The solvent was removed under reduced pressure and purification of the crude product by silica flash chromatography (0→10%) ethyl acetate in petroleum ether afforded the title compound 2-(1,3-dioxolan-2-yl)-4,6-difluorobenzaldehyde (3 g) as a colorless liquid.

$^1$H NMR (300 MHz, CDCl$_3$) δ 10.41 (s, 1H), 7.35 (d, J=9.6 Hz, 1H), 6.95-6.85 (m, 1H), 6.53 (s, 1H), 4.08 (s, 4H).

Step 2: 1-(2-(1,3-dioxolan-2-yl)-4,6-difluorophenyl)ethan-1-ol

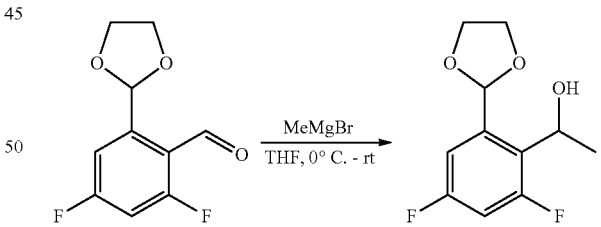

To a solution of 2-(1,3-dioxolan-2-yl)-4,6-difluorobenzaldehyde (from step 1, 1.0 g, 4.67 mmol) in dry tetrahydrofuran (10 mL) at 0° C. was added methyl magnesium bromide (2.33 mL, 3 M in ether, 4.67 mmol). The resulting solution was stirred at room temperature for 1 hr. The reaction mixture was quenched with saturated ammonium chloride (10 mL) at 0° C. and diluted with ethyl acetate (100 mL). The organic phase was separated, washed with brine and dried over Na$_2$SO$_4$. The solvent was removed under reduced pressure to afford the title compound 1-(2-(1,3-dioxolan-2-yl)-4,6-difluorophenyl)ethan-1-ol (950 mg) as a colorless liquid. The crude compound was carried forward to the next step without further purification.

¹H NMR (300 MHz, CDCl₃) δ 7.17 (dd, J=2.4, 6.3 Hz, 1H), 6.89-6.72 (m, 1H), 6.17 (s, 1H), 5.31 (dd, J=6.9, 13.5 Hz, 1H), 4.15-4.02 (m, 4H), 2.64-2.59 (m. 1H), 1.58 (d, J=9.0 Hz, 3H).

Step 3: 2-(3,5-difluoro-2-(1-fluoroethyl)phenyl)-1,3-dioxolane

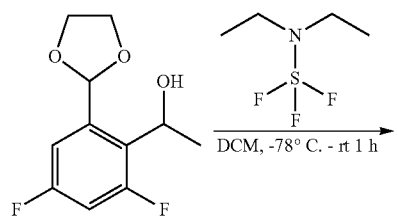

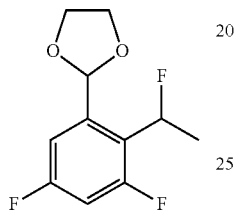

To a solution of 1-(2-(1,3-dioxolan-2-yl)-4,6-difluorophenyl)ethan-1-ol (from step 2, 950 mg, 4.13 mmol) in dichloromethane (10 mL) at −78° C. was added diethylaminosulfur trifluoride (1.0 g, 6.13 mmol). The resulting solution was stirred at room temperature for 1 hr. The reaction mixture was quenched with saturated ammonium chloride (10 mL) at 0° C. and diluted with ethyl acetate (100 mL). The organic phase was separated, washed with brine and dried over Na₂SO₄. The solvent was removed under reduced pressure to afford the title compound 2-(3,5-difluoro-2-(1-fluoroethyl)phenyl)-1,3-dioxolane (600 mg) as a thick yellow liquid. The crude compound was carried forward to the next step without further purification.

¹H NMR (300 MHz, CDCl₃) δ 7.20 (dd, J=2.4, 6.3 Hz, 1H), 6.87-6.75 (m, 1H), 6.15-5.98 (m, 1H), 6.11 (s, 1H), 4.15-4.02 (m, 4H), 1.70 (dd, J=6.6, 22.8 Hz, 3H).

Step 4: 3,5-difluoro-2-(1-fluoroethyl)benzaldehyde

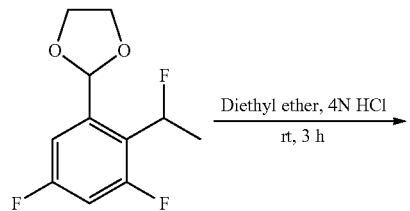

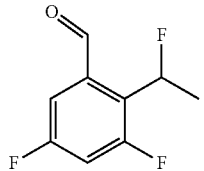

To a solution of 2-(3,5-difluoro-2-(1-fluoroethyl)phenyl)-1,3-dioxolane (from step 3, 600 mg, 2.58 mmol) in diethyl ether (10 mL) was added 4N HCl (2 mL) at room temperature. The resulting solution was stirred at room temperature for 3 hrs. This was washed with water (50 mL), saturated NaHCO₃ solution (100 mL), brine and dried over Na₂SO₄. The solvent was removed under reduced pressure which afforded the title compound 3,5-difluoro-2-(1-fluoroethyl)benzaldehyde (200 mg) as a colorless liquid. (Note: The obtained aldehyde is volatile in nature)

¹H NMR (300 MHz, CDCl₃) δ 10.44 (d, J=3.0 Hz, 1H), 7.20 (d, J=9.3 Hz, 1H), 7.10-6.98 (m, 1H), 6.43-6.19 (m, 1H), 1.78 (dd, J=7.2, 23.1 Hz, 3H).

Step 5: 3-ethyl 5-methyl 2-(acetoxymethyl)-4-(3,5-difluoro-2-(1-fluoroethyl)phenyl)-6-(fluoromethyl)-1,4-dihydropyridine-3,5-dicarboxylate

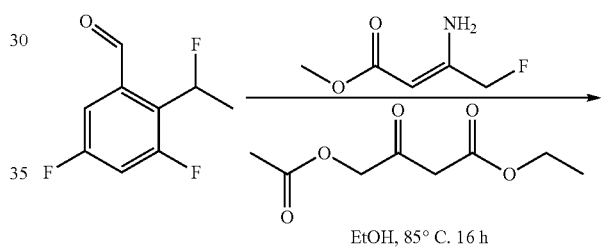

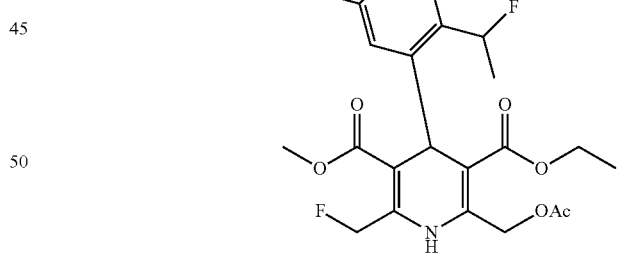

Title compound was synthesized using step 1 of general procedure I (using the aldehyde from step 4, (200 mg, 1.06 mmol)) to give 3-ethyl 5-methyl 2-(acetoxymethyl)-4-(3,5-difluoro-2-(1-fluoroethyl)phenyl)-6-methyl-1,4-dihydropyridine-3,5-dicarboxylate as a mixture of diastereomers. The crude product was carried forward to the next step without purification.

LCMS Rt=2.272 min; MS m/z 472.3 [M−H]−; [Method 7]

Step 6: methyl 4-(3,5-difluoro-2-(1-fluoroethyl)phenyl)-2-(fluoromethyl)-5-oxo-1,4,5,7-tetrahydrofuro[3,4-b]pyridine-3-carboxylate

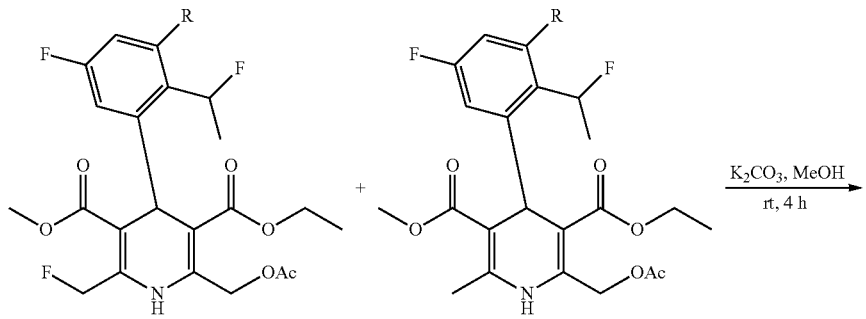

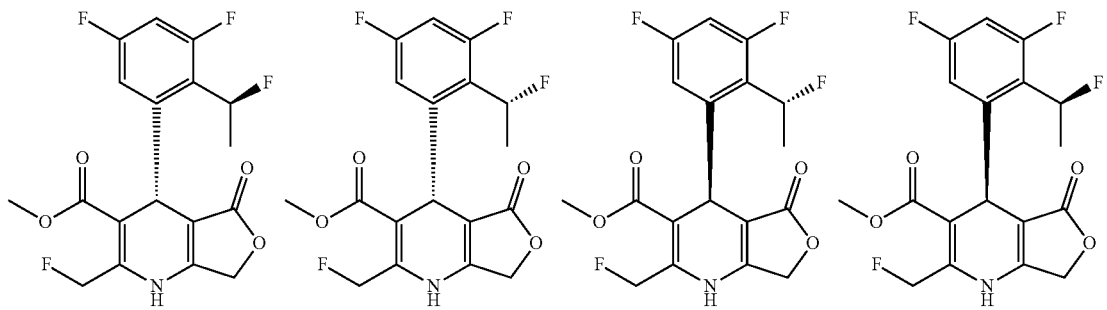

Title compound was synthesized using step 2 of general procedure I (using the mixture of intermediates from step 5, 800 mg, 1.75 mmol) gave methyl 4-(3,5-difluoro-2-(1-fluoroethyl)phenyl)-2-(fluoromethyl)-5-oxo-1,4,5,7-tetrahydrofuro[3,4-b]pyridine-3-carboxylate (2 g crude) an off white solid.

The diastereomeric mixture was separated into its two isomers using combi-flash chromatography (0→80%) to give 100 mg of first diastereomer as a white solid and 80 mg of second diastereomer as a white solid.

Peak-1: 100 mg and Peak-2: 80 mg was further separated its enantiomers using preparative chiral HPLC [Method 7] to obtain four isomers.

Example 5

21 mg of first eluting enantiomer obtained as a white solid.

Chiral HPLC Rt=4.418 min; [chiral analytical method 2]

LCMS Rt=1.514 min; MS m/z 384.0 [M–H]–; [Method 7]

$^1$H NMR: (400 MHz, CD3OD) δ 6.87-6.74 (m, 2H), 6.46-6.18 (m, 1H), 5.75 (t, J=1.0 Hz, 1H), 5.63 (dd, J=1.6, 0.7 Hz, 1H), 5.20-5.12 (m, 1H), 4.91-4.81 (m, 2H), 3.53 (s, 3H), 1.83 (ddd, J=22.7, 6.6, 1.4 Hz, 3H).

Example 5b 22 mg of second eluting enantiomer obtained as a white solid.

Chiral HPLC Rt=4.792 min; [chiral analytical method 2]

LCMS Rt=1.513 min; MS m/z 384.0 [M–H]–; [Method 7]

$^1$H NMR (400 MHz, CD3OD) δ 6.87-6.74 (m, 2H), 6.46-6.18 (m, 1H), 5.75 (t, J=1.0 Hz, 1H), 5.63 (dd, J=1.6, 0.7 Hz, 1H), 5.20-5.12 (m, 1H), 4.91-4.81 (m, 2H), 3.53 (s, 3H), 1.83 (ddd, J=22.7, 6.6, 1.4 Hz, 3H).

Example 5c 18 mg of third eluting enantiomer obtained as a white solid.

Chiral HPLC Rt=6.777 min; [chiral analytical method 2]

LCMS Rt=1.476 min; MS m/z 384.1 [M–H]–; [Method 7]

$^1$H NMR: (400 MHz, CDCl3) δ 6.77-6.63 (m, 2H), 6.48 (dd, J=44.3, 6.6 Hz, 1H), 5.85-5.77 (m, 1H), 5.70 (d, J=4.5 Hz, 1H), 5.10 (s, 1H), 4.83-4.77 (m, 2H), 3.56 (s, 3H), 1.79 (ddd, J=22.5, 6.7, 1.1 Hz, 3H).

Example 5d 16 mg of fourth eluting enantiomer obtained as a white solid using chiral HPLC method 7.

Chiral HPLC Rt=7.475 min; [chiral analytical method 2]

LCMS Rt=2.00 min; MS m/z 384.2 [M–H]–; [Method 9]

$^1$H NMR (400 MHz, CDCl3) δ 6.77-6.63 (m, 2H), 6.48 (dd, J=44.3, 6.6 Hz, 1H), 5.85-5.77 (m, 1H), 5.70 (d, J=4.5 Hz, 1H), 5.10 (s, 1H), 4.83-4.77 (m, 2H), 3.56 (s, 3H), 1.79 (ddd, J=22.5, 6.7, 1.1 Hz, 3H).

Example 6: methyl (R)-4-(2-((S)-1,2-difluoroethyl)-3-fluorophenyl)-2-(fluoromethyl)-5-oxo-1,4,5,7-tetrahydrofuro[3,4-b]pyridine-3-carboxylate

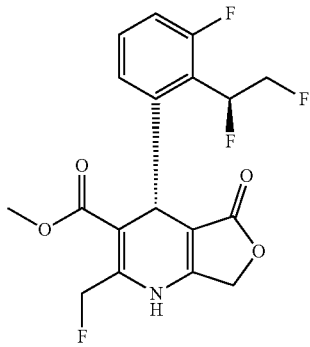

Step 1: 1-(2-(1,3-dioxolan-2-yl)-6-fluorophenyl)-2-fluoroethan-1-one

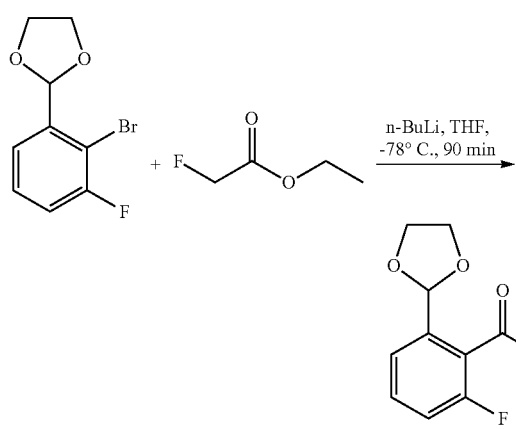

A solution of 2-(2-bromo-3-fluorophenyl)-1,3-dioxolane (from step 1, Example 1, 26 g, 105.23 mmol) in THF (250 mL) under nitrogen atmosphere was cooled to −78° C. Then n-butyllithium in n-hexane solution (44.19 mL, 2.5M, 110.49 mmol) was added, reaction stirred for 30 min at −78° C. Then ethyl 2-fluoroacetate (22.33 g, 210.47 mmol) was added to the reaction and the resulting mixture stirred for another 60 min. at −78° C. The reaction mixture was quenched with saturated ammonium chloride solution (100 mL) and extracted with ethyl acetate (2×250 mL). Combined organic phases were washed with water (250 mL), brine (250 mL) and dried over $Na_2SO_4$. The solvent was removed under reduced pressure and purification of the crude product by silica flash chromatography (0→10%) ethyl acetate in petroleum ether afforded the title compound 1-(2-(1,3-dioxolan-2-yl)-6-fluorophenyl)-2-fluoroethan-1-one (16.2 g) as a colorless liquid.

$^1$H NMR (400 MHz, CDCl3) δ 7.45 (m, 1H), 7.37 (d, J=7.8, 1H), 7.13 (dd, J=9.3, 8.2 Hz, 1H), 6.02 (s, 1H), 5.23 (d, J=1.4 Hz, 1H), 5.11 (d, J=1.3 Hz, 1H), 4.08-3.87 (m, 4H).

Step 2: 1-(2-(1,3-dioxolan-2-yl)-6-fluorophenyl)-2-fluoroethan-1-ol

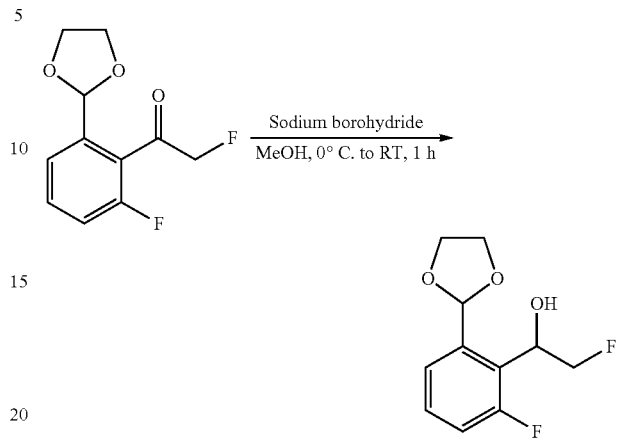

To a stirred solution of 1-(2-(1,3-dioxolan-2-yl)-6-fluorophenyl)-2-fluoroethan-1-one (from step 1, 19.6 g, 85.89 mmol) in methanol (100 mL) was added sodium borohydride (3.9 g, 103.07 mmol) at 0° C. under nitrogen atmosphere. The resulting mixture was stirred at room temperature for 1 h. Reaction mixture was quenched with ice water and extracted with ethyl acetate (2×250 mL). Combined organic phases were washed with water (250 mL), followed by brine (250 mL) and dried over $Na_2SO_4$. The solvent was removed under reduced pressure and purification of the crude product by silica flash chromatography (0→30%) ethyl acetate in petroleum ether afforded the title compound 1-(2-(1,3-dioxolan-2-yl)-6-fluorophenyl)-2-fluoroethan-1-ol (18 g) as a colorless liquid.

$^1$H NMR (400 MHz, CDCl3) δ 7.44 (dd, J=7.9, 1.2 Hz, 1H), 7.33 (dd, J=8.0, 8.0 Hz, 1H), 7.10 (dd, J=8.2, 1.3 Hz, 1H), 6.13 (s, 1H), 5.47 (m, 1H), 4.98-4.51 (m, 2H), 4.22-3.97 (m, 4H), 3.04 (m, 1H).

Step 3: 2-(2-(1,2-difluoroethyl)-3-fluorophenyl)-1,3-dioxolane

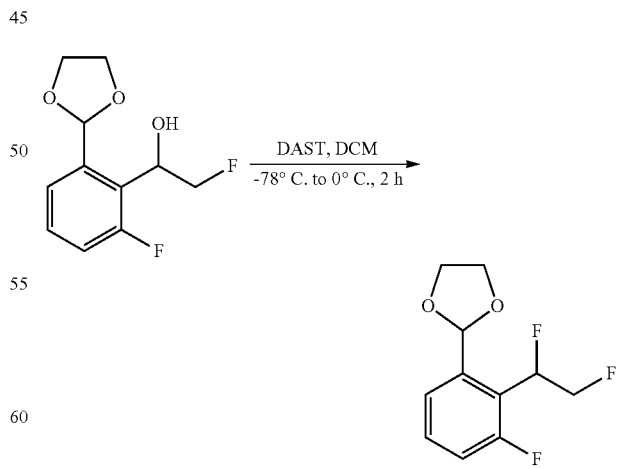

A solution of 1-(2-(1,3-dioxolan-2-yl)-6-fluorophenyl)-2-fluoroethan-1-ol (from step 2, 18 g, 78.18 mmol) in dichloromethane (150 mL) was cooled to −78° C. then diethylaminosulfur trifluoride (DAST) (15.49 mL, 117.28 mmol)

was added and the resulting reaction mixture was stirred at −78° C. for 1 h. The reaction mixture was slowly brought to 0° C. and stirred for another 1 h. Water (150 mL) was added and product was extracted with dichloromethane (2×200 mL). The combined organic phases were combined, washed with saturated sodium bicarbonate solution (2×200 mL), water (200 mL), brine (200 mL) and dried over Na$_2$SO$_4$. The solvent was removed under reduced pressure and purification of the crude product by silica flash chromatography (0→10%) ethyl acetate in petroleum ether afforded the title compound 2-(2-(1,2-difluoroethyl)-3-fluorophenyl)-1,3-dioxolane (12.4 g) as a colorless liquid.

$^1$H NMR (400 MHz, CDCl3) δ 7.45 (d, J=7.8 Hz, 1H), 7.42-7.35 (m, 1H), 7.12 (dd, J=10.6, 8.2 Hz, 1H), 6.21 (m, 1H), 6.04 (s, 1H), 5.22-4.85 (m, 1H), 4.75-4.42 (m, 1H), 4.20-3.97 (m, 4H).

Step 4: 2-(1,2-difluoroethyl)-3-fluorobenzaldehyde

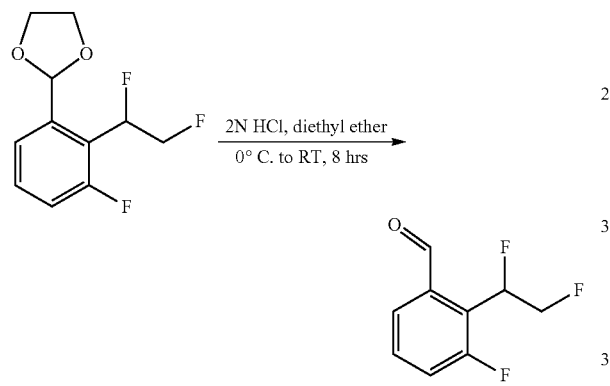

To a solution of 2-(2-(1,2-difluoroethyl)-3-fluorophenyl)-1,3-dioxolane (from step 3, 12.4 g, 53.40 mmol) in diethyl ether (150 mL) was added 2N HCl (100 mL) at 0° C. The resulting reaction mixture was stirred at room temperature for 8 hrs. Reaction mixture was extracted with diethyl ether (200 mL), washed with water (2×100 mL), brine (100 mL) and dried over Na$_2$SO$_4$. The solvent was removed under reduced pressure and purified by silica flash chromatography (0→10%) ethyl acetate in petroleum ether which afforded the title compound 2-(1,2-difluoroethyl)-3-fluorobenzaldehyde (10 g) as a colorless liquid.

$^1$H NMR (400 MHz, CDCl3) δ 10.30 (s, 1H), 7.88-7.70 (m, 1H), 7.56 (m, 1H), 7.44-7.30 (m, 1H), 6.70-6.36 (m, 1H), 4.95-4.70 (m, 2H)

Step 5: 3-ethyl 5-methyl 2-(acetoxymethyl)-4-(2-(1,2-difluoroethyl)-3-fluorophenyl)-6-(fluoromethyl)-1,4-dihydropyridine-3,5-dicarboxylate

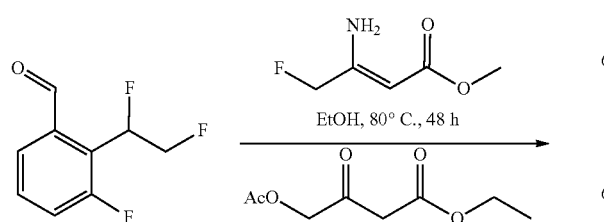

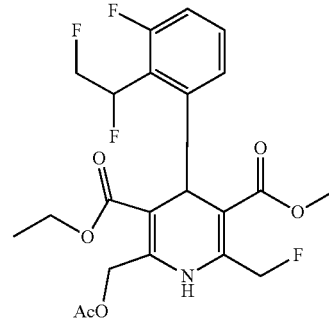

Title compound was synthesized using general step 1 of general procedure I (using the aldehyde from step 4, 9 g, 47.83 mmol) which afforded the title compound 3-ethyl 5-methyl 2-(acetoxymethyl)-4-(2-(1,2-difluoroethyl)-3-fluorophenyl)-6-(fluoromethyl)-1,4-dihydropyridine-3,5-dicarboxylate as a mixture of diastereomers (25.0 g, Crude) as an off white solid.

The crude product was used for the next step without further purification and analysis.

Step 6: methyl 4-(2-(1,2-difluoroethyl)-3-fluorophenyl)-2-(fluoromethyl)-5-oxo-1,4,5,7-tetrahydrofuro[3,4-b]pyridine-3-carboxylate

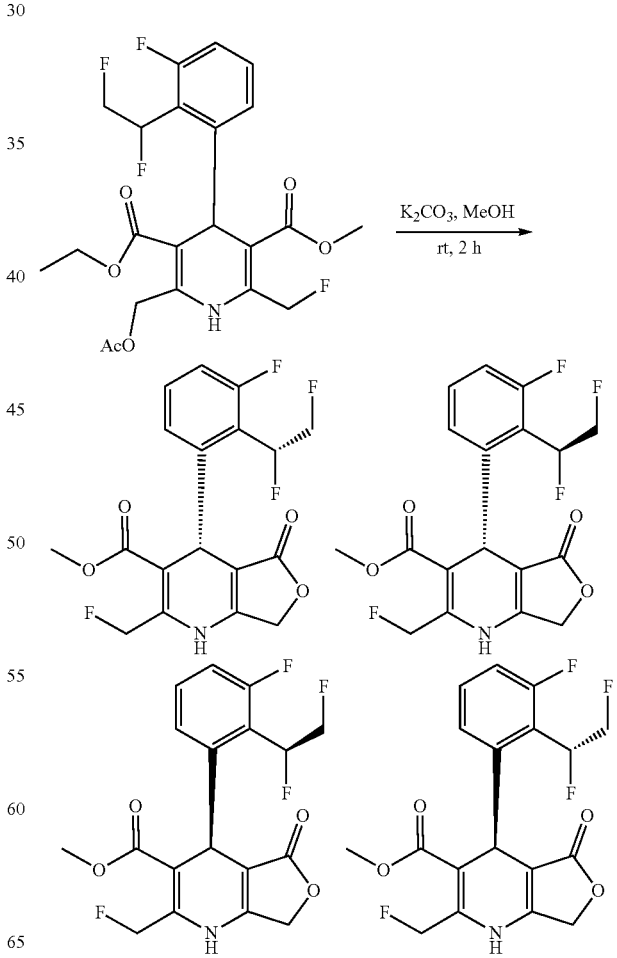

Title compound was synthesized using step 2 of general procedure I (using mixture of intermediates from step 5, 25 g, 52.8 mmol) afforded the title compound methyl 4-(2-(1,2-difluoroethyl)-3-fluorophenyl)-2-(fluoromethyl)-5-oxo-1,4,5,7-tetrahydrofuro[3,4-b]pyridine-3-carboxylate (1 g, crude) as an off white solid. Diastereomeric mixture was separated into its two isomers using silica flash chromatography (0→80%) giving 1.51 g of first diastereomer as a white solid and 820 mg of second diastereomer as a white solid.

Diastereomers from previous separation Peak-1: 200 mg and Peak-2: 200 mg were further separated into their enantiomers using preparative chiral HPLC [Method 7] to obtain four isomers.

Example 6

56 mg of first eluting enantiomer obtained as a white solid.
Chiral HPLC Rt=7.623 min; [chiral analytical method 2]
LCMS Rt=1.445 min; MS m/z 384.0 [M−H]−; [Method 7]
$^1$H NMR (400 MHz, CD3OD) δ 7.41-7.35 (m, 1H), 7.17 (dt, J=7.9, 1.3 Hz, 1H), 6.98 (dd, J=11.4, 8.1 Hz, 1H), 6.66-6.33 (m, 1H), 5.75 (d, J=3.7 Hz, 1H), 5.68-5.56 (m, 1H), 5.18 (s, 1H), 5.15-4.91 (m, 2H), 4.85 (s, 2H), 3.52 (s, 3H).

The stereochemistry of Example 6, methyl 2-methyl-5-oxo-4-phenyl-1,4,5,7-tetrahydrofuro[3,4-b]pyridine-3-carboxylate, was determined by single crystal x-ray crystallographic analysis and it confirmed that active enantiomer is the R-enantiomer (FIG. 7).

Example 6b 54 mg of second eluting enantiomer obtained as a white solid.
Chiral HPLC Rt=8.757 min; [chiral analytical method 2]
LCMS Rt=1.443 min; MS m/z 386.3 [M+H]+; [Method 7]
$^1$H NMR: (400 MHz, CD3OD) δ 7.41-7.35 (m, 1H), 7.17 (dt, J=7.9, 1.3, 1.3 Hz, 1H), 7.10-6.88 (m, 1H), 6.67-6.26 (m, 1H), 5.82-5.70 (m, 1H), 5.69-5.57 (m, 1H), 5.18 (s, 1H), 5.15-4.91 (m, 2H), 4.85 (d, J=0.7 Hz, 2H), 3.52 (s, 3H).

Example 6c 67 mg of third eluting enantiomer obtained as a white solid.
Chiral HPLC=Rt=10.574 min; [chiral analytical method 2]
LCMS Rt=1.379 min; MS m/z 384.0 [M−H]−; [Method 7]
$^1$H NMR (400 MHz, CD3OD) δ 7.41-7.35 (m, 1H), 7.13 (dt, J=7.9, 1.3, 1.3 Hz, 1H), 6.97 (dd, J=11.3, 8.2 Hz, 1H), 6.60 (ddd, J=47.2, 18.0, 8.4 Hz, 1H), 5.75 (s, 1H), 5.63 (s, 1H), 5.14 (s, 1H), 5.12-4.92 (m, 1H), 4.84 (s, 2H), 4.70 (ddd, J=44.6, 32.7, 10.8 Hz, 1H), 3.53 (s, 3H).

Example 6d 69 mg of fourth eluting enantiomer obtained as a white solid.
Chiral HPLC Rt=13.93 min [chiral analytical method 2]
LCMS Rt=1.379 min; MS m/z 384.0 [M−H]−; [Method 7]
$^1$H NMR (400 MHz, CD3OD) δ 7.41-7.35 (m, 1H), 7.13 (dt, J=7.8, 1.3 Hz, 1H), 6.97 (dd, J=11.3, 8.2 Hz, 1H), 6.60 (ddd, J=47.1, 17.9, 8.3 Hz, 1H), 5.75 (s, 1H), 5.63 (s, 1H), 5.17-5.11 (m, 1H), 5.11-4.92 (m, 1H), 4.84 (s, 2H), 4.70 (ddd, J=45.1, 33.0, 11.1 Hz, 1H), 3.53 (s, 3H).

Example 7: methyl (R)-4-(2-((R or S)-1,2-difluoroethyl)-3-fluorophenyl)-2-(fluoromethyl)-5-oxo-4,5,6,7-tetrahydro-1H-cyclopenta[b]pyridine-3-carboxylate

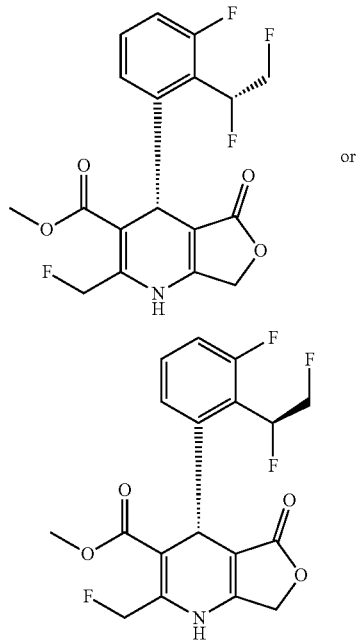

Step 1: 3-ethoxycyclopent-2-en-1-one

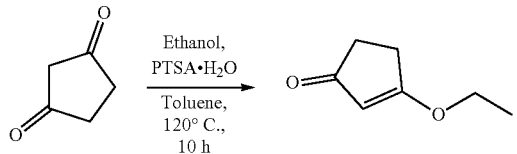

To a stirred solution of cyclopentane-1,3-dione (5.0 g, 50.96 mmol) in toluene (70 mL) was added pTSA (193 mg, 1.019 mmol) and EtOH (22.61 ml, 387.35 mmol) at room temperature. The resulting mixture was stirred at 120° C. for 10 hrs using Dean-stark apparatus. The solvent was removed under reduced pressure giving the crude compound. Crude product was purified by silica flash chromatography (0→50%) ethyl acetate in petroleum ether to afford the title compound 3-ethoxycyclopent-2-en-1-one (4.3 g) as a brown solid.

$^1$H NMR (400 MHz, CDCl3) δ 5.26 (s, 1H), 4.02 (q, J=6.6 Hz, 2H), 2.60-2.55 (m, 2H), 2.44-2.40 (m, 2H), 1.39 (t, J=7.2 Hz, 3H).

Step 2: 3-aminocyclopent-2-en-1-one

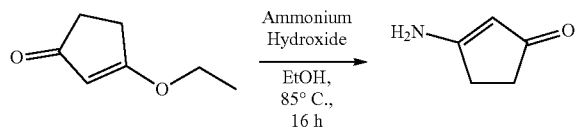

To a stirred solution of 3-ethoxycyclopent-2-en-1-one (from step 1, 4.3 g, 34.08 mmol) in ethanol (50 mL) was added ammonium hydroxide solution (25 mL, 387.35 mmol) at room temperature. The resulting mixture was stirred at 85° C. for 16 hrs. Solvent removal under reduced pressure afforded the title compound 3-aminocyclopent-2-en-1-one (3.2 g) as a brown solid.

LCMS Rt=0.114 min; MS m/z 98.2 [M+H]+; [Method 1]

Step 3: methyl 4-(2-(1,2-difluoroethyl)-3-fluorophenyl)-2-(fluoromethyl)-5-oxo-4,5,6,7-tetrahydro-1H-cyclopenta[b]pyridine-3-carboxylate

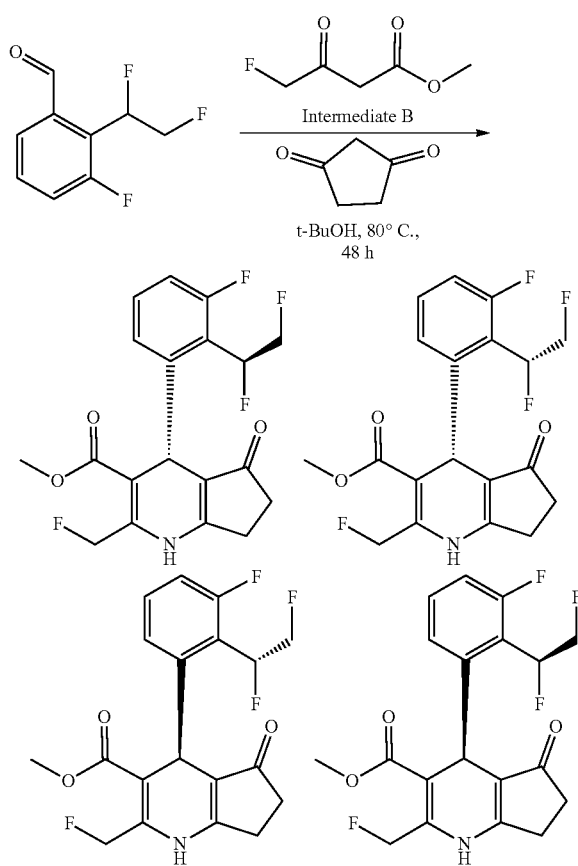

To solution of aldehyde (from example 6, step 4, 3.0 g, 15.944 mmol) was added methyl (Z)-3-amino-4-fluorobut-2-enoate (intermediate B, 2.54 g, 19.133 mmol) and cyclopentane-1,3-dione (1.56 g, 15.944 mmol) in t-butanol (25 mL). The reaction mixture was stirred at 80° C. for 48 hrs. The solvent was removed under reduced pressure resulting in crude compound. Crude product was purified by silica flash chromatography (0→70%) ethyl acetate in petroleum ether affording the title compound methyl 4-(2-(1,2-difluoroethyl)-3-fluorophenyl)-2-(fluoromethyl)-5-oxo-4,5,6,7-tetrahydro-1H-cyclopenta[b]pyridine-3-carboxylate (500 mg, crude) as an off white solid and as a mixture of diastereomers. Diastereomeric mixture was separated into its two isomers using silica flash chromatography (0→80%) giving 12 mg of the first diastereomer as a white solid and 15 mg of the second diastereomer as a white solid.

Diastereomers from first separation Peak-1: 12 mg and Peak-2: 15 mg were further separated into their enantiomers using preparative chiral HPLC [Method 7] to obtain four isomers.

Example 7

2 mg of first eluting enantiomer obtained as a white solid.

Chiral HPLC Rt=9.084 min; [chiral analytical method 4]

LCMS Rt=1.477 min; MS m/z 384.05 [M+H]+; [method 2]

$^1$H NMR (400 MHz, Methanol-d4) δ 7.36-7.24 (m, 1H), 7.06 (d, J=7.8 Hz, 1H), 6.92 (dd, J=11.4, 8.2 Hz, 1H), 6.87-6.60 (m, 1H), 5.72 (s, 1H), 5.60 (s, 1H), 5.05 (s, 1H), 4.69 (ddd, J=44.8, 32.9, 10.8 Hz, 2H), 3.54 (s, 3H), 2.70 (t, J=5.0 Hz, 2H), 2.43-2.29 (m, 2H).

Example 7b 4 mg of second eluting enantiomer obtained as a white solid.

Chiral HPLC Rt=10.439 min; [chiral analytical method 4]

LCMS Rt=1.477 min; MS m/z 384.2 [M+H]+; [method 2]

$^1$H NMR (400 MHz, Methanol-d4) δ 7.37-7.23 (m, 1H), 7.10-7.02 (m, 1H), 6.92 (dd, J=11.4, 8.1 Hz, 1H), 6.86-6.60 (m, 1H), 5.72 (s, 1H), 5.60 (s, 1H), 5.05 (s, 1H), 4.69 (ddd, J=44.9, 33.5, 11.1 Hz, 2H), 3.54 (s, 3H), 2.76-2.66 (m, 2H), 2.42-2.27 (m, 2H).

Example 7c 4 mg of third eluting enantiomer obtained as a white solid.

Chiral HPLC Rt=12.453 min; [chiral analytical method 4]

LCMS Rt=1.327 min; MS m/z 384.2 [M+H]+; [method 2]

$^1$H NMR (400 MHz, Methanol-d4) δ 7.32 (tdd, J=8.1, 5.6, 1.5 Hz, 1H), 7.08 (dt, J=7.8, 1.3 Hz, 1H), 6.93 (dd, J=11.5, 8.1 Hz, 1H), 6.60-6.38 (m, 1H), 5.81-5.69 (m, 1H), 5.69-5.54 (m, 1H), 5.13-5.07 (m, 2H), 5.07-4.93 (m, 1H), 3.53 (s, 3H), 2.75-2.67 (m, 2H), 2.45-2.22 (m, 2H).

Example 7d 4 mg of fourth eluting enantiomer obtained as a white solid.

Chiral HPLC Rt=13.173 min; [chiral analytical method 4]

LCMS Rt=1.33 min; MS m/z 384.2 [M+H]+; [method 2]

$^1$H NMR (400 MHz, Methanol-d4) δ 7.40-7.25 (m, 1H), 7.14-7.05 (m, 1H), 6.93 (dd, J=11.4, 8.2 Hz, 1H), 6.60-6.38 (m, 1H), 5.80-5.66 (m, 1H), 5.66-5.53 (m, 1H), 5.13-5.07 (m, 2H), 5.07-4.94 (m, 1H), 3.53 (s, 3H), 2.71 (t, J=4.8 Hz, 2H), 2.44-2.21 (m, 2H).

Example 8: methyl (R)-4-(3-fluoro-2-((R or S)-1-fluoroethyl)phenyl)-2-(fluoromethyl)-5-oxo-1,4,5,7-tetrahydrofuro[3,4-b]pyridine-3-carboxylate

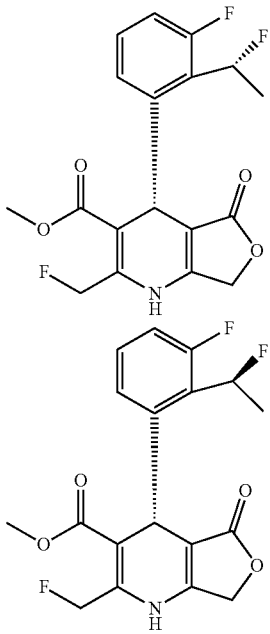

Step 1: 1-(2-(1,3-dioxolan-2-yl)-6-fluorophenyl)ethan-1-ol

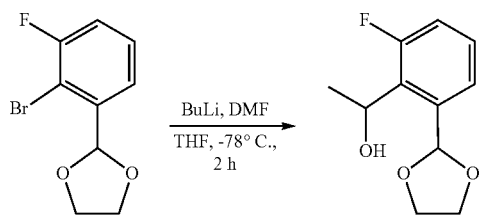

A solution of 2-(2-bromo-3-fluorophenyl)-1,3-dioxolane (from step 1, Ex 1, 30 g, 121.42 mmol) in THF (300 mL) under nitrogen atmosphere was cooled to −78° C. Then n-butyllithium in n-hexane solution (58.3 mL, 2.5M, 147.71 mmol) was added over 10 min, and the resulting mixture was stirred for 1 hr at −78° C. Acetaldehyde (6.42 g, 145.71 mmol) was added and the resulting mixture stirred for 1 hr at −78° C. The reaction mixture was quenched with saturated ammonium chloride solution (50 mL) and extracted with ethyl acetate (2×100 mL). Combined organic phases were washed with water (50 mL), brine (50 mL) and dried over $Na_2SO_4$. The solvent was removed under reduced pressure and purification of the crude product by silica flash chromatography (0→10%) ethyl acetate in petroleum ether afforded the title compound 1-(2-(1,3-dioxolan-2-yl)-6-fluorophenyl)ethan-1-ol (15 g) as a colorless liquid.

$^1$H NMR (400 MHz, $CDCl_3$) δ 7.38 (d, J=8.0 Hz, 1H), 7.30-7.18 (m, 1H), 7.10-7.01 (m, 1H), 6.15 (s, 1H), 5.30-5.25 (m, 1H), 4.15-3.95 (m, 4H), 2.75-2.69 (m, 1H), 1.58 (dd, J=6.6, 22.8 Hz, 3H).

Step 2: 2-(3-fluoro-2-(1-fluoroethyl)phenyl)-1,3-dioxolane

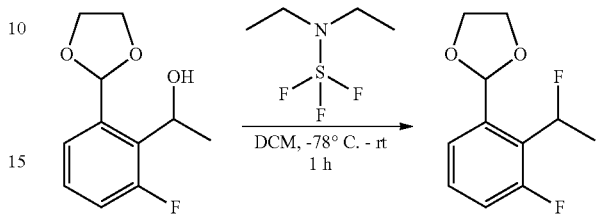

To a solution of 1-(2-(1,3-dioxolan-2-yl)-6-fluorophenyl)ethan-1-ol (from step 1, 15 g, 70.68 mmol) in dichloromethane (150 mL) at −78° C. was added diethylaminosulfur trifluoride (19.3 mL, 141.37 mmol). The resulting solution was stirred at room temperature for 1 hr. The reaction mixture was quenched with saturated ammonium chloride (20 mL) at 0° C. and diluted with ethyl acetate (100 mL). The organic phase was separated, washed with brine and dried over $Na_2SO_4$. The solvent was removed under reduced pressure and purification of the crude product by silica flash chromatography (0→10%) ethyl acetate in petroleum ether afforded the title compound 2-(3-fluoro-2-(1-fluoroethyl)phenyl)-1,3-dioxolane (8.5 g) as a colorless liquid.

$^1$H NMR (300 MHz, $CDCl_3$) δ 7.38 (d, J=7.5 Hz, 1H), 7.30-7.18 (m, 1H), 7.13-7.01 (m, 1H), 6.20-5.95 (m, 1H), 6.10 (s, 1H), 4.16-4.02 (m, 4H), 1.74 (dd, J=7.2, 23.1 Hz, 3H).

Step 3: 3-fluoro-2-(1-fluoroethyl)benzaldehyde

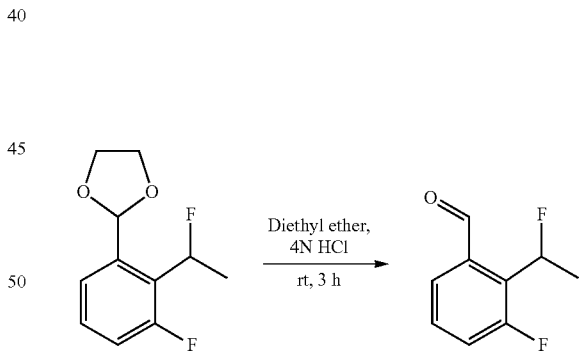

To a solution of 2-(3-difluoro-2-(1-fluoroethyl)phenyl)-1,3-dioxolane (from step 2, 8.5 g, 69.38 mmol) and in diethyl ether (150 mL) was added 4N HCl (85 mL) at room temperature. The resulting solution was stirred at room temperature for 3 hrs. This was washed with water (100 mL), saturated $NaHCO_3$ solution (200 mL), brine and dried over $Na_2SO_4$. The solvent was removed under reduced pressure affording the title compound 3-difluoro-2-(1-fluoroethyl) benzaldehyde (6.5 g) as a colorless liquid. (Note: The obtained aldehyde is volatile in nature).

$^1$H NMR (300 MHz, CDCl3) δ 10.44 (d, J=1.0 Hz, 1H), 7.74 (d, J=7.7 Hz, 1H), 7.45-7.42 (m, 1H), 7.35-7.30 (m, 1H), 6.45-6.38 (m, 1H), 1.92-1.72 (m, 3H).

Step 4: 3-ethyl 5-methyl 2-(acetoxymethyl)-4-(3-fluoro-2-(1-fluoroethyl)phenyl)-6-(fluoromethyl)-1,4-dihydropyridine-3,5-dicarboxylate

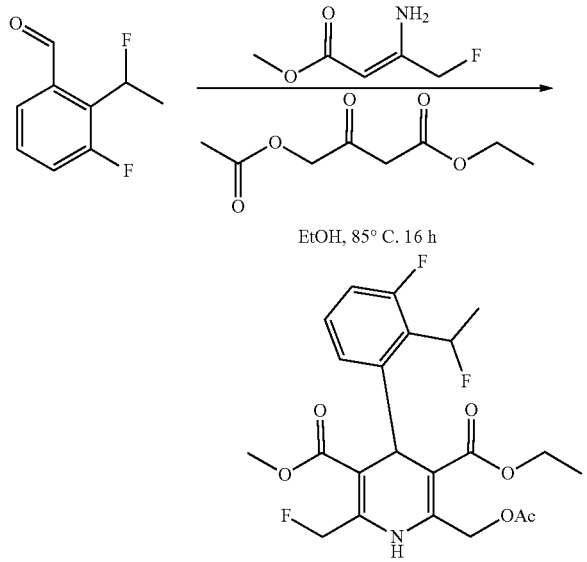

Title compound was synthesized using step 1 of general procedure I (using the aldehyde from step 3, 10 g, 58.76 mmol)) to give 3-ethyl 5-methyl 2-(acetoxymethyl)-4-(3-fluoro-2-(1-fluoroethyl)phenyl)-6-(fluoromethyl)-1,4-dihydropyridine-3,5-dicarboxylate as a mixture of diastereomers (13 g, crude).

LCMS Rt=1.795 min; MS m/z 454.2 [M–H]–; [Method 9]

Step 5: methyl 4-(3-fluoro-2-(1-fluoroethyl)phenyl)-2-(fluoromethyl)-5-oxo-1,4,5,7-tetrahydrofuro[3,4-b]pyridine-3-carboxylate

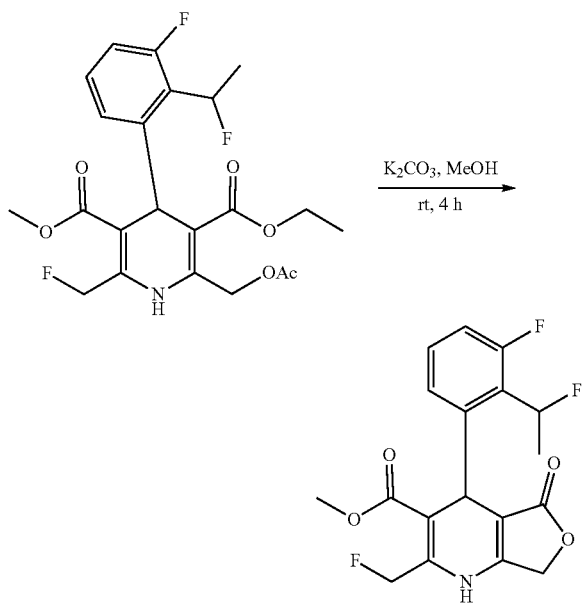

Title compound was synthesized using step 2 of general procedure I (using the mixture of intermediates from step 4 (13.0 g, 28.54 mmol)) affording the title compound methyl 4-(3-fluoro-2-(1-fluoroethyl)phenyl)-2-(fluoromethyl)-5-oxo-1,4,5,7-tetrahydrofuro[3,4-b]pyridine-3-carboxylate (5 g, crude) as an off white solid. Diastereomeric mixture was separated by silica flash chromatography (0→80%) ethyl acetate in hexane to give 1.04 g of first diastereomer and 1.45 g of second diastereomer.

Diastereomers were separated further using chiral SFC: Column 2.1×25.0 cm Chiralcel OX—H; CO2 Co-solvent (Solvent B) Methanol Isocratic Method 25% Co-solvent at 80 g/min System Pressure 100 bar Example 8

37 mg of the title compound as the first eluting stereoisomer

LCMS Rt=1.95 min; MS m/z 366.3 [M–H]–; [Method 4]
SFC Rt=1.12 min; Mobile Phase: 20% MeOH (0.1% Isopropylamine) in CO$_2$ 4 mL/min; Column: Chiralcel OX—H 4.6×100 mm
$^1$H NMR (400 MHz, DMSO-d6) δ 10.12 (d, J=3.3 Hz, 1H), 7.34 (qd, J=7.0, 2.9 Hz, 1H), 7.21-6.91 (m, 2H), 6.35 (dq, J=45.6, 6.6 Hz, 1H), 5.87-5.45 (m, 2H), 5.03 (s, 1H), 4.86 (d, J=2.8 Hz, 2H), 3.44 (s, 3H), 1.80 (dd, J=22.9, 6.6 Hz, 3H).

Example 8b 38 mg as the second eluting stereoisomer
LCMS Rt=1.95 min; MS m/z 366.3 [M–H]–; [Method 4]
SFC Rt=1.52 min; Mobile Phase: 20% MeOH (0.1% Isopropylamine) in CO$_2$ 4 mL/min; Column: Chiralcel OX—H 4.6×100 mm
$^1$H NMR: (400 MHz, DMSO-d6) δ 10.12 (d, J=3.3 Hz, 1H), 7.56-7.23 (m, 1H), 7.25-6.94 (m, 2H), 6.35 (dd, J=45.5, 6.9 Hz, 1H), 5.66 (dd, J=47.9, 2.7 Hz, 2H), 5.03 (s, 1H), 4.86 (d, J=2.6 Hz, 2H), 3.44 (s, 3H), 1.80 (dd, J=22.8, 6.5 Hz, 3H).

Example 8c 42 mg as the third eluting stereoisomer
LCMS Rt=1.88 min; MS m/z 366.3 [M–H]–; [Method 4]
SFC Rt=2.08 min; Mobile Phase: 20% MeOH (0.1% Isopropylamine) in CO$_2$ 4 mL/min; Column: Chiralcel OX—H 4.6×100 mm
$^1$H NMR (400 MHz, DMSO-d6) δ 10.13 (d, J=3.3 Hz, 1H), 7.33 (td, J=8.0, 5.4 Hz, 1H), 7.23-6.92 (m, 2H), 6.49 (dd, J=44.7, 6.8 Hz, 1H), 5.68 (d, J=47.8 Hz, 2H), 4.97 (s, 1H), 4.83 (s, 2H), 3.44 (s, 3H), 1.70 (dd, J=22.7, 6.6 Hz, 3H).

Example 8d 40 mg: as the fourth eluting stereoisomer
LCMS Rt=1.88 min; MS m/z 366.3 [M–H]–; [Method 4]
SFC Rt=3.01 min; Mobile Phase: 20% MeOH (0.1% Isopropylamine) in CO$_2$ 4 mL/min; Column: Chiralcel OX—H 4.6×100 mm
$^1$H NMR: (400 MHz, DMSO-d6) δ 10.13 (d, J=3.4 Hz, 1H), 7.33 (td, J=8.0, 5.4 Hz, 1H), 7.20-6.93 (m, 2H), 6.69-6.31 (m, 1H), 5.68 (d, J=47.8 Hz, 2H), 4.97 (s, 1H), 4.83 (s, 2H), 3.44 (s, 3H), 1.70 (dd, J=22.8, 6.5 Hz, 3H).

The stereochemistry of Example 8, methyl (R)-4-(3-fluoro-2-((R)-1-fluoroethyl)phenyl)-2-(fluoromethyl)-5- oxo-1,4,5,7-tetrahydrofuro[3,4-b]pyridine-3-carboxylate, was determined by single crystal x-ray crystallographic analysis and it confirmed that active enantiomer is the R-enantiomer (FIG. 8).

Example 9: methyl (R)-4-(2-(difluoromethoxy)phenyl)-2-(fluoromethyl)-5-oxo-1,4,5,7-tetrahydrofuro[3,4-b]pyridine-3-carboxylate

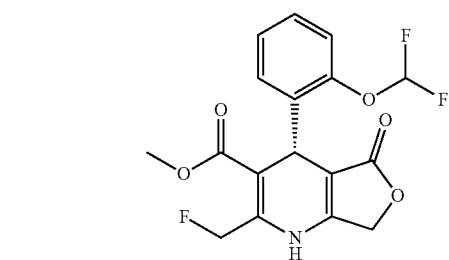

Step 1: 3-ethyl 5-methyl 2-(acetoxymethyl)-4-(2-(difluoromethoxy)phenyl)-6-(fluoromethyl)-1,4-dihydropyridine-3,5-dicarboxylate

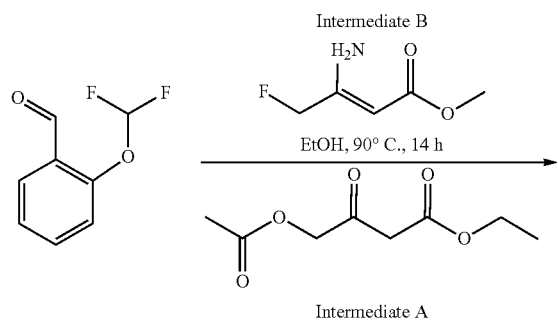

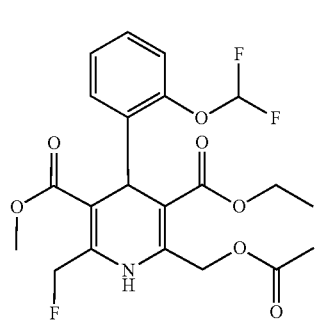

Title compound was synthesized using step 1 of general procedure I (using 2-(difluoromethoxy)benzaldehyde, (350 mg, 2.033 mmol), Intermediate A, (382.3 mg, 2.033 mmol) and Intermediate B, (275.65 mg, 2.033 mmol)) to give 3-ethyl 5-methyl 2-(acetoxymethyl)-4-(2-(difluoromethoxy)phenyl)-6-(fluoromethyl)-1,4-dihydropyridine-3,5-dicarboxylate (600 mg, crude). Without analysis, it was carried forward to the next step.

Step 2: methyl 4-(2-(difluoromethoxy)phenyl)-2-(fluoromethyl)-5-oxo-1,4,5,7-tetrahydro furo[3,4-b]pyridine-3-carboxylate

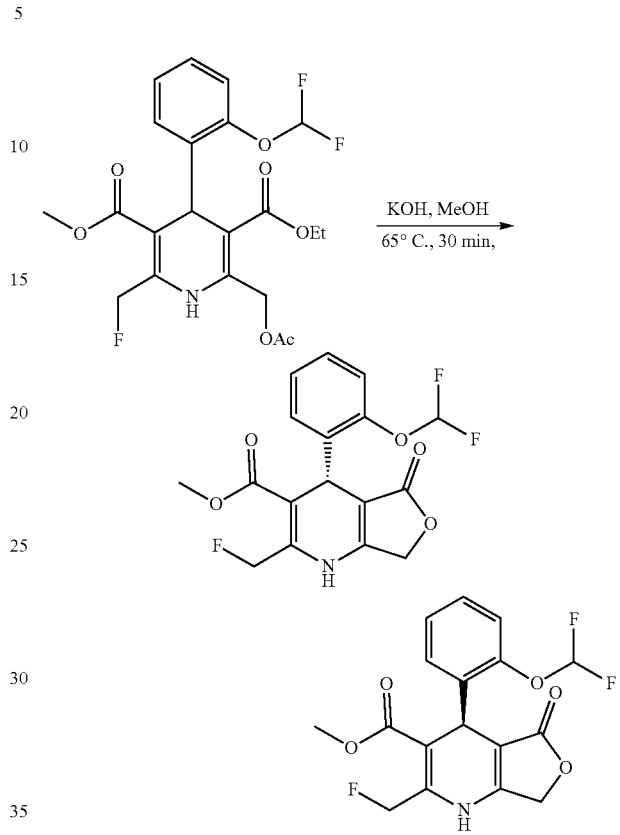

To a crude intermediate (600 mg, 1.30 mmol) from step 1 in methanol (20 mL) was added potassium hydroxide (293.44 mg, 5.22 mmol). The resulting solution was stirred at 65° C. for 30 min. Water was added to reaction mixture and solid was precipitated out and filtered. The solid was washed with diethyl ether and the solid was collected and dried under reduced pressure which afforded the title compound methyl 4-(2-(difluoromethoxy)phenyl)-2-(fluoromethyl)-5-oxo-1,4,5,7-tetrahydro furo[3,4-b]pyridine-3-carboxylate (100 mg).

90 mg of racemic mixture was separated into its enantiomers using chiral HPLC [method 4].

Example 9

40 mg of first eluting enantiomer as a white solid, 44% yield.

Chiral HPLC Rt=6.481 min; [chiral analytical method 1]
LCMS Rt=1.473 min; MS m/z 370 [M+H]+; [Method 7]
$^1$H NMR (400 MHz, CDCl3) δ 7.30 (dd, J=7.5, 1.9 Hz, 1H), 7.24-7.12 (m, 2H), 7.06 (d, J=8.0 Hz, 1H), 6.81-6.43 (m, 1H), 5.82-5.69 (m, 1H), 5.68-5.56 (m, 1H), 5.19 (s, 1H), 4.77 (d, J=1.6 Hz, 2H), 3.55 (d, J=0.7 Hz, 3H). Exchangeable NH proton not seen.

The stereochemistry of Example 9, methyl (R)-4-(2-(difluoromethoxy)phenyl)-2-(fluoromethyl)-5-oxo-1,4,5,7-tetrahydrofuro[3,4-b]pyridine-3-carboxylate, was determined by single crystal x-ray crystallographic analysis and it confirmed that active enantiomer is the R-enantiomer (FIG. 9).

Example 9b 38 mg of second eluting enantiomer as a white solid, 42% yield.

Chiral HPLC Rt=10.303 min; [chiral analytical method 1]

LCMS Rt=1.475 min; MS m/z 370.1 [M+H]+; [Method 7]

$^1$H NMR: (400 MHz, CDCl3) δ 7.30 (dd, J=7.5, 1.9 Hz, 1H), 7.24-7.12 (m, 2H), 7.06 (d, J=8.0 Hz, 1H), 6.81-6.43 (m, 1H), 5.82-5.69 (m, 1H), 5.68-5.56 (m, 1H), 5.19 (s, 1H), 4.77 (d, J=1.6 Hz, 2H), 3.55 (d, J=0.7 Hz, 3H).

Example 10: methyl (R)-4-(3,5-difluoro-2-(trifluoromethyl)phenyl)-2-(fluoromethyl)-5-oxo-1,4,5,7-tetrahydrofuro[3,4-b]pyridine-3-carboxylate

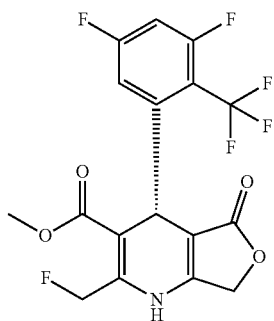

Step 1: 1-bromo-3,5-difluoro-2-(trifluoromethyl)benzene

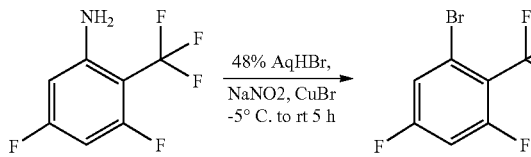

A solution of 3,5-difluoro-2-(trifluoromethyl)aniline (10 g, 50.735 mmol) in 48% aqueous HBr/H$_2$O (80 mL/80 mL) was cooled to −5° C., then NaNO$_2$ (8.74 g in 100 mL H$_2$O, 126.83 mmol) was added slowly over a period of 5 min, then the resulting mixture was stirred for 1 h at −5° C. The reaction mixture was treated with CuBr (10.92 g, 76.103 mmol) portion wise at −5° C. The reaction mixture was slowly raised to room temperature and stirred for 4 hrs. The reaction mixture was extracted with hexane (3×200 mL). The organic phases were combined, washed with saturated brine solution (100 mL) and dried over Na$_2$SO$_4$. The solvent was removed under reduced pressure and purification of the crude product by silica flash chromatography in petroleum ether afforded the title compound 1-bromo-3,5-difluoro-2-(trifluoromethyl)benzene (8 g) as a colorless liquid.

$^1$H NMR (400 MHz, CDCl3) δ 7.31 (dt, J=7.6, 2.2 Hz, 1H), 6.95-6.88 (m, 1H).

Step 2: 1,5-difluoro-2-(trifluoromethyl)-3-vinylbenzene

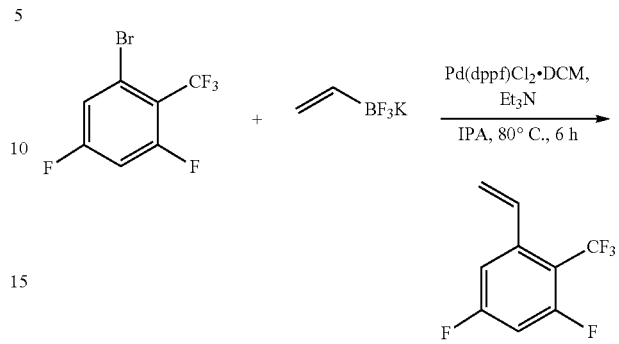

To a solution of 1-bromo-3,5-difluoro-2-(trifluoromethyl)benzene (from step 1, 12.0 g, 45.99 mmol) and trifluoro(vinyl)-14-borane in Isopropyl alcohol (120 mL) was added potassium salt (12.3 g, 91.98 mmol) and triethylamine (19.16 mL, 137.98 mmol). The resulting solution was purged by argon for 10 min, after that [1,1'-Bis (diphenylphosphino)ferrocene]dichloropalladium(II).DCM (3.75 g, 4.599 mmol) was added. The reaction mixture was stirred at 80° C. for 6 hrs. The reaction mixture was filtered through a celite pad and washed with ethyl acetate (100 mL) and dried over Na$_2$SO$_4$. The solvent was removed under reduced pressure and purification of the crude product by silica flash chromatography in petroleum ether afforded the title compound 1,5-difluoro-2-(trifluoromethyl)-3-vinylbenzene (6.5 g) as a colorless liquid.

$^1$H NMR (300 MHz, CDCl3) δ 7.16-6.97 (m, 2H), 6.85-6.80 (m, 1H), 5.67 (d, J=17.2 Hz, 1H), 5.49 (d, J=10.9 Hz, 1H).

Step 3: 3,5-difluoro-2-(trifluoromethyl)benzaldehyde

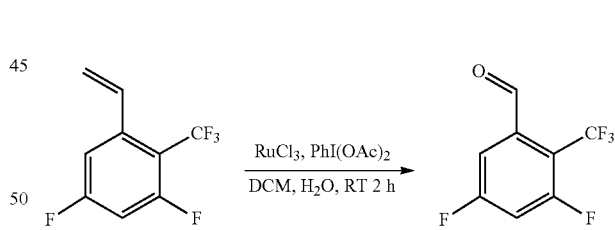

1,5-difluoro-2-(trifluoromethyl)-3-vinylbenzene (from step 2, 6.5 g, 31.23 mmol) and RuCl$_3$·XH$_2$O (647 mg, 3.123 mmol) was added to a solution of diacetoxyiodo benzene (20 g, 62.46 mmol) in dichloromethane: H$_2$O (130 mL:30 mL). The resulting solution was stirred at room temperature for 2 h. The reaction mixture was filtered through a celite pad and washed with dichloromethane (200 mL) and dried over Na$_2$SO$_4$. The solvent was removed under reduced pressure and purification of the crude product by silica flash chromatography (0→5%) ethyl acetate in petroleum ether afforded the title compound 3,5-difluoro-2-(trifluoromethyl)benzaldehyde (3.0 g) as a colorless liquid. $^1$H NMR (300 MHz, CDCl3) δ 10.34 (m, 1H), 7.82-7.52 (m, 1H), 7.22-7.07 (m, 1H).

Step 4: 3-ethyl 5-methyl 2-(acetoxymethyl)-4-(3,5-difluoro-2-(trifluoromethyl)phenyl)-6-(fluoromethyl)-1,4-dihydropyridine-3,5-dicarboxylate

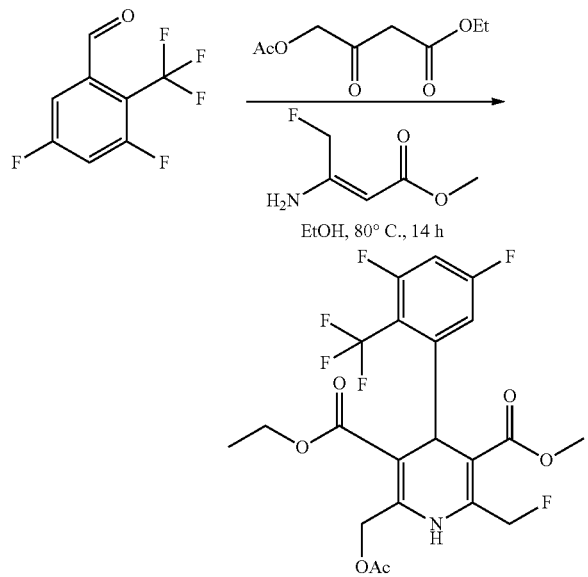

Title compound was synthesized using step 1 of general procedure I (using the aldehyde from step 3 (400 mg, 1.903 mmol)) to give 3-ethyl 5-methyl 2-(acetoxymethyl)-4-(3,5-difluoro-2-(trifluoromethyl)phenyl)-6-(fluoromethyl)-1,4-dihydropyridine-3,5-dicarboxylate (900 mg, crude).

LCMS Rt=1.76 min; MS m/z 496.0 [M+H]+; [Method 7]

Step 5: methyl 4-(3,5-difluoro-2-(trifluoromethyl)phenyl)-2-(fluoromethyl)-5-oxo-1,4,5,7-tetrahydrofuro[3,4-b]pyridine-3-carboxylate

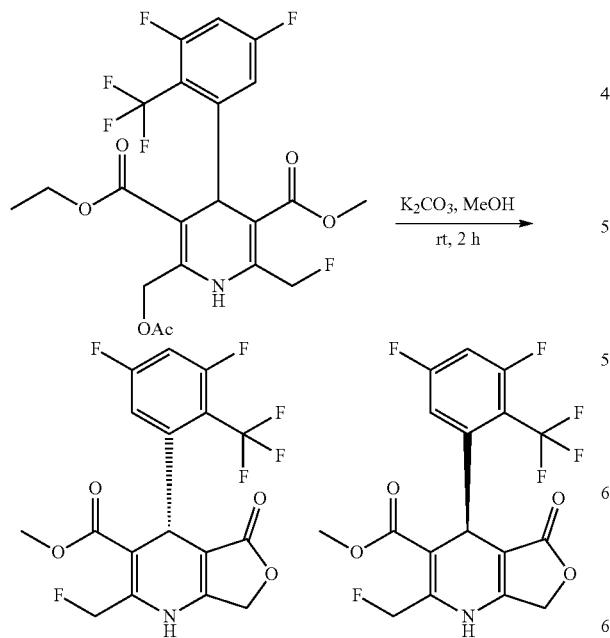

Title compound was synthesized using step 2 of general procedure I (using intermediate from step 4 (900 mg, 1.8 mmol)). Crude product by silica flash chromatography (0→50%) ethyl acetate in petroleum ether afforded the title compound methyl 4-(3,5-difluoro-2-(trifluoromethyl)phenyl)-2-(fluoromethyl)-5-oxo-1,4,5,7-tetrahydrofuro[3,4-b]pyridine-3-carboxylate (90 mg) as an off white solid. Racemic mixture was separated into its enantiomers using chiral HPLC [method 7].

Example 10

30 mg of first eluting enantiomer obtained as a white solid.
Chiral HPLC Rt=5.502 min; [chiral analytical method 2]
LCMS Rt=1.542 min; MS m/z 406 [M−H]−; [Method 7]
$^1$H NMR: (400 MHz, CDCl3) δ 7.30 (d, J=7.2 Hz, 1H), 6.87 (d, J=9.5 Hz, 1H), 6.85-6.75 (m, 1H), 5.79 (t, J=1.2, 1.2 Hz, 1H), 5.67 (t, J=1.1 Hz, 1H), 5.62 (s, 1H), 4.80 (d, J=1.2 Hz, 2H), 3.54 (s, 3H).

Example 10b 30 mg of second eluting enantiomer obtained as a white solid.
Chiral HPLC Rt=6.935 min; [chiral analytical method 1]
LCMS Rt=1.542 min; MS m/z 406 [M−H]−; [Method 7]
$^1$H NMR: (400 MHz, CDCl3) δ 7.30 (d, J=7.2 Hz, 1H), 6.87 (d, J=9.5 Hz, 1H), 6.85-6.75 (m, 1H), 5.79 (t, J=1.2, 1.2 Hz, 1H), 5.67 (t, J=1.1 Hz, 1H), 5.62 (s, 1H), 4.80 (d, J=1.2 Hz, 2H), 3.54 (s, 3H).

Example 11: methyl (R)-4-(2-(2,2-difluoroethyl)-3-fluorophenyl)-2-(fluoromethyl)-5-oxo-1,4,5,7-tetrahydrofuro[3,4-b]pyridine-3-carboxylate

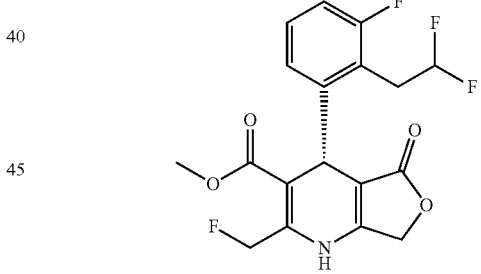

Step 1: 2-(1,3-dioxolan-2-yl)-6-fluorobenzaldehyde

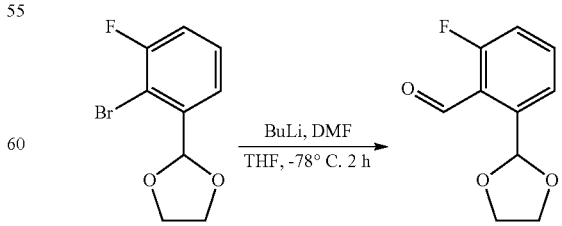

A solution of 2-(2-bromo-3-fluorophenyl)-1,3-dioxolane (from step 1, example 1, 7 g, 28.45 mmol) in THF (70 mL) under nitrogen atmosphere was cooled to −78° C. Then n-butyllithium in n-Hexane solution (13.66 mL, 2.5M, 58.5 mmol) was added over 10 min, the resulting mixture was stirred for 45 min at −78° C. DMF (2.5 g, 34.15 mmol) was added to and resulting mixture stirred for 1.15 h at −78° C. The reaction mixture was quenched with saturated ammonium chloride solution (50 mL) and extracted with ethyl acetate (2×100 mL). Combined organic phases were washed with water (50 mL), followed by brine (50 mL) and dried over Na$_2$SO$_4$. The solvent was removed under reduced pressure and purification of the crude product by silica flash chromatography (0→50%) ethyl acetate in petroleum ether afforded the title compound 2-(1,3-dioxolan-2-yl)-6-fluorobenzaldehyde (5 g) as a colorless liquid.

$^1$H NMR (300 MHz, CDCl3) δ 10.52 (s, 1H), 7.67-7.53 (m, 2H), 7.22-7.12 (m, 1H), 6.50 (s, 1H), 4.27-3.99 (m, 4H).

Step 2: 2-(2-(2,2-difluorovinyl)-3-fluorophenyl)-1,3-dioxolane

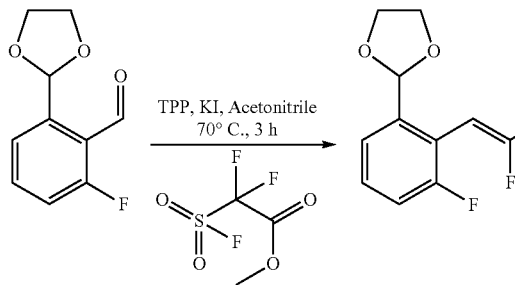

A solution of acetonitrile (65 mL), triphenylphosphine (28.1 g, 107.1 mmol), potassium iodide (11.85 g, 71.4 mmol) and 2-(1,3-dioxolan-2-yl)-6-fluorobenzaldehyde (from step 1, 7 g, 35.7 mmol) was heated to 70° C. under nitrogen atmosphere and stirred for 30 min. Methyl 2,2-difluoro-2-(fluorosulfonyl)acetate (12 g, 62.4 mmol) was added slowly over a period of 10 min (mass color was turned to yellow during addition). The resulting mixture was stirred for another 3 hrs at 70° C., then cooled to room temperature and diluted with diethyl ether. Precipitated solids were filtered and washed with diethyl ether (100 mL). The solvent was removed under reduced pressure and purification of the crude product by silica flash chromatography (0→5%) ethyl acetate in petroleum ether afforded the title compound 2-(2-(2,2-difluorovinyl)-3-fluorophenyl)-1,3-dioxolane (6.9 g) as a light yellow liquid.

$^1$H NMR: (300 MHz, CDCl3) δ 7.39 (dd, J=7.8, 1.4 Hz, 1H), 7.31 (m, 1H), 7.11 (m, 1H), 5.87 (s, 1H), 5.39 (m, 1H), 4.21-3.95 (m, 4H).

Step 3: 2-(2-(2,2-difluoroethyl)-3-fluorophenyl)-1,3-dioxolane

To a solution of 2-(2-(2,2-difluorovinyl)-3-fluorophenyl)-1,3-dioxolane (from step 2, 3 g, 13.04 mmol) in ethyl acetate (60 mL) was added 10% Pd—C (1 g). The resulting reaction mixture was kept in Parr-Shaker for 48 hrs at 60 psi of pressure under hydrogen atmosphere at room temperature. The reaction mixture was filtered on a celite pad, and washed with ethyl acetate (30 mL). The filtrate was concentrated under reduced pressure and purification of the crude product by silica flash chromatography (0→30%) ethyl acetate in petroleum ether afforded the title compound 2-(2-(2,2-difluoroethyl)-3-fluorophenyl)-1,3-dioxolane (3 g) as a colorless liquid.

$^1$H NMR (300 MHz, CDCl3) δ 7.42-7.35 (m, 1H), 7.34-7.27 (m, 1H), 7.15-7.08 (m, 1H), 6.31-5.78 (m, 2H), 4.19-4.02 (m, 4H), 3.38 (m, 2H).

Step 4: 2-(2,2-difluoroethyl)-3-fluorobenzaldehyde

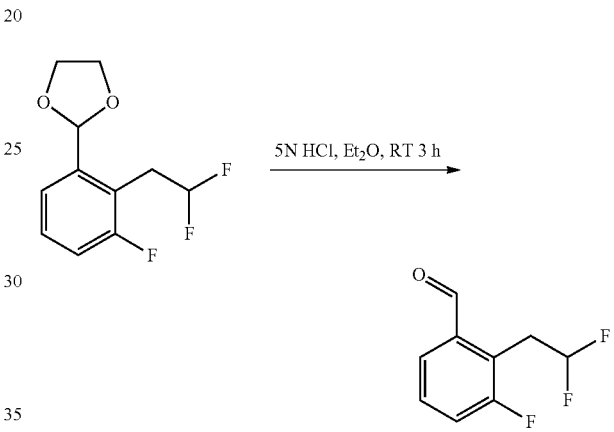

To a solution of 2-(2-(2,2-difluoroethyl)-3-fluorophenyl)-1,3-dioxolane (from step 3, 3 g, 12.93 mmol) in diethyl ether (40 mL) was added 6N HCl (5 mL). The resulting solution was stirred at room temperature for 3 hrs. This was washed with water (50 mL), saturated NaHCO$_3$ solution (100 mL), brine and dried over Na$_2$SO$_4$. The solvent was removed under reduced pressure and purification of the crude product by silica flash chromatography (0→5%) ethyl acetate in petroleum ether afforded the title compound 2-(2,2-difluoroethyl)-3-fluorobenzaldehyde (1.9 g) as a colorless liquid.

$^1$H NMR (400 MHz, CDCl3) δ 10.14 (d, J=1.6 Hz, 1H), 7.70-7.63 (m, 1H), 7.52 (td, J=8.0, 7.9, 5.2 Hz, 1H), 7.35-7.30 (m 1H), 6.03 (m, 1H), 3.83-3.58 (m, 2H).

Step 5: 3-ethyl 5-methyl 2-(acetoxymethyl)-4-(2-(2,2-difluoroethyl)-3-fluorophenyl)-6-(fluoromethyl)-1,4-dihydropyridine-3,5-dicarboxylate

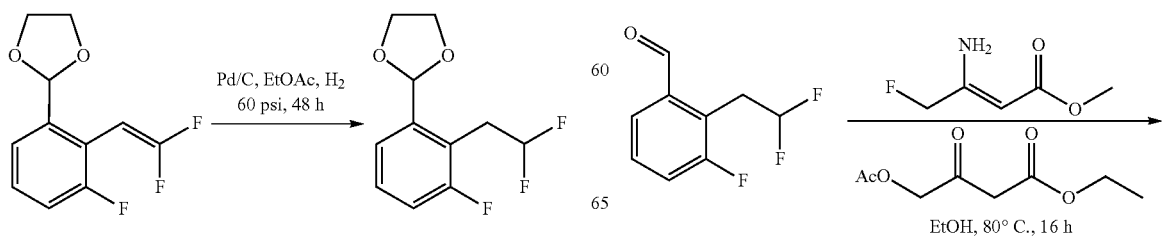

-continued

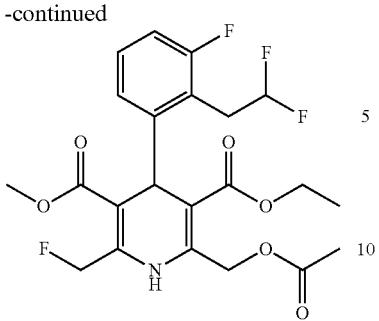

Title compound was synthesized using step 1 of general procedure I (using aldehyde from step 4, 400 mg, 2.12 mmol) to give tittle compound 3-ethyl 5-methyl 2-(acetoxymethyl)-4-(2-(2,2-difluoroethyl)-3-fluorophenyl)-6-(fluoromethyl)-1,4-dihydropyridine-3,5-dicarboxylate (1 g, crude). LCMS Rt=1.764 min; MS m/z 473.4 [M+H]+; [Method 7]

Step 6: methyl 4-(2-(2,2-difluoroethyl)-3-fluorophenyl)-2-(fluoromethyl)-5-oxo-1,4,5,7-tetrahydrofuro[3,4-b]pyridine-3-carboxylate

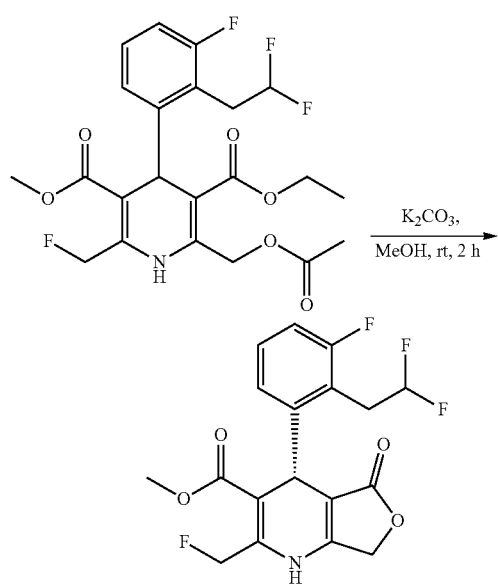

Title compound was synthesized using step 2 of general procedure I (using intermediate from step 5, 1 g, 2.11 mmol). Crude product was purified by silica flash chromatography (0→50%) ethyl acetate in petroleum ether affording the title compound methyl 4-(2-(2,2-difluoroethyl)-3-fluorophenyl)-2-(fluoromethyl)-5-oxo-1,4,5,7-tetrahydrofuro[3,4-b]pyridine-3-carboxylate (85 mg) as an off white solid. Racemic mixture was separated into its enantiomers using chiral preparative HPLC [method 6].

Example 11

30 mg of first eluting enantiomer obtained as a white solid.
Chiral HPLC Rt=6.325 min; [chiral analytical method 2]
LCMS Rt=1.508 min; MS m/z 386.0 [M+H]+; [Method 7]
$^1$H NMR (400 MHz, CDCl3) δ 7.34-7.27 (m, 1H), 7.21 (m, 1H), 7.01-6.89 (m, 2H), 6.55-6.17 (m, 1H), 5.81 (dd, J=1.7, 0.8 Hz, 1H), 5.69 (t, J=1.1 Hz, 1H), 5.08 (s, 1H), 4.78 (d, J=0.9 Hz, 2H), 3.94-3.73 (m, 1H), 3.60-3.55 (m, 1H), 3.54 (s, 3H).

Example 11 b 30 mg of first eluting enantiomer obtained as a white solid.
Chiral HPLC Rt=8.402 min; [chiral analytical method 2]
LCMS Rt=1.508 min; MS m/z 386.4 [M+H]+; [Method 7]
$^1$H NMR (400 MHz, CDCl3) δ 7.34-7.27 (m, 1H), 7.21 (td, J=8.0, 8.0, 5.6 Hz, 1H), 7.01-6.89 (m, 2H), 6.55-6.17 (m, 1H), 5.81 (dd, J=1.7, 0.8 Hz, 1H), 5.69 (t, J=1.1, 1.1 Hz, 1H), 5.08 (s, 1H), 4.78 (d, J=0.9 Hz, 2H), 3.94-3.73 (m, 1H), 3.60-3.55 (m, 1H), 3.54 (s, 3H).

Example 12: methyl (R)-4-(2-(2,2-difluoroethyl)-3,5-difluorophenyl)-2-(fluoromethyl)-5-oxo-1,4,5,7-tetrahydrofuro[3,4-b]pyridine-3-carboxylate

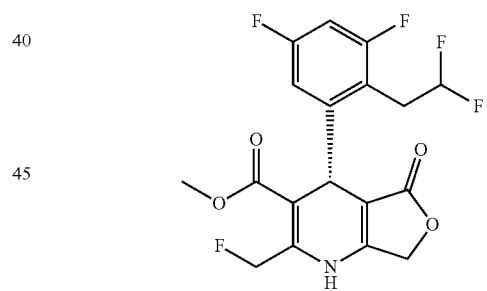

Step 2: 2-(3,5-difluoro-2-vinylphenyl)-1,3-dioxolane

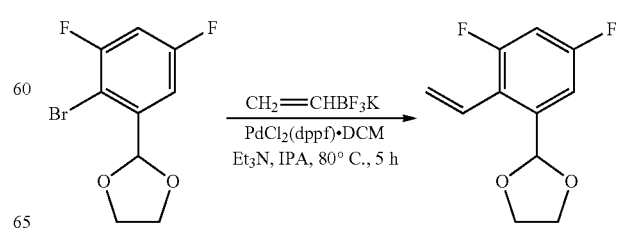

A solution of 2-(2-bromo-3,5-difluorophenyl)-1,3-dioxolane (from step 1, example 3, 5 g, 18.94 mmol) and potassium vinyltrifluoroborate (5.8 g, 37.89 mmol), triethylamine (7.91 mL, 56.82 mmol) in isopropyl alcohol (50 mL) was degassed for 10 min using Argon gas and was added [1,1'-Bis (diphenylphosphino)ferrocene]dichloropalladium(II).DCM (1.55 g, 1.89 mmol). The resulting solution was degassed again with Argon gas for 10 min and stirred at 80° C. for 5 hrs. The reaction mixture was filtered and washed with ethyl acetate (100 mL). The filtrate was dissolved in water (1 L) and extracted into ethyl acetate (2 L). EtOAc was washed with brine and dried over $Na_2SO_4$. The solvent was removed under reduced pressure and purification of the crude product by silica flash chromatography (0→10%) ethyl acetate in petroleum ether afforded the title compound 2-(3,5-difluoro-2-vinylphenyl)-1,3-dioxolane (3.45 g) as a colorless liquid. Note: Compound is volatile in nature, hexane present in the compound.

$^1$H NMR (300 MHz, $CDCl_3$) δ 7.20-7.16 (m, 1H), 6.94-6.83 (m, 1H), 6.82 (dd, J=17.7, 11.7 Hz, 1H), 5.60 (dd, J=1.2, 11.7 Hz, 1H), 5.66-5.60 (m, 1H), 5.95 (s, 1H), 4.18-4.02 (m, 4H).

Step 3:
2-(1,3-dioxolan-2-yl)-4,6-difluorobenzaldehyde

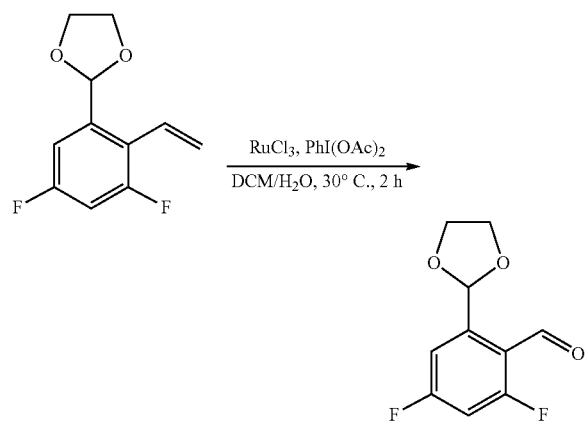

To a solution of 2-(3,5-difluoro-2-vinylphenyl)-1,3-dioxolane (from step 2, 5 g, 23.58 mmol) and ruthenium chloride·$XH_2O$ (490 mg, 2.35 mmol) in dichloromethane (50 mL) and water (10 mL) was added (diacetoxyiodo) benzene (11.4 g, 35.37 mmol). The resulting solution was stirred at 30° C. for 2 hrs. The reaction mixture was filtered and washed with ethyl acetate (200 mL). The filtrate was dissolved in water (200 mL) and product extracted into ethyl acetate (500 mL). Organics were washed with brine and dried over $Na_2SO_4$. The solvent was removed under reduced pressure and purification of the crude product by silica flash chromatography (0→10%) ethyl acetate in petroleum ether afforded the title compound 2-(1,3-dioxolan-2-yl)-4,6-difluorobenzaldehyde (3 g) as a colorless liquid. Note: Compound is volatile in nature, hexane present in the compound.

$^1$H NMR (300 MHz, $CDCl_3$) δ 10.41 (s, 1H), 7.35 (d, J=9.6 Hz, 1H), 6.95-6.85 (m, 1H), 6.53 (s, 1H), 4.08 (s, 4H).

Step 4: 2-(2-(2,2-difluorovinyl)-3,5-difluorophenyl)-1,3-dioxolane

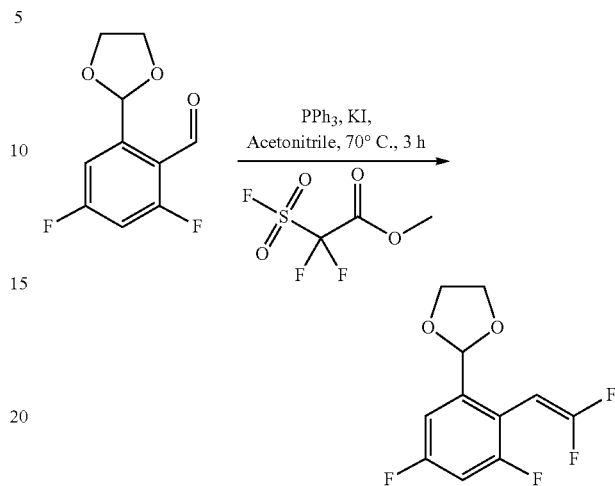

To acetonitrile (4.5 mL) under nitrogen atmosphere was added triphenylphosphine (1.83 g, 7.0 mmol), potassium iodide (775 mg, 4.66 mmol) and 2-1,3-dioxolan-2-yl)-6-fluorobenzaldehyde (from step 3, 500 mg, 2.33 mmol). Reaction stirred for 30 min at 70° C. Then 2-(1,3-dioxolan-2-yl)-4,6-difluorobenzaldehyde (783 mg, 4.07 mmol) was added slowly over a period of 10 min (mass color turned to yellow during addition) and the resulting mixture was stirred at 70° C. for another 3 hrs. Then the reaction mixture was cooled to room temperature and diluted with diethyl ether, precipitated solids were filtered, and washed with diethyl ether (100 mL). The solvent was removed under reduced pressure and purification of the crude product by silica flash chromatography (0→5%) ethyl acetate in petroleum ether afforded the title compound 2-(2-(2,2-difluorovinyl)-3,5-difluorophenyl)-1,3-dioxolane (400 mg) as a light yellow liquid.

$^1$H NMR (300 MHz, CDCl3) δ 7.19-7.12 (m, 1H), 6.89-6.80 (m, 1H), 5.85 (d, J=0.9 Hz, 1H), 5.31 (dt, J=26.1, 1.5 Hz, 1H), 4.16-3.98 (m, 4H).

Step 5: 2-(2-(2,2-difluoroethyl)-3,5-difluorophenyl)-1,3-dioxolane

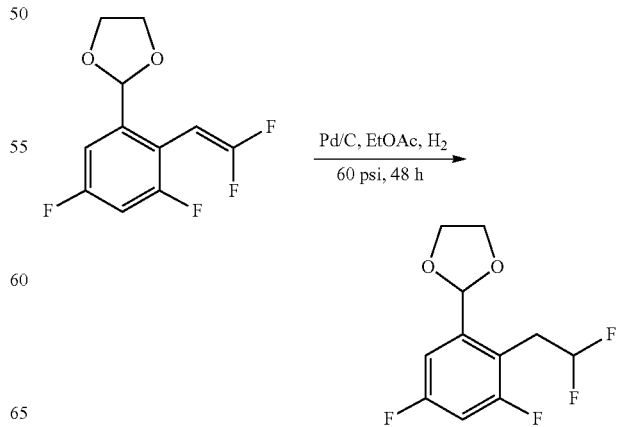

To a solution of 2-(2-(2,2-difluorovinyl)-3,5-difluorophenyl)-1,3-dioxolane (from step 4, 400 mg, 1.61 mmol) in ethyl acetate (10 mL) was added 10% Pd—C (180 mg). The resulting reaction mixture was kept in Parr-Shaker for 48 hrs at 60 psi pressure at room temperature under hydrogen atmosphere. The reaction mixture was filtered through a celite pad and washed with ethyl acetate (30 mL). The filtrate was concentrated under reduced pressure and purification of the crude product by silica flash chromatography (0→30%) ethyl acetate in petroleum ether afforded the title compound 2-(2-(2,2-difluoroethyl)-3,5-difluorophenyl)-1,3-dioxolane (400 mg) as a colorless liquid.

$^1$H NMR (300 MHz, CDCl3) δ 7.22-7.12 (m, 1H), 6.81-6.75 (m, 1H), 6.26-5.75 (m, 2H), 4.20-3.99 (m, 4H), 3.36-3.33 (m, 2H).

Step 6: 2-(2,2-difluoroethyl)-3,5-difluorobenzaldehyde

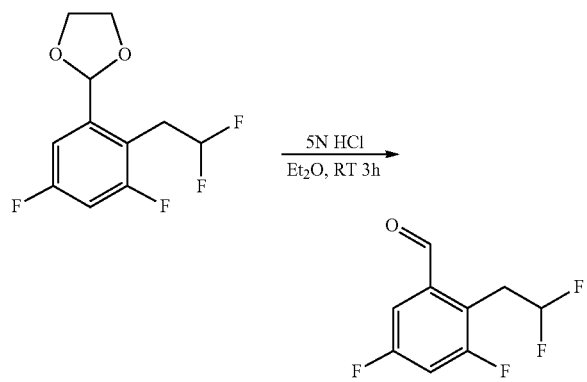

To a solution of 2-(2-(2,2-difluoroethyl)-3,5-difluorophenyl)-1,3-dioxolane (from step 5, 400 mg, 1.6 mmol) in diethyl ether (10 mL) was added 5N HCl (1 mL). The resulting solution was stirred at room temperature for 3 hrs. This was washed with water (50 mL), saturated NaHCO3 solution (100 mL), and brine and dried over Na2SO4. The solvent was removed under reduced pressure and purification of the crude product by silica flash chromatography (0→5%) ethyl acetate in petroleum ether afforded the title compound 2-(2,2-difluoroethyl)-3,5-difluorobenzaldehyde (250 mg) as a colorless liquid.

$^1$H NMR (300 MHz, CDCl3) δ 10.11 (d, J=1.3 Hz, 1H), 7.51-7.34 (m, 1H), 7.20-7.07 (m, 1H), 6.31-5.73 (m, 1H), 3.79-3.56 (m, 2H).

Step 7: 3-ethyl 5-methyl 2-(acetoxymethyl)-4-(2,2-difluoroethyl)-3,5-difluorophenyl)-6-(fluoromethyl)-1,4-dihydropyridine-3,5-dicarboxylate

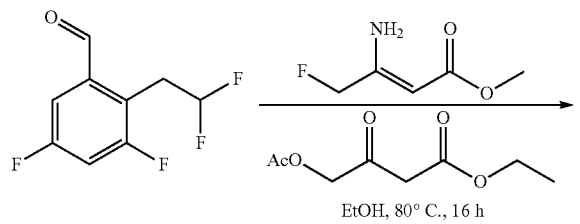

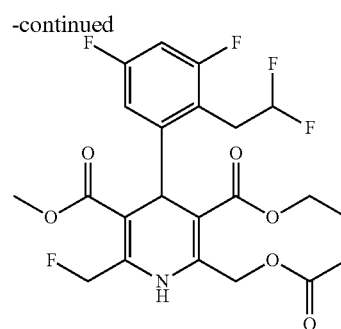

Title compound was synthesized using step 1 of general procedure I (using the aldehyde from step 6 (250 mg, 1.21 mmol)) to give tittle compound 3-ethyl 5-methyl 2-(acetoxymethyl)-4-(2-(2,2-difluoroethyl)-3,5-difluorophenyl)-6-(fluoromethyl)-1,4-dihydropyridine-3,5-dicarboxylate (800 mg, crude).

LCMS Rt=1.77 min; MS m/z 491.0 [M+]+; [Method 7]

Step 8: methyl 4-(2-(2,2-difluoroethyl)-3,5-difluorophenyl)-2-(fluoromethyl)-5-oxo-1,4,5,7-tetrahydrofuro[3,4-b]pyridine-3-carboxylate

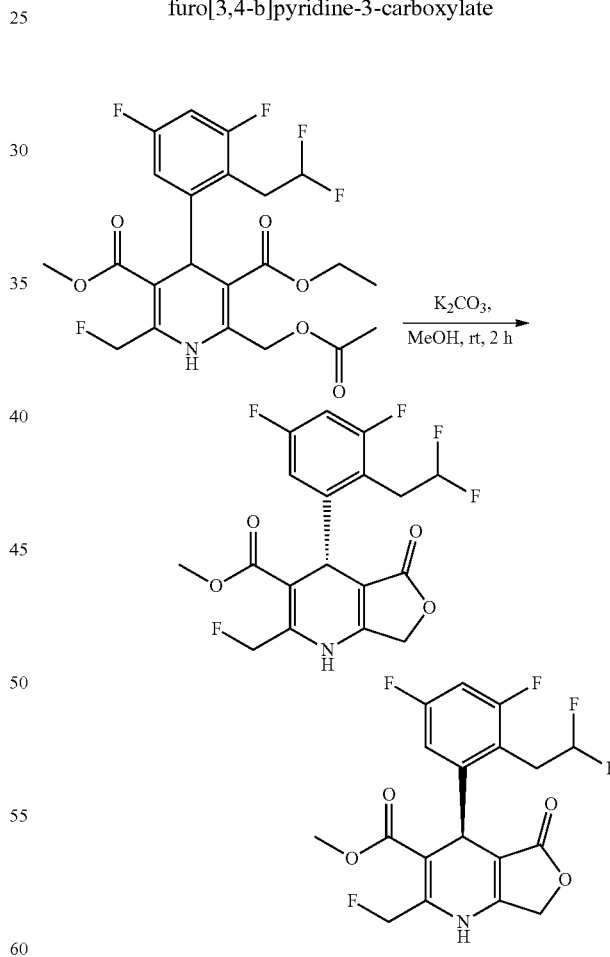

Title compound was synthesized using step 2 of general procedure I (using intermediate from step 7, 800 mg, 1.62 mmol). Crude product was purified by silica flash chromatography (0→50%) ethyl acetate in petroleum ether to afford the title compound methyl 4-(2-(2,2-difluoroethyl)-3,5-difluorophenyl)-2-(fluoromethyl)-5-oxo-1,4,5,7-tetrahydrofuro[3,4-b]pyridine-3-carboxylate (44 mg) as an off white solid. Racemic mixture was separated into its enantiomers using chiral preparative HPLC [method 6].

Example 12

11 mg of first eluting enantiomer obtained as a white solid.

Chiral HPLC Rt=5.674 min; [chiral analytical method 2]
LCMS Rt=1.561 min; MS m/z 403.9 [M+]+; [Method 7]
$^{1}$H NMR (400 MHz, CD3OD) δ 6.87-6.76 (m, 2H), 6.64-6.26 (m, 1H), 5.76 (s, 1H), 5.64 (s, 1H), 5.13 (d, J=1.4 Hz, 1H), 4.87-4.83 (m, 2H), 3.50-3.36 (m, 1H), 3.70 (s, 2H), 3.53 (s, 3H).

Example 12b 10 mg of second eluting enantiomer obtained as a white solid.

Chiral HPLC Rt=7.215 min; [chiral analytical method 2]
LCMS Rt=1.557 min; MS m/z 403.9 [M+]+; [Method 7]
$^{1}$H NMR (400 MHz, CD3OD) δ 6.87-6.76 (m, 2H), 6.64-6.26 (m, 1H), 5.76 (s, 1H), 5.64 (s, 1H), 5.13 (d, J=1.4 Hz, 1H), 4.87-4.83 (m, 2H), 3.50-3.36 (m, 1H), 3.70 (s, 2H), 3.53 (s, 3H).

Example 13: methyl (R)-4-(2-cyclopropyl-3,5-difluorophenyl)-2-(fluoromethyl)-5-oxo-1,4,5,7-tetrahydrofuro[3,4-b]pyridine-3-carboxylate

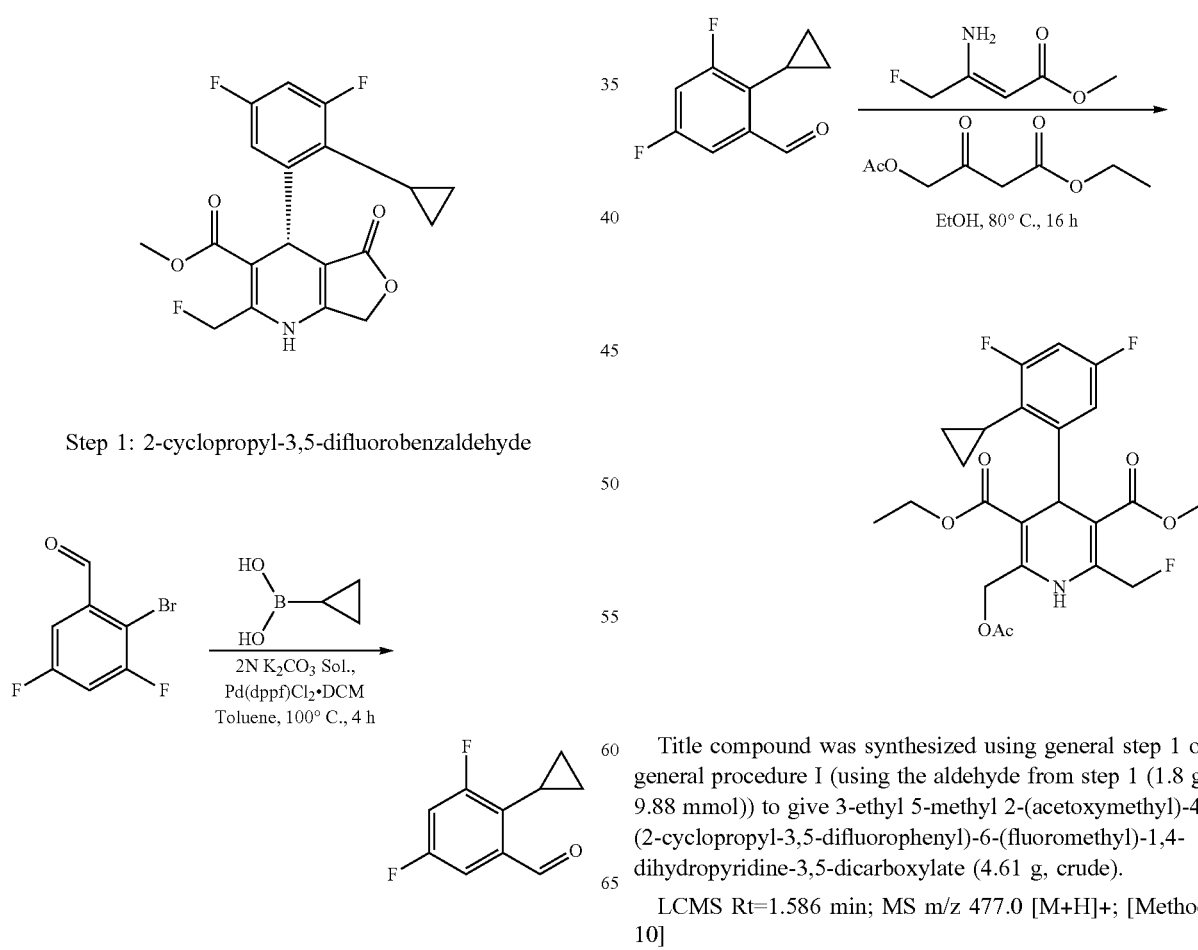

Step 1: 2-cyclopropyl-3,5-difluorobenzaldehyde

To a solution of 2-bromo-3,5-difluorobenzaldehyde (10 g, 45.20 mmol) and cyclopropylboronic acid (4.67 g, 54.2 mmol) in toluene (100 mL) was added 2N K$_2$CO$_3$ (102 mL, 204 mmol) and [1,1'-Bis(diphenylphosphino)ferrocene]dichloropalladium(II).DCM (3.17 g, 3.88 mmol). The resulting solution was degassed with Argon gas for 10 min and stirred at 100° C. for 4 hrs. The reaction mixture was filtered and washed with ethyl acetate (200 mL). The filtrate was added to water (500 mL) and product extracted into ethyl acetate (2 L). EtOAc phase was washed with brine and dried over Na$_2$SO$_4$. The solvent was removed under reduced pressure and purification of the crude product by silica flash chromatography (0→1%) ethyl acetate in petroleum ether afforded the title compound 2-cyclopropyl-3,5-difluorobenzaldehyde (8 g) as a colorless liquid.

$^{1}$H NMR (300 MHz, CDCl$_3$) δ 10.71 (d, J=3 Hz, 1H), 7.40-730 (m, 1H), 7.05-6.90 (m, 1H), 2.05-1.95 (m, 1H), 1.19-1.09 (m, 2H), 0.85-0.75 (m, 2H).

Step 2: 3-ethyl 5-methyl 2-(acetoxymethyl)-4-(2-cyclopropyl-3,5-difluorophenyl)-6-(fluoromethyl)-1,4-dihydropyridine-3,5-dicarboxylate Title compound was synthesized using general step 1 of general procedure I (using the aldehyde from step 1 (1.8 g, 9.88 mmol)) to give 3-ethyl 5-methyl 2-(acetoxymethyl)-4-(2-cyclopropyl-3,5-difluorophenyl)-6-(fluoromethyl)-1,4-dihydropyridine-3,5-dicarboxylate (4.61 g, crude).

LCMS Rt=1.586 min; MS m/z 477.0 [M+H]+; [Method 10]

Step 3: methyl 4-(2-cyclopropyl-3,5-difluorophenyl)-2-(fluoromethyl)-5-oxo-1,4,5,7-tetrahydrofuro[3,4-b]pyridine-3-carboxylate

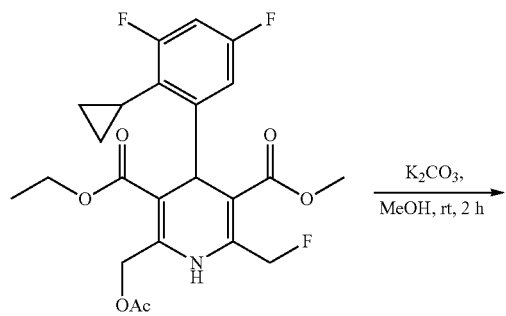

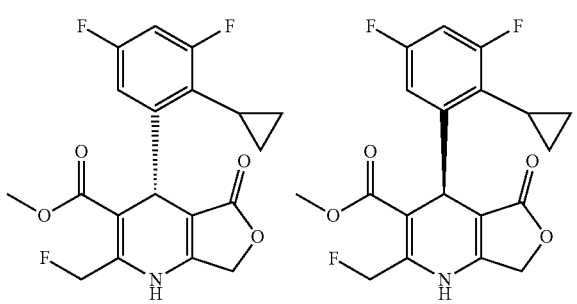

Title compound was synthesized using step 2 of general procedure I (using intermediate from step 2, 4.61 g, 9.871 mmol). Crude product was purified by silica flash chromatography (0→50%) ethyl acetate in petroleum ether which afforded the title compound methyl 4-(2-cyclopropyl-3,5-difluorophenyl)-2-(fluoromethyl)-5-oxo-1,4,5,7-tetrahydrofuro[3,4-b]pyridine-3-carboxylate (350 mg) as an off white solid.

Racemic mixture was separated into its enantiomers using chiral preparative HPLC [method 9].

Example 13

135 mg of first eluting enantiomer obtained as a white solid.

Chiral HPLC Rt=5.33 min; [chiral analytical method 2]

LCMS Rt=1.591 min; MS m/z 380.2 [M+H]+; [Method 7]

¹H NMR (300 MHz, CD3OD) δ 6.78-6.70 (m, 1H), 6.66 (m, 1H), 5.75 (s, 1H), 5.61 (d, J=14.1 Hz, 2H), 4.84 (q, J=1.7, 1.7, 0.9 Hz, 2H), 3.53 (s, 3H), 2.08 (m, 1H), 1.18 (m, 1H), 1.07-0.87 (m, 2H), 0.75 (m, 1H).

Example 14: methyl (R)-4-(2-cyclopropyl-3,5-difluorophenyl)-2-(fluoromethyl)-5-oxo-4,5,6,7-tetrahydro-1H-cyclopenta[b]pyridine-3-carboxylate

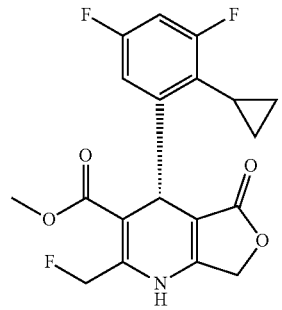

Step 2: methyl 4-(2-cyclopropyl-3,5-difluorophenyl)-2-(fluoromethyl)-5-oxo-4,5,6,7-tetrahydro-1H-cyclopenta[b]pyridine-3-carboxylate To solution of aldehyde (from step 1, example 13, 300 mg, 1.64 mmol) was added methyl (Z)-3-amino-4-fluorobut-2-enoate (intermediate B, 220 mg, 1.64 mmol) and cyclopentane-1,3-dione (161 mg, 1.64 mmol) in ethanol (5 mL). The reaction mixture was stirred at 80° C. for 16 hrs. The solvent was removed under reduced pressure giving crude compound. Crude product was purified by silica flash chromatography (0→70%) ethyl acetate in petroleum ether affording the title compound methyl 4-(2-cyclopropyl-3,5-difluorophenyl)-2-(fluoromethyl)-5-oxo-4,5,6,7-tetrahydro-1H-cyclopenta[b]pyridine-3-carboxylate (55 mg) as an off white solids. Racemic mixture was separated into its enantiomers using chiral preparative HPLC [method 3].

Example 14

17 mg of first eluting enantiomer obtained as a white solid.

Chiral HPLC Rt=8.588 min; [chiral analytical method 3]

LCMS Rt=1.548 min; MS m/z 378.0 [M+H]+; [Method 7]

¹H NMR (400 MHz, CDCl3) δ 7.21 (d, J=7.2 Hz, 1H), 6.65-6.48 (m, 2H), 5.78 (d, J=0.9 Hz, 1H), 5.65 (d, J=0.8 Hz, 1H), 5.60-5.52 (m, 1H), 3.56 (s, 3H), 2.75-2.56 (m, 2H), 2.52-2.32 (m, 2H), 2.20-2.13 (m, 1H), 1.34-1.13 (m, 1H), 1.05-0.98 (m, 2H), 0.83-0.69 (m, 1H).

Example 14b 17 mg of second eluting enantiomer obtained as a white solid.
Chiral HPLC Rt=11.651 min; [chiral analytical method 3]
LCMS Rt=1.548 min; MS m/z 378.0 [M+H]+; [Method 7]
¹H NMR (400 MHz, CDCl3) δ 7.21 (d, J=7.2 Hz, 1H), 6.65-6.48 (m, 2H), 5.78 (d, J=0.9 Hz, 1H), 5.65 (d, J=0.8 Hz, 1H), 5.60-5.52 (m, 1H), 3.56 (s, 3H), 2.75-2.56 (m, 2H), 2.52-2.32 (m, 2H), 2.20-2.13 (m, 1H), 1.34-1.13 (m, 1H), 1.05-0.98 (m, 2H), 0.83-0.69 (m, 1H).

Example 15: methyl (R)-4-(2-(difluoromethyl)-3-fluorophenyl)-2-(fluoromethyl)-5-oxo-1,4,5,7-tetrahydrofuro[3,4-b]pyridine-3-carboxylate

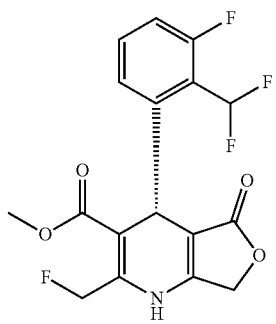

Step 1: 2-(difluoromethyl)-1-fluoro-3-vinylbenzene

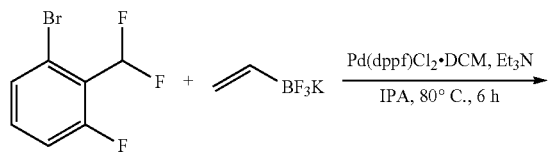

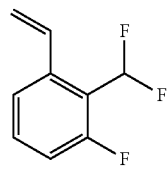

To a solution of 1-bromo-2-(difluoromethyl)-3-fluorobenzene (2.0 g, 8.889 mmol) was added potassium vinyltrifluoroborate (2.38 g, 17.78 mmol) and triethylamine (3.7 mL, 26.66 mmol) in isopropyl alcohol (20 mL). The resulting solution was purged by argon for 10 min and [1,1'-Bis(diphenylphosphino)ferrocene]dichloropalladium(II).DCM (725 mg, 0.889 mmol) was added. The reaction mixture was stirred at 80° C. for 6 hrs. The reaction mixture was filtered through a celite pad and washed with ethyl acetate (100 mL) and dried over Na2SO4. The solvent was removed under reduced pressure and purification of the crude product by silica flash chromatography in petroleum ether afforded the title compound 2-(difluoromethyl)-1-fluoro-3-vinylbenzene (1.2 g) as a colorless liquid.
¹H NMR (400 MHz, CDCl3) δ 7.48-7.40 (m, 1H), 7.30-7.15 (m, 1H), 7.04 (t, J=53.4 Hz, 1H), 7.04-6.90 (m, 2H), 5.44 (d, J=11.2 Hz, 1H), 5.70 (d, J=11.2 Hz, 1H).

Step 2: 2-(difluoromethyl)-3-fluorobenzaldehyde

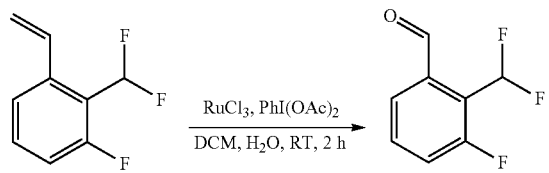

To a solution of 2-(difluoromethyl)-1-fluoro-3-vinylbenzene (from step 1, 1.2 g, 6.970 mmol), was added RuCl3·XH2O (145 mg, 0.697 mmol) and diacetoxyiodobenzene (6.73 g, 20.91 mmol) in dichloromethane: H2O (20 mL: 6 mL). The resulting solution was stirred at room temperature for 2 hrs. The reaction mixture was filtered through a celite pad and washed with dichloromethane (200 mL) and dried over Na2SO4. The solvent was removed under reduced pressure and purification of the crude product by silica flash chromatography (0→5%) ethyl acetate in petroleum ether afforded the title compound 2-(difluoromethyl)-3-fluorobenzaldehyde (500 mg) as a colorless liquid.
¹H NMR (400 MHz, CDCl3) δ 10.42 (t, J=2.0 Hz, 1H), 8.44 (d, J=8.0 Hz, 1H), 7.70-7.59 (m, 1H), 7.45-7.35 (m, 1H), 7.30 (t, J=53.2 Hz, 1H).

Step 3: 3-ethyl 5-methyl 2-(acetoxymethyl)-4-(2-(difluoromethyl)-3-fluorophenyl)-6-(fluoromethyl)-1,4-dihydropyridine-3,5-dicarboxylate

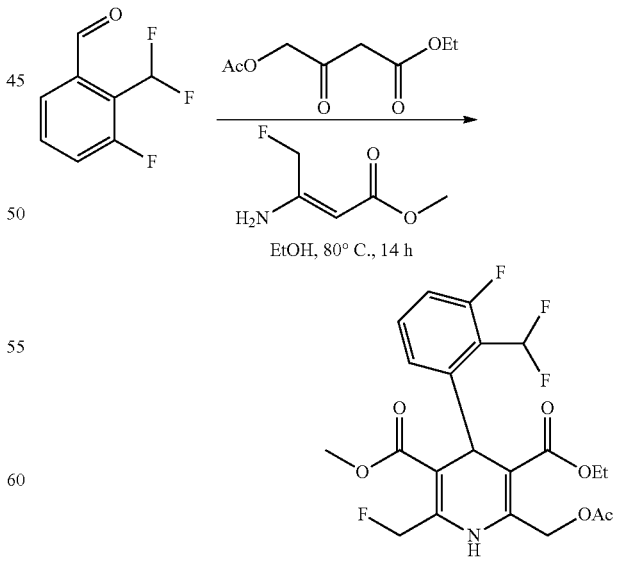

Title compound was synthesized using step 1 of general procedure I (using the aldehyde from step 2, 500 mg, 2.871 mmol) to give 3-ethyl 5-methyl 2-(acetoxymethyl)-4-(2-

(difluoromethyl)-3-fluorophenyl)-6-(fluoromethyl)-1,4-dihydropyridine-3,5-dicarboxylate (1.5 g, crude).

LCMS Rt=1.716 min; MS m/z 460.1 [M+H]+; [Method 7]

Step 4: methyl 4-(2-(difluoromethyl)-3-fluorophenyl)-2-(fluoromethyl)-5-oxo-1,4,5,7-tetrahydrofuro[3,4-b]pyridine-3-carboxylate

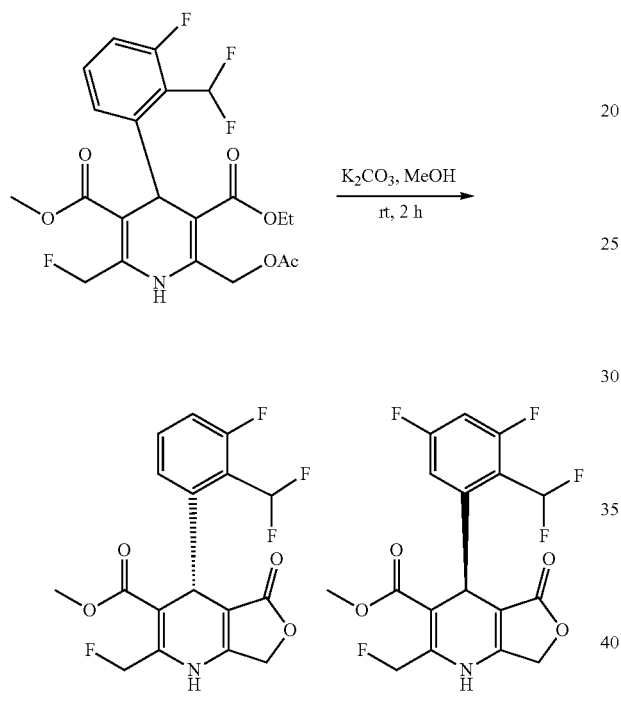

Title compound was synthesized using step 2 of general procedure I (using intermediate from step 3, 1.0 g, 2.177 mmol). Crude product purification by silica flash chromatography (0→50%) ethyl acetate in petroleum ether afforded the title compound methyl 4-(2-(difluoromethyl)-3-fluorophenyl)-2-(fluoromethyl)-5-oxo-1,4,5,7-tetrahydrofuro[3,4-b]pyridine-3-carboxylate (280 mg) as an off white solid. Racemic mixture was separated into its enantiomers using chiral preparative HPLC [method 5].

Example 15

90 mg of first eluting enantiomer obtained as a white solid.

Chiral HPLC Rt=10.05 min; [Chiral analytical method 2]

LCMS Rt=1.947 min; MS m/z 372.2 [M+H]+; [Method 9]

$^1$H NMR (400 MHz, CDCl3) δ 7.44-7.28 (m, 2H), 7.09-6.96 (m, 2H), 5.80 (d, J=0.8 Hz, 1H), 5.68 (d, J=0.9 Hz, 1H), 5.20 (s, 1H), 4.80 (d, J=1.1 Hz, 2H), 3.54 (s, 3H). Exchangeable NH proton not seen in spectra.

Example 15b 90 mg of second eluting enantiomer obtained as a white solid.

Chiral HPLC Rt=12.05 min; [Chiral analytical method 2]

LCMS Rt=2.09 min; MS m/z 372.2 [M+H]+; [Method 9]

$^1$H NMR (400 MHz, CDCl3) δ 7.43-7.33 (m, 2H), 7.10-6.93 (m, 2H), 5.80 (d, J=0.8 Hz, 1H), 5.68 (d, J=0.9 Hz, 1H), 5.20 (s, 1H), 4.80 (d, J=0.9 Hz, 2H), 3.54 (s, 3H).

Example 16: methyl (R)-4-(2-((R or S)-1,2-difluoroethyl)-3,5-difluorophenyl)-2-(fluoromethyl)-5-oxo-1,4,5,7-tetrahydrofuro[3,4-b]pyridine-3-carboxylate

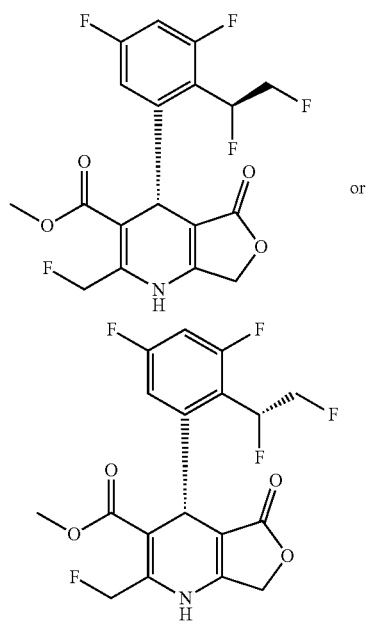

Step 1: 2-(2-bromo-3,5-difluorophenyl)-1,3-dioxolane

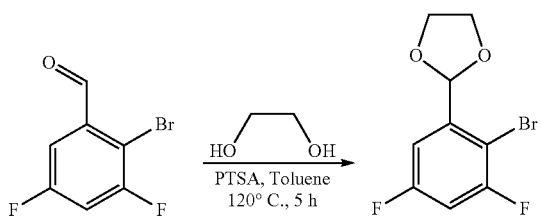

The title compound was synthesized following a procedure similar to step 1 of example 1 using 15 g of 2-bromo-3,5-difluorobenzaldehyde to obtain 15 g of desired product 2-(2-bromo-3,5-difluorophenyl)-1,3-dioxolane.

$^1$H NMR (300 MHz, CDCl3) δ 7.23-7.18 (m, 1H), 6.95-6.90 (m, 1H), 6.08 (t, J=1.1 Hz, 1H), 4.24-3.99 (m, 4H).

Step 2: (3-bromo-4-(1,3-dioxolan-2-yl)-2,6-difluorophenyl)trimethylsilane

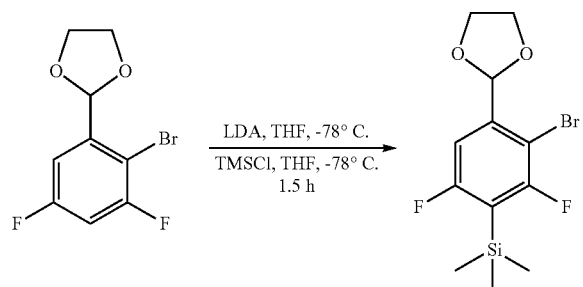

To a solution of 2-(2-bromo-3,5-difluorophenyl)-1,3-dioxolane (from step 1, 15.0 g, 56.59 mmol) in freshly distilled THF (150 mL) under inert atmosphere was added lithium diisopropylamide (31.1 mL, 2.0 M in hexane, 62.25 mmol) at −78° C. and stirred for 30 min. Trimethylsilyl chloride (7.37 g, 67.91 mmol) was added to the reaction mixture and stirred for 1 h at −78° C. The reaction mixture was quenched with saturated NH$_4$Cl solution (250 mL) and product extracted into ethyl acetate (2×500 mL). The combined EtOAc phases were washed with brine solution (250 mL) and dried over Na$_2$SO$_4$. The solvent was removed under reduced pressure and purification of the crude product by silica flash chromatography in petroleum ether (100%) afforded the title compound (3-bromo-4-(1,3-dioxolan-2-yl)-2,6-difluorophenyl)trimethylsilane (9.0 g) as a colorless liquid.

$^1$H NMR (300 MHz, CDCl3) δ 7.08 (dd, J=8.9, 1.6 Hz, 1H), 6.07 (d, J=1.3 Hz, 1H), 4.33-3.89 (m, 4H), 0.37 (t, J=1.6 Hz, 9H).

Step 3: 1-(6-(1,3-dioxolan-2-yl)-2,4-difluoro-3-(trimethylsilyl)phenyl)-2-fluoroethan-1-one

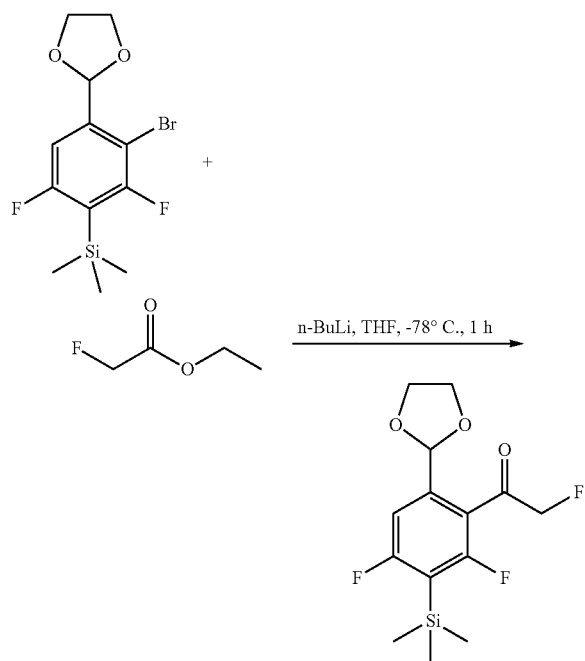

To a solution of (3-bromo-4-(1,3-dioxolan-2-yl)-2,6-difluorophenyl)trimethylsilane (from step 2, 5.0 g, 14.961 mmol) in freshly distilled THF (50 mL) under inert atmosphere was added n-butyl lithium (6.0 mL, 2.5M in hexane, 14.961 mmol) slowly at −78° C. Then ethyl 2,2-difluoroacetate (3.1 g, 29.9 mmol) was added to reaction mixture and stirred for 1 h at −78° C. The reaction was quenched with saturated NH$_4$Cl solution (250 mL) and extracted into ethyl acetate (2×200 mL). The combined EtOAc phases were washed with brine solution (50 mL) and dried over Na$_2$SO$_4$. The solvent was removed under reduced pressure and purification of the crude product by silica flash chromatography (0→10%) ethyl acetate in petroleum ether afforded the title compound 1-(6-(1,3-dioxolan-2-yl)-2,4-difluoro-3-(trimethylsilyl)phenyl)-2-fluoroethan-1-one (2.5 g) as a colorless liquid.

$^1$H NMR (300 MHz, CDCl3) δ 7.04 (dt, J=8.9, 0.8 Hz, 1H), 6.02 (s, 1H), 5.22 (d, J=1.6 Hz, 1H), 5.07 (d, J=1.6 Hz, 1H), 4.03-3.79 (m, 4H), 0.37 (s, 9H).

Step 4: 1-(6-(1,3-dioxolan-2-yl)-2,4-difluoro-3-(trimethylsilyl)phenyl)-2-fluoroethan-1-ol

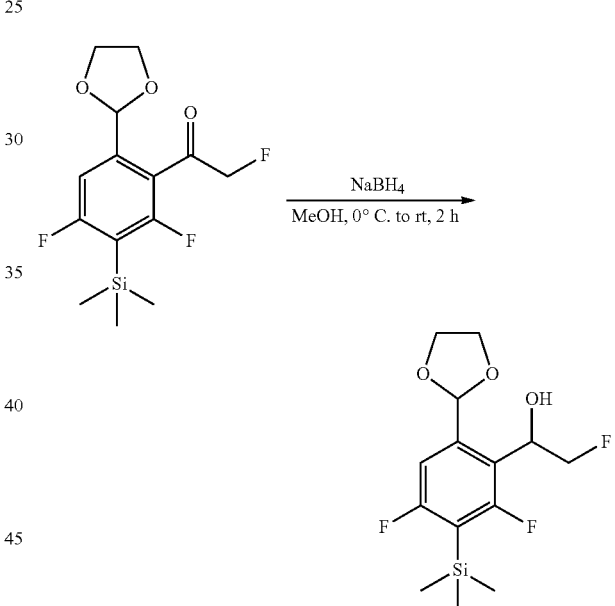

To a solution of 1-(6-(1,3-dioxolan-2-yl)-2,4-difluoro-3-(trimethylsilyl)phenyl)-2-fluoroethan-1-one (from step 3, 2.5 g, 7.854 mmol) in methanol (20 mL) was added sodium borohydride (594.2 mg, 15.70 mmol) portion wise at 0° C. Temperature was allowed to rise to room temperature slowly over 1 hour and stirred at room temperature for another for 2 hrs. The reaction mixture was quenched with saturated ammonium chloride solution (50 mL) and extracted into ethyl acetate (200 mL). EtOAc was washed with brine solution (50 mL) and dried over Na$_2$SO$_4$. The solvent was removed under reduced pressure and purification of the crude product by silica flash chromatography (0→30%) ethyl acetate in petroleum ether afforded the title compound 1-(6-(1,3-dioxolan-2-yl)-2,4-difluoro-3-(trimethylsilyl)phenyl)-2-fluoroethan-1-ol (2.5 g) as a colorless liquid.

$^1$H NMR (400 MHz, CDCl3) δ 7.12 (dd, J=9.4, 1.2 Hz, 1H), 6.15 (s, 1H), 5.42-5.35 (m, 1H), 4.93-4.47 (m, 2H), 4.19-3.88 (m, 4H), 2.96 (dd, J=6.1, 2.8 Hz, 1H), 0.36 (s, 9H).

Step 5: (3-(1,2-difluoroethyl)-4-(1,3-dioxolan-2-yl)-2,6-difluorophenyl)trimethylsilane

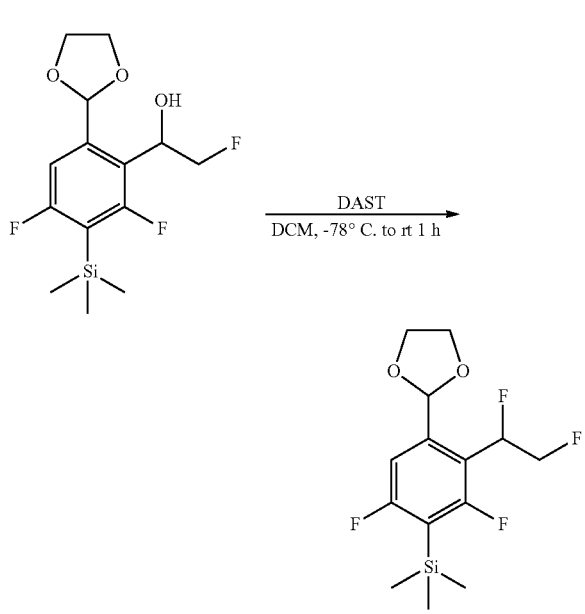

To a solution of 1-(6-(1,3-dioxolan-2-yl)-2,4-difluoro-3-(trimethylsilyl)phenyl)-2-fluoroethan-1-ol (from step 4, 2.0 g, 6.24 mmol) in dichloromethane (20 mL) was added diethylaminosulfur trifluoride (DAST) (1.24 mL, 9.36 mmol) at 0° C. Reaction was allowed to warm to room temperature and stirred for 1 h. To the reaction mixture was added water (50 mL) and product extracted into dichloromethane (3×50 mL). DCM phases were combined and washed with saturated NaHCO₃ solution (50 mL), brine and dried over Na₂SO₄. The solvent was removed under reduced pressure and purification of the crude product by silica flash chromatography (0→2%) ethyl acetate in petroleum ether afforded the title compound (3-(1,2-difluoroethyl)-4-(1,3-dioxolan-2-yl)-2,6-difluorophenyl)trimethylsilane (1.1 g) as a colorless liquid.

$^1$H NMR (400 MHz, CDCl3) δ 7.23-7.04 (m, 1H), 6.24-6.05 (m, 1H), 6.04 (s, 1H), 5.15-4.89 (m, 1H), 4.70-4.39 (m, 1H), 4.14-3.99 (m, 4H), 0.36 (s, 9H).

Step 6: 2-(1,2-difluoroethyl)-3,5-difluoro-4-(trimethylsilyl)benzaldehyde

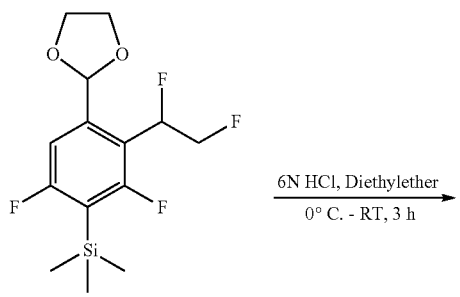

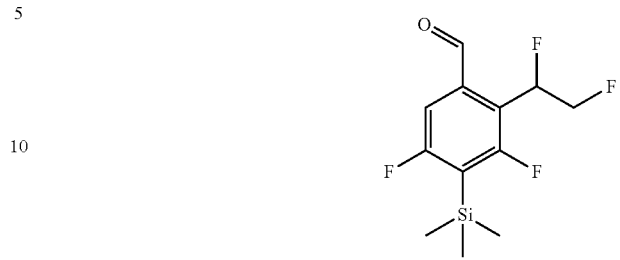

To a solution of (3-(1,2-difluoroethyl)-4-(1,3-dioxolan-2-yl)-2,6-difluorophenyl)trimethylsilane (from step 5, 1.1 g, 3.41 mmol) in diethyl ether (10 mL) was added 6N HCl (11 mL). The resulting solution was stirred at room temperature for 3 hrs. This was washed with water (50 mL), saturated NaHCO₃ solution (100 mL), and brine and dried over Na₂SO₄. The solvent was removed under reduced pressure affording the title compound 2-(1,2-difluoroethyl)-3,5-difluoro-4-(trimethylsilyl)benzaldehyde (900 mg) as a colorless liquid. Without further purification and analysis, product was used for the next step.

Step 7: 2-(1,2-difluoroethyl)-3,5-difluorobenzaldehyde

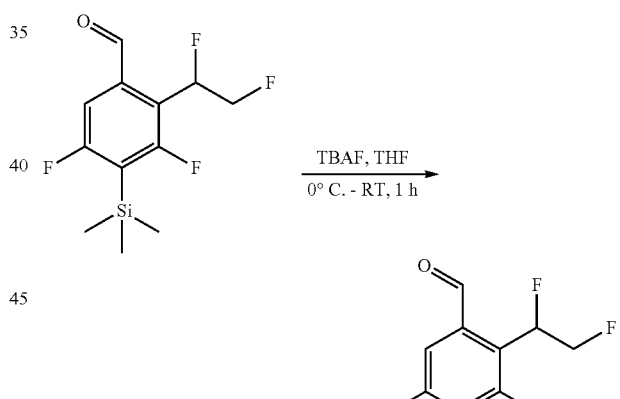

To a solution of (2-(1,2-difluoroethyl)-3,5-difluoro-4-(trimethylsilyl)benzaldehyde (from step 6, 900 mg, 3.23 mmol) in THF (20 mL), was added TBAF (8.0 mL, 1.0M in THF, 8.08 mmol). The resulting solution was stirred at room temperature for 1 h. Reaction mixture was diluted with EtOAc (50 mL) and this was washed with water (50 mL), saturated NaHCO₃ solution (100 mL), and brine and dried over Na₂SO₄. The solvent was removed under reduced pressure and purification of the crude product by silica flash chromatography (5→10%) ethyl acetate in petroleum ether afforded the title compound 2-(1,2-difluoroethyl)-3,5-difluorobenzaldehyde (400 mg) as a colorless liquid.

$^1$H NMR (600 MHz, CDCl3) δ 10.41-10.14 (m, 1H), 7.54 (d, J=8.3 Hz, 1H), 7.15-7.06 (m, 1H), 6.34-6.30 (m, 1H), 4.95-4.67 (m, 2H).

Step 8: 3-ethyl 5-methyl 2-(acetoxymethyl)-4-(2-(1,2-difluoroethyl)-3,5-difluorophenyl)-6-(fluoromethyl)-1,4-dihydropyridine-3,5-dicarboxylate

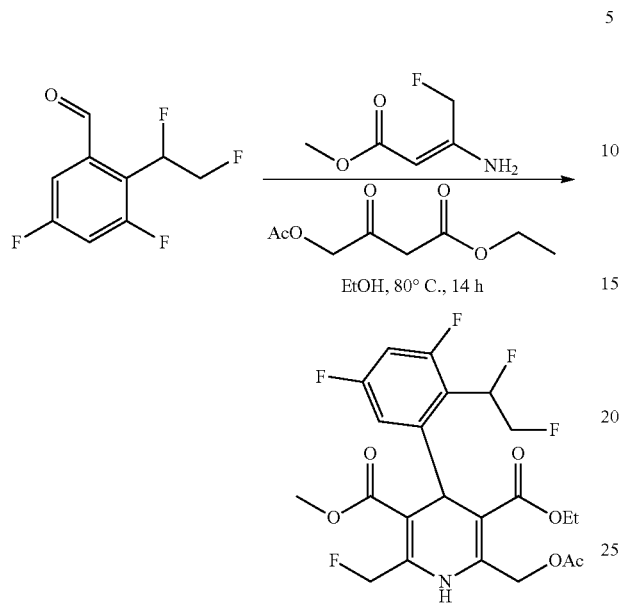

Title compound was synthesized using step 1 of general procedure I (using the aldehyde from step 7, 490 mg, 2.377 mmol) to give 3-ethyl 5-methyl 2-(acetoxymethyl)-4-(2-(1,2-difluoroethyl)-3,5-difluorophenyl)-6-(fluoromethyl)-1,4-dihydropyridine-3,5-dicarboxylate (1.0 g, crude). Without further purification and analysis product was used for the next step.

Step 9: methyl 4-(2-(1,2-difluoroethyl)-3,5-difluorophenyl)-2-(fluoromethyl)-5-oxo-1,4,5,7-tetrahydrofuro[3,4-b]pyridine-3-carboxylate

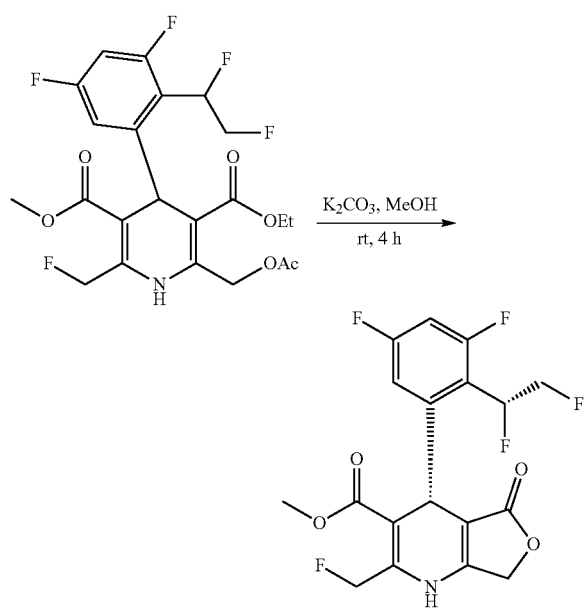

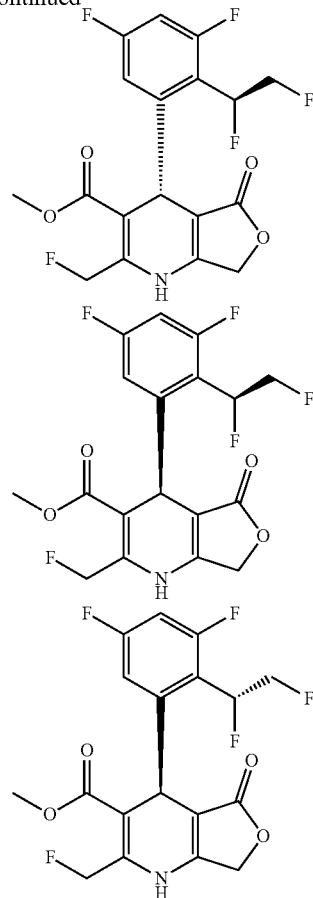

Title compound was synthesized using step 2 of general procedure I (using intermediate from step 8, 1.0 g, 2.03 mmol). Crude product by silica flash chromatography (0→50%) ethyl acetate in petroleum ether afforded the title compound methyl 4-(2-(1,2-difluoroethyl)-3,5-difluorophenyl)-2-(fluoromethyl)-5-oxo-1,4,5,7-tetrahydrofuro[3,4-b]pyridine-3-carboxylate (1.0 g, crude) as an off white solid. Diastereomeric mixture was separated into its two isomers using silica flash chromatography (0→80%) to give 70 mg of first diastereomer as a white solid and 50 mg of second diastereomer as a white solid. Diastereomers from first separation Peak-1: 70 mg and Peak-2: 50 mg were further separated into their enantiomers using preparative chiral SFC [Method 8] to obtain four isomers.

Example 16

25 mg of second eluting enantiomer obtained as a white solid
Chiral HPLC Rt=12.95 min; [chiral analytical method 3]
LCMS Rt=1.52 min; MS m/z 402.2 [M−H]−; [Method 7]
$^1$H NMR (600 MHz, CDCl3) δ 7.29 (d, J=6.8 Hz, 1H), 6.80-6.69 (m, 2H), 6.41 (dd, J=48.5, 17.2 Hz, 1H), 5.80 (s, 1H), 5.72 (s, 1H), 5.36-4.69 (m, 5H), 3.59 (s, 3H).

Example 16b 25 mg of first eluting enantiomer obtained as a white solid
Chiral HPLC RT 10.54 min; [chiral analytical method 3]
LCMS Rt=1.52 min; MS m/z 402.0 [M−H]−; [Method 7]

¹H NMR (600 MHz, CDCl3) δ 7.29 (d, J=6.8 Hz, 1H), 6.80-6.69 (m, 2H), 6.41 (dd, J=48.5, 17.2 Hz, 1H), 5.80 (s, 1H), 5.72 (s, 1H), 5.36-4.69 (m, 5H), 3.59 (s, 3H).

Example 16c 15 mg of third eluting enantiomer as a white solid

Chiral HPLC Rt=14.54 min; [chiral analytical method 3]

LCMS Rt=1.472 min; MS m/z 402.0 [M–H]–; [Method 7]

¹H NMR (400 MHz, CD3OD) δ 6.92-6.80 (m, 2H), 6.70-6.48 (m, 1H), 5.76 (s, 1H), 5.64 (s, 1H), 5.48 (s, 1H), 5.16 (s, 1H), 5.15-4.51 (m, 4H), 3.55 (s, 3H).

Example 16d 15 mg of fourth eluting enantiomer as a white solid

Chiral HPLC Rt=18.97 min; [chiral analytical method 3]

LCMS Rt=1.466 min; MS m/z 402.2 [M–H]–; [Method 7]

¹H NMR (400 MHz, CD3OD) δ 6.92-6.80 (m, 2H), 6.70-6.48 (m, 1H), 5.76 (s, 1H), 5.64 (s, 1H), 5.48 (s, 1H), 5.16 (s, 1H), 5.15-4.51 (m, 4H), 3.55 (s, 3H).

Example 17: methyl (R)-4-(3-fluoro-2-(trifluoromethyl)phenyl)-2-(fluoromethyl)-5-oxo-1,4,5,7-tetrahydrofuro[3,4-b]pyridine-3-carboxylate

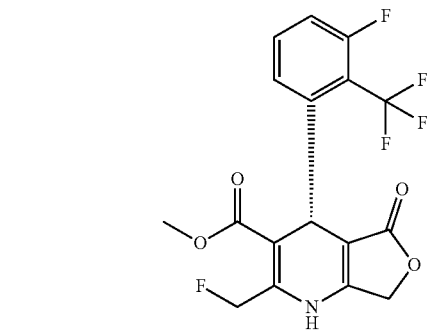

Step 1: 3-ethyl 5-methyl 2-(acetoxymethyl)-4-(3-fluoro-2-(trifluoromethyl)phenyl)-6-(fluoromethyl)-1,4-dihydropyridine-3,5-dicarboxylate

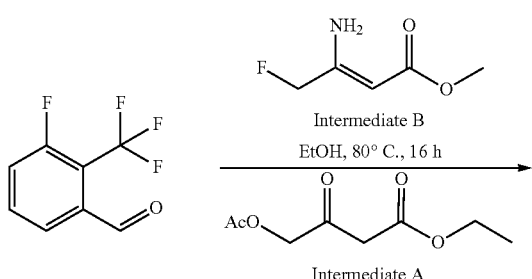

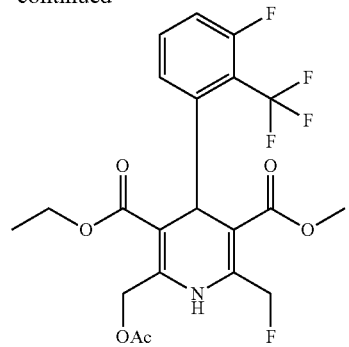

Title compound was synthesized using general procedure I (using commercially available 3-fluoro-2-(trifluoromethyl)benzaldehyde, 1.4 g, 7.28 mmol) to give 3-ethyl 5-methyl 2-(acetoxymethyl)-4-(3-fluoro-2-(trifluoromethyl)phenyl)-6-(fluoromethyl)-1,4-dihydropyridine-3,5-dicarboxylate (2 g, crude). Without further purification and analysis, the product was used for the next step.

Step 2: methyl 4-(3-fluoro-2-(trifluoromethyl)phenyl)-2-(fluoromethyl)-5-oxo-1,4,5,7-tetrahydrofuro[3,4-b]pyridine-3-carboxylate

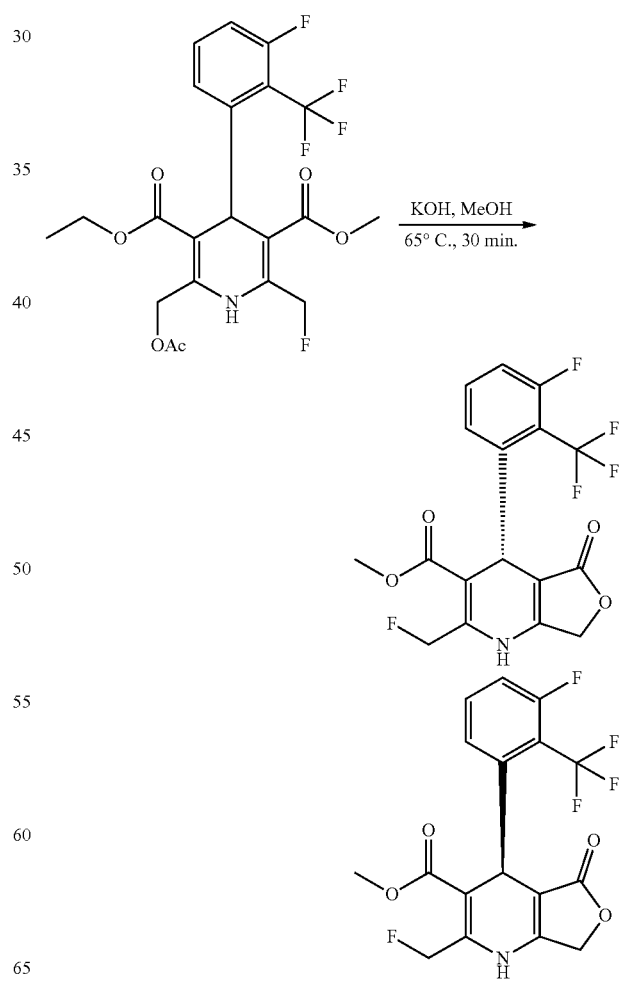

Title compound was synthesized using step 2 of general procedure I (from step 2, 2 g, 4.18 mmol). Crude product purification by silica flash chromatography (0→70%) ethyl acetate in petroleum ether afforded the title compound methyl 4-(3-fluoro-2-(trifluoromethyl)phenyl)-2-(fluoromethyl)-5-oxo-1,4,5,7-tetrahydrofuro[3,4-b]pyridine-3-carboxylate (240 mg) as an off white solid. Racemic mixture was separated into its enantiomers using preparative chiral HPLC [method 5].

Example 17

80 mg of first eluting enantiomer as a white solid, 33% yield.

Chiral HPLC Rt=7.549 min; [chiral analytical method 1]
LCMS Rt=1.485 min; MS m/z 390.1 [M+H]+; [Method 7]
$^1$H NMR (600 MHz, CD3OD) δ 7.62-7.46 (m, 1H), 7.35-7.30 (m, 1H), 7.20-7.02 (m, 1H), 5.75-5.69 (m, 1H), 5.68-5.60 (m, 1H), 5.58-5.50 (m, 1H), 4.84 (d, J=5.1 Hz, 2H), 3.47 (s, 3H).

Example 18: methyl (R)-4-(2-(difluoromethyl)-3,5-difluorophenyl)-2-(fluoromethyl)-5-oxo-1,4,5,7-tetrahydrofuro[3,4-b]pyridine-3-carboxylate

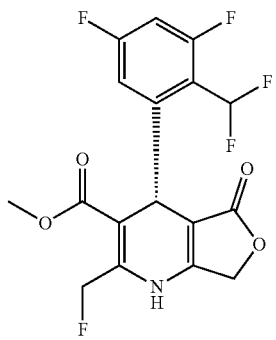

Step 1: 2-(2-bromo-3,5-difluorophenyl)-1,3-dioxolane

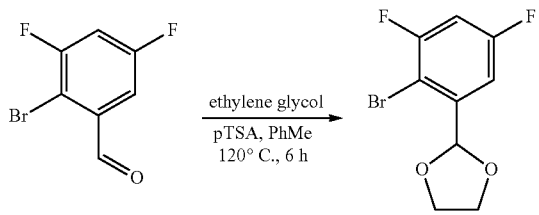 [SMILES: O=Cc1cc(F)cc(F)c1Br ; Fc1cc(F)c(Br)c(C2OCCO2)c1]

The title compound was synthesized following a procedure similar to step 1 of example 1 using 15 g of 2-bromo-3,5-difluorobenzaldehyde obtained 15.4 g of 2-(2-bromo-3,5-difluorophenyl)-1,3-dioxolane.

$^1$H NMR (300 MHz, CDCl$_3$) δ 7.20-7.15 (m, 1H), 6.49-6.87 (m, 1H), 6.08 (s, 1H), 4.17-4.04 (m, 4H).

Step 2: 2-(3,5-difluoro-2-vinylphenyl)-1,3-dioxolane

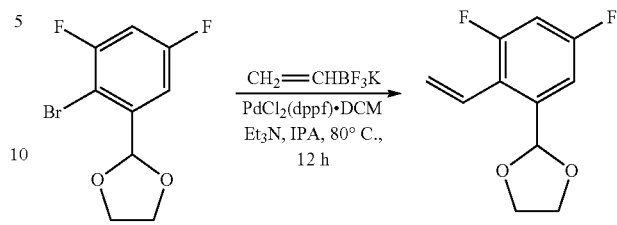

The title compound was synthesized following a procedure similar to step 2 of example 1 using 2-(2-bromo-3,5-difluorophenyl)-1,3-dioxolane giving 2-(3,5-difluoro-2-vinylphenyl)-1,3-dioxolane (3.0 g). $^1$H NMR (300 MHz, CDCl$_3$) δ 7.20-7.16 (m, 1H), 6.94-6.83 (m, 1H), 6.82 (dd, J=17.7, 11.7 Hz, 1H), 5.60 (dd, J=1.2, 11.7 Hz, 1H), 5.66-5.60 (m, 1H), 5.95 (s, 1H), 4.18-4.02 (m, 4H).

Step 3: 2-(1,3-dioxolan-2-yl)-4,6-difluorobenzaldehyde

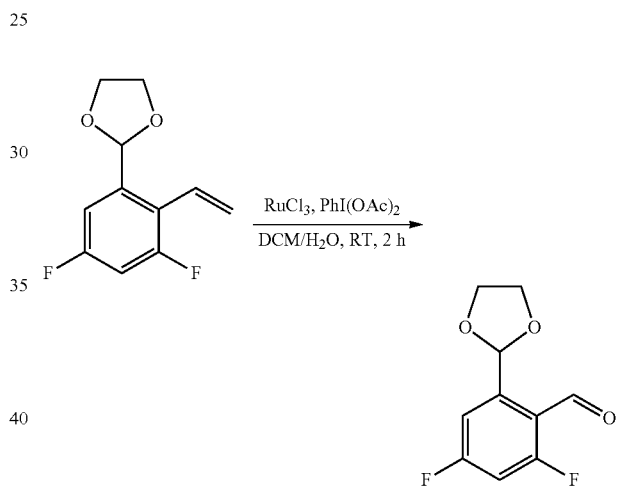

The title compound was synthesized following a procedure similar to step 1 of example 5 giving 2 2-(1,3-dioxolan-2-yl)-4,6-difluorobenzaldehyde (1.0 g).
$^1$H NMR (300 MHz, CDCl$_3$) δ 10.41 (s, 1H), 7.35 (d, J=9.6 Hz, 1H), 6.95-6.85 (m, 1H), 6.53 (s, 1H), 4.08 (s, 4H).

Step 4: 2-(2-(difluoromethyl)-3,5-difluorophenyl)-1,3-dioxolane

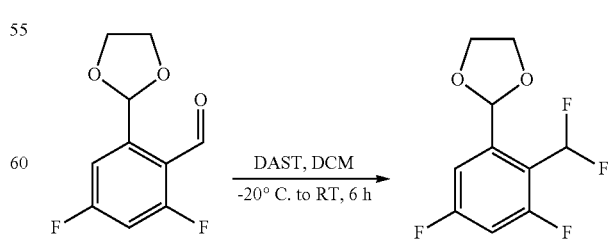

The title compound was synthesized following a procedure similar to step 3 of example 5 giving 2-(2-(difluoromethyl)-3,5-difluorophenyl)-1,3-dioxolane (570 mg)

$^1$H NMR (300 MHz, CDCl3) δ 7.29-7.25 (m, 1H), 7.06 (t, J=1.1 Hz, 1H), 6.95-6.84 (m, 1H), 6.13 (t, J=1.2 Hz, 1H), 4.30-3.86 (m, 4H).

Step 5: 2-(difluoromethyl)-3,5-difluorobenzaldehyde

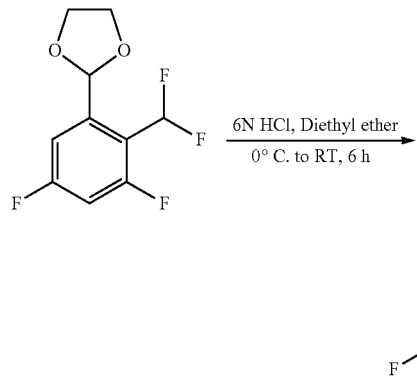

To a solution of 2-(2-(difluoromethyl)-3,5-difluorophenyl)-1,3-dioxolane (from step 4, 570 mg, 2.41 mmol) in diethyl ether (10 mL) was added 6N HCl (10 mL) at 0° C. The resulting reaction mixture was stirred at room temperature for 6 hrs. Reaction mixture was extracted into diethyl ether (50 mL) and washed with water (30 mL). Organic phase was washed with saturated NaHCO$_3$ solution (30 mL), brine (30 mL) and dried over Na$_2$SO$_4$. The solvent was removed under reduced pressure resulting in crude compound 2-(difluoromethyl)-3,5-difluorobenzaldehyde (360 mg) as a colorless liquid.

$^1$H NMR (300 MHz, CDCl3) δ 10.42 (s, 1H), 7.74-7.54 (m, 1H), 7.25 (dd, J=46.8, 10.4 Hz, 1H), 7.15-7.10 (m, 1H).

Step 6: 3-ethyl 5-methyl 2-(acetoxymethyl)-4-(2-(difluoromethyl)-3,5-difluorophenyl)-6-(fluoromethyl)-1,4-dihydropyridine-3,5-dicarboxylate

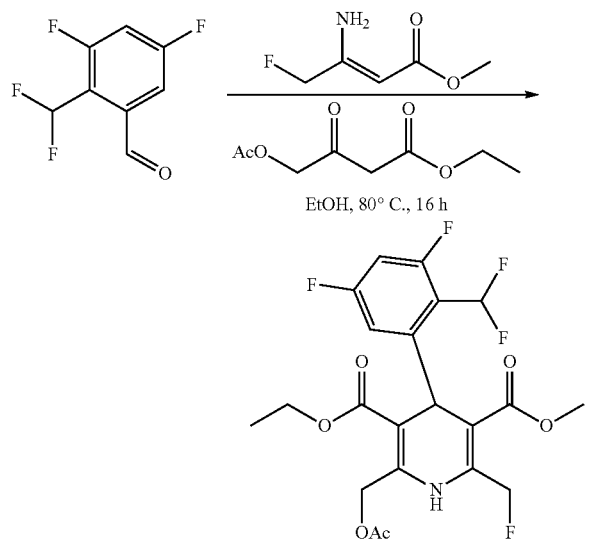

Title compound was synthesized using step 1 of general procedure I (using the aldehyde from step 5, 360 mg, 1.87 mmol) to give 3-ethyl 5-methyl 2-(acetoxymethyl)-4-(2-(difluoromethyl)-3,5-difluorophenyl)-6-(fluoromethyl)-1,4-dihydropyridine-3,5-dicarboxylate (720 mg, crude).

LCMS Rt=1.698 min; MS m/z 476.1 [M–H]–; [Method 7]

Step 7: methyl 4-(2-(difluoromethyl)-3,5-difluorophenyl)-2-(fluoromethyl)-5-oxo-1,4,5,7-tetrahydrofuro[3,4-b]pyridine-3-carboxylate

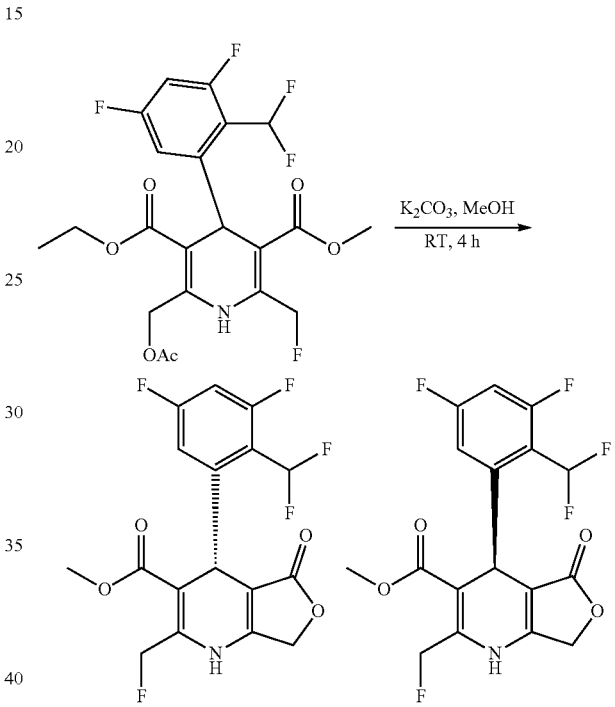

Title compound was synthesized using step 2 of general procedure I (using intermediate from step 6, 720 mg, 1.50 mmol). Crude product purification by silica flash chromatography (0→70%) ethyl acetate in petroleum ether afforded the title compound methyl 4-(2-(difluoromethyl)-3,5-difluorophenyl)-2-(fluoromethyl)-5-oxo-1,4,5,7-tetrahydrofuro[3,4-b]pyridine-3-carboxylate (120 mg) as an off white solid. Racemic mixture was separated into its enantiomers using chiral preparative HPLC [method 7].

Example 18

30 mg of first eluting enantiomer obtained as a white solid, 25% yield.

Chiral HPLC Rt=17.629 min; [chiral analytical method 1]

LCMS Rt=1.454 min; MS m/z 388.2 [M–H]–; [Method 7]

$^1$H NMR (400 MHz, CD3OD) δ 7.40-7.38 (m, 1H), 6.93 (dd, J=10.3, 7.6 Hz, 2H), 5.77 (d, J=0.8 Hz, 1H), 5.65 (d, J=0.7 Hz, 1H), 5.27 (d, J=1.6 Hz, 1H), 4.89-4.86 (m, 2H), 3.51 (s, 3H).

Example 18b 36 mg of second eluting enantiomer obtained as a white solid, 30% yield.

Chiral HPLC Rt=19.634 min; [chiral analytical method 1]

LCMS Rt=1.454 min; MS m/z 388.0 [M−H]−; [Method 7]

¹H NMR (400 MHz, CD3OD) δ 7.40-7.38 (m, 1H), 6.93 (dd, J=10.3, 7.6 Hz, 2H), 5.77 (d, J=0.8 Hz, 1H), 5.65 (d, J=0.7 Hz, 1H), 5.27 (d, J=1.6 Hz, 1H), 4.89-4.86 (m, 2H), 3.51 (s, 3H).

Example 19: methyl (R)-4-(2-(difluoromethoxy)-3-fluorophenyl)-2-(fluoromethyl)-5-oxo-1,4,5,7-tetrahydrofuro[3,4-b]pyridine-3-carboxylate

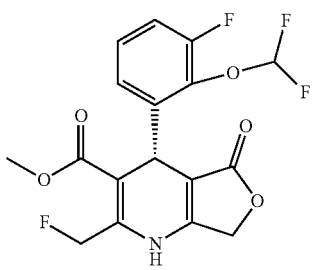

Title compound was prepared using general procedure II using commercially available 2-(difluoromethoxy)-3-fluorobenzaldehyde (249 mg, 1.311 mmol). Crude was purified by automated flash column chromatography eluting with 0-100% gradient of EtOAc in heptane on a 24 g Si-column and further purified by mass directed reverse phase prep chromatography; Conditions: Xbridge C18 OBD 30×50 mm 5 um column ACN/H2O w/NH3OH 5 mL/min 1.5 mL injection. The racemate was separated into its individual enantiomers using chiral SFC (Mobile Phase: 5-25% MeOH in C02 80 g/min; Column: (RR) Whelk-O1 21×250 mm).

Example 19

8.6 mg of second eluting enantiomer (4%)

Chiral SFC Rt=2.61 min (Mobile Phase: 5-55% MeOH in Column: (RR) Whelk-O1 4.6×100 mm 5 um column; 6 mins run)

LCMS Rt=1.94 min; MS m/z 388.2 [M+H]+; [Method 4]

¹H NMR (400 MHz, Methylene Chloride-d2) δ 7.46 (d, J=6.8 Hz, 1H), 7.29-7.05 (m, 3H), 6.93 (t, J=74.16 Hz, 1H), 5.88-5.56 (m, 2H), 5.23 (s, 1H), 4.81 (s, 2H), 3.57 (s, 3H).

Example 19b 9.5 mg of first eluting enantiomer (4%)

Chiral SFC Rt=2.41 min (Mobile Phase: 5-55% MeOH in Column: (RR) Whelk-O1 4.6×100 mm 5 um column; 6 mins run)

LCMS Rt=1.90 min; MS m/z 388.2 [M+H]+; [Method 4]

¹H NMR (400 MHz, Methylene Chloride-d2) δ 7.46 (d, J=6.8 Hz, 1H), 7.29-7.05 (m, 3H), 6.93 (t, J=74.16 Hz, 1H), 5.88-5.56 (m, 2H), 5.23 (s, 1H), 4.81 (s, 2H), 3.57 (s, 3H).

Example 20: methyl (R)-4-(2-(difluoromethoxy)-5-fluorophenyl)-2-(fluoromethyl)-5-oxo-1,4,5,7-tetrahydrofuro[3,4-b]pyridine-3-carboxylate

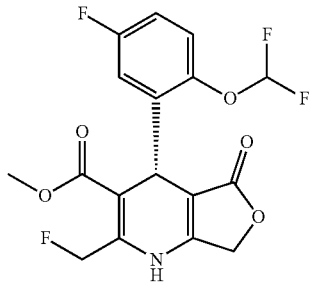

Title compound was prepared using general procedure II using commercially available 2-(difluoromethoxy)-5-fluorobenzaldehyde (229 mg, 1.206 mmol). Crude was purified by automated flash column chromatography eluting with 0-100% gradient of EtOAc in heptane on a 24 g Si-column and further purified by mass directed reverse phase prep chromatography; Conditions: Xbridge C18 OBD 30×50 mm 5 um column ACN/H2O w/NH3OH 5 mL/min 1.5 mL injection. The racemate was separated into its individual enantiomers using chiral SFC (Mobile Phase: 5-25% MeOH in C02 80 g/min; Column: (RR) Whelk-O1 21×250 mm).

Example 20

10 mg of second eluting enantiomer

Chiral SFC Rt=2.51 min (Mobile Phase: 5-55% MeOH in Column: (RR) Whelk-O1 4.6×100 mm 5 um column; 6 mins run)

LCMS Rt=1.91 mins; MS m/z 388.1 [M+H]+; [Method 4]

¹H NMR (400 MHz, DMSO-d₆) δ 10.11 (d, J=3.3 Hz, 1H), 7.32-6.85 (m, 4H), 5.79-5.65 (m, 1H), 5.65-5.48 (m, 1H), 5.05 (s, 1H), 4.83 (s, 2H), 3.45 (s, 3H).

Example 20b 12 mg of first eluting enantiomer

Chiral SFC Rt=2.31 min (Mobile Phase: 5-55% MeOH in Column: (RR) Whelk-O1 4.6×100 mm 5 um column; 6 mins run)

LCMS Rt=1.91 mins; MS m/z 388.0 [M+H]+; [Method 4]

¹H NMR (400 MHz, DMSO-d₆) δ 10.11 (d, J=2.0 Hz, 1H), 7.33-6.80 (m, 4H), 5.77-5.65 (m, 1H), 5.64-5.51 (m, 1H), 5.05 (s, 1H), 4.83 (s, 2H), 3.45 (s, 3H).

Example 21: methyl (R)-4-(2-cyclopropyl-5-fluorophenyl)-2-(fluoromethyl)-5-oxo-1,4,5,7-tetrahydrofuro[3,4-b]pyridine-3-carboxylate

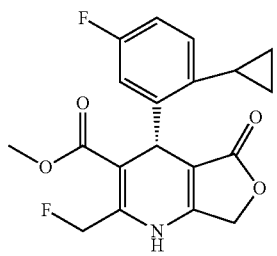 [SMILES: COC(=O)C1=C(CF)NC2=C(C(=O)OC2)[C@H]1c1cc(F)ccc1C1CC1]

Step 1: 2-cyclopropyl-5-fluorobenzaldehyde

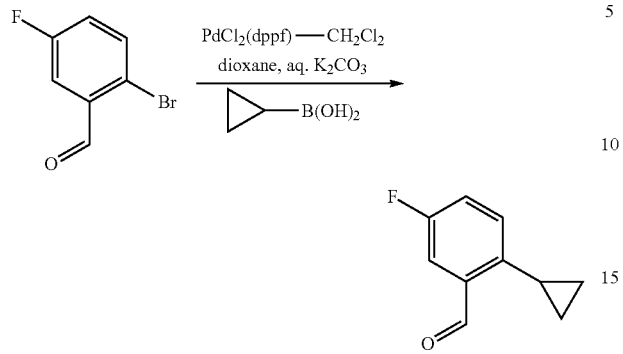

A degassed solution of 2-bromo-5-fluorobenzaldehyde (2.03 g, 10.00 mmol), cyclopropane boronic acid (1.031 g, 12.00 mmol), and $PdCl_2(dppf)$-$CH_2Cl_2$ adduct (0.817 g, 1.000 mmol) in dioxane (20 mL) and 2.0 M aq. $K_2CO_3$ (10.00 mL, 20.00 mmol) was stirred and heated to 80° C. At completion, the reaction mixture was cooled to room temperature then partitioned between water and ethyl acetate. The organics phase was washed with water and brine, then dried over $MgSO_4$ and concentrated. The crude was purified by silica flash chromatography [0-20% Ethyl acetate in heptane] to provide 800 mg of title compound, 49% yield. Crude product was taken on without further purification.

Step 2: methyl 4-(2-cyclopropyl-5-fluorophenyl)-2-(fluoromethyl)-5-oxo-1,4,5,7-tetrahydrofuro[3,4-b]pyridine-3-carboxylate

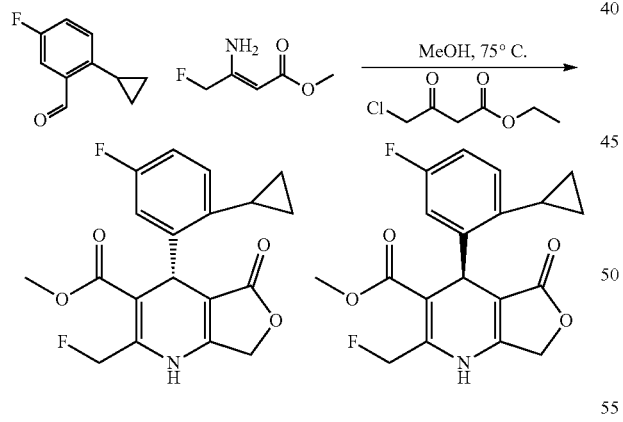

The title compound was prepared according to general procedure II from ethyl 4-chloro-3-oxobutanoate (346 mg, 2.10 mmol), 2-cyclopropyl-5-fluorobenzaldehyde (345 mg, 2.10 mmol) prepared in step 1, and methyl (Z)-3-amino-4-fluorobut-2-enoate (Intermediate B, 280 mg, 2.10 mmol). Racemic methyl 4-(2-cyclopropyl-5-fluorophenyl)-2-(fluoromethyl)-5-oxo-1,4,5,7-tetrahydrofuro[3,4-b]pyridine-3-carboxylate was separated into its enantiomers using chiral SFC (Mobile Phase: 25% Methanol with 0.2% $NH_4OH/CO_2$ at 80 g/min; Column: (SS) Whelk-O1 4.6×100 mm).

Example 21

21.4 mg First eluting enantiomer as a white solid (5.6%).
Chiral SFC Rt=2.41 min (Mobile Phase: 5-55% MeOH w/10 mM $NH_4OH/CO2$ 5 mL/min 120 bar;
Column: (SS) Whelk-O1 4.6×100 mm 5 μm).
LCMS Rt=0.95 min; MS m/z 362.5 [M+H]+; [Method 4].
$^1$H NMR (400 MHz, DMSO-d6) δ ppm 10.08 (s, 1H), 7.08-6.95 (m, 1H), 6.93-6.82 (m, 2H), 5.78-5.58 (m, 2H), 5.37 (s, 1H), 4.90-4.77 (m, 2H), 3.45 (s, 3H), 1.00-0.80 (m, 3H), 0.54-0.46 (m, 1H). Benzylic CH on cyclopropyl is hidden under DMSO peak.

Example 21b 10.3 mg Second eluting enantiomer as a white solid (2.7%).
Chiral SFC Rt=2.69 min (Mobile Phase: 5-55% MeOH w/10 mM $NH_4OH/CO2$ 5 mL/min 120 bar;
Column: (SS) Whelk-O1 4.6×100 mm 5 μm).
LCMS Rt=0.95 min; MS m/z 362.5 [M+H]+; [Method 4].
$^1$H NMR (400 MHz, DMSO-d6) δ ppm 10.08 (s, 1H), 7.08-6.95 (m, 1H), 6.93-6.82 (m, 2H), 5.78-5.58 (m, 2H), 5.37 (s, 1H), 4.90-4.77 (m, 2H), 3.45 (s, 3H), 1.00-0.80 (m, 3H), 0.54-0.46 (m, 1H).

Example 22: methyl (R)-4-(2-cyclopropylphenyl)-2-(fluoromethyl)-5-oxo-1,4,5,7-tetrahydrofuro[3,4-b]pyridine-3-carboxylate

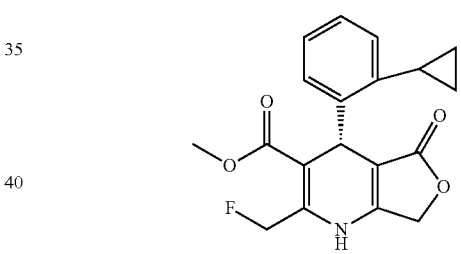

Step 1: 2-cyclopropylbenzaldehyde

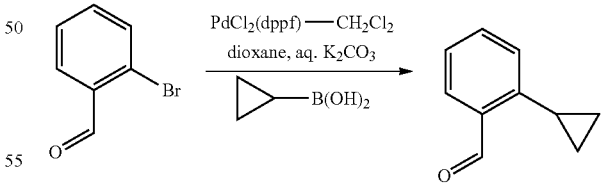

A degassed solution of the 2-bromobenzaldehyde (1 g, 5.40 mmol), cyclopropane boronic acid (0.557 g, 6.49 mmol), PdCl2 (dppf).CH2Cl2 adduct (0.441 g, 0.540 mmol) in Dioxane (15 mL) and 2.0 M aq K2CO3 (5.40 mL, 10.81 mmol) was stirred and heated to 80° C. At completion, the reaction mixture was cooled to room temperature then partitioned between water and ethyl acetate. The organics phase was washed with water and brine, then dried over MgSO4 and concentrated. The crude was purified by silica flash chromatography [0-20% Ethyl acetate in heptane] to provide 420 mg of the title compound, 53% yield. Crude product was taken on without further purification.

Step 2: methyl 4-(2-cyclopropylphenyl)-2-(fluoromethyl)-5-oxo-1,4,5,7-tetrahydrofuro[3,4-b]pyridine-3-carboxylate

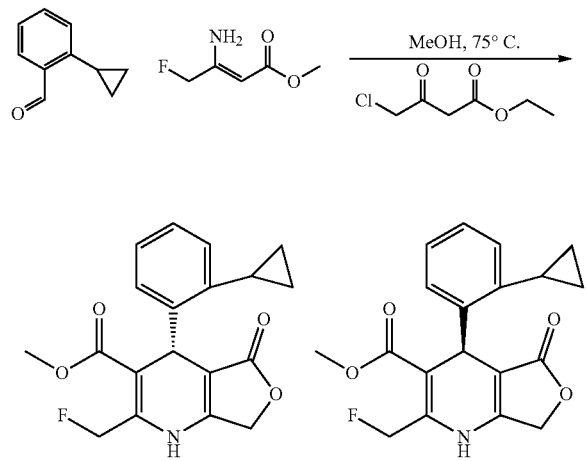

The title compound was prepared according to general procedure II from ethyl 4-chloro-3-oxobutanoate (0.204 mL, 1.500 mmol) 2-cyclopropylbenzaldehyde (219 mg, 1.5 mmol) prepared in step 1 and methyl (Z)-3-amino-4-fluorobut-2-enoate (Intermediate B, 200 mg, 1.50 mmol). Racemic methyl-4-(2-cyclopropyl phenyl)-2-(fluoromethyl)-5-oxo-1,4,5,7-tetrahydrofuro[3,4-b]pyridine-3-carboxylate was separated into its enantiomers using chiral SFC (Mobile Phase: 5-55% Methanol with 10 mM NH$_4$OH/CO$_2$ at 3 mL/min; Column: (SS) WHO; 1 4.6×100 mm).

Example 22

7.9 mg First eluting enantiomer as a white solid (3.0%).
Chiral SFC Rt=2.77 min
LCMS Rt=0.93 min; MS m/z 344.5 [M+H]+; [Method 4].
$^1$H NMR (400 MHz, METHANOL-d4) δ ppm 6.91-7.23 (m, 4H), 5.73 (d, J=1.96 Hz, 1H), 5.61 (d, J=2.93 Hz, 1H), 5.48 (s, 1H), 4.82 (s, 2H), 3.50 (s, 3H), 2.53-2.65 (m, 1H), 0.86-0.99 (m, 3H), 0.58 (d, J=5.87 Hz, 1H).

Example 22b 7.5 mg Second eluting enantiomer as a white solid (2.9%).
Chiral SFC Rt=3.19 min
LCMS Rt=0.93 min; MS m/z 344.5 [M+H]+; [Method 4].
$^1$H NMR (400 MHz, METHANOL-d4) δ ppm 6.91-7.23 (m, 4H), 5.73 (d, J=1.96 Hz, 1H), 5.61 (d, J=2.93 Hz, 1H), 5.48 (s, 1H), 4.82 (s, 2H), 3.50 (s, 3H), 2.53-2.65 (m, 1H), 0.86-0.99 (m, 3H), 0.58 (d, J=5.87 Hz, 1H).

Example 23: Methyl (R)-4-(5-fluoro-2-(trifluoromethyl)phenyl)-2-(fluoromethyl)-5-oxo-1,4,5,7-tetrahydrofuro[3,4-b]pyridine-3-carboxylate

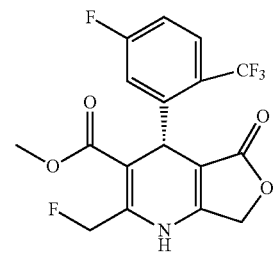 [SMILES: COC(=O)C1=C(CF)NC2=C(C(=O)OC2)[C@H]1c1cc(F)ccc1C(F)(F)F]

The title compound was prepared according to general procedure II from ethyl 4-chloro-3-oxobutanoate (0.318 mL, 2.342 mmol), commercially available 5-fluoro-2-(trifluoromethyl) benzaldehyde (450 mg, 2.342 mmol) and methyl (Z)-3-amino-4-fluorobut-2-enoate (Intermediate B, 312 mg, 2.342 mmol). Racemic methyl 4-(5-fluoro-2-(trifluoromethyl)phenyl)-2-(fluoromethyl)-5-oxo-1,4,5,7-tetrahydrofuro[3,4-b]pyridine-3-carboxylate was separated into its enantiomers using chiral SFC (Mobile Phase: 15% Methanol with 0.2% Ammonium Hydroxide/CO$_2$ at 80 g/min; Column: 2.0×25.0 cm ChromegaChiral CC4).

Example 23

12.2 mg First eluting enantiomer as a white solid (2.7%).
Chiral SFC Rt=1.29 min (Column: 4.6×100 mm Chiralcel OZ—H; isocratic 15% Methanol with 0.1% Isopropylamine; 125 bar
LCMS Rt=0.92 min; MS m/z 390.0 [M+H]+; [Method 4].
$^1$H NMR (400 MHz, DMSO-d$_6$) δ ppm 10.16 (br s, 1H), 7.70 (dd, J=8.80, 5.38 Hz, 1H), 7.20-7.30 (m, 2H), 5.72 (s, 1H), 5.60 (s, 1H), 5.20 (s, 1H), 4.74-4.91 (m, 2H), 3.38 (s, 3H).

Example 23b 14.0 mg Second eluting enantiomer as a white solid (3.0%).
Chiral SFC Rt=1.74 min (Column: 4.6×100 mm Chiralcel OZ—H; isocratic 15% Methanol with 0.1% Isopropylamine; 125 bar)
LCMS Rt=0.92 min; MS m/z 390.0 [M+H]+; [Method 4].
$^1$H NMR (400 MHz, DMSO-d$_6$) δ ppm 10.16 (br s, 1H), 7.70 (dd, J=8.80, 5.38 Hz, 1H), 7.20-7.30 (m, 2H), 5.72 (s, 1H), 5.60 (s, 1H), 5.20 (s, 1H), 4.74-4.91 (m, 2H), 3.38 (s, 3H).

Example 24: Methyl (R)-2-(fluoromethyl)-5-oxo-4-(2-(trifluoromethyl)phenyl)-1,4,5,7-tetrahydrofuro[3,4-b]pyridine-3-carboxylate

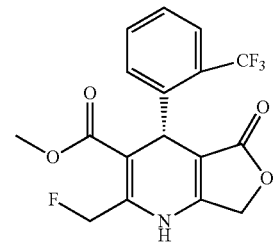 [SMILES: COC(=O)C1=C(CF)NC2=C(C(=O)OC2)[C@H]1c1ccccc1C(F)(F)F]

The title compound was prepared according to general procedure II from ethyl 4-chloro-3-oxobutanoate (0.286 mL, 2.10 mmol), commercially available 2-trifluoromethylbenzaldehyde (366 mg, 2.10 mmol) and methyl (Z)-3-amino-4-fluorobut-2-enoate (Intermediate B, 280 mg, 2.10 mmol). Racemic methyl 2-(fluoromethyl)-5-oxo-4-(2-(trifluoromethyl)phenyl)-1,4,5,7-tetrahydrofuro[3,4-b]pyridine-3-carboxylate was separated into its enantiomers using chiral SFC (Mobile Phase: 20% Methanol with 0.2% Ammonium Hydroxide at 80 g/min; Column: 2.0×25.0 cm Chromega-Chiral CC4).

Example 24

7.9 mg First eluting enantiomer as a white solid (2.0%).
Chiral SFC Rt=1.19 min (Mobile Phase: 20% Methanol with 0.1% Isopropylamine/$CO_2$ at 4 mL/min;
Column: Chiralcel OZ—H; 1 4.6×100 mm).
LCMS Rt=0.91 min; MS m/z 370.0 [M+H]+; [Method 4].
$^1$H NMR (400 MHz, DMSO-$d_6$) δ ppm 10.12 (br s, 1H), 7.60 (d, J=7.82 Hz, 2H), 7.49 (d, J=7.83 Hz, 1H), 7.31-7.42 (m, 1H), 5.70 (s, 1H), 5.58 (s, 1H), 5.19 (s, 1H), 4.81 (s, 2H), 3.37 (s, 3H).

Example 24b 9.3 mg Second eluting enantiomer as a white solid (2.4%).
Chiral SFC Rt=1.72 min (Mobile Phase: 20% Methanol with 0.1% Isopropylamine/$CO_2$ at 4 mL/min;
Column: Chiralcel OZ—H; 1 4.6×100 mm).
LCMS Rt=0.91 min; MS m/z 370.0 [M+H]+; [Method 4].
$^1$H NMR (400 MHz, DMSO-$d_6$) δ ppm 10.12 (br s, 1H), 7.60 (d, J=7.82 Hz, 2H), 7.49 (d, J=7.83 Hz, 1H), 7.31-7.42 (m, 1H), 5.70 (s, 1H), 5.58 (s, 1H), 5.19 (s, 1H), 4.81 (s, 2H), 3.37 (s, 3H).

Example 25: Methyl (R)-4-(3-fluoro-2-(2,2,2-trifluoroethyl)phenyl)-2-(fluoromethyl)-5-oxo-4,5,6,7-tetrahydro-1H-cyclopenta[b]pyridine-3-carboxylate

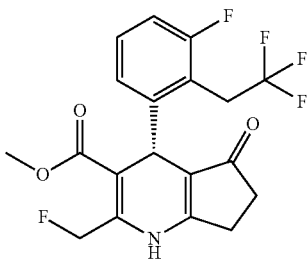 [SMILES: COC(=O)C1=C(CF)NC2=C(C(=O)CC2)[C@H]1c1cccc(F)c1CC(F)(F)F]

Step 1: 2-(2-bromo-3-fluorophenyl)-1,3-dioxolane

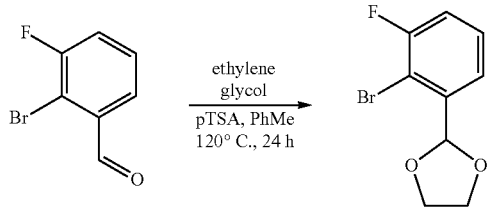 [SMILES: O=Cc1cccc(F)c1Br ; Fc1cccc(C2OCCO2)c1Br]

To a solution of 2-bromo-3-fluorobenzaldehyde (60 g, 295.56 mmol) and ethylene glycol (65.4 mL, 1182.2 mmol) in toluene (600 mL) was added p-toluenesulfonic acid monohydrate (28.11 g, 147.78 mmol). The resulting solution was stirred at 120° C. for 24 hrs using dean-stark apparatus. The solvent was added to water (2 L) and extracted into EtOAc (3 L). EtOAc was washed with saturated $NaHCO_3$ solution (1 L), brine and dried over $Na_2SO_4$. The solvent was removed under reduced pressure and purification of the crude product by silica flash chromatography (0→10%) ethyl acetate in petroleum ether afforded the title compound 2-(2-bromo-3-fluorophenyl)-1,3-dioxolane (60 g) as a colorless liquid.
$^1$H NMR (400 MHz, $CDCl_3$) δ 7.42-7.37 (m, 1H), 7.34-7.29 (m, 1H), 7.16-7.10 (m, 1H), 6.10 (s, 1H), 4.19-4.09 (m, 4H).

Step 2: 2-(1,3-dioxolan-2-yl)-6-fluorobenzaldehyde

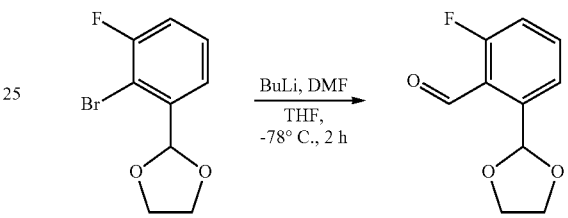

To a solution of 2-(2-bromo-3-fluorophenyl)-1,3-dioxolane (from step 1, 7 g, 28.45 mmol) in THF (70 mL) under nitrogen atmosphere was cooled to −78° C. Then n-butyllithium in n-Hexane solution (13.66 mL, 2.5M, 58.5 mmol) was added over 10 min. The resulting mixture was stirred for 45 min at −78° C., then DMF (2.5 g, 34.15 mmol) was added and resulting mixture stirred for 1.15 h at −78° C. The reaction mixture was quenched with saturated ammonium chloride solution (50 mL) and extracted with ethyl acetate (2×100 mL). Combined organic phases were washed with water (50 mL), followed by brine (50 mL) and dried over $Na_2SO_4$. The solvent was removed under reduced pressure and purification of the crude product by silica flash chromatography (0→50%) ethyl acetate in petroleum ether afforded the title compound 2-(1,3-dioxolan-2-yl)-6-fluorobenzaldehyde (5 g) as a colorless liquid.
$^1$H NMR (300 MHz, Chloroform-d) δ 10.52 (s, 1H), 7.67-7.53 (m, 2H), 7.22-7.12 (m, 1H), 6.50 (s, 1H), 4.27-3.99 (m, 4H).

Step 3: 2-(2-(2,2-difluorovinyl)-3-fluorophenyl)-1,3-dioxolane

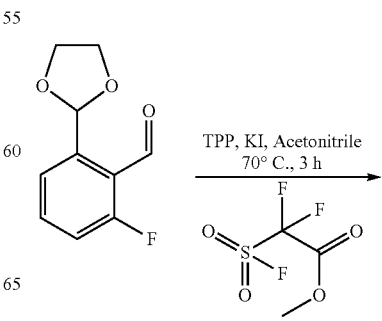

-continued

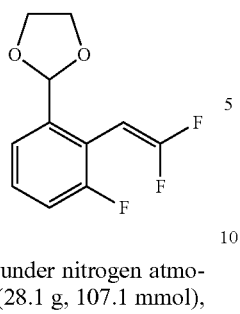

To solution of acetonitrile (65 mL) under nitrogen atmosphere was added triphenylphosphine (28.1 g, 107.1 mmol), potassium iodide (11.85 g, 71.4 mmol) and 2-(1,3-dioxolan-2-yl)-6-fluorobenzaldehyde (from step 2, 7 g, 35.7 mmol). Reaction stirred for 30 min at 70° C., then methyl 2,2-difluoro-2-(fluorosulfonyl)acetate (12 g, 62.4 mmol) was added slowly over a period of 10 min (mass color was turned to yellow while addition). Resulting mixture was stirred for another 3 hrs at 70° C., then cooled to room temperature, diluted with diethyl ether, precipitated solids were removed by filtration and washed with diethyl ether (100 mL). The resulting solvent was removed under reduced pressure and purification of the crude product by silica flash chromatography (0→5%) ethyl acetate in petroleum ether afforded the title compound 2-(2-(2,2-difluorovinyl)-3-fluorophenyl)-1,3-dioxolane (6.9 g) as a light yellow liquid.

$^1$H NMR (300 MHz, Chloroform-d) δ 7.39 (dd, J=7.8, 1.4 Hz, 1H), 7.31 (m, 1H), 7.11 (m, 1H), 5.87 (s, 1H), 5.39 (m, 1H), 4.21-3.95 (m, 4H).

Step 4: 2-(3-fluoro-2-(2,2,2-trifluoroethyl)phenyl)-1,3-dioxolane

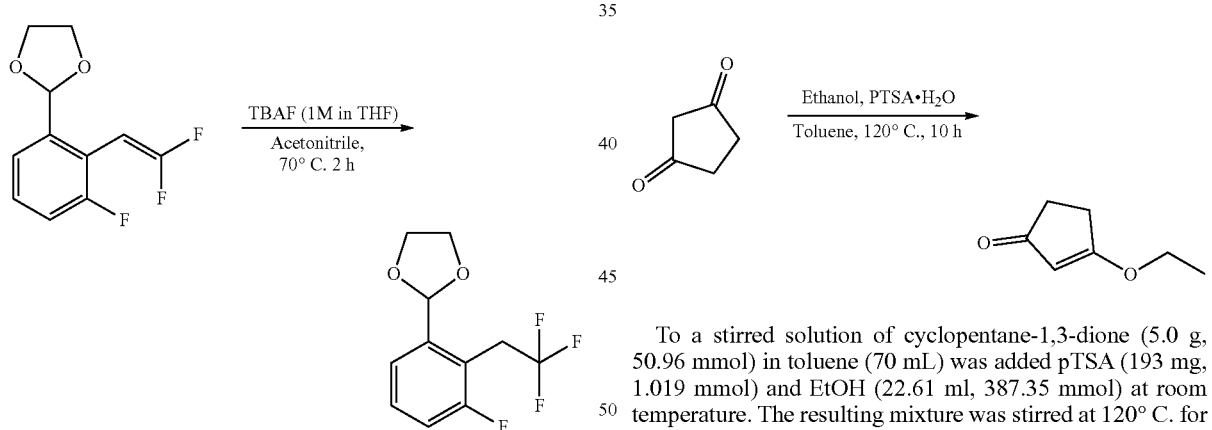

A solution of 2-(2-(2,2-difluorovinyl)-3-fluorophenyl)-1,3-dioxolane (from step 3, 2.7 g, 11.73 mmol) and tetrabutylammonium fluoride in THF (13.7 g, 1M, 13.7 mmol) was heated to 70° C. in closed system for 2 hrs. Reaction was allowed to cool, diluted with diethyl ether and this washed with water (50 mL), saturated NaHCO$_3$ solution (100 mL), and brine and dried over Na$_2$SO$_4$. The solvent was removed under reduced pressure and purification of the crude product by silica flash chromatography (0→10%) ethyl acetate in petroleum ether afforded the title compound 2-(3-fluoro-2-(2,2,2-trifluoroethyl)phenyl)-1,3-dioxolane (1.2 g) as a colorless liquid.

$^1$H NMR (300 MHz, Chloroform-d) δ 7.49-7.42 (m, 1H), 7.35 (m, 1H), 7.17-7.05 (m, 1H), 6.03 (s, 1H), 4.25-3.90 (m, 4H), 3.75 (m, 2H).

Step 5: 3-fluoro-2-(2,2,2-trifluoroethyl)benzaldehyde

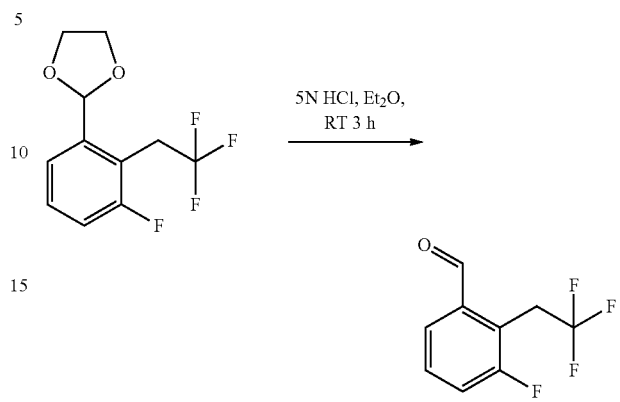

To a solution of 2-(3-fluoro-2-(2,2,2-trifluoroethyl)phenyl)-1,3-dioxolane (from step 4, 2 g, 8.0 mmol) in diethyl ether (40 mL) was added 6N HCl (5 mL). The resulting solution was stirred at room temperature for 3 hrs. This was washed with water (50 mL), saturated NaHCO$_3$ solution (100 mL), brine and dried over Na$_2$SO$_4$. The solvent was removed under reduced pressure and purification of the crude product by silica flash chromatography (0→5%) ethyl acetate in petroleum ether afforded the title compound 3-fluoro-2-(2,2,2-trifluoroethyl)benzaldehyde (1.2 g) as a colorless liquid. The crude product was taken as such to next step without further purification.

Step 6: 3-ethoxycyclopent-2-en-1-one

To a stirred solution of cyclopentane-1,3-dione (5.0 g, 50.96 mmol) in toluene (70 mL) was added pTSA (193 mg, 1.019 mmol) and EtOH (22.61 ml, 387.35 mmol) at room temperature. The resulting mixture was stirred at 120° C. for 10 hrs using Dean-stark apparatus. The solvent was removed under reduced pressure. Crude product was purified by silica flash chromatography (0→50%) ethyl acetate in petroleum ether to afford the title compound 3-ethoxycyclopent-2-en-1-one (4.3 g) as a brown solid.

$^1$H NMR (400 MHz, CDCl3) δ 5.26 (s, 1H), 4.02 (q, J=6.6 Hz, 2H), 2.60-2.55 (m, 2H), 2.44-2.40 (m, 2H), 1.39 (t, J=7.2 Hz, 3H).

Step 7: 3-aminocyclopent-2-en-1-one

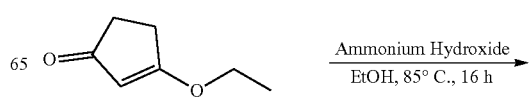

107

-continued

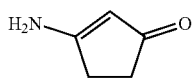

To a stirred solution of 3-ethoxycyclopent-2-en-1-one (from step 6, 4.3 g, 34.08 mmol) in ethanol (50 mL) was added ammonium hydroxide solution (25 mL, 387.35 mmol) at room temperature. The resulting mixture was stirred at 85° C. for 16 hrs. Solvent removal under reduced pressure afforded the title compound 3-aminocyclopent-2-en-1-one (3.2 g) as a brown solid.

LCMS Rt=0.114 min; MS m/z 98.2 [M+H]+; [Method 7]

Step 8: methyl 4-(3-fluoro-2-(2,2,2-trifluoroethyl)phenyl)-2-(fluoromethyl)-5-oxo-4,5,6,7-tetrahydro-1H-cyclopenta[b]pyridine-3-carboxylate

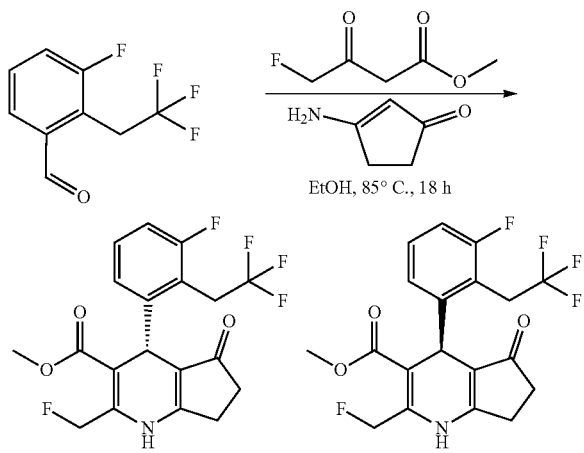

To solution of the aldehyde (from step 5, 200 mg, 0.9708 mmol), methyl 4-fluoro-3-oxobutanoate (method 2, step 1 of intermediate B, 130 mg, 0.9708 mmol) in EtOH (2 mL) was added 3-aminocyclopent-2-en-1-one (from step 7, 94 mg, 0.9708 mmol). The reaction mixture was stirred at 80° C. for 18 hrs. The solvent was removed under reduced pressure. Crude product was purified by silica flash chromatography (0→70%) ethyl acetate in petroleum ether afforded the title compound as an off white solid. Racemic mixture was separated into its enantiomers using chiral preparative HPLC [method 6].

Example 25

Second eluting enantiomer obtained as a white solid (25 mg).

Chiral HPLC Rt=7.610 min; [chiral analytical method 4]

LCMS Rt=1.533 min; MS m/z 401.75 [M+]+; [Method 12]

$^1$H NMR (400 MHz, CD3OD) δ 7.31-7.25 (m, 1H), 7.04 (d, J=8 Hz, 1H), 6.97-6.90 (m, 1H), 5.76 (d, J=3.2 Hz, 1H), 5.64 (d, J=2.8 Hz, 2H), 5.08 (s, 1H), 4.79-4.60 (m, 2H), 3.70-3.55 (m, 2H), 3.44 (s, 3H), 2.66-2.61 (m, 2H).

108

Example 25b

First eluting enantiomer as a white solid (24 mg).

Chiral HPLC Rt 7.103 min; [chiral analytical method 4]

LCMS Rt=1.533 min; MS m/z 401.75 [M+]+; [Method 12]

$^1$H NMR (400 MHz, CD3OD) δ 7.31-7.25 (m, 1H), 7.04 (d, J=8 Hz, 1H), 6.97-6.90 (m, 1H), 5.76 (d, J=3.2 Hz, 1H), 5.64 (d, J=2.8 Hz, 2H), 5.08 (s, 1H), 4.79-4.60 (m, 2H), 3.70-3.55 (m, 2H), 3.44 (s, 3H), 2.66-2.61 (m, 2H).

Example 26: methyl (R)-4-(2-(2,2-difluoroethyl)-3-fluorophenyl)-2-(fluoromethyl)-5-oxo-4,5,6,7-tetrahydro-1H-cyclopenta[b]pyridine-3-carboxylate

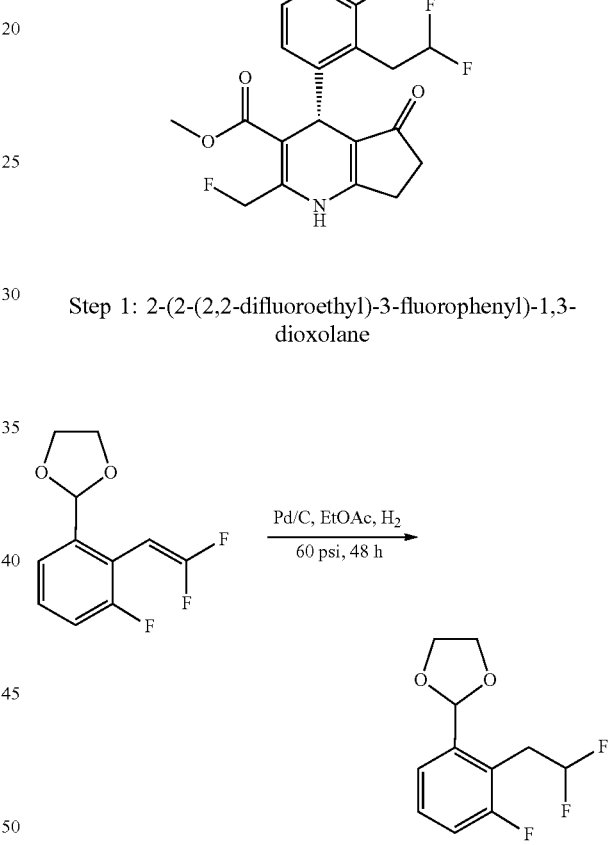

Step 1: 2-(2-(2,2-difluoroethyl)-3-fluorophenyl)-1,3-dioxolane

To a solution of 2-(2-(2,2-difluorovinyl)-3-fluorophenyl)-1,3-dioxolane (from example 25, step 3, 3 g, 13.04 mmol) in ethyl acetate (60 mL) was added 10% Pd—C (1 g). The resulting reaction mixture was kept in Parr-Shaker for 48 hrs at 60 psi of pressure under hydrogen atmosphere at room temperature. The reaction mixture was filtered through a celite pad, washed with ethyl acetate (30 mL). The filtrate was concentrated under reduced pressure and purification of the crude product by silica flash chromatography (0→30%) ethyl acetate in petroleum ether afforded the title compound 2-(2-(2,2-difluoroethyl)-3-fluorophenyl)-1,3-dioxolane (3 g) as a colorless liquid.

$^1$H NMR (300 MHz, CDCl3) δ 7.42-7.35 (m, 1H), 7.34-7.27 (m, 1H), 7.15-7.08 (m, 1H), 6.31-5.78 (m, 2H), 4.19-4.02 (m, 4H), 3.38 (m, 2H).

Step 2: 2-(2,2-difluoroethyl)-3-fluorobenzaldehyde

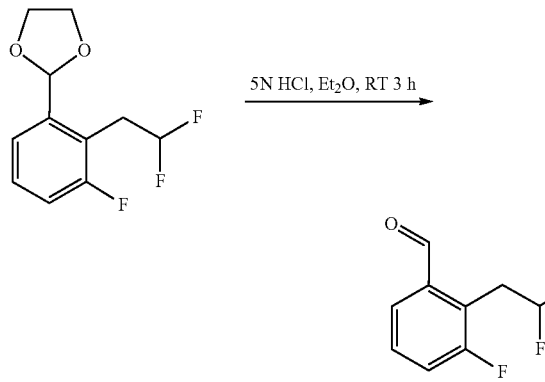

To a solution of 2-(2-(2,2-difluoroethyl)-3-fluorophenyl)-1,3-dioxolane (from step 1, 3 g, 12.93 mmol) in diethyl ether (40 mL) was added 6N HCl (5 mL). The resulting solution was stirred at room temperature for 3 hrs. This was washed with water (50 mL), saturated NaHCO₃ solution (100 mL), and brine and dried over Na₂SO₄. The solvent was removed under reduced pressure and purification of the crude product by silica flash chromatography (0→5%) ethyl acetate in petroleum ether afforded the title compound 2-(2,2-difluoroethyl)-3-fluorobenzaldehyde (1.9 g) as a colorless liquid.

¹H NMR (400 MHz, CDCl3) δ 10.14 (d, J=1.6 Hz, 1H), 7.70-7.63 (m, 1H), 7.52 (td, J=8.0, 7.9, 5.2 Hz, 1H), 7.35-7.30 (m 1H), 6.03 (m, 1H), 3.83-3.58 (m, 2H).

Step 3: methyl (R)-4-(2-(2,2-difluoroethyl)-3-fluorophenyl)-2-(fluoromethyl)-5-oxo-4,5,6,7-tetrahydro-1H-cyclopenta[b]pyridine-3-carboxylate and methyl (S)-4-(2-(2,2-difluoroethyl)-3-fluorophenyl)-2-(fluoromethyl)-5-oxo-4,5,6,7-tetrahydro-1H-cyclopenta[b]pyridine-3-carboxylate

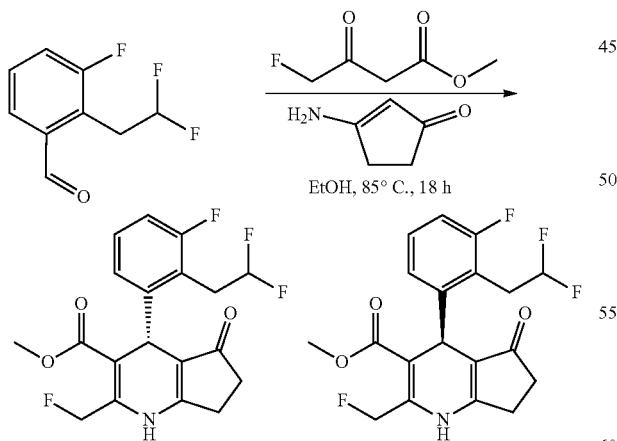

To solution of the aldehyde (from step 2, 200 mg, 1.063 mmol), methyl 4-fluoro-3-oxobutanoate (Method 2, step 1 of intermediate B, 142 mg, 1.063 mmol) in EtOH (2 mL) was added 3-aminocyclopent-2-en-1-one (example 25, step 7, 103 mg, 1.063 mmol). The reaction mixture was stirred at 80° C. for 18 hrs. The solvent was removed under reduced pressure gave crude compound. Crude product was purified by silica flash chromatography (0→70%) ethyl acetate in petroleum ether afforded the title compound as an off white solid (100 mg). Racemic mixture was separated into its enantiomers using chiral preparative HPLC [method 6].

Example 26

First eluting enantiomer obtained as a white solid (25 mg).
Chiral HPLC Rt 7.341 min; [chiral analytical method 4]
LCMS Rt=1.505 min; MS m/z 384.2 [M+1]+; [Method 12]
¹H NMR (400 MHz, CD3OD) δ 7.25-7.17 (m, 1H), 7.01 (d, J=8 Hz, 1H), 6.92-6.85 (m, 1H), 6.80-6.40 (m, 1H), 5.76 (d, J=3.2 Hz, 1H), 5.64 (d, J=2.8 Hz, 1H), 5.08 (s, 1H), 4.79-4.60 (m, 2H), 3.70-3.55 (m, 2H), 3.60-3.40 (m, 1H), 3.52 (s, 3H), 2.75-2.65 (m, 2H).

Example 26b

Second eluting enantiomer obtained as a white solid (26 mg).
Chiral HPLC Rt 9.044 min; [chiral analytical method 4]
LCMS Rt=1.505 min; MS m/z 384.2 [M+1]+; [Method 12]
¹H NMR (400 MHz, CD3OD) δ 7.25-7.17 (m, 1H), 7.01 (d, J=8 Hz, 1H), 6.92-6.85 (m, 1H), 6.80-6.40 (m, 1H), 5.76 (d, J=3.2 Hz, 1H), 5.64 (d, J=2.8 Hz, 1H), 5.08 (s, 1H), 4.79-4.60 (m, 2H), 3.70-3.55 (m, 2H), 3.60-3.40 (m, 1H), 3.52 (s, 3H), 2.75-2.65 (m, 2H).

Example 27: methyl (R)-4-(3-fluoro-2-((R or S)-1-fluoroethyl)phenyl)-2-(fluoromethyl)-5-oxo-4,5,6,7-tetrahydro-1H-cyclopenta[b]pyridine-3-carboxylate

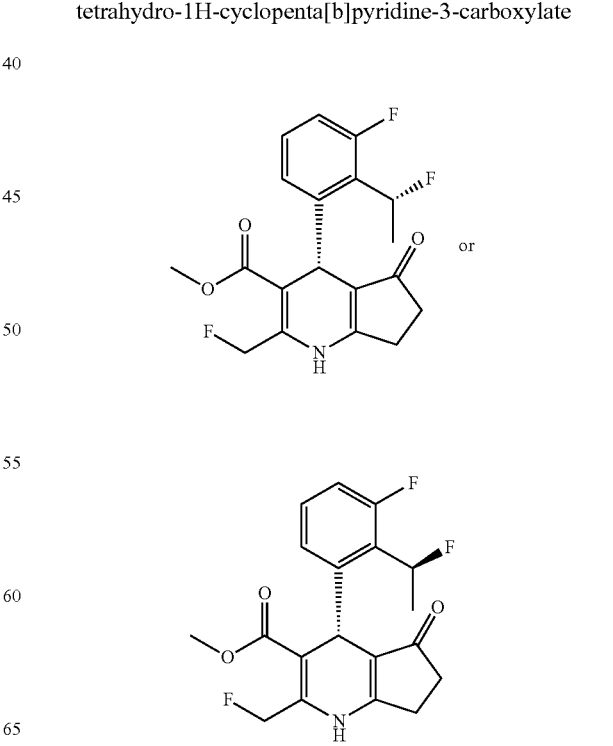

Step 1: 1-(2-(1,3-dioxolan-2-yl)-6-fluorophenyl)ethan-1-ol

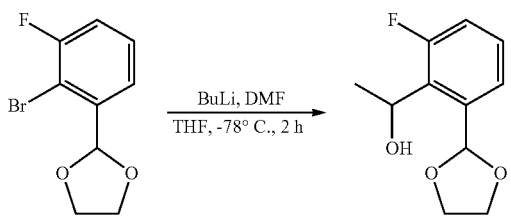

To a solution of 2-(2-bromo-3-fluorophenyl)-1,3-dioxolane (from example 25, step 1, 30 g, 121.42 mmol) in THF (300 mL) under nitrogen atmosphere at −78° C. was added n-BuLi in n-Hexane solution (58.3 mL, 2.5M, 147.71 mmol) dropwise over 10 min. The resulting mixture was stirred for 1 h at −78° C. then acetaldehyde (6.42 g, 145.71 mmol) was added and reaction stirred for 1 h at −78° C. The reaction mixture was quenched with saturated ammonium chloride solution (50 mL) and extracted with ethyl acetate (2×100 mL). Combined organic phases were washed with water (50 mL), washed with brine (50 mL) and dried over $Na_2SO_4$. The solvent was removed under reduced pressure and purification of the crude product by silica flash chromatography (0→10%) ethyl acetate in petroleum ether afforded the title compound 1-(2-(1,3-dioxolan-2-yl)-6-fluorophenyl)ethan-1-ol (15 g) as a colorless liquid.

$^1$H NMR (400 MHz, $CDCl_3$) δ 7.38 (d, J=8.0 Hz, 1H), 7.30-7.18 (m, 1H), 7.10-7.01 (m, 1H), 6.15 (5, 1H), 5.30-5.25 (m, 1H), 4.15-3.95 (m, 4H), 2.75-2.69 (m. 1H), 1.58 (dd, J=6.6, 22.8 Hz, 3H).

Step-2: 2-(3-fluoro-2-(1-fluoroethyl)phenyl)-1,3-dioxolane

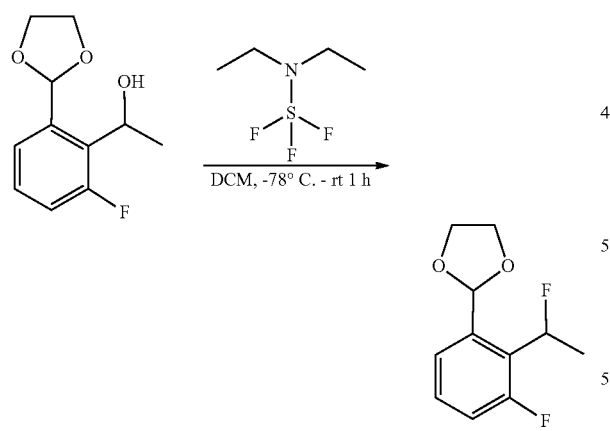

To a solution of 1-(2-(1,3-dioxolan-2-yl)-6-fluorophenyl)ethan-1-ol (from step 1, 15 g, 70.68 mmol) in dichloromethane (150 mL) at −78° C. was added diethylaminosulfur trifluoride (19.3 mL, 141.37 mmol). The resulting solution was allowed to warm to RT and stirred for 1 hr. The reaction mixture was quenched with saturated ammonium chloride (20 mL) at 0° C. and diluted with ethyl acetate (100 mL).

The organic layer was separated, washed with brine and dried over $Na_2SO_4$. The solvent was removed under reduced pressure and purification of the crude product by silica flash chromatography (0→10%) ethyl acetate in petroleum ether afforded the title compound 2-(3-fluoro-2-(1-fluoroethyl)phenyl)-1,3-dioxolane (8.5 g) as a colorless liquid.

$^1$H NMR (300 MHz, $CDCl_3$) δ 7.38 (d, J=7.5 Hz, 1H), 7.30-7.18 (m, 1H), 7.13-7.01 (m, 1H), 6.20-5.95 (m, 1H), 6.10 (s, 1H), 4.16-4.02 (m, 4H), 1.74 (dd, J=7.2, 23.1 Hz, 3H).

Step-3: 3-fluoro-2-(1-fluoroethyl)benzaldehyde

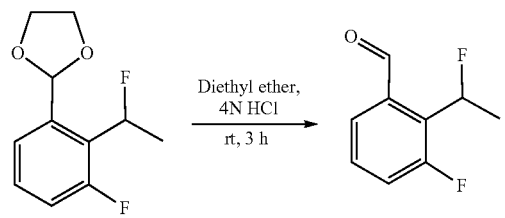

To a solution of 2-(3-fluoro-2-(1-fluoroethyl)phenyl)-1,3-dioxolane (from step 2, 8.5 g, 69.38 mmol) in diethyl ether (150 mL) was added 4N HCl (85 mL) at room temperature. The resulting solution was stirred at room temperature for 3 hrs. This was washed with water (100 mL), saturated $NaHCO_3$ solution (200 mL), and brine and dried over $Na_2SO_4$. The solvent was removed under reduced pressure to afford the title compound 3-fluoro-2-(1-fluoroethyl)benzaldehyde (6.5 g) as a colorless liquid. (Note: The obtained aldehyde is volatile in nature).

Step-4: methyl 4-(3-fluoro-2-((R or S)-1-fluoroethyl)phenyl)-2-(fluoromethyl)-5-oxo-4,5,6,7-tetrahydro-1H-cyclopenta[b]pyridine-3-carboxylate

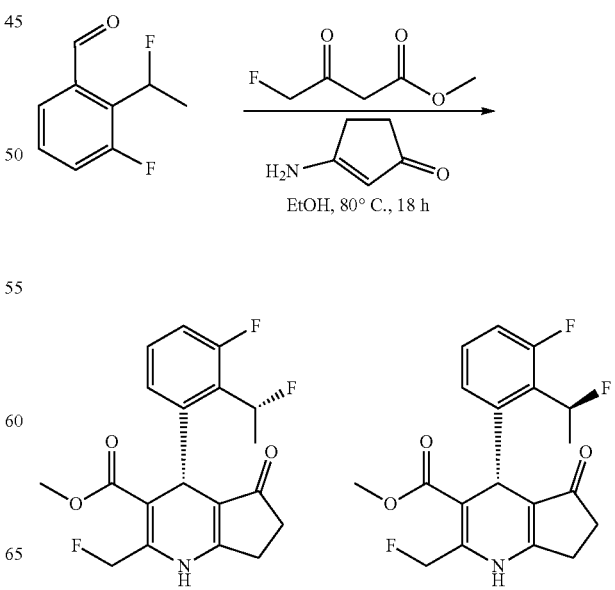

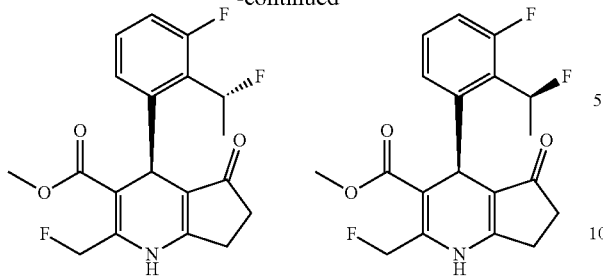

To solution of the aldehyde (from step 3, 1 g, 5.876 mmol), methyl 4-fluoro-3-oxobutanoate (Method 2, step 1 of intermediate B, 780 mg, 5.876 mmol) in EtOH (10 mL) was added 3-aminocyclopent-2-en-1-one (example 25, step 7, 570 mg, 5.876 mmol). The reaction mixture was stirred at 80° C. for 18 hrs. The solvent was removed under reduced pressure and crude product was purified by silica flash chromatography (0→70%) ethyl acetate in petroleum ether afforded the title compound as an off white solids as a diastereomeric mixture of methyl 4-(3-fluoro-2-(1-fluoroethyl)phenyl)-2-(fluoromethyl)-5-oxo-4,5,6,7-tetrahydro-1H-cyclopenta[b]pyridine-3-carboxylate (220 mg).

Diastereomeric mixture was separated into its two isomers using chiral prep-purification [method 2].

First peak from diastereomer separation was separated into its enantiomers Peak 1 and Peak 2 using chiral prep-purification [method 5].

Example 27

Second eluting enantiomer obtained as a white solid (55 mg)

Chiral HPLC Rt=5.729 min; [chiral analytical method 2]
LCMS Rt=2.25 min; MS m/z 364.1 [M–H]–; [Method 7]
$^1$H NMR (400 MHz, CDCl3) δ 7.25-7.15 (m, 2H), 6.96-6.75 (m, 2H), 6.52-6.30 (m, 1H), 5.79 (s, 1H), 5.67 (s, 1H), 5.05 (s, 1H), 3.59 (s, 3H), 2.80-2.60 (m, 2H), 2.50-2.35 (m, 2H), 2.01 (dd, J=6.4, 23.2 HZ, 3H).

Example 27b

First eluting enantiomer obtained as a white solid (55 mg).
Chiral HPLC Rt=5.678 min; [chiral analytical method 2]
LCMS Rt=2.25 min; MS m/z 364.1 [M–H]–; [Method 7]
$^1$H NMR (400 MHz, CDCl3) δ 7.25-7.15 (m, 2H), 6.96-6.75 (m, 2H), 6.52-6.30 (m, 1H), 5.79 (s, 1H), 5.67 (s, 1H), 5.05 (s, 1H), 3.59 (s, 3H), 2.80-2.60 (m, 2H), 2.50-2.35 (m, 2H), 2.01 (dd, J=6.4, 23.2 HZ, 3H).

Second peak from diastereomer separation was separated into its enantiomers peak 3 and peak 4 using chiral prep-purification [method 10].

Example 27c

Third eluting enantiomer as a white solid (10 mg).
Chiral HPLC Rt=8.702 min; [chiral analytical method 2]
LCMS Rt=2.22 min; MS m/z 364.1 [M–H]–; [Method 7]
$^1$H NMR (400 MHz, CDCl3) δ 7.25-7.15 (m, 2H), 6.96-6.75 (m, 2H), 6.80-6.60 (m, 1H), 5.79 (s, 1H), 5.69 (s, 1H), 5.03 (s, 1H), 3.54 (s, 3H), 2.75-2.58 (m, 2H), 2.50-2.45 (m, 2H), 1.83 (dd, J=6.4, 22.4 HZ, 3H).

Example 27d

Fourth eluting enantiomer as a white solid (10 mg).
Chiral HPLC Rt=9.851 min; [chiral analytical method 2]
LCMS Rt=2.22 min; MS m/z 364.1 [M–H]–; [Method 7]
$^1$H NMR (400 MHz, CDCl3) δ 7.25-7.15 (m, 2H), 6.96-6.75 (m, 2H), 6.80-6.60 (m, 1H), 5.79 (s, 1H), 5.69 (s, 1H), 5.03 (s, 1H), 3.54 (s, 3H), 2.75-2.58 (m, 2H), 2.50-2.45 (m, 2H), 1.83 (dd, J=6.4, 22.4 HZ, 3H).

Example 28: methyl (R)-4-(2-cyclopropyl-3-fluorophenyl)-2-(fluoromethyl)-5-oxo-4,5,6,7-tetrahydro-1H-cyclopenta[b]pyridine-3-carboxylate

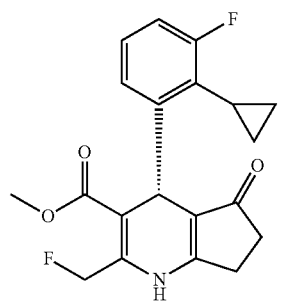 [SMILES: COC(=O)C1=C(CF)NC2=C(C(=O)CC2)[C@H]1c1cccc(F)c1C1CC1]

Step 1: 2-cyclopropyl-3-fluorobenzaldehyde

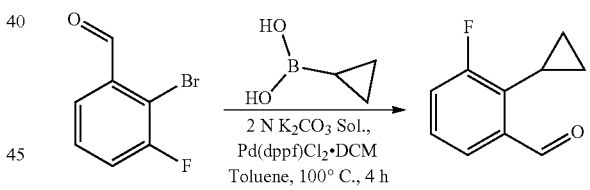

To a solution of 2-bromo-3-fluorobenzaldehyde (15 g, 73.88 mmol) and cyclopropylboronic acid (7.61 g, 88.66 mmol) in toluene (160 mL) was added 2N K$_2$CO$_3$ (25.5 mL, 182.16 mmol) and [1,1'-Bis(diphenylphosphino)ferrocene]dichloropalladium(II).DCM (6.03 g, 7.38 mmol). The resulting solution was degassed with Argon gas for 10 min and stirred at 100° C. for 4 hrs. The reaction mixture was filtered and washed with ethyl acetate (200 mL). The filtrate was added to water (500 mL) and product extracted into ethyl acetate (2 L). EtOAc phase was washed with brine and dried over Na$_2$SO$_4$. The solvent was removed under reduced pressure and purification of the crude product by silica flash chromatography (0→1%) ethyl acetate in petroleum ether afforded the title compound 2-cyclopropyl-3-fluorobenzaldehyde (11.2 g) as a colorless liquid.

$^1$H NMR (300 MHz, CDCl$_3$) δ 10.70 (s, 1H), 7.63 (dd, J=1.2, 7.8 Hz, 1H), 7.35-7.15 (m, 2H), 2.14-2.02 (m, 1H), 1.19-1.09 (m, 2H), 0.85-0.75 (m, 2H).

115

Step 2: methyl 4-(2-cyclopropyl-3-fluorophenyl)-2-(fluoromethyl)-5-oxo-4,5,6,7-tetrahydro-1H-cyclopenta[b]pyridine-3-carboxylate

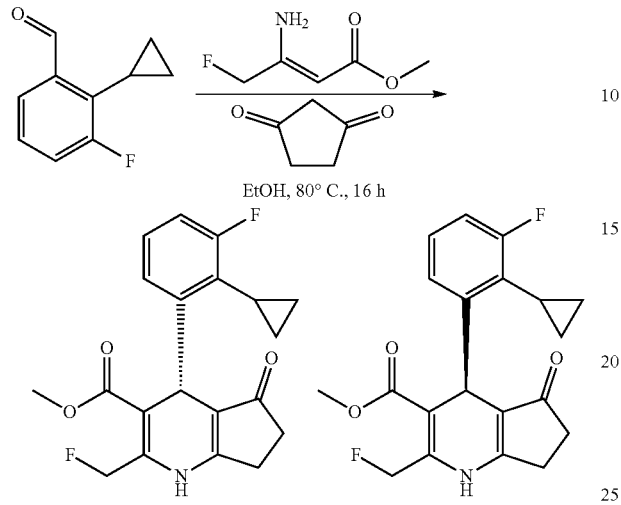

To a solution of the aldehyde (from step 1, 900 mg, 5.481 mmol), methyl (Z)-3-amino-4-fluorobut-2-enoate (intermediate B, 537.76 mg, 5.481 mmol) in ethanol (5 mL) was added cyclopentane-1,3-dione (875.68161 mg, 5.481 mmol) The reaction mixture was stirred at 80° C. for 16 hrs. The solvent was removed under reduced pressure and crude product was purified by silica flash chromatography (0→70%) ethyl acetate in petroleum ether afforded the title compound methyl-4-(2-cyclopropyl-3-fluorophenyl)-2-(fluoromethyl)-5-oxo-4,5,6,7-tetrahydro-1H-cyclopenta[b]pyridine-3-carboxylate (130 mg) as an off white solids. Racemic mixture was separated into its enantiomers using chiral preparative H PLC [method 11].

Example 28

First eluting enantiomer obtained as a white solid (46 mg).

Chiral HPLC Rt=10.37 min; [chiral analytical method 3]

LCMS Rt=1.47 min; MS m/z 360.2 [M+H]+; [Method 7]

$^1$H NMR (400 MHz, CDCl3) δ 7.10-7.01 (m, 1H), 6.95-6.90 (m, 1H), 6.78-6.71 (m, 1H), 5.68 (d, J=0.9 Hz, 1H), 5.58-5.52 (m, 2H), 3.53 (s, 3H), 2.70-2.65 (m, 2H), 2.45-2.12 (m, 4H), 1.34-1.25 (m, 1H), 1.05-0.89 (m, 2H), 0.80-0.69 (m, 1H).

Example 28b

Second eluting enantiomer obtained as a white solid (48 mg).

Chiral HPLC Rt=15.216 min; [chiral analytical method 3]

LCMS Rt=1.47 min; MS m/z 360.2 [M+H]+; [Method 7]

$^1$H NMR (400 MHz, CDCl3) δ 7.10-7.01 (m, 1H), 6.95-6.90 (m, 1H), 6.78-6.71 (m, 1H), 5.68 (d, J=0.9 Hz, 1H), 5.58-5.52 (m, 2H), 3.53 (s, 3H), 2.70-2.65 (m, 2H), 2.45-2.12 (m, 4H), 1.34-1.25 (m, 1H), 1.05-0.89 (m, 2H), 0.80-0.69 (m, 1H).

116

Example 29: methyl (R)-4-(3,5-difluoro-2-((S or R)-1-fluoroethyl)phenyl)-2-(fluoromethyl)-5-oxo-4,5,6,7-tetrahydro-1H-cyclopenta[b]pyridine-3-carboxylate

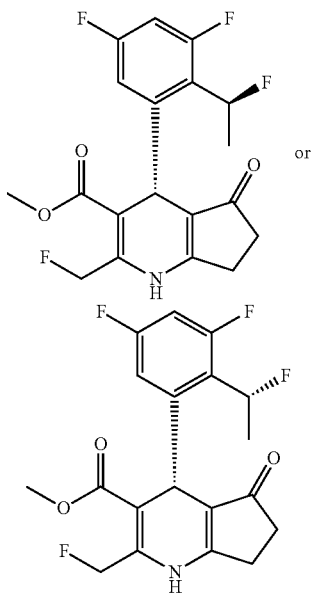

Step 1: 2-(1,3-dioxolan-2-yl)-4,6-difluorobenzaldehyde

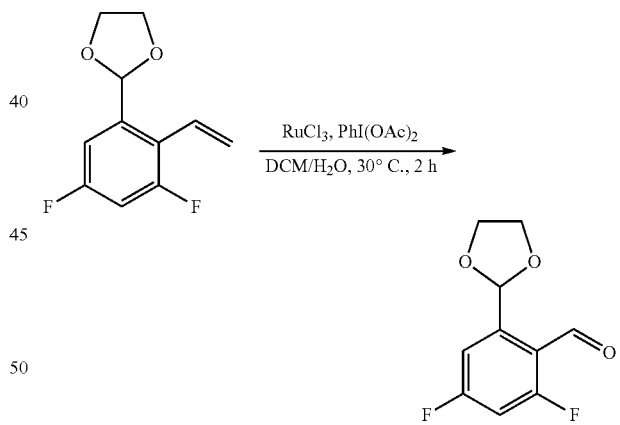

To a solution of 2-(3,5-difluoro-2-vinylphenyl)-1,3-dioxolane (step 2 from example 3, 5 g, 23.58 mmol) and ruthenium chloride·XH$_2$O (490 mg, 2.35 mmol) in dichloromethane (50 mL) and water (10 mL) was added diacetoxyiodo benzene (11.4 g, 35.37 mmol). The resulting solution was stirred at 30° C. for 2 hrs. The reaction mixture was filtered and washed with ethyl acetate (200 mL). The filtrate was dissolved in water (200 mL) and extracted into ethyl acetate (500 mL) and dried over Na$_2$SO$_4$. The solvent was removed under reduced pressure and purification of the crude product by silica flash chromatography (0→10%) ethyl acetate in petroleum ether afforded the title compound 2-(1,3-dioxolan-2-yl)-4,6-difluorobenzaldehyde (3 g) as a colorless liquid.

$^1$H NMR (300 MHz, CDCl$_3$) δ 10.41 (s, 1H), 7.35 (d, J=9.6 Hz, 1H), 6.95-6.85 (m, 1H), 6.53 (s, 1H), 4.08 (s, 4H).

Step 2: 1-(2-(1,3-dioxolan-2-yl)-4,6-difluorophenyl)ethan-1-ol

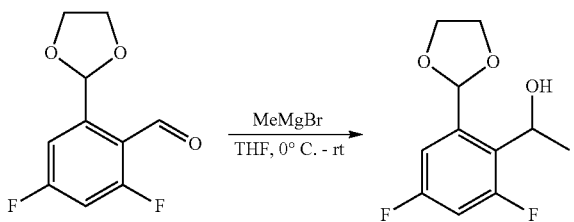 [SMILES: "MeMgBr" ; O=Cc1c(F)cc(F)cc1C1OCCO1 ; CC(O)c1c(F)cc(F)cc1C1OCCO1]

To a solution of 2-(1,3-dioxolan-2-yl)-4,6-difluorobenzaldehyde (from step 1, 1.0 g, 4.67 mmol) in dry tetrahydrofuran (10 mL) at 0° C. was added methyl magnesium bromide (2.33 mL, 3 M in ether, 4.67 mmol). The resulting solution was stirred at room temperature for 1 hrs. The reaction mixture was quenched with saturated ammonium chloride (10 mL) at 0° C. and diluted with ethyl acetate (100 mL). The organic layer was separated and dried over Na$_2$SO$_4$. The solvent was removed under reduced pressure afforded the title compound 1-(2-(1,3-dioxolan-2-yl)-4,6-difluorophenyl)ethan-1-ol (950 mg) as a colorless liquid. The crude compound was carry forwarded to next step without further purification.

$^1$H NMR (300 MHz, CDCl$_3$) δ 7.17 (dd, J=2.4, 6.3 Hz, 1H), 6.89-6.72 (m, 1H), 6.17 (s, 1H), 5.31 (dd, J=6.9, 13.5 Hz, 1H), 4.15-4.02 (m, 4H), 2.64-2.59 (m. 1H), 1.58 (d, J=9.0 Hz, 3H).

Step 3: 2-(3,5-difluoro-2-(1-fluoroethyl)phenyl)-1,3-dioxolane

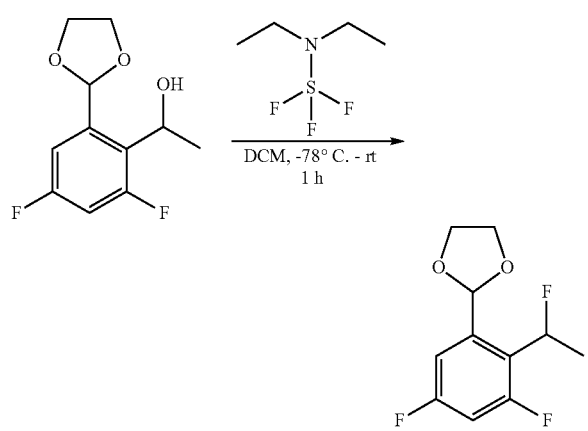

To a solution of 1-(2-(1,3-dioxolan-2-yl)-4,6-difluorophenyl)ethan-1-ol (from step 2, 950 mg, 4.13 mmol) in dichloromethane (10 mL) at −78° C. was added diethylaminosulfur trifluoride (1.0 g, 6.13 mmol). The resulting solution was stirred at room temperature for 1 hr. The reaction mixture was quenched with saturated ammonium chloride (100 mL) at 0° C. and diluted with ethyl acetate (100 mL). The organic layer was separated and dried over Na$_2$SO$_4$. The solvent was removed under reduced pressure afforded the title compound 2-(3,5-difluoro-2-(1-fluoroethyl)phenyl)-1,3-dioxolane (600 mg) as a thick yellow liquid. The crude compound was carry forwarded to next step without further purification.

$^1$H NMR (300 MHz, CDCl$_3$) δ 7.20 (dd, J=2.4, 6.3 Hz, 1H), 6.87-6.75 (m, 1H), 6.15-5.98 (m, 1H), 6.11 (s, 1H), 4.15-4.02 (m, 4H), 1.70 (dd, J=6.6, 22.8 Hz, 3H).

Step 4: 3,5-difluoro-2-(1-fluoroethyl) benzaldehyde

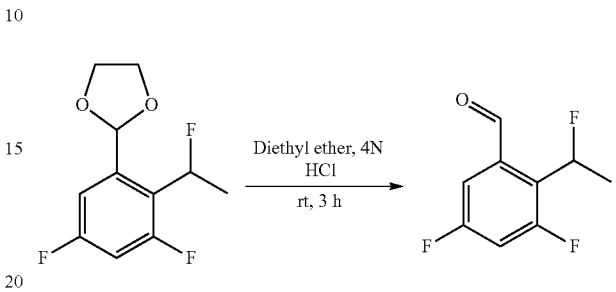

To a solution of 2-(3,5-difluoro-2-(1-fluoroethyl)phenyl)-1,3-dioxolane (from step 3, 600 mg, 2.58 mmol) in diethyl ether (10 mL) was added 4N HCl (2 mL) at room temperature. The resulting solution was stirred at room temperature for 3 hrs. This was washed with water (50 mL) and saturated NaHCO$_3$ solution (100 mL) and dried over Na$_2$SO$_4$. The solvent was removed under reduced pressure afforded the title compound 3,5-difluoro-2-(1-fluoroethyl)benzaldehyde (200 mg) as a colorless liquid. (Note: The obtained aldehyde is volatile nature)

$^1$H NMR (300 MHz, CDCl$_3$) δ 10.44 (d, J=3.0 Hz, 1H), 7.20 (d, J=9.3 Hz, 1H), 7.10-6.98 (m, 1H), 6.43-6.19 (m, 1H), 1.78 (dd, J=7.2, 23.1 Hz, 3H).

Step 5: 3-ethoxycyclopent-2-en-1-one

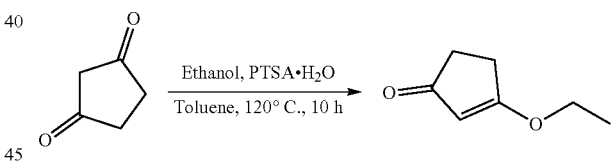

To a stirred solution of cyclopentane-1,3-dione (5.0 g, 50.96 mmol) in toluene (70 mL) was added pTSA (193 mg, 1.019 mmol) and EtOH (22.61 ml, 387.35 mmol) at room temperature. The resulting mixture was stirred at 120° C. for 10 hrs using Dean-stark apparatus. The solvent was removed under reduced pressure gave crude compound. Crude product was purified by silica flash chromatography (0→50%) ethyl acetate in petroleum ether to afford the title compound 3-ethoxycyclopent-2-en-1-one (4.3 g) as a brown solid.

$^1$H NMR (400 MHz, CDCl3) δ 5.26 (s, 1H), 4.02 (q, J=6.6 Hz, 2H), 2.60-2.55 (m, 2H), 2.44-2.40 (m, 2H), 1.39 (t, J=7.2 Hz, 3H).

Step 6: 3-aminocyclopent-2-en-1-one

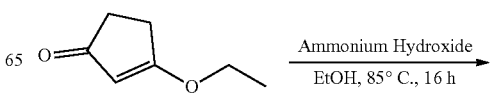

-continued

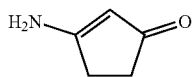

To a stirred solution of 3-ethoxycyclopent-2-en-1-one (from step 5, 4.3 g, 34.08 mmol) in ethanol (50 mL) was added ammonium hydroxide solution (25 mL, 387.35 mmol) at room temperature. The resulting mixture was stirred at 85° C. for 16 hrs. Solvent removal under reduced pressure afforded the title compound 3-aminocyclopent-2-en-1-one (3.2 g) as a brown solid.

LCMS RT=0.114 min; MS m/z 98.2 [M+H]+; [Method 7]

Step 7: methyl 4-(3,5-difluoro-2-(1-fluoroethyl)phenyl)-2-(fluoromethyl)-5-oxo-4,5,6,7-tetrahydro-1H-cyclopenta[b]pyridine-3-carboxylate

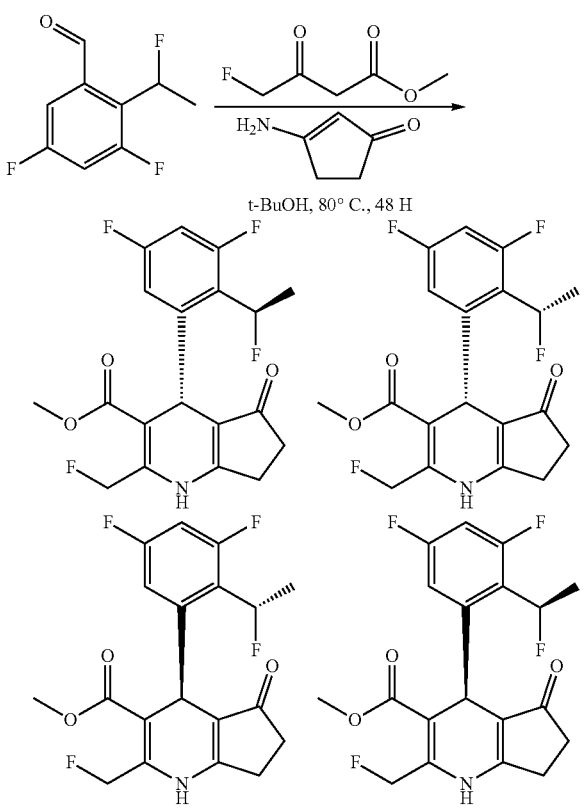

To a solution of the aldehyde (from step 4, 700 mg, 3.7204 mmol), methyl 4-fluoro-3-oxobutanoate (step 1; method 2 of intermediate B, 598.73 mg, 4.4645 mmol) and 3-aminocyclopent-2-en-1-one (step 6, 361.32 mg, 3.7204 mmol) in t-butanol (15 mL). The reaction mixture was stirred at 80° C. for 48 hrs. The solvent was removed under reduced pressure gave crude compound. Crude product was purified by silica flash chromatography (0→50%) ethyl acetate in petroleum ether afforded the title compound methyl 4-(3,5-difluoro-2-(1-fluoroethyl)phenyl)-2-(fluoromethyl)-5-oxo-4,5,6,7-tetrahydro-1H-cyclopenta[b]pyridine-3-carboxylate (580 mg) as an off white solids and as mixture of diastereomers and off white solid first diastereomer (320 mg, Peak-1). The mixture (580 mg) was further purified by prep-HPLC purification (Method 8) gave off white solid second diastereomer (80 mg, Peak-2).

Peak-1: 160 mg and Peak-2: 80 mg was further separated into its enantiomers using preparative chiral HPLC [Method 11] to obtain four isomers of example 29

Example 29

50 mg of first eluting enantiomer obtained as a white solid using chiral HPLC [method 11].

LCMS RT=1.445 min; MS m/z 382.1 [M−H]−; [Method 7]

This was further purified by preparative HPLC purification [Method 9] gave off white solid (25 mg).

Chiral HPLC: RT: 8.905 min; [chiral analytical method 3]

LCMS RT=1.445 min; MS m/z 382.1 [M−H]−; [Method 13]

$^1$H NMR (400 MHz, DMSO-d6) δ 10.10 (s, 1H), 7.06 (ddd, J=11.6, 8.8, 2.6 Hz, 1H), 6.82-6.68 (m, 1H), 6.36 (dq, J=45.3, 6.5 Hz, 1H), 5.75-5.64 (m, 1H), 5.63-5.50 (m, 1H), 4.97 (s, 1H), 3.45 (s, 3H), 2.70-2.59 (m, 2H), 2.25-2.09 (m, 2H), 1.84 (dd, J=23.0, 6.5 Hz, 3H).

Example 29b 55 mg of second eluting enantiomer obtained as a white solid using chiral HPLC [method 11].

Chiral HPLC: RT: 10.197 min; [chiral analytical method 3]

LCMS RT=1.510 min; MS m/z 382.1 [M−H]−; [Method 13]

$^1$H NMR (400 MHz, DMSO-d6) δ 10.10 (s, 1H), 7.06 (ddd, J=11.6, 8.8, 2.6 Hz, 1H), 6.82-6.67 (m, 1H), 6.36 (dq, J=45.4, 6.6 Hz, 1H), 5.75-5.64 (m, 1H), 5.63-5.48 (m, 1H), 4.97 (s, 1H), 3.45 (s, 3H), 2.71-2.59 (m, 2H), 2.27-2.16 (m, 2H), 1.84 (dd, J=23.0, 6.5 Hz, 3H).

Example 29c 24.2 mg of third eluting enantiomer obtained as a white solid using chiral HPLC [method 11].

Chiral HPLC: RT: 14.455 min; [chiral analytical method 3]

LCMS RT=1.504 min; MS m/z 382.0 [M−H]−; [Method 10]

$^1$H NMR (400 MHz, DMSO-d6) δ 10.13 (s, 1H), 7.14-6.96 (m, 1H), 6.75 (d, J=9.8 Hz, 1H), 6.63 (dq, J=44.2, 6.8 Hz, 1H), 5.71 (s, 1H), 5.59 (s, 1H), 4.88 (s, 1H), 3.47 (s, 3H), 2.62 (q, J=4.5 Hz, 2H), 2.25 (t, J=4.9 Hz, 2H), 1.68 (dd, J=22.8, 6.5 Hz, 3H).

Example 29d 32.4 mg of fourth eluting enantiomer obtained as a white solid using chiral HPLC [method 11].

Chiral HPLC: RT: 18.561 min [chiral analytical method 3]

LCMS RT=1.514 min; MS m/z 382.0 [M−H]−; [Method 10]

$^1$H NMR (400 MHz, DMSO-d6) δ 10.13 (s, 1H), 7.05-7.00 (m, 1H), 6.75 (d, J=9.7 Hz, 1H), 6.62 (dt, J=44.2, 6.6 Hz, 1H), 5.71 (s, 1H), 5.59 (s, 1H), 4.88 (s, 1H), 3.47 (s, 3H), 2.62 (q, J=4.6 Hz, 2H), 2.25 (t, J=4.9 Hz, 2H), 1.68 (dd, J=22.8, 6.4 Hz, 3H).

Example 30: methyl (R)-4-(2-ethylphenyl)-2-(fluoromethyl)-5-oxo-1,4,5,7-tetrahydrofuro[3,4-b]pyridine-3-carboxylate

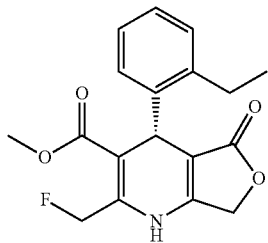 [SMILES: CCc1ccccc1[C@H]1C(C(=O)OC)=C(CF)NC2=C1C(=O)OC2]

Step 1: methyl 4-(2-ethylphenyl)-2-(fluoromethyl)-5-oxo-1,4,5,7-tetrahydrofuro[3,4-b]pyridine-3-carboxylate

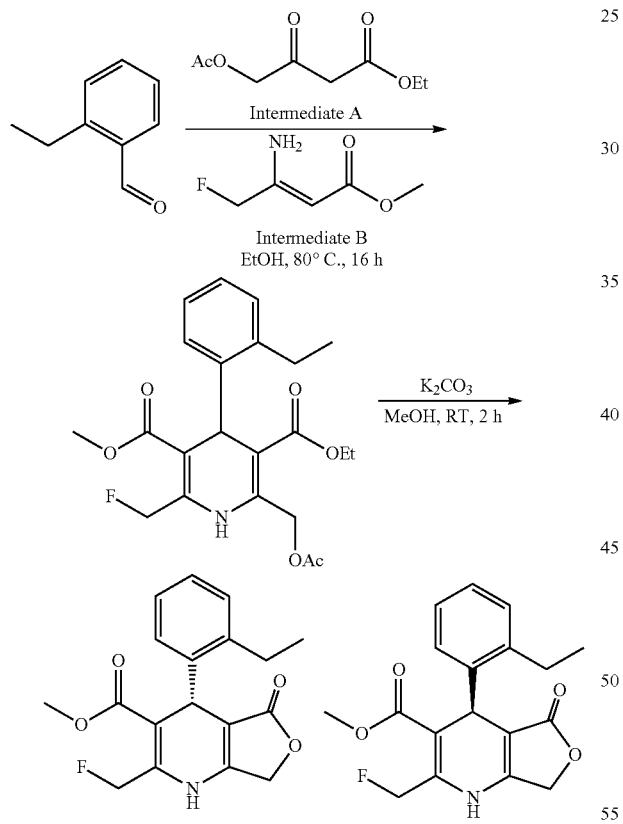

The title compound was synthesized using general method I (using 2-ethylbenzaldehyde, 0.2 g, 1.44 mmol). Crude product was purified by silica column chromatography (2→3% methanol in DCM) which afforded the title compound as a cream color solid. Methyl methyl 4-(2-ethylphenyl)-2-(fluoromethyl)-5-oxo-1,4,5,7-tetrahydrofuro[3,4-b]pyridine-3-carboxylate (0.165 g, 43%). LCMS Rt=1.506 min; MS m/z 331.85 [M+H]+; [Method 10]

The racemic sample was separated into its enantiomers by chiral HPLC (Column: LUX CELLULOSE-4, (250 MM×21.2 MM×5 MICRON); Mobile Phase: N-HEXANE (A) EtOH: MeOH, 1:1 (B), FLOW: 15 mL).

Example 30

The first eluting enantiomer, 30 mg as a pale yellow solid.

Chiral HPLC Rt=5.952 min (Column: LUX CELLULOSE-4 (150×4.6 mm×5µ); Mobile Phase: A=n-HEXANE, B: ETHANOL:METHANOL (50:50); Flow: 1.0 mL/min).

LCMS Rt=1.53 min; MS m/z 332.0 [M+H]+; [Method 7]

$^1$H NMR (400 MHz, DMSO-$d_6$) δ 10.03 (s, 1H), 7.13-7.10 (m, 4H), 5.71 (s, 1H), 5.59 (s, 1H), 4.98 (s, 1H), 4.82 (s, 2H), 3.44 (s, 3H), 2.98-2.92 (m, 2H), 1.25 (t, J=7.8 Hz, 3H).

Example 30b

The second eluting enantiomer, 29 mg as a pale yellow solid.

Chiral HPLC Rt=7.581 min (Column: LUX CELLULOSE-4 (150×4.6 mm×5µ); Mobile Phase: A=n-HEXANE, B: ETHANOL:METHANOL (50:50); Flow: 1.0 ml/min).

LCMS Rt=1.528 min; MS m/z 332.0 [M+H]+; [Method 7]

$^1$H NMR (400 MHz, DMSO-$d_6$) δ 10.03 (s, 1H), 7.13-7.10 (m, 4H), 5.71 (s, 1H), 5.59 (s, 1H), 4.98 (s, 1H), 4.82 (s, 2H), 3.44 (s, 3H), 2.98-2.92 (m, 2H), 1.25 (t, J=7.8 Hz, 3H).

Example 31: methyl (R)-2-(difluoromethyl)-4-(3-fluoro-2-((R or S)-1-fluoroethyl)phenyl)-5-oxo-1,4,5,7-tetrahydrofuro[3,4-b]pyridine-3-carboxylate

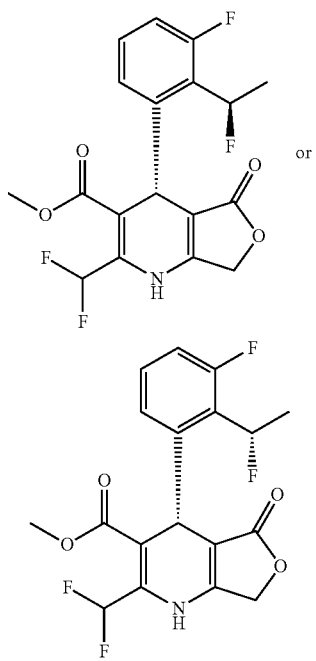

Step 1: 5-ethyl 3-methyl 2-(dimethoxymethyl)-4-(3-fluoro-2-(1-fluoroethyl)phenyl)-6-methyl-1,4-dihydropyridine-3,5-dicarboxylate

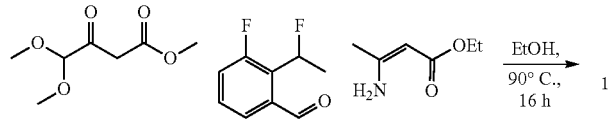

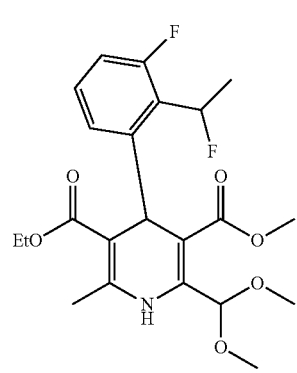

A stirred solution of methyl 4,4-dimethoxy-3-oxobutanoate (2.0 g, 11.35 mmol), 3-fluoro-2-(1-fluoroethyl)benzaldehyde (from example 27 step 3, 1.93 g, 11.35 mmol) and ethyl (Z)-3-aminobut-2-enoate (1.46 g, 11.35 mmol) in ethanol (20 mL) was heated to 90° C. for 16 h. Reaction mixture was concentrated under reduced pressure to afford crude compound as a brown colored liquid. Crude compound was purified by silica flash chromatography (9→10% ethyl acetate in hexane to afford title compound as yellow sticky liquid. 5-ethyl 3-methyl 2-(dimethoxymethyl)-4-(3-fluoro-2-(1-fluoroethyl)phenyl)-6-methyl-1,4-dihydropyridine-3,5-dicarboxylate (1.7 g, 34%).

Compound taken directly on as crude without further analysis

Step 2: 3-ethyl 5-methyl 4-(3-fluoro-2-(1-fluoroethyl)phenyl)-6-formyl-2-methyl-1,4-dihydropyridine-3,5-dicarboxylate

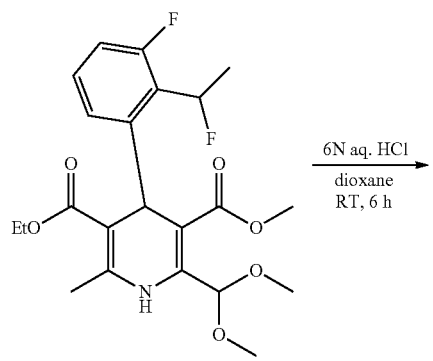

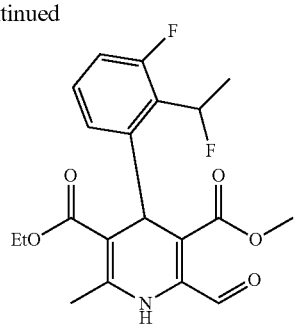

A stirred solution of 5-ethyl 3-methyl 2-(dimethoxymethyl)-4-(3-fluoro-2-(1-fluoroethyl) phenyl)-6-methyl-1,4-dihydropyridine-3,5-dicarboxylate (from step 1, 1.7 g, 3.86 mmol) in 1,4-Dioxane (10.0 mL) was cooled to 0° C. 6 N aqueous hydrochloric acid solution (15.0 mL) was added at 0° C. and reaction mixture was stirred at room temperature for 16 h. Reaction mixture was diluted with water and product extracted into ethyl acetate. Combined organic layers were washed with saturated solution of sodium bicarbonate, dried over anhydrous sodium sulfate, filtered and the solvent removed under reduced pressure. Crude compound was purified by silica flash chromatography (12→15% ethyl acetate in hexane) to afford the diastereomer 1 (400 mg, 26%) and diastereomer 2 (300 mg, 20%) of title compound as yellow sticky liquid.

Diastereomer 1

LCMS Rt=1.606 min; MS m/z 392.0 [M–H]–; [Method 10]

¹H NMR (300 MHz, DMSO-d₆) δ 10.13 (s, 1H), 9.05 (s, 1H), 7.33 (dd, J=13.8, 7.2 Hz, 1H), 7.10-7.02 (m, 2H), 6.45-6.23 (m, 1H), 5.19 (s, 1H), 4.06-3.98 (m, 2H), 3.63 (s, 3H), 2.35 (s, 3H), 1.76 (dd, J=22.8, 6.6 Hz, 3H), 1.13 (t, J=6.9 Hz, 3H)

Diastereomer 2

LCMS Rt=1.461 min; MS m/z 392.0 [M–H]–; [Method 14]

¹H NMR (300 MHz, DMSO-d₆) δ 10.12 (s, 1H), 9.07 (s, 1H), 7.33 (dd, J=13.8, 7.2 Hz, 1H), 7.10-7.03 (m, 2H), 6.44-6.22 (m, 1H), 5.18 (s, 1H), 4.13-3.87 (m, 2H), 3.67 (s, 3H), 2.35 (s, 3H), 1.74 (dd, J=22.8, 6.6 Hz, 3H), 1.11 (t, J=6.9 Hz, 3H).

Step 3: 5-ethyl 3-methyl 2-(difluoromethyl)-4-(3-fluoro-2-(1-fluoroethyl)phenyl)-6-methyl-1,4-dihydropyridine-3,5-dicarboxylate

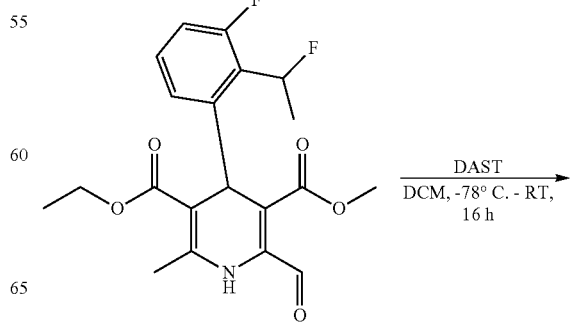

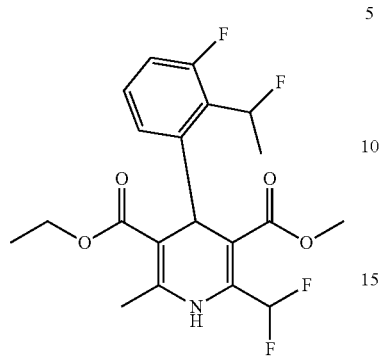
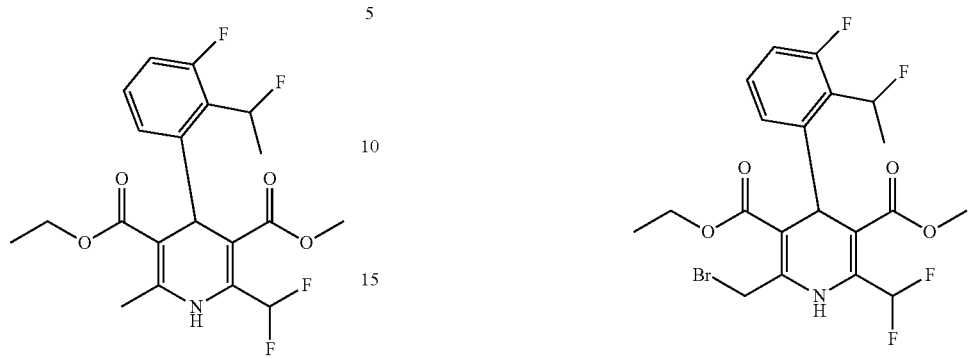

A stirred solution of 3-ethyl 5-methyl 4-(3-fluoro-2-(1-fluoroethyl)phenyl)-6-formyl-2-methyl-1,4-dihydropyridine-3,5-dicarboxylate (from diastereoisomer 1 of step 2, 0.40 g, 1.01 mmol) in dichloromethane (5.0 mL) was cooled to −78° C. Diethylaminosulfur trifluoride (0.16 mL, 1.22 mmol) was added portion wise at −78° C. and the reaction mixture was stirred at room temperature for 16 h. Reaction mixture was quenched by ice cold water and product extracted into dichloromethane. The combined organic layers were washed with saturated sodium bicarbonate solution, dried over anhydrous sodium sulfate, filtered and the solvent removed under reduced pressure to afford the title compound as brown sticky liquid. 5-ethyl 3-methyl 2-(difluoromethyl)-4-(3-fluoro-2-(1-fluoroethyl)phenyl)-6-methyl-1,4-dihydropyridine-3,5-dicarboxylate (0.3 g).

LCMS Rt=1.632 min; MS m/z 414.0 [M−H]−; [Method 10]

$^1$H NMR (300 MHz, DMSO-d$_6$) δ 9.38 (s, 1H), 7.58-7.23 (m, 2H), 7.09-7.01 (m, 2H), 6.43-6.22 (m, 1H), 5.12 (s, 1H), 4.08-3.97 (m, 2H), 3.58 (s, 3H), 2.34 (s, 3H), 1.75 (dd, J=23.1, 6.0 Hz, 3H), 1.13 (t, J=6.9 Hz, 3H)

A solution of 5-ethyl 3-methyl 2-(difluoromethyl)-4-(3-fluoro-2-(1-fluoroethyl)phenyl)-6-methyl-1,4-dihydropyridine-3,5-dicarboxylate (from step 3, 0.3 g, 0.722 mmol) in dichloromethane (5.0 mL) was cooled to −78° C. Pyridinium tribromide (0.254 g, 0.794 mmol) was added at −78° C. and stirred for 1 h, at same temperature. Then the reaction mixture was stirred at room temperature for 30 minutes. Reaction mixture was diluted with ice cold water and product extracted into dichloromethane. Combined organic layers were dried over anhydrous sodium sulfate, filtered and the solvent removed under reduced pressure. Crude compound was purified by silica flash chromatography (10→12% ethyl acetate in Hexane) to afford the title compound as yellow sticky liquid. 3-ethyl 5-methyl 2-(bromomethyl)-6-(difluoromethyl)-4-(3-fluoro-2-(1-fluoroethyl)phenyl)-1,4-dihydropyridine-3,5-dicarboxylate (0.2 g, 56%)

LCMS Rt=1.653 min; MS m/z 491.95 [M−H]−; [Method 10]

$^1$H NMR (400 MHz, DMSO-d$_6$) δ 9.73 (s, 1H), 7.40-7.34 (m, 2H), 7.11-7.02 (m, 2H), 6.40-6.24 (m, 1H), 5.16 (s, 1H), 4.73 (dd, J=34, 9.2 Hz, 2H), 4.14-4.05 (m, 2H), 3.58 (s, 3H), 1.75 (dd, J=22.4, 6.4 Hz, 3H), 1.18 (t, J=7.4 Hz, 3H)

Step 4: 3-ethyl 5-methyl 2-(bromomethyl)-6-(difluoromethyl)-4-(3-fluoro-2-(1-fluoroethyl)phenyl)-1,4-dihydropyridine-3,5-dicarboxylate Step 5: methyl 2-(difluoromethyl)-4-(3-fluoro-2-(1-fluoroethyl)phenyl)-5-oxo-1,4,5,7-tetrahydrofuro[3,4-b]pyridine-3-carboxylate

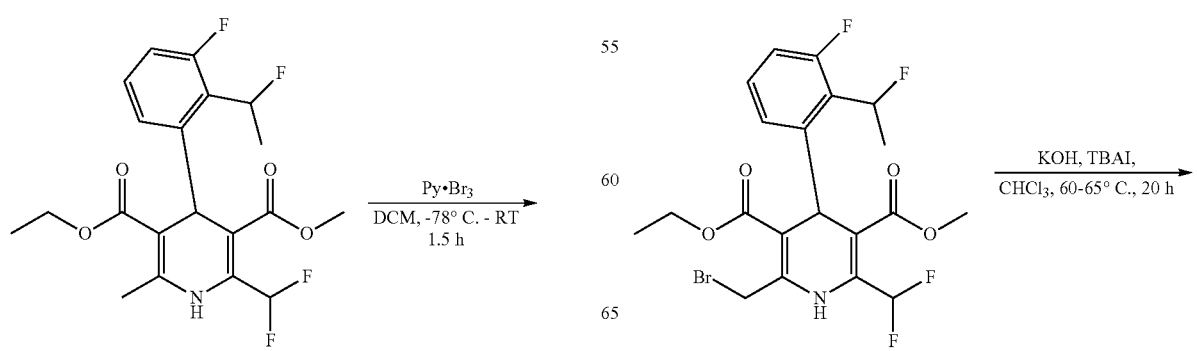

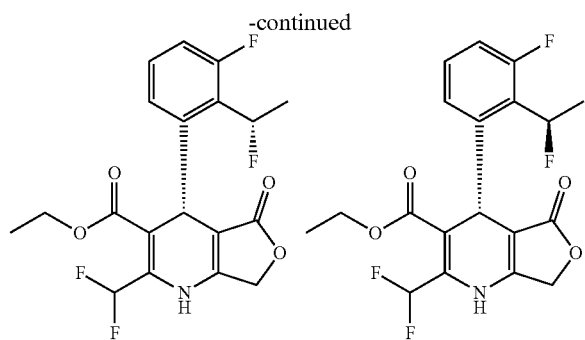

To a solution of 3-ethyl 5-methyl 2-(bromomethyl)-6-(difluoromethyl)-4-(3-fluoro-2-(1-fluoroethyl)phenyl)-1,4-dihydropyridine-3,5-dicarboxylate (from step 4, 0.1 g, 0.202 mmol) in chloroform (5.0 mL), was added potassium hydroxide (0.005 g, 0.101 mmol) at room temperature.

The reaction mixture was heated to 60° C. and stirred for 8 h. Tetra-n-butylammonium iodide (0.007 g, 0.020 mmol) was added at room temperature and the reaction mixture was heated to 65° C. for 12 h. Reaction mixture was diluted with water and product extracted into dichloromethane. Combined organic layers were washed with brine, dried over anhydrous sodium sulfate filtered and the solvent removed under reduced pressure. Crude product was purified by Prep HPLC (Column: ZORBAX XDB (250 mm×21.2 mm), 5.0µ; Mobile phase: A=WATER B=ACN; Flow: 18 ml/min) to afford the title compound as a cream color solid. methyl 2-(difluoromethyl)-4-(3-fluoro-2-(1-fluoroethyl)phenyl)-5-oxo-1,4,5,7-tetrahydrofuro[3,4-b]pyridine-3-carboxylate (20 mg, 26%).

LCMS Rt=1.503 min; MS m/z 384.05 [M−H]−; [Method 10]

The racemic sample was separated into its enantiomers by chiral HPLC (Column: CHIRALPAK IJ, 250 MM×4.3 MM×5 MICRON; Mobile Phase: A=HEXANE, B=0.1% HCOOH IN MeOH:EtOH, 1:1, FLOW: 5 mL).

Example 31

First eluting peak of chiral HPLC, 3.4 mg as a cream color solid.

Chiral HPLC Rt=6.393 min (Column: CHIRAL PAK IJ (250×4.6 mm×5µ); Mobile Phase: A: n-HEXANE B: Ethanol; FLOW: 1.0 mL/min.

LCMS Rt=1.502 min; MS m/z 384.05 [M−H]− [Method 10]

$^1$H NMR (300 MHz, DMSO-$d_6$) δ 10.43 (s, 1H), 7.64-7.28 (m, 2H), 7.10-7.02 (m, 2H), 6.44-6.22 (m, 1H), 5.13 (s, 1H), 4.88 (s, 2H), 3.49 (s, 3H), 1.80 (dd, J=22.8, 6.0 Hz, 3H)

Example 31b

Second eluting peak of chiral HPLC, 3 mg as a cream color solid.

Chiral HPLC Rt=7.605 min (Column: CHIRAL PAK IJ (250×4.6 mm×5µ); Mobile Phase: A: n-HEXANE B: Ethanol; FLOW: 1.0 mL/min.

LCMS Rt=1.500 min; MS m/z 384.05 [M−H]−. [Method 10]

$^1$H NMR (300 MHz, DMSO-$d_6$) δ 10.42 (s, 1H), 7.59-7.32 (m, 2H), 7.10-7.02 (m, 2H), 6.42-6.25 (m, 1H), 5.13 (s, 1H), 4.88 (dd, J=19.2, 16.4 Hz, 2H), 3.49 (s, 3H), 1.80 (dd, J=23.2, 6.4 Hz, 3H).

Crystalline Forms
X-Ray Powder Diffraction Measurements (XRPD)

XRPD was performed with a Bruker D8 Advance diffractometer equipped with a nickel filter monochromator and a LYNXEYE (1D mode) detector with an open angle: 2.948° using Cu-Kalpha$_{1,2}$ radiation (wavelength 0.15419 nm). The diffractogram was recorded at a tube voltage of 40 kV and a tube current of 40 mA, applying a step size of 0.0164° (2-theta value) with 0.3 seconds per step in the angular range of 2° to 40° 2-Theta at ambient conditions. The scan time was 768 seconds. A typical precision of the 2-theta values is in the range of ±0.2° 2-Theta, preferably of ±0.1° 2-Theta. Thus, for example, the diffraction peak of crystalline Form A of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate that appears for example at 10.4° 2-Theta can appear in the range of from (10.4−0.2°) to (10.4+0.2)° 2-Theta, preferably from (10.4−0.1°) to (10.4+0.1)° 2-Theta on most X-ray diffractometers under standard conditions.

Crystalline Form A

Crude methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate (130 g, 0.35 mol) was slurried in ethyl ether (520 ml) for 3 hours at room temperature to obtain a suspension which was filtered. The wetcake was then dried under vacuum at 60° C. for 72 hours to provide methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Form A (100 g, 0.27 mol) with the yield of 77%.

Crystalline Form B

Crystalline Form B was prepared by dissolving 100 mg of Form A in sufficient isopropyl acetate to obtain a solution. Then sufficient heptane was added at 55° C. until a cloudy suspension was obtained. The suspension was kept at a certain time at 55° C. and then cooled 25° C. and equilibrated for 2 to 4 hours at 25° C. The solid part was isolated and analysed by XRPD, which confirmed the presence of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Form B.

Alternative synthesis: 400 mL heptane was added into a 500 mL reactor and heated to 55° C. 20 g Form A was added into 60 mL isopropyl acetate at room temperature. About 2 g of Form B was added as seed into the reactor at 55° C. and the resulting mixture was equilibration for 30 min at 55° C. Then the isopropyl acetate solution of Form A free form was added dropwise into the reactor within 2 hours using a syringe pump. The resulting mixture was equilibrated at 55° C. for 2 hours. The mixture was then cooled to 25° C. within 6 hours and then equilibrated at 25° C. for further 10 hours. The suspension was then filtrated and the wet cake was dried at 50° C. under vacuum for 4 hours. About 21 g of final product was obtained, which was confirmed by XRPD to correspond to Form B. The water content by KF was 0.3%.

Crystalline Form C

About 100 mg of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate and various stoichiometric amounts of citric acid (base: acid ratios of 4:1, 3:1, 2:1 or 1:1) were crystallized in tert-butyl methyl ether. The solid forms obtained corresponded to methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate Form C.

Alternative synthesis: 40 mL of heptane was added into a 100 mL EasyMax reactor at 25° C. 2 g of Form A was dissolved in 5 mL isopropyl acetate at room temperature.

Then 20 mg of seeds of Form C were added to the reactor at 25° C. The resulting mixture was equilibrated for 30 min at 25° C. The isopropyl acetate solution of Form A free form was added dropwise to the reactor within 2 hours period using a syringe pump. The resulting mixture was equilibrated at 25° C. for 2 hours. The in process control showed a mixture of Form C and Hydrate A. The solid material was then slurried in 10 mL isopropyl acetate/heptane (1/7) for 2 days. The suspension was then filtrated and dried at 40° C. for 18 hours. The XRPD of the final product corresponded to Form C. The water content by KF was 0.3%.

Crystalline Form Hydrate A 1.97 g of Form A was weighted into a 100 mL EasyMax glass vial and dispersed in 35 mL of water, the suspension was stirred at 300 rpm by overhead stirring under 50° C. for 3 hours, then cool to 25° C. in 6 hours at about 0.07° C./min, after that, kept stirring at 25° C. for 24 hours. The solid material was isolated by filtration. The XRPD of the solid form corresponded to Hydrate A.

Alternative synthesis: Hydrate A was obtained e.g. by evaporation crystallization of a clear saturated solution of Crystalline Form B in acetone, acetonitrile/water (99.5:0.5), ethyl acetate or water. Hydrate A shows a loss of mass by TGA of about 4.1%, which is close to a monohydrate (calculated water content of 4.7%). Hydrate A is slightly hygroscopic. The water uptake between 10% to 95% RH is about 0.2% at 25° C.

Crystalline Form Hydrate B 2 g of Form A was weighted into a 100 mL EasyMax glass vial and dispersed in 30 mL of methanol, the suspension was stirred at 300 rpm by overhead stirring under 25° C. for 20 hours. The solid material was isolated by filtration and the solids were exposed to 92% RH for 1 days. The solid material corresponded to Hydrate B as confirmed by XRPD.

Alternative synthesis: Hydrate B was obtained by air drying of Crystalline Form B in methanol solvate. Hydrate B shows a loss of mass by TGA of about 4.4%, which is also close to a monohydrate (calculated water content of 4.7%). Hydrate B starts to dehydrate below 20% RH and loses about 4.4% of water until 0% RH. Upon subsequent increase of the relative humidity it only takes up about 3% of water at 25° C.

Differential Scanning Calorimetry

Differential scanning calorimetry was performed using a TA Discovery DSC with a temperature range of 30 to 300 C at a scan rate of 10 C/min under nitrogen with a flow rate of 25 mL/min. The sample mass used was about 2 mg.

Biological Data

Many known calcium channel activators have shown complex mechanisms of activating $Ca_V1.2$. These molecules not only increase peak currents, but also have additional mechanisms that increase intracellular calcium concentration, for example, by shifting the voltage sensitivity of the channel to more negative membrane potentials. FIG. 6 illustrates these additional mechanisms by depicting simulated cardiac action potentials from an epicardial environment and showing the impact of shifting the voltage of $Ca_V1.2$ activation to more negative membrane potentials at a Potential (mV) versus Time (ms). These additional mechanisms could drive or facilitate cardiovascular effects such as increase in blood pressure, change in heart rate or contractility, and/or arrhythmia due to QT prolongation. For example, the O'Hara-Rudy model was used to investigate the effect of $Ca_V1.2$ modulation on action potential duration and arrhythmic liability. It was identified that a >12 mV hyperpolarizing shift in the activation curve could potentially lead to >15% QT prolongation and an increased risk of arrhythmia. Therefore, minimizing any shifts in voltage sensitivity may lead to compounds with a reduced risk of QT prolongation and cardiac arrhythmia.

The compounds of formula (I) are highly potent $Ca_V1.2$ activators having a biophysical profile which minimizes the cardiovascular risks outlined above. First, the compounds of formula (I) limit their effects on the voltage sensitivity by minimizing hyperpolarizing shifts to <9 mV to mitigate for an arrhythmia potential. Second, the compounds of formula (I) increase $Ca_V1.2$ peak currents by no more than 2.5 fold, thereby limiting over-activation of the channel. Third, the compounds of formula (I) do not delay $Ca_V1.2$ channel inactivation, a pathophysiological mechanism underlying cardiac symptoms of Timothy Syndrome. Moreover, compounds of formula (I) are designed to maximize brain exposure by showing no significant efflux in the brain.

Generation and Maintenance of the $Ca_V1.2$-HEK293 (AUX) Cell Line

The monoclonal $Ca_V1.2$-HEK293(AUX) cell line constitutively expresses human $Ca_V1.2$ alpha1C (α1C) subunit (CACNA1C) and has doxycycline-inducible expression of the alpha2delta (α2Δ2) auxiliary subunit (CACNA2D2) and beta2 (β2) auxiliary subunit (CACNB2). To generate the cell line, expression vectors pcDNA5.0/FRT-TO-CACNA2D2-FCS-P2A-CACNB2 and pCMV6-entry-CACNA1C were established via gene synthesis and cloning. Here, pcDNA5.0/FRT-TO plasmid is from Invitrogen, pCMV6-entry is from Origene, FCS stands for Furin Cleavage Site, P2A is a peptide self-cleavage sequence derived from porcine teschovirus-1, and FRT is the Flippase recognition target site. Next, parental line Flp-In™ 293 T-Rex (Invitrogen) was transfected with pcDNA5.0/FRT-TO-CACNA2D2-FCS-P2A-CACNB2 and Flippase vector pOG44 (Invitrogen) to establish targeted integration of the CACNA2D2-FCS-P2A-CACNB2 expression cassette into the pre-engineered FRT site in Flp-In™ 293 T-Rex. This intermediate cell line was then transfected with pCMV6-entry-CACNA1C to establish stable CACNA1C expression. Clonal isolation was achieved under Neomycin selection. A cell clone (2-19B) with good voltage-dependent Barium current (see electrophysiology methods below) was selected for characterization of $Ca_V1.2$ activators.

To maintain the cell line, cells were passaged twice per week. At each passage, growth media (Table 6) were completely removed and cells were rinsed sequentially with 10 ml of D-PBS and 5 ml of warm TrypLE™ Express Enzyme (Gibco). Both D-PBS and TrypLE™ Express Enzyme were immediately removed after rinsing. Plates were then placed at room temperature for 3-5 minutes. Next, 10 mL of warm 37° C. complete media was added to flush the cell-growing surface and collect dissociated cells. Cells were counted and seeded into new flasks, targeting a density of 2-3×10⁶ cells per T175 cm² flask.

TABLE 6

| Growth medium for HEK293-$Ca_V1.2$(AUX) cells | |
|---|---|
| Reagent | Concentration |
| DMEM | |
| Heat inactivated fetal bovine serum | 10% |
| Hygromycin B | 100 ug/ml |
| Blasticidin | 10 ug/ml |
| Geneticin (G418) | 200 ug/mL |

Electrophysiological Characterization of $Ca_V1.2$ Activators Using $Ca_V1.2$-HEK293(AUX) Cell Line and QPatch 24 hours prior an electrophysiology experiment, doxycycline (1 μg/ml) was added to the growth medium (Table 6), and 25 μM of verapamil was co-applied to prevent calcium influx triggered cell death. Cell confluency should reach 70%-80% right before the experiment.

To harvest cells (from a T175 cm² flask as an example), growth media were removed completely, and the cells were rinsed with 10 mL of D-PBS. D-PBS was aspirated, and 10 mL of Detachin (Genlantis) was added and the plate was placed in a 37° C. incubator for 10 minutes. Detached cells were placed into a 15 mL conical tube and spun at 1000 rpm for 2 minutes. Supernatant was removed, and cells were re-suspended in QPatch complete media (Table 7) to desired cell density of 1.5-3 million cells per QPatch run. Each experimental run uses 1.5 mL of cells.

The cells suspension was taken to the Sophion QPatch platform that uses whole-cell voltage clamp to measure barium currents conducted through $Ca_V1.2$ on single-hole QPlates. Extracellular and intracellular patch clamp solutions are described in Tables 7 and 8, respectively. A dose-response assay protocol was used to determine the maximal fold change of peak inward current (Emax) and potency ($EC_{50}$) of each compound. The protocol had eight liquid periods. The first liquid period was to stabilize current amplitude, which was monitored using repetitive 200-ms voltage pulses stepping from −80 mV to 0 mV. The second liquid period was to determine baseline current amplitude in the presence of vehicle control, using a single 20-ms voltage pulse stepping from −80 mV to 0 mV. The third through eighth liquid periods were used to ascertain a 6-dose response to compound treatments, also using single 20-ms voltage pulses stepping from −80 mV to 0 mV. The $EC_{50}$ was generated using the following equation $I_{concentration} = I_{base} + (I_{full} - I_{base}) * c^n / (XC_{50}^n \, c^n)$, where c is the concentration and n is the Hill coefficient constant. $I_{full}$ is the maximal current achievable, and $I_{base}$ is 0. A channel biophysics assay protocol was used to determine channel gating properties including current-voltage relationship (IV curves), half-way channel activation voltage ($V_{1/2}$), rate of channel inactivation (tau), and amplitude of tail current. Among these, V112 was derived from fitting equation $G(V) = G_{Vmin} + (G_{Vmax} - G_{Vmin})/(1 + \exp(-(V - V_{1/2})/V_{slope}))$, where G stands for conductance, $G_{Vmin}$ equals 0, $G_{Vmax}$ is the maximal conductance, and $V_{slope}$ is a slope factor. G(V) was pre-calculated from equation $G(V) = I(V)/(V - 0.06)$, for each experimentally applied depolarization potential (V) and the corresponding current amplitude (I(V)), and 0.06 in the equation was the experimentally determined reversal potential in volts. The protocol had four liquid periods. The first liquid period was to stabilize current amplitude, which was monitored using repetitive 200-ms voltage pulses stepping from −80 mV to 0 mV. Upon stabilization of current amplitude, a baseline value for the tau of inactivation was determined, via a single-exponential fit of the inactivation phase of the current trace. The second liquid period was to measure the baseline values constituting the current-voltage relationship in the presence of vehicle control, and the third liquid period was to measure the compound effect on the current-voltage relationship. During each of these two liquid periods, cells were given ten 20-ms voltage pulses, each stepping from −80 mV to an incremental value that ranges from −55 mV to +35 mV (increment size 10 mV). During the fourth liquid period a 200-ms voltage pulse from −80 mV to 0 mV was delivered again to measure the compound effect on tau of inactivation.

TABLE 6

QPatch complete media:

| Reagent | Concentration |
|---|---|
| CHO-Serum free Media (SFM) | |
| 1M HEPES | 25 mM |

TABLE 7

Extracellular solution for QPatch experiments

| Chemical | Concentration (mM) |
|---|---|
| Sodium Chloride | 145 |
| Barium Chloride | 10 |
| Potassium Chloride | 4 |
| HEPES (4-(2-hydroxyethyl)-1-piperazineethanesulfonic acid)) | 10 |
| HEPES | 10 | pH to 7.4 with NaOH for a final osmolarity of ~315 mOSm, filter solution through 0.2 μM filter.

TABLE 8

Intracellular solution for QPatch experiments. The solution is a mix of 80% part two (stored at −80° C.) and 20% part one:

| Chemical | Concentration (mM) |
|---|---|
| Part One: | |
| Cesium Fluoride | 135 |
| HEPES (4-(2-hydroxyethyl)-1-piperazineethanesulfonic acid)) | 10 |
| Sodium Chloride | 10 |
| EGTA (Ethylene glycol-bis(2-aminoethylether)-N,N,N',N'-tetraacetic acid) | 1 | pH to 7.2 with CsOH for a final osmolarity of ~295 mOSm, filter solution through 0.2 μM filter.

| Chemical | Concentration (mM) |
|---|---|
| Part Two: | |
| Cesium Chloride | 140 |
| EGTA (Ethylene glycol-bis(2-aminoethylether)-N,N,N',N'-tetraacetic acid) | 10 |
| HEPES (4-(2-hydroxyethyl)-1-piperazineethanesulfonic acid)) | 10 |
| Adenosine 5'-triphosphate magnesium salt | 5 | pH to 7.2 with KOH for a final osmolarity of ~295 mOSm, filter solution through 0.2 μM filter.

Assessment of Compound Exposure—cFos Induction (PK-PD) Relationship in Wild-Type Mice Animal maintenance and ethics. All animals were housed with regulated temperature and light cycle (22° C., 12-hour light/12-hour dark cycle) with unrestricted access to food and water. All animal experiments were performed in accordance with institutional guidelines for the care and use of laboratory animals as approved by the Institutional Animal Care and Use Committee (IACUC) of the Novartis Institutes for BioMedical Research, Inc. (Cambridge, MA, USA).

Compound administration and brain tissue collection. Wild-type C57BL/6J male mice were obtained from Jackson laboratories (Bar Harbor, ME). The acute, single-dose effects of $Ca_V1.2$ activators of the present disclosure were evaluated in male eight-week old mice (n=6 mice per compound). Each compound was dissolved in 10% PEG300, 10% Solutol, 10% Cremophore EL, and 70% Phosphate Buffered Saline and administered intraperitoneal (i.p.) at a concentration of 1 mg/kg up to 30 mg/kg depending on the compound. Animals were euthanized one hour after compound administration via exsanguination under deep anesthesia. Blood was collected in EDTA tubes for downstream analysis of drug levels. Brains were rapidly removed from the skull, and the cerebral cortex and cerebellum were regionally dissected. Cerebellar samples were snap frozen in liquid nitrogen to assess compound exposure. Cortical samples for cFos assessment were placed in 500 µl of RNAlater solution (ThermoFisher) to preserve the integrity of RNA in the sample. Samples remained in RNAlater for at least 24 hours at 4° C. before moving to −80° C. for storage before processing.

Quantification of cFos mRNA induction. Tissue homogenization was performed using TissueLyser system for 96 well plates (Qiagen). First, frozen cortical samples were thawed, removed from RNAlater, and placed into TissueLyser tubes along with Buffer RLT containing 0.5% Reagent DX and one 5 mm TissueLyser metal bead. The TissueLyser tubes were loaded into a TissueLyser II tissue homogenizer for 3 rounds of homogenization, with each round lasting 5 minutes at 30 Hz bead-beating frequency. Total RNA was purified from the homogenate using RNeasy 96 Plus kit (Qiagen), RNA concentration and A260/A280 ratio were quantified via the Nanodrop (ThermoFisher), and all samples were normalized to 100 ng/µL concentration. RNA was reverse transcribed into cDNA using the Superscript III First-strand synthesis SuperMix Kit (ThermoFisher). For each sample, 6 µL of RNA (600 ng total) was mixed with 1 µL of Oligo dT and 1 µl of annealing buffer and heated to 65° C. for 5 minutes. Next, 10 µL of 2× First-Strand Reaction Mix and 2 µl of the Enzyme mix were added to achieve a total reaction volume of 20 uL. The samples were heated to 50° C. for 50 minutes then 85° C. for 5 minutes to complete cDNA synthesis.

Quantitative PCR was performed on the cDNA samples using Quantitect Multiplex RT-PCR kit (Qiagen) in a 384-well assay format. Each PCR well contained 2 µl of cDNA (60 ng total), 10 µL of RT-PCR mastermix, 1 µL of cFos FAM Taqman probe (Mm00487425_m1 (FAM) #4351368), 1 µL of GAPDH VIC Taqman probe (Mm99999915-g1 (VIC) #4448486), 0.2 µl of Multiplex RT mix and 5.8 µl of RNase-free water. On the ViiA7 Real-Time PCR system (ThermoFisher), the samples were heated to 95° C. for 15 minutes then cycled between 94° C. for 45 seconds and 60° C. for 45 seconds for 45 cycles. cFos Ct values were exported, normalized to GAPDH Ct values, and converted to relative fold change in expression using the delta-delta Ct relative quantification method. cFos fold changes between compound treatments and vehicle were analyzed by one-way ANOVA, followed by Tukey's post-hoc comparisons.

Quantification of compound exposure. Cerebellar tissue samples were homogenized in 4 ml of 20% acetonitrile and 80% Phosphate buffered saline for every 1 g of tissue (5× dilution). Tissue was homogenized using either of the following three methods: hand held probe system, TissueLyser system with 5 mm steel bead at a frequency of 30 s$^{-1}$ for 4 min, or OMNI Bead Ruptor Elite homogenizer for 30 seconds to 1 minute depending on tissue type. Tissue samples were added to a 96-well plate (12.5 uL sample) and processed for quantification by mass spectrometry.

Results

TABLE 9

Compound data

| Example | Qpatch EC50 (µM) | Qpatch Emax | Biophysics voltage shift (mV) | Brain:blood ratio | %↑cFOS mRNA cortex (3 mg/kg ip) | %↑cFOS mRNA cortex (10 mg/kg ip) |
| --- | --- | --- | --- | --- | --- | --- |
| 1 | 0.024 | 1.9 | −5.9 | 2.9 | 254% | nd |
| 2 | 0.012 | 2.3 | −4.5 | 1.5 | 378% | nd |
| 3 | 0.05 | 1.6 | 0.1 | 2.8 | 204% | nd |
| 4 | 0.02 | 1.9 | −4.4 | 1.4 | 161% | nd |
| 5 | 0.02 | 1.9 | −4.6 | 3.3 | 400% | nd |
| 6 | 0.017* | 1.4* | −6.3 | 1.5 | 199% | nd |
| 7 | 0.03 | 1.8 | −6.3 | nd | 262% | nd |
| 8 | 0.02 | 2.0 | −5.4 | 3.5 | 496% | nd |
| 9 | 0.10 | 1.5 | −4.5 | 1.5 | 290% | 525% |
| 10 | 0.04 | 1.8 | −2.3 | 0.9 | 225% | nd |
| 11 | 0.07 | 2.0 | −5.0 | 1.1 | 160% | nd |
| 12 | 0.08 | 2.3 | −3.4 | nd | nd | nd |
| 13 | 0.02* | 1.6* | −0.7 | 3.5 | 225% | 444% |
| 14 | 0.09 | 1.9 | −5.5 | nd | nd | nd |
| 15 | 0.29 | 1.3 | −5.7 | 1.7 | 176% | 294% |
| 16 | 0.01 | 1.5 | −5.8 | 3.2 | 234% | nd |
| 17 | 0.12 | 1.2 | −6.8 | 2.1 | 201% | nd |
| 18 | 0.21 | 1.8 | −5.2 | 1.0 | 173% | 280% |
| 19 | 0.06 | 1.8 | −6.7 | nd | nd | nd |
| 20 | 0.22 | 3.0 | −8.5 | nd | nd | nd |
| 21 | 0.03 | 2.8 | −8.1 | nd | nd | nd |
| 22 | 0.05 | 2.8 | −8.6 | nd | nd | nd |
| 23 | 0.12 | 3.5 | −6.2 | 1.2 | 365 | nd |
| 24 | 0.16 | 2.4 | −7.5 | nd | nd | nd |
| 25 | 0.04 | 1.7 | −4.2 | nd | nd | nd |
| 26 | 0.30 | 2.0 | −4.3 | nd | nd | nd |
| 27 | 0.03 | 1.5 | −8.7 | nd | nd | nd |
| 28 | 0.06 | 1.9 | −7.2 | 1.1 | 293% | nd |
| 29 | 0.05 | 1.4 | TBD | nd | nd | nd |

TABLE 9-continued

| | | | | | %↑cFOS | %↑cFOS |
| | Qpatch | | Biophysics | | mRNA | mRNA |
| | EC50 | Qpatch | voltage | Brain:blood | cortex | cortex |
| Example | (µM) | Emax | shift (mV) | ratio | (3 mg/kg ip) | (10 mg/kg ip) |
|---|---|---|---|---|---|---|
| 30 | 0.09 | 1.8 | nd | nd | nd | nd |
| 31 | 0.29 | 1.6 | nd | nd | nd | nd |

Qpatch was conducted as a 6-point dose response with 10 individual determinations at each concentration.
Unless stated only one experimental replicate (n = 1)
*n = 2
n = 3
nd = not determined Comparative Examples Other $Ca_V1.2$ activators are known, however these compounds are not as potent and/or do not have the desired biophysical properties needed to activate the channel and have sufficient brain exposure, while at the same time minimizing cardiovascular risks, such as increase in blood pressure, altered heart rate or contractility, and/or arrhythmia due to QT prolongation.

TABLE 10

Comparative examples to other known CaV1.2 activators

| Structure Name | Qpatch EC50 (µM) | Qpatch Emax | Biophysics voltage shift (mV) | Brain:blood ratio |
|---|---|---|---|---|

Reported calcium channel activators (single enantiomers of reported racemates) showing various Qpatch profiles (Emax & V-shift)

| | | | | |
|---|---|---|---|---|
| (BayK8644) | 0.021 | 3.9 | −10.11 | Not determined |
| (RS30124) | 0.045 | 4.3 | −15.4 | Not determined |

TABLE 10-continued
| | | | Biophysics | |
|---|---|---|---|---|
| | Qpatch EC50 | | voltage shift | Brain:blood |
| Structure Name | (μM) | Qpatch Emax | (mV) | ratio |
Comparative examples to other known CaV1.2 activators
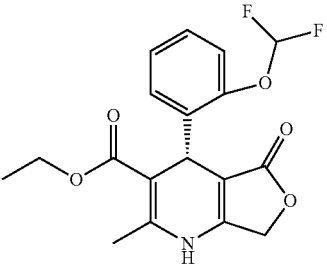
(CGP028392)
0.28  2.2  −6.7  0.23
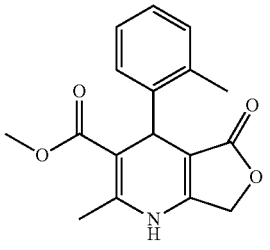
CAS# 85825-32-7
2.24  Not determined  Not determined  Not determined
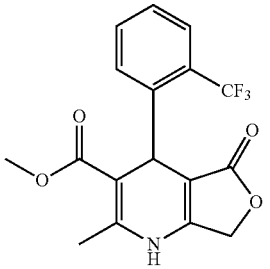
CAS# 85825-31-6
0.36  1.4  −4.3  Not determined
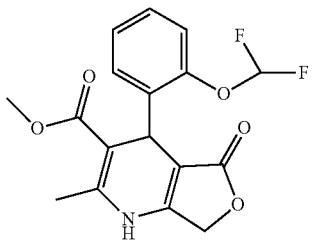
CAS# 92638-18-1
0.51  1.7  −7.1  Not determined TABLE 10-continued Comparative examples to other known CaV1.2 activators

| Structure Name | Qpatch EC50 (μM) | Qpatch Emax | Biophysics voltage shift (mV) | Brain:blood ratio |
|---|---|---|---|---|
| 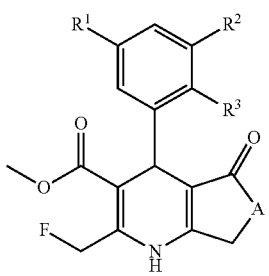 | 0.93 | 1.9 | Not determined | Not determined |

What is claimed is:

1. A compound according to formula (I) or a pharmaceutically acceptable salt thereof

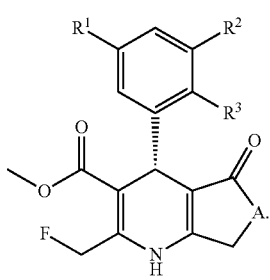
(I)

wherein:

A is O;

$R^1$ is H or F;

$R^2$ is H or F; and $R^3$ is methyl substituted with 1 or 3 F, ethyl substituted with 1 to 3 F, or cyclopropyl optionally substituted with 1 to 3 F.

2. The compound of claim 1, wherein the compound is a compound of formula (Ia) or a pharmaceutically acceptable salt thereof (Ia)

3. The compound of claim 1, wherein the compound is a compound of formula (Ib) or a pharmaceutically acceptable salt thereof

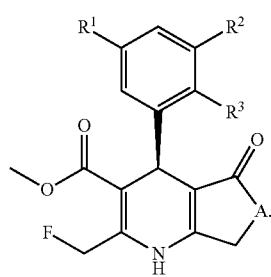
(Ib)

4. The compound of claim 1, wherein $R^2$ is F.

5. The compound of claim 1, wherein $R^2$ is H.

6. The compound of claim 1, wherein $R^3$ is cyclopropyl substituted with 1 to 3 F.

7. The compound of claim 1, wherein $R^3$ is $CF_3$.

8. The compound of claim 1, wherein $R^3$ is ethyl substituted with 1 or 2 F or cyclopropyl either unsubstituted or substituted with 2 F.

9. The compound of claim 8, wherein $R^2$ is F.

10. The compound of claim 8, wherein $R^3$ is ethyl substituted with 1 to 3 F.

11. A compound selected from the group consisting of:
methyl (R)-4-(2-((R)-2,2-difluorocyclopropyl)-3-fluorophenyl)-2-(fluoromethyl)-5-oxo-1,4,5,7-tetrahydrofuro[3,4-b]pyridine-3-carboxylate;
methyl (R)-4-(2-((S)-2,2-difluorocyclopropyl)-3-fluorophenyl)-2-(fluoromethyl)-5-oxo-1,4,5,7-tetrahydrofuro[3,4-b]pyridine-3-carboxylate;
methyl (R)-4-(2-cyclopropyl-3-fluorophenyl)-2-(fluoromethyl)-5-oxo-1,4,5,7-tetrahydrofuro[3,4-b]pyridine-3-carboxylate;
Methyl (R)-4-(2-((R)-2,2-difluorocyclopropyl)-3,5-difluorophenyl)-2-(fluoromethyl)-5-oxo-1,4,5,7-tetrahydrofuro[3,4-b]pyridine-3-carboxylate;
Methyl (R)-4-(2-((S)-2,2-difluorocyclopropyl)-3,5-difluorophenyl)-2-(fluoromethyl)-5-oxo-1,4,5,7-tetrahydrofuro[3,4-b]pyridine-3-carboxylate;
methyl (R)-4-(3,5-difluoro-2-((R)-1-fluoroethyl)phenyl)-2-(fluoromethyl)-5-oxo-1,4,5,7-tetrahydrofuro[3,4-b]pyridine-3-carboxylate;
methyl (R)-4-(3,5-difluoro-2-((S)-1-fluoroethyl)phenyl)-2-(fluoromethyl)-5-oxo-1,4,5,7-tetrahydrofuro[3,4-b]pyridine-3-carboxylate;

methyl (R)-4-(2-((S)-1,2-difluoroethyl)-3-fluorophenyl)-2-(fluoromethyl)-5-oxo-1,4,5,7-tetrahydrofuro[3,4-b]pyridine-3-carboxylate;
methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate;
methyl (R)-4-(3-fluoro-2-((S)-1-fluoroethyl)phenyl)-2-(fluoromethyl)-5-oxo-1,4,5,7-tetrahydrofuro[3,4-b]pyridine-3-carboxylate;
methyl (R)-4-(3,5-difluoro-2-(trifluoromethyl)phenyl)-2-(fluoromethyl)-5-oxo-1,4,5,7-tetrahydrofuro[3,4-b]pyridine-3-carboxylate;
methyl (R)-4-(2-(2,2-difluoroethyl)-3,5-difluorophenyl)-2-(fluoromethyl)-5-oxo-1,4,5,7-tetrahydrofuro [3,4-b]pyridine-3-carboxylate;
methyl (R)-4-(2-cyclopropyl-3,5-difluorophenyl)-2-(fluoromethyl)-5-oxo-1,4,5,7-tetrahydrofuro[3,4-b]pyridine-3-carboxylate;
methyl (R)-4-(2-((R)-1,2-difluoroethyl)-3,5-difluorophenyl)-2-(fluoromethyl)-5-oxo-1,4,5,7-tetrahydrofuro[3,4-b]pyridine-3-carboxylate;
methyl (R)-4-(2-((S)-1,2-difluoroethyl)-3,5-difluorophenyl)-2-(fluoromethyl)-5-oxo-1,4,5,7-tetrahydrofuro[3,4-b]pyridine-3-carboxylate;
methyl (R)-4-(3-fluoro-2-(trifluoromethyl)phenyl)-2-(fluoromethyl)-5-oxo-1,4,5,7-tetrahydrofuro[3,4-b]pyridine-3-carboxylate;
methyl (R)-4-(2-cyclopropyl-5-fluorophenyl)-2-(fluoromethyl)-5-oxo-1,4,5,7-tetrahydrofuro[3,4-b]pyridine-3-carboxylate;
methyl (R)-4-(2-cyclopropylphenyl)-2-(fluoromethyl)-5-oxo-1,4,5,7-tetrahydrofuro[3,4-b]pyridine-3-carboxylate;
methyl (R)-4-(5-fluoro-2-(trifluoromethyl)phenyl)-2-(fluoromethyl)-5-oxo-1,4,5,7-tetrahydrofuro[3,4-b]pyridine-3-carboxylate;
methyl (R)-2-(fluoromethyl)-5-oxo-4-(2-(trifluoromethyl)phenyl)-1,4,5,7-tetrahydrofuro[3,4-b]pyridine-3-carboxylate; and pharmaceutically acceptable salts thereof.

12. A crystalline form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate.

13. A crystalline hydrated form of methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate.

14. A pharmaceutical composition comprising a compound according to claim 1 and a pharmaceutically acceptable excipient.

15. A method for the treatment of schizophrenia, bipolar disorder, major depressive disorder, substance use disorder, ADHD, Phelan-McDermid Syndrome, autism spectrum disorder, multiple sclerosis, frontotemporal dementia, Alzheimer's disease, Brugada Syndrome, Short QT syndrome, or early repolarization syndrome comprising administration of an effective amount of a compound according to claim 1, or a pharmaceutically acceptable salt thereof to a patient in need of treatment thereof.

16. A method for the treatment of schizophrenia, bipolar disorder, major depressive disorder, substance use disorder, ADHD, Phelan-McDermid Syndrome, autism spectrum disorder, multiple sclerosis, frontotemporal dementia, Alzheimer's disease, Brugada Syndrome, Short QT syndrome, or early repolarization syndrome comprising administration of a compound according to claim 11, or a pharmaceutically acceptable salt thereof to a patient in need of treatment thereof.

17. The compound of claim 1, wherein the compound is methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate or a pharmaceutically acceptable salt thereof.

18. The method of claim 16, wherein the compound is methyl (R)-4-(3-fluoro-2-((R)-1-fluoroethyl)phenyl)-2-(fluoromethyl)-5-oxo-1,4,5,7-tetrahydrofuro[3,4-b]pyridine-3-carboxylate or a pharmaceutically acceptable salt thereof.

19. The method of claim 16, wherein the method is for the treatment of schizophrenia.

20. The method of claim 16, wherein the method is for the treatment of bipolar disorder.

21. The method of claim 18, wherein the method is for the treatment of schizophrenia.

22. The method of claim 18, wherein the method is for the treatment of bipolar disorder.

* * * * *